United States Patent
Liu et al.

(10) Patent No.: US 11,084,818 B2
(45) Date of Patent: Aug. 10, 2021

(54) NITROGEN-CONTAINING HETEROCYCLIC COMPOUND, PREPARATION METHOD, INTERMEDIATE, PHARMACEUTICAL COMPOSITION AND USE

(71) Applicant: HEPO PHARMACEUTICAL CO., LTD., Nanjing (CN)

(72) Inventors: Xuemei Liu, Shanghai (CN); Pengfei Qian, Shanghai (CN)

(73) Assignee: HEPO PHARMACEUTICAL CO., LTD., Nanjing (CN)

( * ) Notice: Subject to any disclaimer, the term of this patent is extended or adjusted under 35 U.S.C. 154(b) by 0 days.

(21) Appl. No.: 16/348,504

(22) PCT Filed: Nov. 10, 2017

(86) PCT No.: PCT/CN2017/110493
§ 371 (c)(1),
(2) Date: May 9, 2019

(87) PCT Pub. No.: WO2018/086593
PCT Pub. Date: May 17, 2018

(65) Prior Publication Data
US 2020/0062758 A1    Feb. 27, 2020

(30) Foreign Application Priority Data
Nov. 11, 2016 (CN) .......................... 201610994573.X

(51) Int. Cl.
| | |
|---|---|
| *C07D 473/06* | (2006.01) |
| *C07D 239/48* | (2006.01) |
| *C07D 471/04* | (2006.01) |
| *C07D 473/18* | (2006.01) |
| *C07D 473/22* | (2006.01) |
| *C07D 473/28* | (2006.01) |
| *C07D 519/00* | (2006.01) |

(52) U.S. Cl.
CPC ......... *C07D 473/06* (2013.01); *C07D 239/48* (2013.01); *C07D 471/04* (2013.01); *C07D 473/18* (2013.01); *C07D 473/22* (2013.01); *C07D 473/28* (2013.01); *C07D 519/00* (2013.01)

(58) Field of Classification Search
CPC ... C07D 473/04; C07D 473/06; A61K 31/522
USPC .......................... 544/265; 514/263.2, 263.22
See application file for complete search history.

(56) References Cited

U.S. PATENT DOCUMENTS

| | | |
|---|---|---|
| 5,658,918 A | 8/1997 | Okamoto et al. |
| 2007/0213361 A1 | 9/2007 | Iida |
| 2009/0047249 A1 | 2/2009 | Graupe et al. |
| 2017/0273983 A1 | 9/2017 | Ding et al. |

FOREIGN PATENT DOCUMENTS

| | | |
|---|---|---|
| CN | 1114318 A | 1/1996 |
| CN | 2005121130 A2 | 12/2005 |
| CN | 101027295 A | 8/2007 |
| JP | 2010532353 A | 10/2010 |
| WO | 2015023958 A1 | 2/2015 |

(Continued)

OTHER PUBLICATIONS

"Burger's Medicinal Chemistry and Drug Discovery," 5th Ed. Part 1, Wolf, et.al., pp. 975-977 (1995).*
Banker, et. al., (1996), Modern Pharmaceuticals, p. 596.*
Chawla et. al.; CRIPS 5(1); 2004; p. 9-12.*
Newman, et. al., Drug Discovery Today 8(19); 2003; pp. 898-905.*
Eva M.Y. Moresco et al., "Toll-like receptors", Current Biology, vol. 21, No. 13, 2011, pp. R488-493.
M. Fukata et al., "The role of pattern recognition receptors in intestinal inflammation", Mucosal Immunology, vol. 6, No. 3, 2013, pp. 451-463.

(Continued)

*Primary Examiner* — Jeffrey H Murray
(74) *Attorney, Agent, or Firm* — Houston Beshining Law Office PLLC; Liangang Ye

(57) ABSTRACT

Disclosed are a nitrogen-containing heterocyclic compound, a preparation method thereof, an intermediate thereof, a pharmaceutical composition thereof and a use thereof. The nitrogen-containing heterocyclic compound is a compound of formula I or formula II, a tautomer thereof, an optical isomer thereof, a deuterated compound thereof, a hydrate thereof, a solvate thereof or a pharmaceutically acceptable salt thereof, which can be used for treating a disease associated with TLR7 activity. The nitrogen-containing heterocyclic compound has a relatively high TLR7 agonist activity, high selectivity and good safety.

Formula I

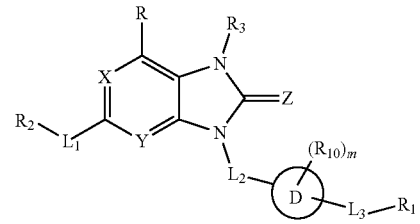

Formula II

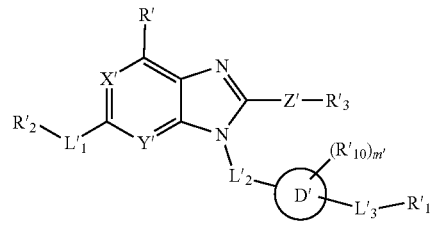

19 Claims, No Drawings

(56) References Cited

FOREIGN PATENT DOCUMENTS

WO 2016023511 A1 2/2016
WO 2017064675 A1 4/2017

OTHER PUBLICATIONS

Keith B. Gorden et al., "Synthetic TLR agonists reveal functional differences between human TLR7 and TLR8", The Journal of Immunology, 2005, pp. 1259-1268.
International Search Report and Written Opinion of PCT/CN2017/110493 dated Feb. 14, 2018.
First Office Action issued in the counterpart Japanese application No. 2019546962 dated Sep. 29, 2020.
Registry (STN) [online], 2009.
Kosaku Hirota et al: "Synthesis and Biological Evaluation of 2,8-Disubstituted 9-Benzyladenines: Discovery of 8-Mercaptoadenines as Potent Interferon-Inducers", Bioorg. Med. Chem. 2003, v.11, pp. 2715-2722.
Extended European Search Report issued in the counterpart European application No. 17869097.0 dated Apr. 17, 2020.
The Second Office Action issued in the counterpart Chinese application No. 2017111075679 dated Apr. 10, 2020.
Nakamura Tomoaki et al: "Synthesis and evaluation of 8-oxoadenine derivatives as potent Toll-like receptor 7 antagonists with high water solubility", Bioorganic & Medicinal Chemistry Letters, Pergamon, Amsterdam, NL, vol. 23, No. 3, Dec. 5, 2012 (Dec. 5, 2012), pp. 669-672.
Second Office Action issued in the counterpart Japanese application No. 2019546962 dated Apr. 6, 2021.

\* cited by examiner

NITROGEN-CONTAINING HETEROCYCLIC COMPOUND, PREPARATION METHOD, INTERMEDIATE, PHARMACEUTICAL COMPOSITION AND USE

RELATED APPLICATION REFERENCE

The present invention is a National Stage of International Application No. PCT/CN2017/110493, filed on Nov. 10, 2017, which claims the priority of the Chinese Patent Application No. CN201610994573.X, filed on Nov. 11, 2016, the contents of which are incorporated herein by its entirety.

FIELD OF INVENTION

The present invention relates to a nitrogen-containing heterocyclic compound, preparation method, intermediate, pharmaceutical composition and use thereof.

PRIOR ARTS

Toll-like receptors (TLRs) are a class of evolutionarily highly conserved natural immune receptors that are widely expressed in a variety of tissues and cells (*Toll-like receptors. Curr Biol,* 2011, 21: R488-93). So far, as a class of well-researched pattern recognition receptors (PRRs), Toll-like receptors can recognize potential pathogenic microorganisms and non-pathogenic commensal bacteria, and perform an important function in removing pathogenic microorganisms, which is the first barrier against the invasion of pathogens (*The role of pattern recognition receptors in intestinal inflammation. Mucosal Immunol,* 2013, 6: 451-63).

Structurally, Toll-like receptors belong to type I transmembrane proteins, which consist of three parts: an extracellular region, a transmembrane region, and an intracellular region. Toll-like receptors may be clarified into two categories. One includes TLR1, TLR2, TLR4, TLR5, TLR6, TLR11, and TLR12, which are mainly expressed on the membrane surface and mainly recognize membrane components of microorganisms such as lipids, lipoproteins, and proteins. The other includes TLR3, TLR7, TLR8, and TLR9, which are mainly expressed in intracellular vesicles, such as endoplasmic reticulum, endosomes, etc., and mainly recognize nucleic acids of pathogenic microorganisms.

TLR7 and TLR8 are highly homologous, and have similar phylogeny and characteristics of recognizing small-molecule compounds, but their functions are quite different. TLR7 agonists are more effective at inducing chemokines regulated by IFN-α and IFN-γ, while TLR8 agonists are biased to induce the inflammatory cytokines TNF-α and IL-12 (*Synthetic TLR agonists reveal functional differences between human TLR7 and TLR8. J Immunol,* 2005, 174: 1259-68). IFN-α is one of the main drugs for the treatment of chronic hepatitis B and hepatitis C, but TNF-α is a pro-inflammatory cytokine and excessive activation may cause serious side effects. At present, several TLR7 agonists, such as Imiquimod, Resiquimod and GS9620, which have been developed and reported, have shown good clinical application prospects. However, the existing TLR7 agonists have the problem of poor selectivity for TLR7. As reported in WO2016023511A1, the $EC_{50}$ of GS9620 for hTLR7 and hTLR8 is 0.517 μM and 7.867 μM, respectively, which shows that its selectivity to TLR7 is poor.

Therefore, it is of great significance to develop a small-molecule compound having high TLR7 agonistic activity, high selectivity and safety.

CONTENT OF THE PRESENT INVENTION

The technical problem to be solved by the present invention is to provide a nitrogen-containing heterocyclic compound, preparation method, intermediate, pharmaceutical composition and use thereof in order to find a structurally novel TLR7 agonist. The nitrogen-containing heterocyclic compound of the present invention has a novel structure, relatively high TLR7 agonist activity, high selectivity and good safety.

The present invention provides a compound of formula I or formula II, a tautomer thereof, an optical isomer thereof, a hydrate thereof, a solvate thereof, a polymorph thereof, a pharmaceutically acceptable salt thereof or a prodrug thereof,

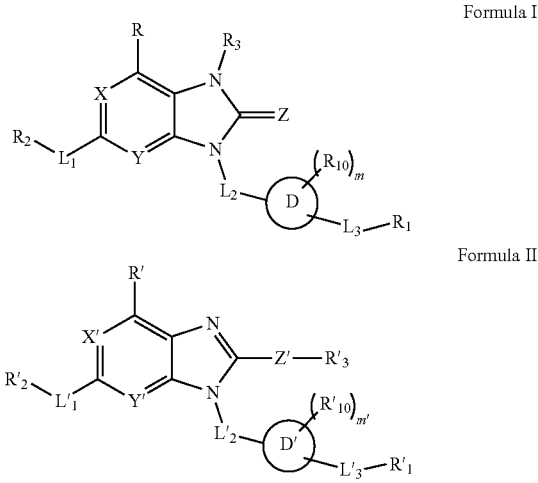

wherein, each of X, Y, X' and Y' is independently selected from C or N (preferably, both X and Y are N, or both X' and Y' are N);

each of $R_2$ and $R'_2$ is independently hydrogen, a $C_1$-$C_{10}$ alkyl, a $C_2$-$C_{10}$ heteroalkyl, a $C_3$-$C_{10}$ cycloalkyl, a $C_3$-$C_{10}$ heterocycloalkyl, a $C_2$-$C_{10}$ alkenyl or a $C_2$-$C_{10}$ alkynyl; wherein, each of the $C_1$-$C_{10}$ alkyl, the $C_2$-$C_{10}$ heteroalkyl, the $C_3$-$C_{10}$ cycloalkyl, the $C_3$-$C_{10}$ heterocycloalkyl, the $C_2$-$C_{10}$ alkenyl and the $C_2$-$C_{10}$ alkynyl is independently substituted by one or more (e.g., 2, 3 or 4) $R_4$; when a plurality of $R_4$ substituents are present, the substituents are the same or different; $R_4$ is selected from the group consisting of hydrogen, hydroxyl, a halogen, a $C_1$-$C_6$ alkyl, a $C_3$-$C_{10}$ cycloalkyl and a $C_3$-$C_{10}$ heterocycloalkyl;

each of $L_1$ and $L'_1$ is independently —O—, —C($R_{a1}R_{a2}$)—, —C(O)—, —S—, —S(O)—, —S(O)$_2$—, —N($R_{a3}$)—, —N($R_{a4}$)C(O)— or —N($R_{a5}$)S(O)$_2$—; wherein, each of $R_{a1}$, $R_{a2}$, $R_{a3}$, $R_{a4}$ and $R_{a5}$ is independently hydrogen or a $C_1$-$C_6$ alkyl (e.g., methyl, ethyl, n-propyl, isobutyl, n-butyl, isobutyl or tert-butyl);

each of $R_1$ and $R'_1$ is independently —$NR_5R_6$;

each of $R_5$ and $R_6$ is independently hydrogen or a $C_1$-$C_{10}$ alkyl; wherein the $C_1$-$C_{10}$ alkyl is substituted by one or more (e.g., 2, 3 or 4) $R_7$; when a plurality of $R_7$ substituents are present, the substituents are the same or different; $R_7$ is selected from the group consisting of hydrogen, hydroxyl, a halogen, a $C_3$-$C_{10}$ cycloalkyl and a $C_3$-$C_{10}$ heterocycloalkyl;

alternatively, $R_5$ and $R_6$ together with the nitrogen atom to which they are attached form a substituted or unsubstituted heterocyclic ring (the heterocyclic ring may be a monocyclic ring, a fused ring, a spiro ring or a bridged ring; the heterocyclic ring may be a heteroaromatic ring or a heteroalicyclic ring; the heterocyclic ring is preferably a 3-10 membered heterocyclic ring; the heteroatom may be selected from the group consisting of O, S and N; the number of the heteroatom is preferably 1, 2 or 3); the substituted heterocyclic ring is substituted by one or more (e.g., 2, 3 or 4) $R_8$; when a plurality of $R_8$ substituents are present, the substituents are the same or different; $R_8$ is selected from the group consisting of a halogen, hydroxyl, a $C_1$-$C_6$ alkyl, a $C_3$-$C_{10}$ cycloalkyl, —C(O)$OR_{b1}$, —C(O)$R_{b2}$, —$NR_{b3}R_{b4}$, —C(O)$NR_{b5}$, —OC(O)$NR_{b6}$ or —$NR_{b7}$C(O)$NR_{b8}$; wherein, each of $R_{b1}$, $R_{b2}$, $R_{b3}$, $R_{b4}$, $R_{b5}$, $R_{b6}$, $R_{b7}$ and $R_{b8}$ is independently hydrogen or a $C_1$-$C_6$ alkyl (e.g., methyl, ethyl, n-propyl, isobutyl, n-butyl, isobutyl or tert-butyl);

Z is C, N, O or S;

Z' is —O—, —S—, —N($R'_4$)— or —C($R'_5R'_6$)—;

each of $R_3$, $R'_3$, $R'_4$, $R'_5$ and $R'_6$ is independently hydrogen, a $C_1$-$C_{10}$ alkyl or a $C_3$-$C_{10}$ cycloalkyl; wherein each of the $C_1$-$C_{10}$ alkyl and the $C_3$-$C_{10}$ cycloalkyl is independently substituted by one or more (e.g., 2, 3 or 4) $R_9$; when a plurality of $R_9$ substituents are present, the substituents are the same or different; $R_9$ is selected from the group consisting of hydrogen, a halogen, a $C_1$-$C_6$ alkyl, a $C_3$-$C_{10}$ cycloalkyl and a $C_3$-$C_{10}$ heterocycloalkyl;

D is a $C_6$-$C_{10}$ arylene (e.g., phenylene) or a $C_5$-$C_{10}$ heteroarylene;

each of $R_{10}$ and $R'_{10}$ is independently a halogen, nitro, cyano, hydroxyl, sulfhydryl, a $C_1$-$C_6$ alkyl, a $C_1$-$C_6$ alkoxy, a $C_3$-$C_{10}$ cycloalkyl, a $C_3$-$C_{10}$ heterocycloalkyl, —C(O)$OR_1$, —C(O)$R_{c2}$, —OC(O)$R_{13}$, —$NR_{c4}R_{c5}$, —$NR_{c6}$C(O)$R_{c7}$, —C(O)$NR_{c8}$, —OC(O)$NR_{c9}$, —$NR_{c10}$C(O)$NR_{c11}$, —$SR_{c12}$, —S(O)$NR_{c13}R_{c14}$, —S(O)$_2NR_{c15}R_{c16}$, —$NR_{c17}$S(O)$_2R_{c18}$ or —$NR_{c19}$S(O)$R_{c20}$; wherein each of $R_{c1}$, $R_{c2}$, $R_{c3}$, $R_{c4}$, $R_{c5}$, $R_{c6}$, $R_{c7}$, $R_{c8}$, $R_{c9}$, $R_{c10}$, $R_{c11}$, $R_{c12}$, $R_{c13}$, $R_{c14}$, $R_{c15}$, $R_{c16}$, $R_{c17}$, $R_{c18}$, $R_{c19}$ and $R_{c20}$ is independently hydrogen or a $C_1$-$C_6$ alkyl (e.g., methyl, ethyl, n-propyl, isobutyl, n-butyl, isobutyl or tert-butyl);

each of m and m' is independently 0, 1, 2, 3 or 4; when a plurality of $R_{10}$ substituents are present on D, the substituents are the same or different; when a plurality of $R'_{10}$ substitutions are present on D', the substituents are the same or different;

each of $L_2$, $L'_2$, $L_3$ and $L'_3$ is independently a $C_1$-$C_6$ alkylene (e.g., —CH$_2$—, —CH$_2$CH$_2$—, —CH(CH$_3$)—, —CH$_2$CH$_2$CH$_2$—, —CH(CH$_3$)CH$_2$— or —CH(CH$_2$CH$_3$)—) or a $C_2$-$C_6$ heteroalkylene (the heteroatom in the $C_2$-$C_6$ heteroalkylene may be selected from the group consisting of O, S and N; the number of the heteroatom may be 1, 2 or 3, e.g., —CH$_2$OCH$_2$—); each of the $C_1$-$C_6$ alkylene and the $C_2$-$C_6$ heteroalkylene is independently substituted by one or more (e.g., 2, 3 or 4) $R_{11}$; when a plurality of $R_{11}$ substitutions are present, the substituents are the same or different; $R_{11}$ is selected from the group consisting of hydrogen, a halogen, cyano, a $C_1$-$C_6$ alkyl, a $C_3$-$C_{10}$ cycloalkyl, a $C_3$-$C_{10}$ heterocycloalkyl, —$OR_{d1}$, —$SR_{d2}$, —$NR_{d3}R_{d4}$; wherein each of $R_{d1}$, $R_{d2}$, $R_{d3}$ and $R_{d4}$ is independently hydrogen or a $C_1$-$C_6$ alkyl (e.g., methyl, ethyl, n-propyl, isobutyl, n-butyl, isobutyl or tert-butyl);

each of R and R' is independently hydrogen, a halogen, hydroxyl, a $C_1$-$C_{10}$ alkyl, a $C_2$-$C_{10}$ heteroalkyl, a $C_3$-$C_{10}$ cycloalkyl, a $C_3$-$C_{10}$ heterocycloalkyl, a $C_2$-$C_{10}$ alkenyl or a $C_2$-$C_{10}$ alkynyl; wherein, each of the $C_1$-$C_{10}$ alkyl, the $C_2$-$C_{10}$ heteroalkyl, the $C_3$-$C_{10}$ cycloalkyl, the $C_3$-$C_{10}$ heterocycloalkyl, the $C_2$-$C_{10}$ alkenyl and the $C_2$-$C_{10}$ alkynyl is independently substituted by one or more (e.g., 2, 3 or 4) $R_{12}$; when a plurality of $R_{12}$ substitutions are present, the substituents are the same or different; $R_{12}$ is selected from the group consisting of hydrogen, a halogen, a $C_1$-$C_6$ alkyl, a $C_3$-$C_{10}$ cycloalkyl and a $C_3$-$C_{10}$ heterocycloalkyl.

When $R_2$, $R'_2$, $R_3$, $R'_3$, $R'_4$, $R_5$, $R_6$, $R'_5$, $R'_6$, R or R' is a $C_1$-$C_{10}$ alkyl; then the $C_1$-$C_{10}$ alkyl is preferably a $C_1$-$C_6$ alkyl; the $C_1$-$C_6$ alkyl is preferably methyl, ethyl, n-propyl, isobutyl, n-butyl, isobutyl or tert-butyl.

When $R_2$, $R'_2$, R or R' is a $C_2$-$C_{10}$ heteroalkyl, then the heteroatom in the $C_2$-$C_{10}$ heteroalkyl group may be selected from the group consisting of O, S and N and the number of heteroatom is preferably 1 to 5 (e.g., 1, 2, 3 or 4). Preferably, the heteroatom in the $C_2$-$C_{10}$ heteroalkyl is O and the number of heteroatom is 1 or 2; more preferably, the $C_2$-$C_{10}$ heteroalkyl is preferably

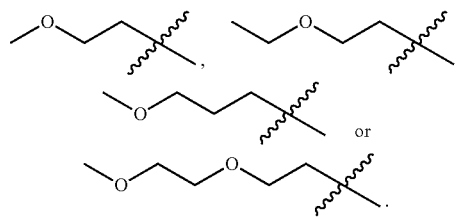

When $R_2$, $R'_2$, $R_3$, $R'_3$, $R'_4$, $R'_5$, $R'_6$, R or R' is a $C_3$-$C_{10}$ cycloalkyl, then the $C_3$-$C_{10}$ cycloalkyl is preferably cyclopropyl, cyclopentyl or cyclohexyl.

When $R_2$, $R'_2$, R or R' is a $C_3$-$C_{10}$ heterocycloalkyl, then the heteroatom in the $C_3$-$C_{10}$ heterocycloalkyl may be selected from the group consisting of O, S and N and the number of the heteroatom is preferably 1 to 3 (e.g., 2); the $C_3$-$C_{10}$ heterocycloalkyl is preferably

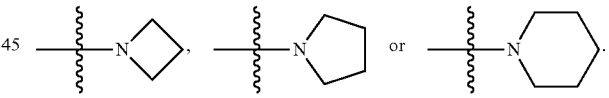

When $R_2$, $R'_2$, R or R' is a $C_2$-$C_{10}$ alkenyl, then the $C_2$-$C_{10}$ alkenyl is preferably vinyl.

When $R_2$, $R'_2$, R or R' is a $C_2$-$C_{10}$ alkynyl, then the $C_2$-$C_{10}$ alkynyl is preferably ethynyl.

When $R_4$, $R_7$, $R_8$, $R_9$, $R_{10}$, $R'_{10}$, $R_{11}$ or $R_{12}$ is a halogen, then the halogen is preferably F, Cl, Br or I.

When $R_4$, $R_7$, $R_8$, $R_9$, $R_{10}$, $R'_{10}$, $R_{11}$ or $R_{12}$ is a $C_3$-$C_{10}$ cycloalkyl, then the $C_3$-$C_{10}$ cycloalkyl is preferably cyclopropyl, cyclopentyl or cyclohexyl.

When $R_4$, $R_7$, $R_9$, $R_{10}$, $R'_{10}$, $R_{11}$ or $R_{12}$ is a $C_3$-$C_{10}$ heterocycloalkyl, then the heteroatom in the $C_3$-$C_{10}$ heterocycloalkyl may be selected from the group consisting of O, S and N; the number of the heteroatom is preferably 1 to 3 (e.g., 2); the heteroatom may be at the ortho-, meta- or para-position of the linking site; the $C_3$-$C_{10}$ heterocycloalkyl may be linked through a carbon atom or an N atom; the $C_3$-$C_{10}$ heterocycloalkyl is preferably

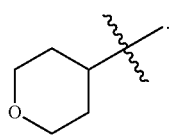 [SMILES: *C1CCOCC1]

When $R_4$, $R_8$, $R_9$, $R_{10}$, $R'_{10}$, $R_{11}$ or $R_{12}$ is a $C_1$-$C_6$ alkyl, then the $C_1$-$C_6$ alkyl is preferably methyl, ethyl, n-propyl, isobutyl, n-butyl, isobutyl or tert-butyl.

When the $R_{10}$ or $R'_{10}$ is a $C_1$-$C_6$ alkoxy, then the $C_1$-$C_6$ alkoxy is preferably methoxy, ethoxy, n-propoxy, isobutoxy, n-butoxy, isobutoxy or tert-butoxy.

In $R_1$ or $R'_1$, when $R_5$ and $R_6$ together with the nitrogen atom to which they are attached form a substituted or unsubstituted heterocyclic ring, then the heterocyclic ring is preferably selected from any one of the following structures:

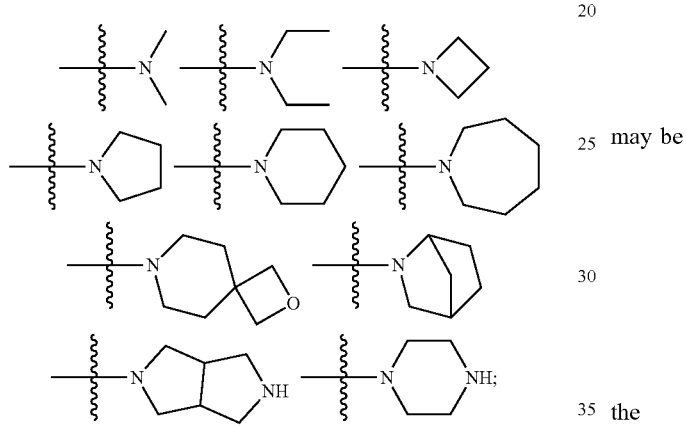

more preferably, the substituted heterocyclic ring is selected from any one of the following structures:

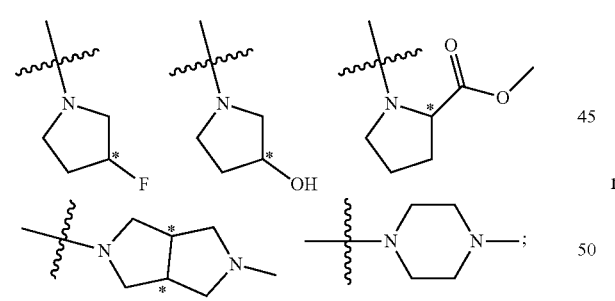

"*" refers to the chiral carbon center, which may be S-configuration carbon, R-configuration carbon or a racemate; e.g., the

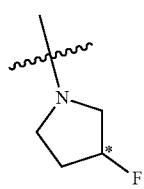 [SMILES: *N1CCC(F)C1]

may be

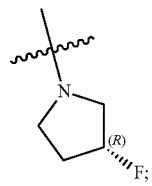

the

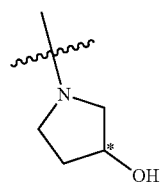 [SMILES: *N1CCC(O)C1]

may be

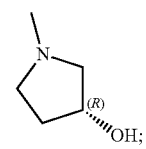

the

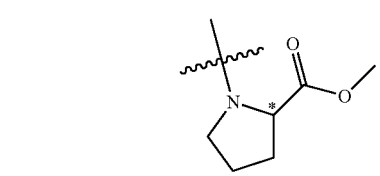 [SMILES: *N1CCCC1C(=O)OC]

may be

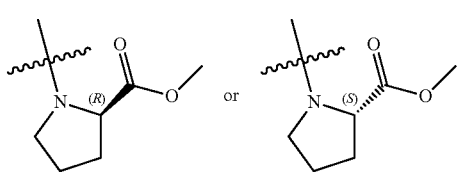

the

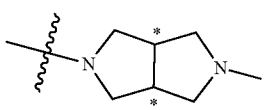

may be

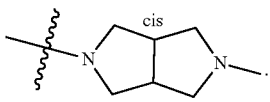 [SMILES: *N1CC2CN(C)CC2C1]

Preferably, the R₂— is preferably selected from any one of the following structures:

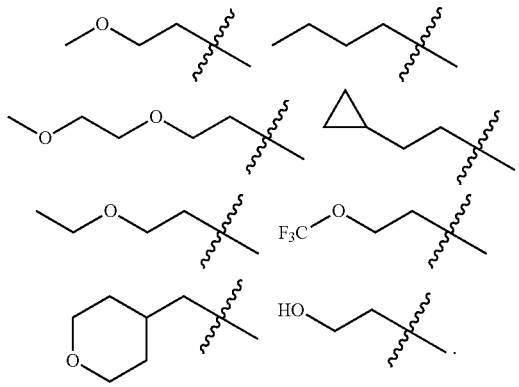

Preferably, the R₂-L₁- is preferably selected from any one of the following structures:

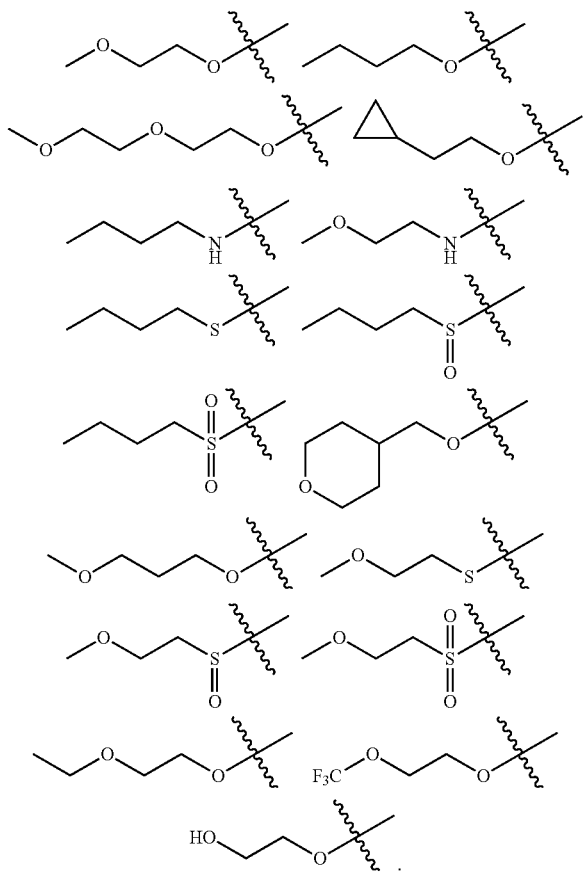

Preferably, when D is phenylene, -L₃-R₁ is at the ortho-, meta- or para-position of L₂.

Preferably, when D' is phenylene, -L'₃-R'₁ is in the ortho-, meta- or para-position of L'₂.

The compound of formula I is preferably

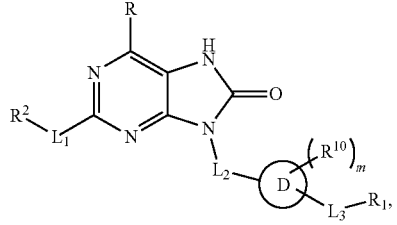

Formula I-1 more preferably

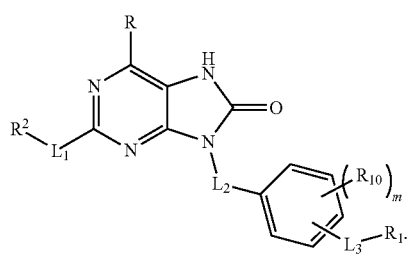

Formula I-2

Preferably, in the formula I-2, R is H and m is 0.

The compound of formula II is preferably

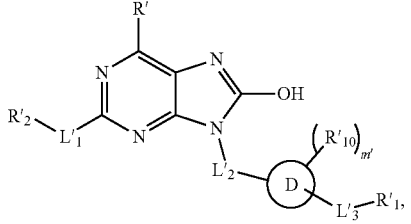

Formula II-1 more preferably

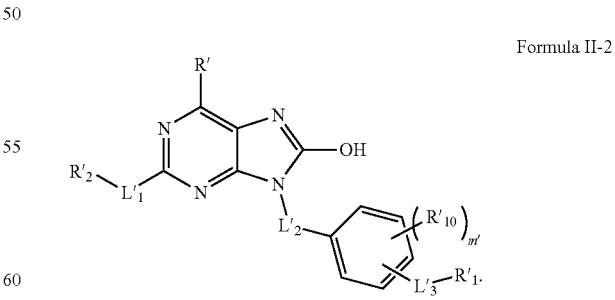

Formula II-2

Preferably, in the formula II-2, R' is H and m is 0.

When $R_2$, $R'_2$, R or R' is a $C_2$-$C_{10}$ heteroalkyl, the heteroatom in the $C_2$-$C_{10}$ heteroalkyl may be selected from the group consisting of O, S and N, the number of heteroatom is preferably 1 to 5 (e.g., 1, 2, 3 or 4). Preferably, the heteroatom in the $C_2$-$C_{10}$ heteroalkyl is O and the number of heteroatom is 1 or 2; more preferably, the $C_2$-$C_{10}$ heteroalkyl is more preferably

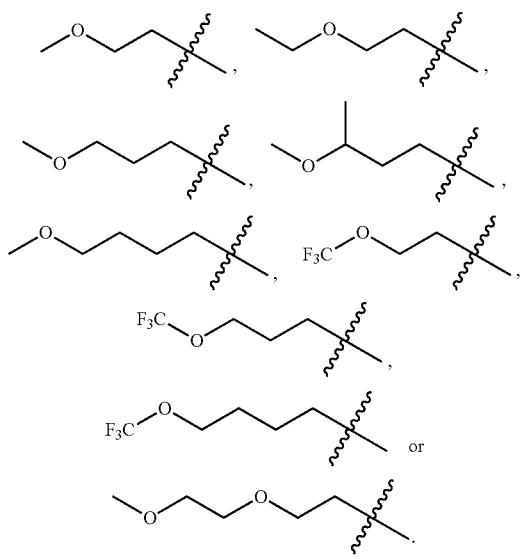

Preferably, the $R_2$— is preferably selected from any one of the following structures:

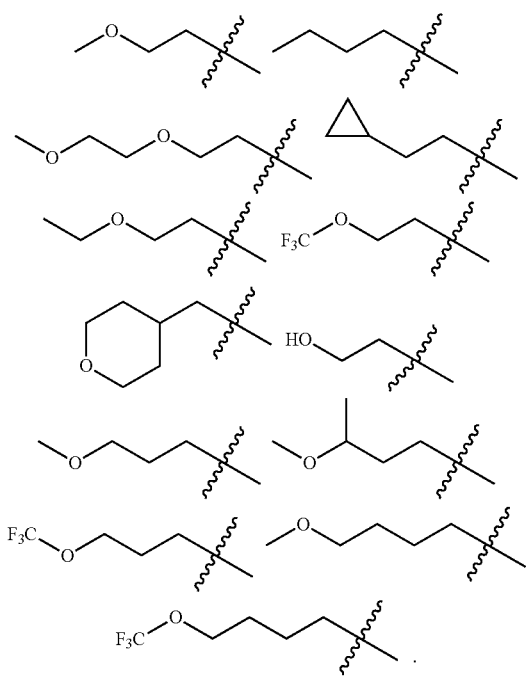

Preferably, the $R_2$-$L_1$- is preferably selected from any one of the following structures:

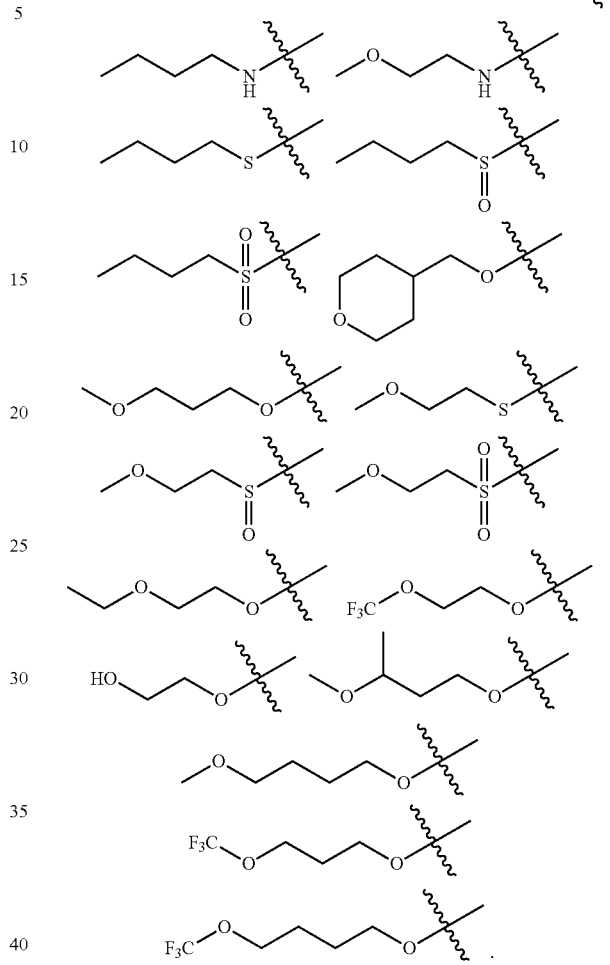

The present invention provides a compound of formula I, a tautomer thereof, an optical isomer thereof, a deuterated compound thereof, a hydrate thereof, a solvate thereof, a polymorph thereof, a pharmaceutically acceptable salt thereof or a prodrug thereof;

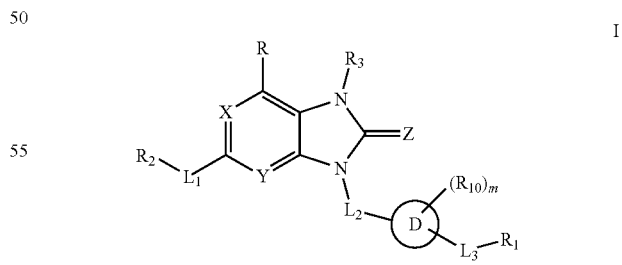

wherein, X and Y are independently C or N (e.g., both X and Y are N; and also e.g., X is N and Y is C);

$R_2$ is hydrogen, a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl; "$R_4$ substituted $C_1$-$C_{10}$ alkyl" is e.g.,

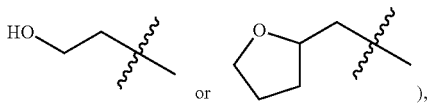

a C$_2$-C$_{10}$ heteroalkyl (wherein, the heteroatom may be selected from the group consisting of O, S and N, and may only be O; the number of the heteroatom may be 1, 2, 3, 4 or 5, and may also be 1 or 2, and may also be 1; when the "C$_2$-C$_{10}$ heteroalkyl" is substituted by a halogen and the heteroatom is O, the terminal may be trifluoromethoxy; the "C$_2$-C$_{10}$ heteroalkyl" may be a C$_2$-C$_5$ heteroalkyl, and may also be

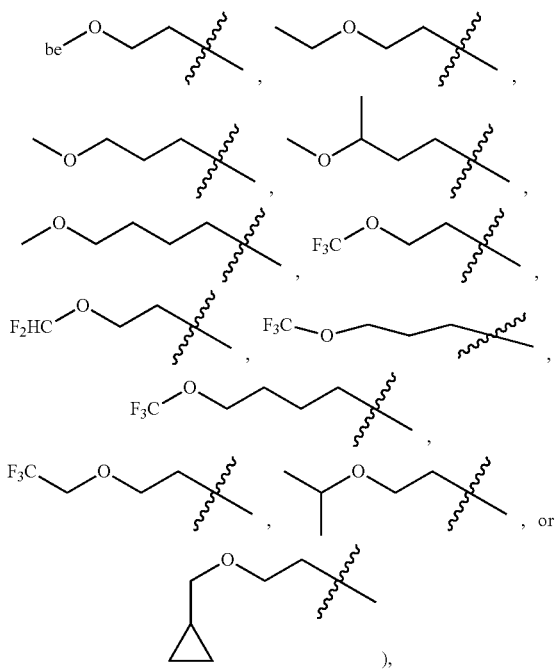

), a C$_3$-C$_{10}$ cycloalkyl, a C$_3$-C$_{10}$ heterocycloalkyl, a C$_2$-C$_{10}$ alkenyl or a C$_2$-C$_{10}$ alkynyl; wherein, the C$_1$-C$_{10}$ alkyl, the C$_2$-C$_{10}$ heteroalkyl, the C$_3$-C$_{10}$ cycloalkyl, the C$_3$-C$_{10}$ heterocycloalkyl, the C$_2$-C$_{10}$ alkenyl and the C$_2$-C$_{10}$ alkynyl are independently substituted by one or more (e.g., 2, 3 or 4) R$_4$; when a plurality of R$_4$ substituents are present, each R$_4$ is the same or different; R$_4$ is independently selected from the group consisting of hydrogen (however, not all the R$_4$ on the C$_1$-C$_{10}$ alkyl is hydrogen), hydroxyl, a halogen (e.g., F, Cl, Br or I, and e.g., F), a C$_1$-C$_6$ alkyl, a C$_3$-C$_{10}$ cycloalkyl (e.g, a C$_3$-C$_6$ cycloalkyl, and e.g., cyclopropyl, cyclobutyl, cyclopentyl or cyclohexyl, and also e.g, cyclopropyl) and a C$_3$-C$_{10}$ heterocycloalkyl (wherein, the heteroatom may be selected from the group consisting of O, S and N, and may only be O; the number of the heteroatom may be 1, 2, 3, 4 or 5, and may be 1; the "C$_3$-C$_{10}$ heterocycloalkyl" may be a C$_4$-C$_5$ heterocycloalkyl, and may be a tetrahydropyranyl or a tetrahydrofuranyl; the tetrahydropyranyl may be tetrahydropyran-4-yl; the tetrahydrofuranyl may be tetrahydrofuran-2-yl);

L$_1$ is —O—, —C(R$_{a1}$R$_{a2}$)—, —C(O)—, —S—, —S(O)—, —S(O)$_2$—, —N(R$_{a3}$)—, —N(R$_{a4}$)C(O)— or —N(R$_{a5}$)S(O)$_2$—; wherein, R$_{a1}$, R$_{a2}$, R$_{a3}$, R$_{a4}$ and R$_{a5}$ are independently hydrogen or a C$_1$-C$_6$ alkyl (e.g., methyl, ethyl, n-propyl, isopropyl, n-butyl, isobutyl or tert-butyl);

R is hydrogen, a halogen, hydroxyl, a C$_1$-C$_{10}$ alkyl (e.g., a C$_1$-C$_6$ alkyl, and e.g., a C$_1$-C$_4$ alkyl, and also e.g., methyl, ethyl, n-propyl, isopropyl, n-butyl, sec-butyl, isobutyl or tert-butyl, and also e.g., methyl), a C$_2$-C$_{10}$ heteroalkyl, a C$_3$-C$_{10}$ cycloalkyl, a C$_3$-C$_{10}$ heterocycloalkyl, a C$_2$-C$_{10}$ alkenyl or a C$_2$-C$_{10}$ alkynyl; wherein, each of the C$_1$-C$_{10}$ alkyl, the C$_2$-C$_{10}$ heteroalkyl, the C$_3$-C$_{10}$ cycloalkyl, the C$_3$-C$_{10}$ heterocycloalkyl, the C$_2$-C$_{10}$ alkenyl and the C$_2$-C$_{10}$ alkynyl is independently substituted by one or more R$_{12}$ (e.g., 2, 3 or 4); when a plurality of R$_{12}$ substitutions are present, each R$_{12}$ is the same or different; R$_{12}$ is independently selected from the group consisting of hydrogen, a halogen, a C$_1$-C$_6$ alkyl, a C$_3$-C$_{10}$ cycloalkyl and a C$_3$-C$_{10}$ heterocycloalkyl;

R$_3$ is hydrogen, a C$_1$-C$_{10}$ alkyl (e.g., a C$_1$-C$_6$ alkyl, and e.g., a C$_1$-C$_4$ alkyl, and also e.g., methyl, ethyl, n-propyl, isopropyl, n-butyl, sec-butyl, isobutyl or tert-butyl, and also e.g., methyl or n-propyl) or a C$_3$-C$_{10}$ cycloalkyl; wherein the C$_1$-C$_{10}$ alkyl and the C$_3$-C$_{10}$ cycloalkyl are independently substituted by one or more (e.g., 2, 3 or 4) R$_9$; when a plurality of R$_9$ substitutions are present, each R$_9$ is the same or different; R$_9$ is independently selected from the group consisting of hydrogen, a halogen, a C$_1$-C$_6$ alkyl, a C$_3$-C$_{10}$ cycloalkyl and a C$_3$-C$_{10}$ heterocycloalkyl;

Z is CH$_2$, NH, O or S (when Z is CH$_2$ and R$_3$ is hydrogen, then the tautomer of the compound I may be

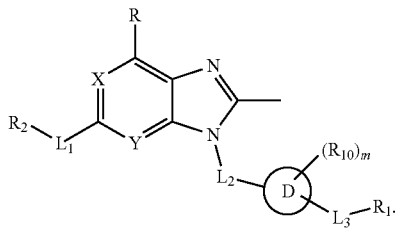

The tautomers of NH, O and S follow the above.);

L$_2$ and L$_3$ are independently a C$_1$-C$_6$ alkylene (e.g., —CH$_2$—, —CH$_2$CH$_2$—, —CH(CH$_3$)—, —CH$_2$CH$_2$CH$_2$—, —CH(CH$_3$)CH$_2$— or —CH(CH$_2$CH$_3$)—; and e.g., L$_2$ is —CH$_2$—; and also e.g., L$_3$ is —CH$_2$—, —CH$_2$CH$_2$—, —CH(CH$_3$)— or —CH(CH$_2$CH$_3$)—; when the "C$_1$-C$_6$ alkylene" contains a chiral carbon atom, the chiral carbon atom is in R-configuration, S-configuration or a mixture thereof <e.g., a racemic carbon atom>) or a C$_2$-C$_6$ heteroalkylene (the heteroatom in the C$_2$-C$_6$ heteroalkylene may be selected from the group consisting of O, S and N; the number of the heteroatom may be 1, 2 or 3, the "C$_2$-C$_6$ heteroalkylene" is e.g., —CH$_2$OCH$_2$—); the C$_1$-C$_6$ alkylene and the C$_2$-C$_6$ heteroalkylene are independently substituted by one or more (e.g., 2, 3 or 4) R$_{11}$; when a plurality of R$_{11}$ substitutions are present, each R$_{11}$ is the same or different; R$_{11}$ is independently selected from the group consisting of hydrogen, a halogen, cyano, a C$_1$-C$_6$ alkyl, a C$_3$-C$_{10}$ cycloalkyl, a C$_3$-C$_{10}$ heterocycloalkyl, —OR$_{d1}$, —SR$_{d2}$, —NR$_{d3}$R$_{d4}$; wherein R$_{d1}$, R$_{d2}$, R$_{d3}$ and R$_{d4}$ are independently hydrogen or a C$_1$-C$_6$ alkyl (e.g., methyl, ethyl, n-propyl, isopropyl, n-butyl, isobutyl or tert-butyl); (e.g., L$_2$, and L$_3$ are independently a C$_1$-C$_6$ alkylene.);

D is a C$_6$-C$_{10}$ arylene (e.g., phenylene; when the C$_6$-C$_{10}$ arylene is phenylene, then the L$_2$ and the L$_3$ may be at the para-position to each other, and may also be at the meta-position) or a $C_5$-$C_{10}$ heteroarylene (e.g., D is a $C_6$-$C_{10}$ arylene);

m is 0, 1, 2, 3 or 4; when a plurality of $R_{10}$ substituents are present on D, each $R_{10}$ is the same or different;

$R_{10}$ is independently a halogen (e.g., F, Cl, Br or I), nitro, cyano, hydroxyl, sulfhydryl, a $R_{10-1}$ substituted or unsubstituted $C_1$-$C_6$ alkyl (the number of the $R_{10-1}$ may be one or more [e.g., 2, 3 or 4]; when a plurality of $R_{10-1}$ are present, each $R_{10-1}$ is the same or different; the "$C_1$-$C_6$ alkyl" may be a $C_1$-$C_4$ alkyl, and may be methyl, ethyl, n-propyl, isopropyl, n-butyl, sec-butyl, isobutyl or tert-butyl; the "$R_{10-1}$ substituted $C_1$-$C_6$ alkyl" is e.g., trifluoromethyl), a $R_{10-2}$ substituted or unsubstituted $C_1$-$C_6$ alkoxy (the number of $R_{10-2}$ may be one or more [e.g., 2, 3 or 4]; when a plurality of $R_{10-2}$ substituents are present, each $R_{10-2}$ is the same or different; the "$C_1$-$C_6$ alkoxy" may be a $C_1$-$C_4$ alkoxy, and may be methoxy, ethoxy, n-propoxy, isopropoxy, n-butoxy, sec-butoxy, isobutoxy or tert-butoxy; the "$R_{10-2}$ substituted $C_1$-$C_6$ alkoxy" is e.g., trifluoromethoxy), a $R_{10-3}$ substituted or unsubstituted $C_3$-$C_{10}$ cycloalkyl (the number of $R_{10-3}$ may be one or more [e.g., 2, 3 or 4]; when a plurality of $R_{10-3}$ substituents are present, each $R_{10-3}$ is the same or different; the "$C_3$-$C_{10}$ cycloalkyl" may be a $C_3$-$C_6$ cycloalkyl, and may be cyclopropyl, cyclobutyl, cyclopentyl or cyclohexyl), a $R_{10-4}$ substituted or unsubstituted $C_3$-$C_{10}$ heterocycloalkyl (the number of $R_{10-4}$ may be one or more [e.g., 2, 3 or 4]; when a plurality of $R_{10-4}$ substituents are present, each $R_{10-4}$ is the same or different;), —C(O)O$R_{c1}$, —C(O)$R_{c2}$, —OC(O)$R_{c3}$, —N$R_{c4}R_{c5}$, —N$R_{c6}$C(O)$R_{c7}$, —C(O)N$R_{c8}$, —OC(O)N$R_{c9}$, —N$R_{c10}$C(O)N$R_{c11}$, —S$R_{c12}$, —S(O)N$R_{c13}R_{c14}$, —S(O)$_2R_{c15}R_{16}$, —N$R_{c17}$S(O)$_2R_{18}$ or —N$R_{c19}$S(O)$R_{c20}$; wherein, $R_{c1}$, $R_{c2}$, $R_{c3}$, $R_{c4}$, $R_{c5}$, $R_{c6}$, $R_{c7}$, $R_{c8}$, $R_{c9}$, $R_{c10}$, $R_{c11}$, $R_{c12}$, $R_{c13}$, $R_{c14}$, $R_{c15}$, $R_{c16}$, $R_{c17}$, $R_{c18}$, $R_{c19}$ and $R_{c20}$ are independently hydrogen or a $C_1$-$C_6$ alkyl (e.g., methyl, ethyl, n-propyl, isopropyl, n-butyl, isobutyl or tert-butyl); all of $R_{10-1}$, $R_{10-2}$, $R_{10-3}$ and $R_{10-4}$ are independently F, Cl, Br or I (e.g., F);

$R_1$ is —N$R_5R_6$;

$R_5$ and $R_6$ are independently hydrogen or a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl or ethyl); wherein the $C_1$-$C_{10}$ alkyl is substituted by one or more (e.g., 2, 3 or 4) $R_7$; when a plurality of $R_7$ are present, each $R_7$ is the same or different; $R_7$ is independently selected from the group consisting of hydrogen, hydroxyl, a halogen, a $C_3$-$C_{10}$ cycloalkyl and a $C_3$-$C_{10}$ heterocycloalkyl;

alternatively, $R_5$ and $R_6$ together with the nitrogen atom to which they are attached form a substituted or unsubstituted heterocyclic ring (the heterocyclic ring may be a monocyclic ring, a fused ring, a spiro ring or a bridged ring, and may be a monocyclic ring; the heterocyclic ring may be heteroaromatic ring or heteroalicyclic ring, and may be heteroalicyclic ring; the heteroalicyclic ring may be heterocycloalkyl or heterocycloalkenyl, and may be heterocycloalkyl; the heterocyclic ring may be a 3-10 membered heterocyclic ring, and may be a 4-9 membered heterocyclic ring, and may also be a 5-7 membered heterocyclic ring; the heteroatom(s) may be selected from the group consisting of O, S and N [N must be present, which is attached to $L_3$], and may only be N; the number of the heteroatom may be 1, 2 or 3, and may be 1 or 2, and may also be 1; the "heterocyclic ring" [whether it is substituted or unsubstituted] may be any one of the following structures:

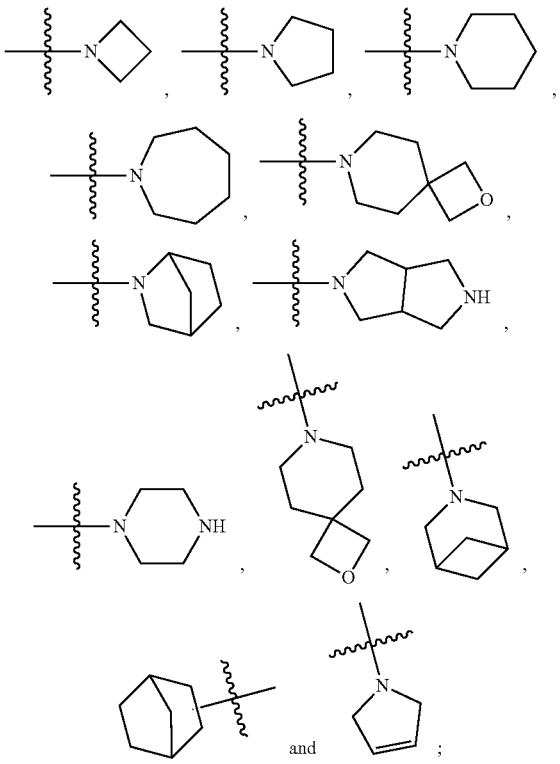

the "substituted heterocyclic ring" may be any one of the following structures:

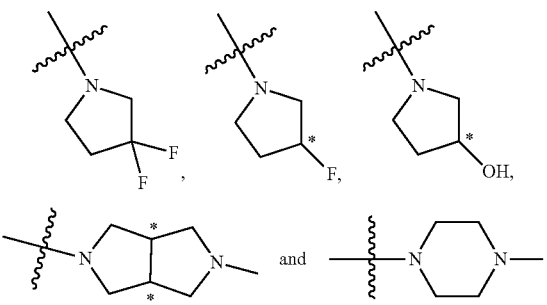

[wherein, all the "*" independently refer to a chiral carbon center, which may be a S-configuration carbon, a R-configuration carbon or a mixture thereof (e.g. a racemate); e.g.,

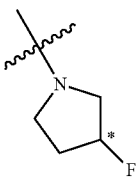 [SMILES: *N1CCC(F)C1]

may be

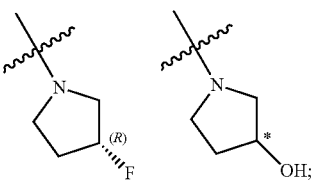

may be

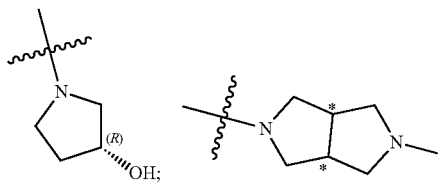

may be

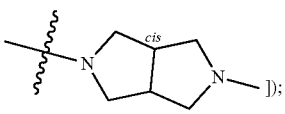 [SMILES: *N1CC2CN(C)CC2C1]

the substituted heterocyclic ring is substituted by one or more (e.g., 2, 3 or 4) $R_8$; when a plurality of $R_8$ substituents are present, each $R_8$ is the same or different; $R_8$ is independently selected from the group consisting of a halogen (e.g., F, Cl, Br or I, and e.g., F), hydroxyl, a $C_1$-$C_6$ alkyl (e.g., a $C_1$-$C_4$ alkyl, and e.g., methyl, ethyl, n-propyl, isopropyl, n-butyl, isobutyl or tert-butyl), a $C_3$-$C_{10}$ cycloalkyl, —C(O)OR$_{b1}$, —C(O)R$_{b2}$, —NR$_{b3}$R$_{b4}$, —C(O)NR$_{b5}$, —OC(O)NR$_{b6}$ or —NR$_{b7}$C(O)NR$_{b8}$; wherein, R$_{b1}$, R$_{b2}$, R$_{b3}$, R$_{b4}$, R$_{b5}$, R$_{b6}$, R$_{b7}$ and R$_{b8}$ are independently hydrogen or a $C_1$-$C_6$ alkyl (e.g., methyl, ethyl, n-propyl, isopropyl, n-butyl, isobutyl or tert-butyl).

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

X and Y may be selected from N.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

$R_2$ may be hydrogen, a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl), a $C_2$-$C_{10}$ heteroalkyl (wherein, the heteroatom may be selected from the group consisting of O, S and N, and may only be O; the number of the heteroatom may be 1, 2, 3, 4 or 5, and may also be 1 or 2, and may also be 1; the "$C_2$-$C_{10}$ heteroalkyl" may be a $C_2$-$C_5$ heteroalkyl; when the "$C_2$-$C_{10}$ heteroalkyl" is substituted by a halogen and the heteroatom is O, then the terminal may be trifluoromethoxy), a $C_3$-$C_{10}$ cycloalkyl, or, a $C_3$-$C_{10}$ heterocycloalkyl; wherein, the $C_1$-$C_{10}$ alkyl, the $C_2$-$C_{10}$ heteroalkyl, the $C_3$-$C_{10}$ cycloalkyl, and, the $C_3$-$C_{10}$ heterocycloalkyl are independently substituted by one or more (e.g., 2, 3 or 4, and e.g., 3) $R_4$; when a plurality of $R_4$ substituents are present, each $R_4$ is the same or different; $R_4$ is independently selected from the group consisting of hydrogen (however, not all the $R_4$ on the $C_1$-$C_{10}$ alkyl is hydrogen), hydroxyl, a halogen (e.g., F, Cl, Br or I, and e.g., F), a $C_1$-$C_6$ alkyl, a $C_3$-$C_{10}$ cycloalkyl (e.g, a $C_3$-$C_6$ cycloalkyl, and e.g., cyclopropyl, cyclobutyl, cyclopentyl or cyclohexyl, and also e.g, cyclopropyl) and a $C_3$-$C_{10}$ heterocycloalkyl (wherein, the heteroatom may be selected from the group consisting of O, S and N, and may only be O; the number of the heteroatom may be 1, 2, 3, 4 or 5, and may be 1; the "$C_3$-$C_{10}$ heterocycloalkyl" may be a $C_4$-$C_5$ heterocycloalkyl, and may be a tetrahydropyranyl or a tetrahydrofuranyl; the tetrahydropyranyl may be tetrahydropyran-4-yl; the tetrahydrofuranyl may be tetrahydrofuran-2-yl);

$R_2$ may be hydrogen, a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl), or, a $C_2$-$C_{10}$ heteroalkyl containing one heteroatom (the heteroatom here only refers to the heteroatom for substituting the —CH$_2$— on the substituted alkyl chain, other than the hetero atom for substituting a hydrogen atom hereinafter [e.g., halogen], wherein, the heteroatom may be O, S or N, and may only be O; the "$C_2$-$C_{10}$ heteroalkyl" may be a $C_2$-$C_5$ heteroalkyl, and may be a $C_3$-$C_4$ heteroalkyl, and may also be 2-methoxyethyl; when the "$C_2$-$C_{10}$ heteroalkyl" is substituted by a halogen and the heteroatom is O, then the terminal may be trifluoromethoxy); wherein, the $C_1$-$C_{10}$ alkyl is substituted by one or more (e.g., 2, 3 or 4, and e.g., 3) $R_4$ (wherein, $R_4$ is independently hydroxyl or a $C_3$-$C_4$ heterocycloalkyl [wherein, the heteroatom may be selected from the group consisting of O, S and N, and may only be O; the number of the heteroatom may be 1 or 2, and may be 1; the "$C_3$-$C_4$ heterocycloalkyl" may be a tetrahydrofuranyl, and may also be tetrahydrofuran-2-yl]); when a plurality of $R_4$ substituents are present, each $R_4$ is the same or different.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

$L_1$ may be —O—.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

R may be hydrogen, a halogen (e.g., F, Cl, Br or I, and e.g., F), or, hydroxyl; and may also be hydrogen.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

$R_3$ may be hydrogen.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

Z may be NH or O, and may also be O.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

$L_2$ may be a $C_1$-$C_6$ alkylene, and may also be —$CH_2$—.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

$L_3$ may be a $C_1$-$C_6$ alkylene.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

D may be a $C_6$-$C_{10}$ arylene (e.g., phenylene; when the $C_6$-$C_{10}$ arylene is phenylene, then the $L_2$ and the $L_3$ may be at the para-position to each other, and may also be at the meta-position).

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

M may be 0 or 1.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

$R_{10}$ may be a halogen, cyano, a $R_{10-1}$ substituted or unsubstituted $C_1$-$C_6$ alkyl, a $R_{10-2}$ substituted or unsubstituted $C_1$-$C_6$ alkoxy, a $R_{10-3}$ substituted or unsubstituted $C_3$-$C_{10}$ cycloalkyl, or, a $R_{10-4}$ substituted or unsubstituted $C_3$-$C_{10}$ heterocycloalkyl, and may also be a halogen (e.g., F, Cl, Br or I, and e.g., F).

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

wherein, X and Y are independently C or N (e.g., both of X and Y are N; and also e.g., X is N and Y is C);

$R_2$ is hydrogen, a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl), a $C_2$-$C_{10}$ heteroalkyl (wherein, the heteroatom may be selected from the group consisting of O, S and N, and may only be O; the number of the heteroatom can be 1, 2, 3, 4 or 5, and may also be 1 or 2, and may also be 1; the "$C_2$-$C_{10}$ heteroalkyl" may be a $C_2$-$C_5$ heteroalkyl; when the "$C_2$-$C_{10}$ heteroalkyl" is substituted by a halogen and the heteroatom is O, then the terminal may be trifluoromethoxy), a $C_3$-$C_{10}$ cycloalkyl, or, a $C_3$-$C_{10}$ heterocycloalkyl; wherein, the $C_1$-$C_{10}$ alkyl, the $C_2$-$C_{10}$ heteroalkyl, the $C_3$-$C_{10}$ cycloalkyl, and, the $C_3$-$C_{10}$ heterocycloalkyl are independently substituted by one or more (e.g., 2, 3 or 4) $R_4$; when a plurality of $R_4$ substituents are present, each $R_4$ is the same or different; $R_4$ is independently selected from the group consisting of hydrogen (however, not all $R_4$ on the $C_1$-$C_{10}$ alkyl is hydrogen), hydroxyl, a halogen (e.g., F, Cl, Br or I, and e.g., F), a $C_1$-$C_6$ alkyl, a $C_3$-$C_{10}$ cycloalkyl (e.g, a $C_3$-$C_6$ cycloalkyl, and e.g., cyclopropyl, cyclobutyl, cyclopentyl or cyclohexyl, and also e.g, cyclopropyl) and a $C_3$-$C_{10}$ heterocycloalkyl (wherein, the heteroatom(s) may be selected from the group consisting of O, S and N, and may only be O; the number of the heteroatom(s) may be 1, 2, 3, 4 or 5, and may be 1; the "$C_3$-$C_{10}$ heterocycloalkyl" may be a $C_4$-$C_5$ heterocycloalkyl, and may be a tetrahydropyranyl or a tetrahydrofuranyl; the tetrahydropyranyl may be tetrahydropyran-4-yl; the tetrahydrofuranyl may be tetrahydrofuran-2-yl);

$L_1$ is —O—;

R is hydrogen, a halogen (e.g., F, Cl, Br or I, and e.g., F), or, hydroxyl;

$R_3$ is hydrogen;

Z is $CH_2$, NH, O or S;

$L_2$ and $L_3$ are independently a $C_1$-$C_6$ alkylene (e.g., —$CH_2$—, —$CH_2CH_2$—, —$CH(CH_3)$—, —$CH_2CH_2CH_2$—, —$CH(CH_3)CH_2$— or —$CH(CH_2CH_3)$—; and e.g., $L_2$ is —$CH_2$—; and also e.g., $L_3$ is —$CH_2$—, —$CH_2CH_2$—, —$CH(CH_3)$— or —$CH(CH_2CH_3)$—; when the "$C_1$-$C_6$ alkylene" contains a chiral carbon atom, the chiral carbon atom is in R-configuration, S-configuration or a mixture thereof <e.g., a racemic carbon atom>);

D is a $C_6$-$C_{10}$ arylene (e.g., phenylene; when the $C_6$-$C_{10}$ arylene is phenylene, then the $L_2$ and the $L_3$ may be at the para-position to each other, and may also be at the meta-position) or a $C_5$-$C_{10}$ heteroarylene; (e.g., D is a $C_6$-$C_{10}$ arylene)

m is 0, 1, 2, 3 or 4; when a plurality of $R_{10}$ substituents are present on D, $R_{10}$(s) are the same or different;

$R_{10}$ is independently a halogen (e.g., F, Cl, Br or I), cyano, a $R_{10-1}$ substituted or unsubstituted $C_1$-$C_6$ alkyl (the number of the $R_{10-1}$ may be one or more [e.g., 2, 3 or 4]; when a plurality of $R_{10-1}$ substituents are present, each $R_{10-1}$ is the same or different; the "$C_1$-$C_6$ alkyl" may be a $C_1$-$C_4$ alkyl, and may be methyl, ethyl, n-propyl, isopropyl, n-butyl, sec-butyl, isobutyl or tert-butyl; the "$R_{10-1}$ substituted $C_1$-$C_6$ alkyl" is e.g., trifluoromethyl), a $R_{10-2}$ substituted or unsubstituted $C_1$-$C_6$ alkoxy (the number of the $R_{10-2}$ may be one or more [e.g., 2, 3 or 4]; when a plurality of $R_{10-2}$ substituents are present, each $R_{10-2}$ is the same or different; the "$C_1$-$C_6$ alkoxy" may be a $C_1$-$C_4$ alkoxy, and may be methoxy, ethoxy, n-propoxy, isopropoxy, n-butoxy, sec-butoxy, isobutoxy or tert-butoxy; the "$R_{10-2}$ substituted $C_1$-$C_6$ alkoxy" is e.g., trifluoromethoxy), a $R_{10-3}$ substituted or unsubstituted $C_3$-$C_{10}$ cycloalkyl (the number of the $R_{10-3}$ may be one or more [e.g., 2, 3 or 4]; when a plurality of $R_{10-3}$ substituents are present, each $R_{10-3}$ is the same or different; the "$C_3$-$C_{10}$ cycloalkyl" may be a $C_3$-$C_6$ cycloalkyl, and may be cyclopropyl, cyclobutyl, cyclopentyl or cyclohexyl), or, a $R_{10-4}$ substituted or unsubstituted $C_3$-$C_{10}$ heterocycloalkyl (the number of the $R_{10-4}$ may be one or more [e.g., 2, 3 or 4]; when a plurality of $R_{10-4}$ substituents are present, each $R_{10-4}$ is the same or different;); all of $R_{10-1}$, $R_{10-2}$, $R_{10-3}$ and $R_{10-4}$ are independently F, Cl, Br or I (e.g., F);

$R_1$ is —$NR_5R_6$;

$R_5$ and $R_6$ are independently hydrogen or a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl or ethyl); wherein the $C_1$-$C_{10}$ alkyl is substituted by one or more (e.g., 2, 3 or 4) $R_7$; when a plurality of $R_7$ substituents are present, each $R_7$ is the same or different; $R_7$ is independently selected from the group consisting of hydrogen, hydroxyl, halogen, $C_3$-$C_{10}$ cycloalkyl and $C_3$-$C_{10}$ heterocycloalkyl;

alternatively, $R_5$ and $R_6$ together with the nitrogen atom to which they are attached form a substituted or unsubstituted heterocyclic ring (the heterocyclic ring may be a monocyclic ring, a fused ring, a spiro ring or a bridged ring, and may be a monocyclic ring; the heterocyclic ring may be a heteroaromatic ring or a heteroalicyclic ring, and may be a heteroalicyclic ring; the heteroalicyclic ring may be a heteroalkyl or a heterocycloalkenyl, and may be a heteroalkyl; the heterocyclic ring may be a 3-10 membered heterocyclic ring, and may be a 4-9 membered heterocyclic ring, and may also be a 5-7 membered heterocyclic ring; the heteroatom may be selected from the group consisting of O, S and N [N must be present, which is attached to $L_3$], and may only be N; the number of the heteroatom may be 1, 2 or 3, and may be 1 or 2, and may also be 1); the substituted heterocyclic ring is substituted by one or more (e.g., 2, 3 or 4) $R_8$; when a plurality of $R_8$ substituents are present, each $R_8$ is the same or different; $R_8$ is independently selected from the group consisting of a halogen (e.g., F, Cl, Br or I, and e.g., F), hydroxyl, a $C_1$-$C_6$ alkyl (e.g., $C_1$-$C_4$ alkyl, and e.g., methyl, ethyl, n-propyl, isopropyl, n-butyl, isobutyl or tert-butyl), or, $C_3$-$C_{10}$ cycloalkyl.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

X and Y are selected from N;

$R_2$ is a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl), or, a $C_2$-$C_{10}$ heteroalkyl containing one heteroatom (the heteroatom here only refers to the heteroatom for substituting the —$CH_2$— on the substituted alkyl chain, other than the hetero atom for substituting a hydrogen atom hereinafter [e.g., halogen], wherein, the heteroatom may be O, S or N, and may be O; the "$C_2$-$C_{10}$ heteroalkyl" may be a $C_2$-$C_5$ heteroalkyl, and may be a $C_3$-$C_4$ heteroalkyl, and may also be 2-methoxyethyl; when the "$C_2$-$C_{10}$ heteroalkyl" is substituted by a halogen and the heteroatom is O, then the terminal may be trifluoromethoxy); wherein, the $C_1$-$C_{10}$ alkyl is substituted by one or more (e.g., 2, 3 or 4) $R_4$ (wherein, $R_4$ is independently hydroxyl or a $C_3$-$C_4$ heterocycloalkyl [wherein, the heteroatom may be selected from the group consisting of O, S and N, and may only be O; the number of the heteroatom may be 1 or 2, and may be 1; the "$C_3$-$C_4$ heterocycloalkyl" may be a tetrahydrofuranyl, and may be a tetrahydrofuran-2-yl]); when a plurality of $R_4$ substituents are present, each $R_4$ is the same or different; the $C_2$-$C_{10}$ heteroalkyl is substituted by one or more (e.g., 2, 3 or 4) $R_4$ (wherein, $R_4$ is independently hydrogen or a halogen [e.g., F, Cl, Br or I, and e.g., F]); when a plurality of $R_4$ substituents are present, each $R_4$ is the same or different;

$L_1$ is —O—;

R is hydrogen, a halogen (e.g., F, Cl, Br or I, and e.g., F), or, hydroxyl;

$R_3$ is hydrogen;

Z is NH or O;

$L_2$ is —$CH_2$—;

$L_3$ is a $C_1$-$C_6$ alkylene (e.g., —$CH_2$—, —$CH_2CH_2$—, —$CH(CH_3)$—, —$CH_2CH_2CH_2$—, —$CH(CH_3)CH_2$— or —$CH(CH_2CH_3)$—; when the "$C_1$-$C_6$ alkylene" contains a chiral carbon atom, the chiral carbon atom is in R-configuration, S-configuration or a mixture thereof <e.g., a racemic carbon atom>);

D is a $C_6$-$C_{10}$ arylene (e.g., phenylene; when the $C_6$-$C_{10}$ arylene is phenylene, the $L_2$ and the $L_3$ may be at the para-position to each other, and may also be at the meta-position);

m is 0 or 1;

$R_{10}$ is a halogen (e.g., F, Cl, Br or I), a $R_{10-1}$ substituted or unsubstituted $C_1$-$C_6$ alkyl (the number of the $R_{10-1}$ may be one or more [e.g., 2, 3 or 4]; when a plurality of $R_{10-1}$ substituents are present, each $R_{10-1}$ is the same or different; the "$C_1$-$C_6$ alkyl" may be a $C_1$-$C_4$ alkyl, and may be methyl, ethyl, n-propyl, isopropyl, n-butyl, sec-butyl, isobutyl or tert-butyl; the "$R_{10-1}$ substituted $C_1$-$C_6$ alkyl" is e.g., trifluoromethyl), a $R_{10-2}$ substituted or unsubstituted $C_1$-$C_6$ alkoxy (the number of the $R_{10-2}$ may be one or more [e.g., 2, 3 or 4]; when a plurality of $R_{10-2}$ substituents are present, each $R_{10-2}$ is the same or different; the "$C_1$-$C_6$ alkoxy" may be a $C_1$-$C_4$ alkoxy, and may be methoxy, ethoxy, n-propoxy, isopropoxy, n-butoxy, sec-butoxy, isobutoxy or tert-butoxy; the "$R_{10-2}$ substituted $C_1$-$C_6$ alkoxy" is e.g., trifluoromethoxy), a $R_{10-3}$ substituted or unsubstituted $C_3$-$C_{10}$ cycloalkyl (the number of the $R_{10-3}$ may be one or more [e.g., 2, 3 or 4]; when a plurality of $R_{10-3}$ substituents are present, each $R_{10-3}$ is the same or different; the "$C_3$-$C_{10}$ cycloalkyl" may be a $C_3$-$C_6$ cycloalkyl, and may be cyclopropyl, cyclobutyl, cyclopentyl or cyclohexyl), or, a $R_{10-4}$ substituted or unsubstituted $C_3$-$C_{10}$ heterocycloalkyl (the number of the $R_{10-4}$ may be one or more [e.g., 2, 3 or 4]; when a plurality of $R_{10-4}$ substituents are present, each $R_{10-4}$ is the same or different;); all of $R_{10-1}$, $R_{10-2}$, $R_{10-3}$ and $R_{10-4}$ are independently F, Cl, Br or I (e.g., F);

$R_1$ is —$NR_5R_6$;

$R_5$ and $R_6$ are independently a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl or ethyl);

alternatively, $R_5$ and $R_6$ together with the nitrogen atom to which they are attached form a substituted or unsubstituted heterocyclic ring (the heterocyclic ring may be a monocyclic ring, a fused ring, a spiro ring or a bridged ring, and may be a monocyclic ring; the heterocyclic ring may be a heteroaromatic ring or a heteroalicyclic ring, and may be a heteroalicyclic ring; the heteroalicyclic ring may be a heteroalkyl or a heterocycloalkenyl, and may be a heteroalkyl; the heterocyclic ring may be a 3-10 membered heterocyclic ring, and may be a 4-9 membered heterocyclic ring, and may also be a 5-7 membered heterocyclic ring; the heteroatom may be selected from the group consisting of O, S and N [N must be present, which is attached to $L_3$], and may only be N; the number of the heteroatom may be 1, 2 or 3, and may be 1 or 2, and may also be 1); the substituted heterocyclic ring is substituted by one or more (e.g., 2, 3 or 4) $R_8$; when a plurality of $R_8$ substituents are present, each $R_8$ is the same or different; $R_8$ is independently selected from the group consisting of a halogen (e.g., F, Cl, Br or I, and e.g., F), hydroxyl, or, a $C_1$-$C_6$ alkyl (e.g., a $C_1$-$C_4$ alkyl, and e.g., methyl, ethyl, n-propyl, isopropyl, n-butyl, isobutyl or tert-butyl, and also e.g., methyl).

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

X and Y are selected from N;

$R_2$ is a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl), or, a $C_2$-$C_{10}$ heteroalkyl containing one heteroatom (the heteroatom here only refers to the heteroatom for substituting the —$CH_2$— on the substituted alkyl chain, other than the hetero atom for substituting a hydrogen atom hereinafter [e.g., halogen], wherein, the heteroatom may be O, S or N, and may be O; the "$C_2$-$C_{10}$ heteroalkyl" may be a $C_2$-$C_5$ heteroalkyl, and may be a $C_3$-$C_4$ heteroalkyl, and may also be 2-methoxyethyl; when the "$C_2$-$C_{10}$ heteroalkyl" is substituted by a halogen and the heteroatom is O, then the terminal may be trifluoromethoxy); wherein, the $C_1$-$C_{10}$ alkyl is substituted by one or more (e.g., 2, 3 or 4) $R_4$ (wherein, the $R_4$ is independently hydroxyl or a $C_3$-$C_4$ heterocycloalkyl [wherein, the heteroatom may be selected from the group consisting of O, S and N, and may only be O; the number of the heteroatom may be 1 or 2, and may be 1; the "$C_3$-$C_4$ heterocycloalkyl" may be a tetrahydrofuranyl, and may be a tetrahydrofuran-2-yl]); when a plurality of $R_4$ substituents are present, each $R_4$ is the same or different; the $C_2$-$C_{10}$ heteroalkyl is substituted by one or more (e.g., 2, 3 or 4) $R_4$ (wherein, the $R_4$ is independently hydrogen or a halogen [e.g., F, Cl, Br or I, and e.g., F]); when a plurality of $R_4$ substituents are present, each $R_4$ is the same or different;

$L_1$ is —O—;
R is hydrogen;
$R_3$ is hydrogen;
Z is O;
$L_2$ is —$CH_2$—;
$L_3$ is a $C_1$-$C_6$ alkylene (e.g., —$CH_2$—, —$CH_2CH_2$—, —$CH(CH_3)$—, —$CH_2CH_2CH_2$—, —$CH(CH_3)CH_2$— or —$CH(CH_2CH_3)$—; when the "$C_1$-$C_6$ alkylene" contains a chiral carbon atom, the chiral carbon atom is in R-configuration, S-configuration or a mixture thereof <e.g., a racemic carbon atom>);

D is a $C_6$-$C_{10}$ arylene (e.g., phenylene; when the $C_6$-$C_{10}$ arylene is phenylene, the $L_2$ and the $L_3$ may be at the para-position to each other, and may also be at the meta-position);

m is 0 or 1;
$R_{10}$ is a halogen (e.g., F, Cl, Br or I, and e.g., F);
$R_1$ is —$NR_5R_6$;
$R_5$ and $R_6$ are independently a $C_1$-$C_{10}$ alkyl (e.g., a $C_1$-$C_6$ alkyl, and e.g., a $C_1$-$C_4$ alkyl, and also e.g., methyl, ethyl, n-propyl, isopropyl, n-butyl, isobutyl or tert-butyl, and also e.g., methyl or ethyl);

alternatively, $R_5$ and $R_6$ together with the nitrogen atom to which they are attached form a substituted or unsubstituted heterocyclic ring (the heterocyclic ring may be a monocyclic ring, a fused ring, a spiro ring or a bridged ring, and may be a monocyclic ring; the heterocyclic ring may be a heteroaromatic ring or a heteroalicyclic ring, and may be a heteroali- cyclic ring; the heteroalicyclic ring may be a heteroalkyl or a heterocycloalkenyl, and may be a heteroalkyl; the heterocyclic ring may be a 3-10 membered heterocyclic ring, and may be a 4-9 membered heterocyclic ring, and may also be a 5-7 membered heterocyclic ring; the heteroatom may be selected from the group consisting of O, S and N [N must be present, which is attached to $L_3$], and may only be N; the number of the heteroatom may be 1, 2 or 3, and may be 1 or 2, and may also be 1); the substituted heterocyclic ring is substituted by one or more (e.g., 2, 3 or 4) $R_8$; when a plurality of $R_8$ substituents are present, each $R_8$ is the same or different; $R_8$ is independently selected from the group consisting of a halogen (e.g., F, Cl, Br or I, and e.g., F), hydroxyl, or, a $C_1$-$C_6$ alkyl (e.g., $C_1$-$C_4$ alkyl, and e.g., methyl, ethyl, n-propyl, isopropyl, n-butyl, isobutyl or tert-butyl, and also e.g., methyl).

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_2$, $R_3$, $R_5$, $R_6$ or R is a $C_1$-$C_{10}$ alkyl; then the $C_1$-$C_{10}$ alkyl is preferably a $C_1$-$C_6$ alkyl; the $C_1$-$C_6$ alkyl is preferably methyl, ethyl, n-propyl, isobutyl, n-butyl, isobutyl or tert-butyl.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_2$ or R is a $C_2$-$C_{10}$ heteroalkyl, then the heteroatom in the $C_2$-$C_{10}$ heteroalkyl group may be selected from the group consisting of O, S and N and the number of heteroatom is preferably 1 to 5 (e.g., 1, 2, 3 or 4). Preferably, the heteroatom in the $C_2$-$C_{10}$ heteroalkyl is O and the number of heteroatom is 1 or 2; more preferably, the $C_2$-$C_{10}$ heteroalkyl is preferably

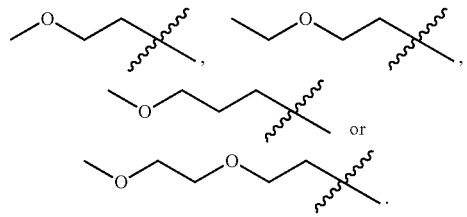

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_2$, $R_3$ or R is a $C_3$-$C_{10}$ cycloalkyl, then the $C_3$-$C_{10}$ cycloalkyl is preferably cyclopropyl, cyclopentyl or cyclohexyl.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_2$ or R is a $C_3$-$C_{10}$ heterocycloalkyl, then the heteroatom in the $C_3$-$C_{10}$ heterocycloalkyl may be selected from the group consisting of O, S and N and the number of the heteroatom is preferably 1 to 3 (e.g., 2); the $C_3$-$C_{10}$ heterocycloalkyl is preferably

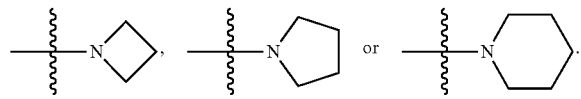

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_2$ or R is a $C_2$-$C_{10}$ alkenyl, then the $C_2$-$C_{10}$ alkenyl is preferably vinyl.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_2$ or R is a $C_2$-$C_{10}$ alkynyl, then the $C_2$-$C_{10}$ alkynyl is preferably ethynyl.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_4$, $R_7$, $R_8$, $R_9$ or $R_{10}$ is a halogen, then the halogen is preferably F, Cl, Br or I.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_4$, $R_7$, $R_8$, $R_9$, $R_{10}$, $R_{11}$ or $R_{12}$ is a $C_3$-$C_{10}$ cycloalkyl, then the $C_3$-$C_{10}$ cycloalkyl is preferably cyclopropyl, cyclopentyl or cyclohexyl.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_4$, $R_7$, $R_8$, $R_9$, $R_{10}$, $R_{11}$ or $R_{12}$ is a $C_3$-$C_{10}$ heterocycloalkyl, then the heteroatom in the $C_3$-$C_{10}$ heterocycloalkyl may be selected from the group consisting of O, S and N; the number of the heteroatom is preferably 1 to 3 (e.g., 2); the heteroatom may be at the ortho-, meta- or para-position of the linking site; the $C_3$-$C_{10}$ heterocycloalkyl may be linked through a carbon atom or an N atom; the $C_3$-$C_{10}$ heterocycloalkyl is preferably

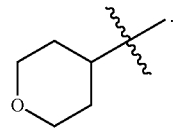

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_4$, $R_7$, $R_8$, $R_9$, $R_{10}$, $R_{11}$ or $R_{12}$ is a $C_1$-$C_6$ alkyl, then the $C_1$-$C_6$ alkyl is preferably methyl, ethyl, n-propyl, isobutyl, n-butyl, isobutyl or tert-butyl.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when the $R_{10}$ is a $C_1$-$C_6$ alkoxy, then the $C_1$-$C_6$ alkoxy is preferably methoxy, ethoxy, n-propoxy, isobutoxy, n-butoxy, isobutoxy or tert-butoxy.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

in $R_1$, when $R_5$ and $R_6$ together with the nitrogen atom to which they are attached form a substituted or unsubstituted heterocyclic ring, then the heterocyclic ring is preferably selected from any one of the following structures:

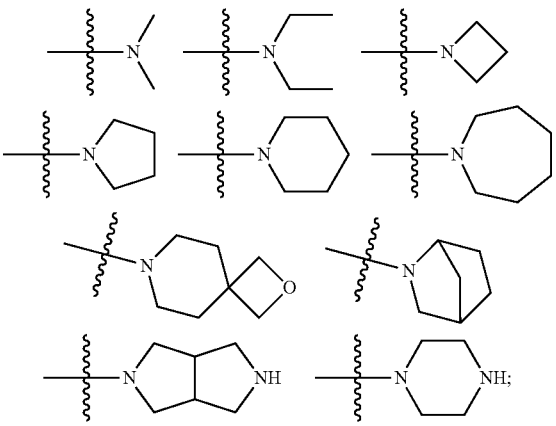

more preferably, the substituted heterocyclic ring is selected from any one of the following structures:

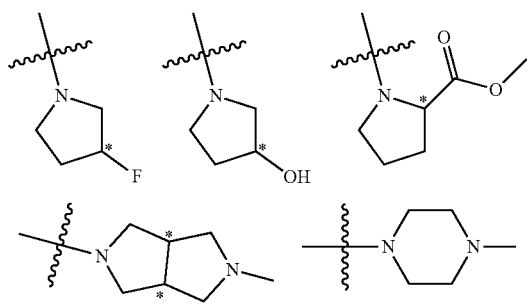

"*" refers to the chiral carbon center, which may be a S-configuration carbon, a R-configuration carbon or a racemate; e.g.,

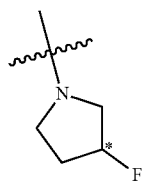 [SMILES: *N1CCC(F)C1]

may be

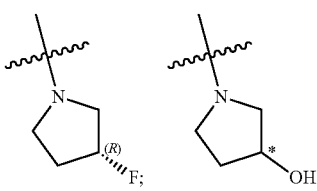

may be

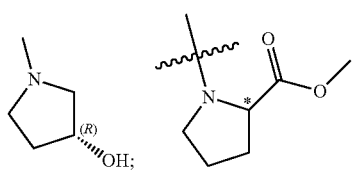

may be

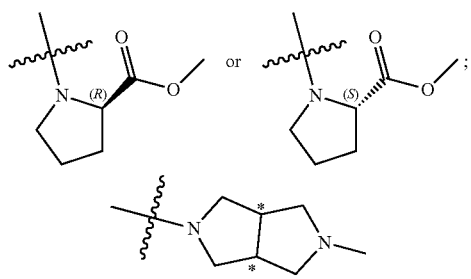

may be

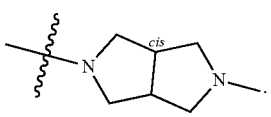 [SMILES: *N1CC2CN(C)CC2C1]

In one embodiment, in the compound I, the tautomer thereof, isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

preferably, the $R_2$— is preferably any one of the following structures:

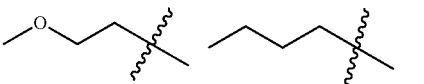
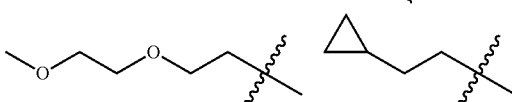
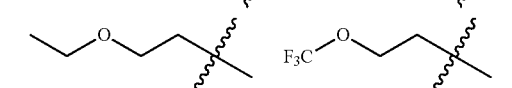
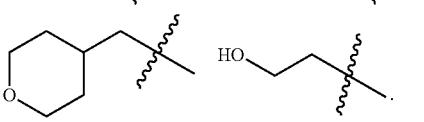

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

preferably, the $R_2$-$L_1$- is preferably any one of the following structures:

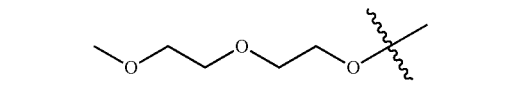
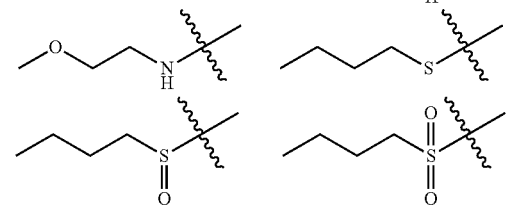

-continued

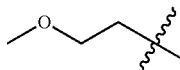

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

preferably, when the D is phenylene, then -$L_3$-$R_1$ is at the ortho-, meta- or para-position of $L_2$.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

the compound of formula I is preferably

Formula 1-1

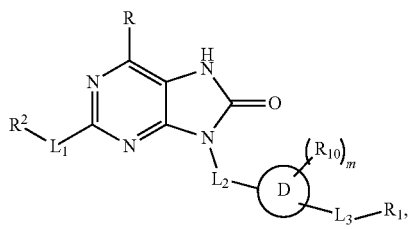

more preferably

Formula I-2

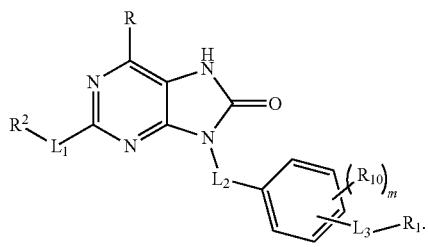

Preferably, in the formula I-2, R is H and m is 0.

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

when $R_2$ or R is a $C_2$-$C_{10}$ heteroalkyl, the heteroatom in the $C_2$-$C_{10}$ heteroalkyl may be selected from the group consisting of O, S and N, the number of heteroatom is preferably 1 to 5 (e.g., 1, 2, 3 or 4). Preferably, the heteroatom in the $C_2$-$C_{10}$ heteroalkyl is O and the number of heteroatom is 1 or 2; more preferably, the $C_2$-$C_{10}$ heteroalkyl is more preferably

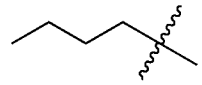

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

preferably, the $R_2$— is preferably selected from any one of the following structures:

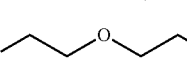

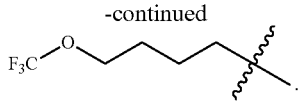

In one embodiment, in the compound I, the tautomer thereof, the optical isomer thereof, the deuterated compound thereof, the hydrate thereof, the solvate thereof, the polymorph thereof, the pharmaceutically acceptable salt thereof or the prodrug thereof, wherein, each group can be described as follows and the undefined ones are as described in any one of the preceding embodiments:

preferably, the $R_2$-$L_1$- is preferably selected from any one of the following structures:

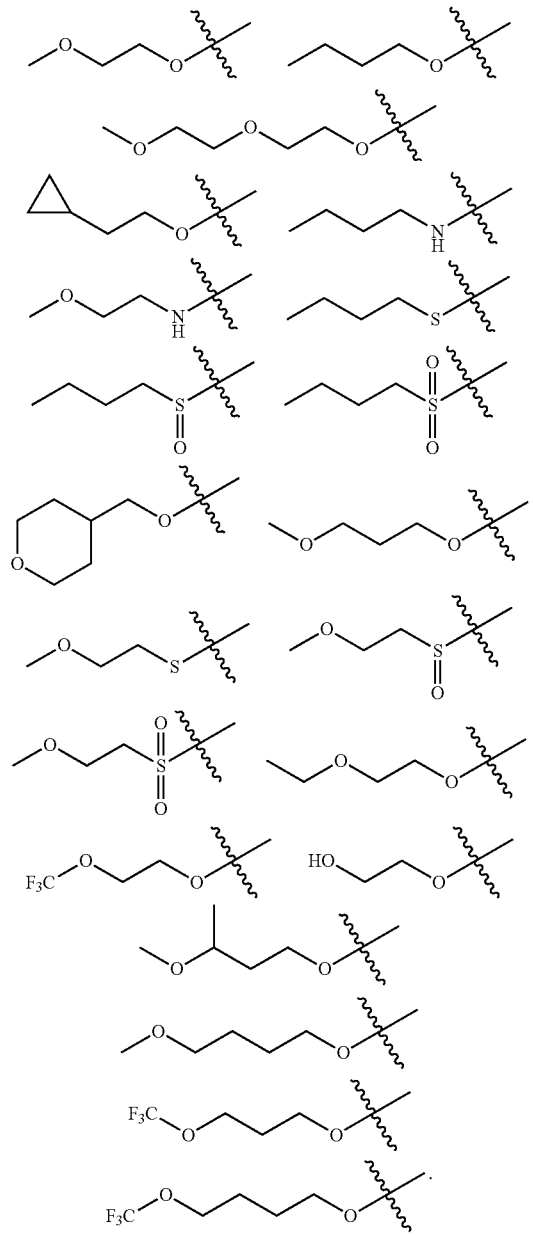

The compound of formula I of the present invention may be selected from any one of the following compounds:

Example 1

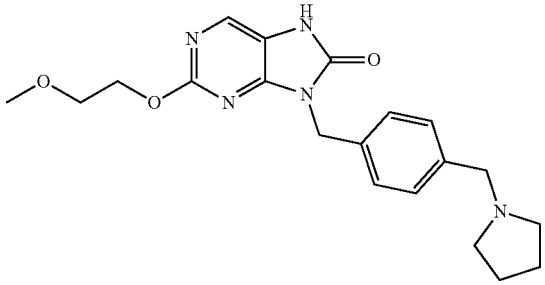

Example 2

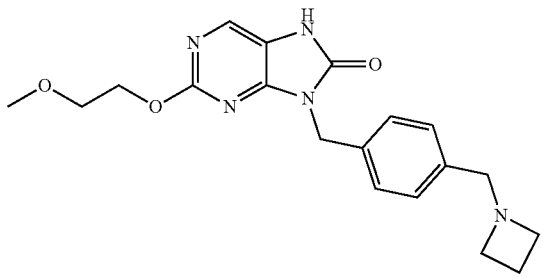

Example 3

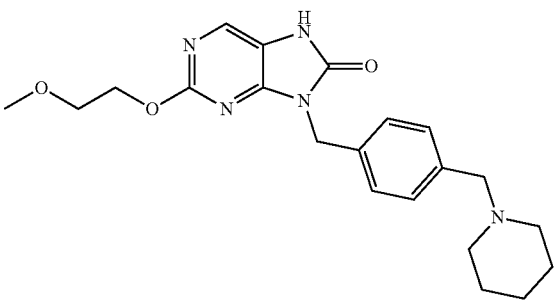

Example 4

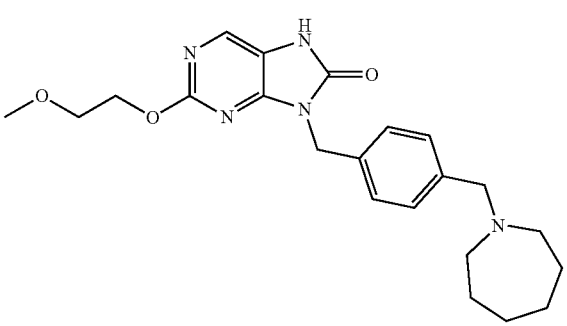

Example 5

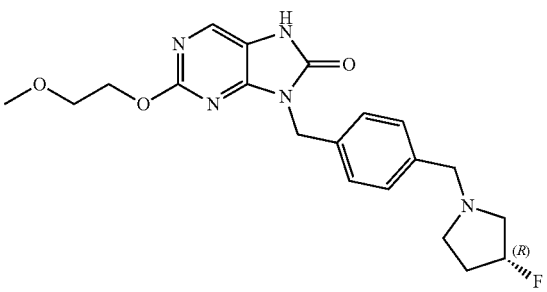

Example 6
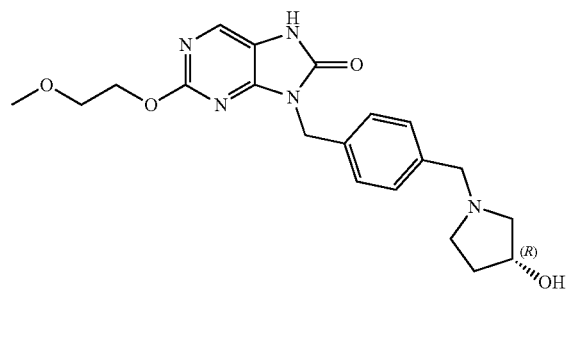
Example 7
Example 8
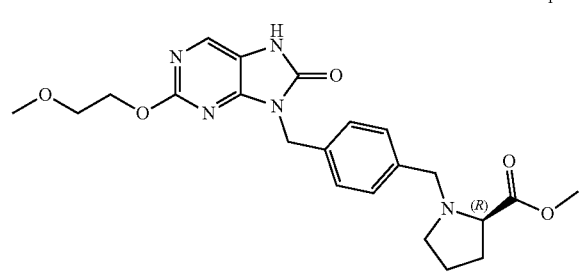
Example 9
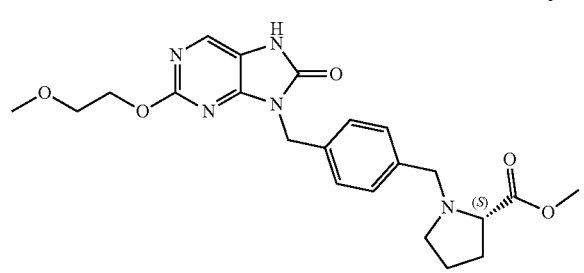
Example 10
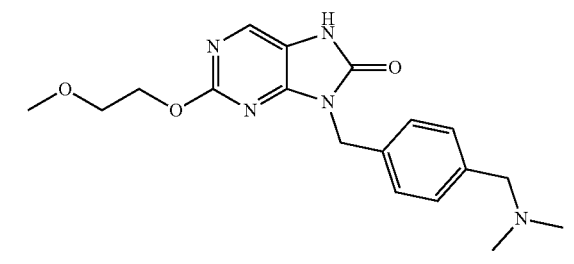
Example 11
Example 12
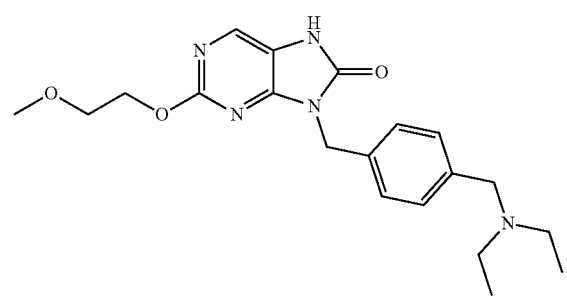
Example 13
Example 14

Example 15
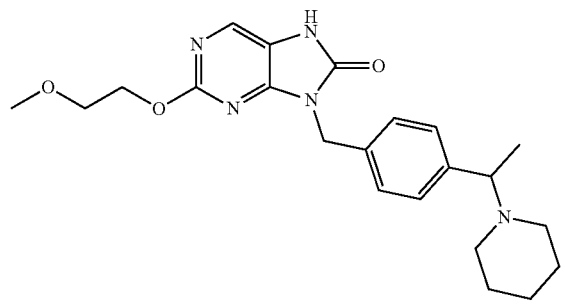
Example 16
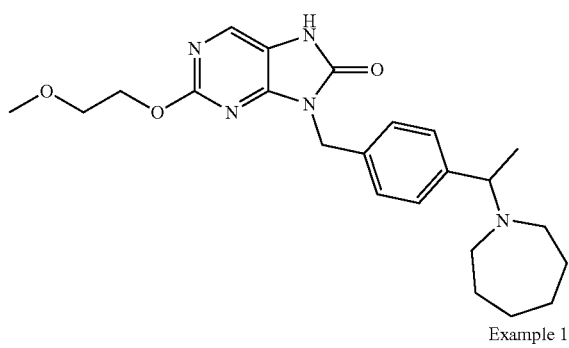
Example 17
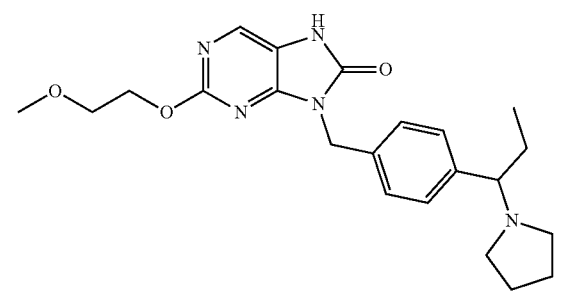
Example 18
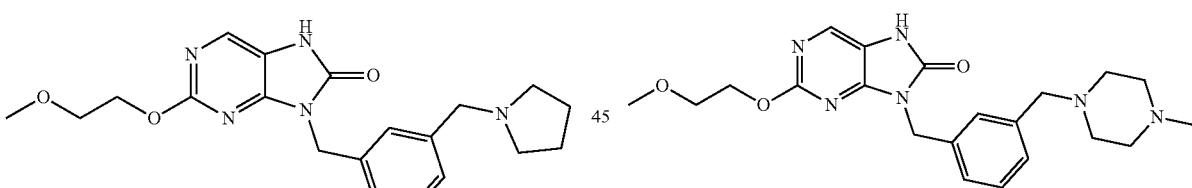
Example 19
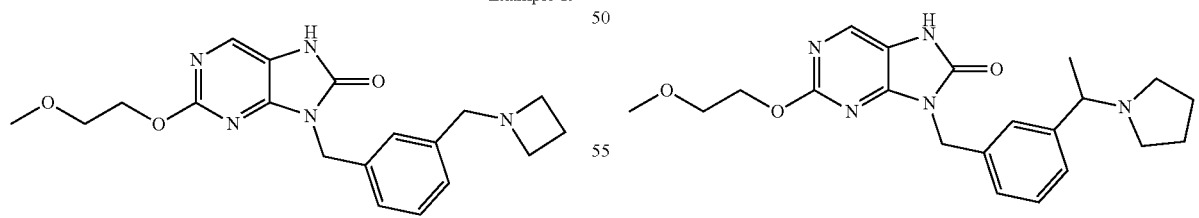
Example 20
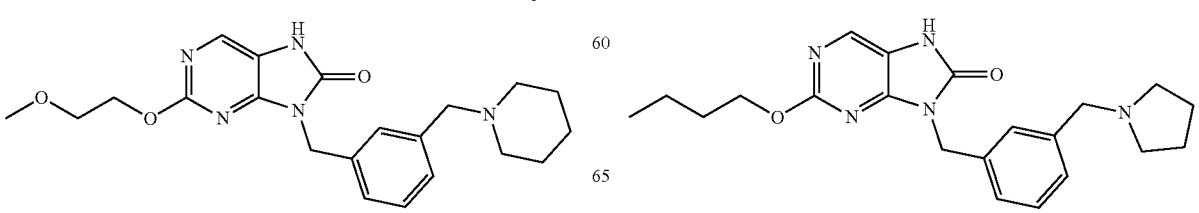
Example 21
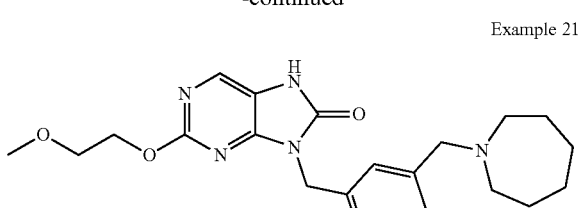
Example 22
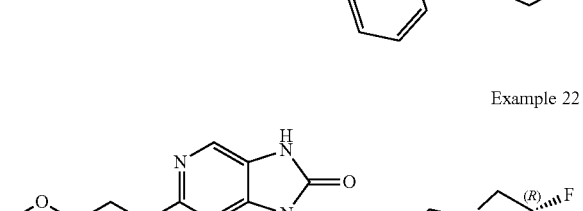
Example 23
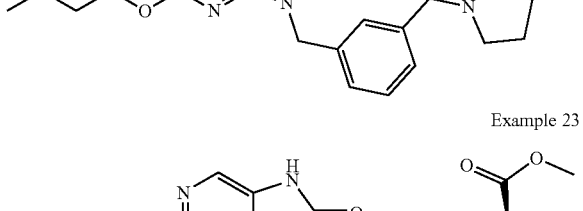
Example 24
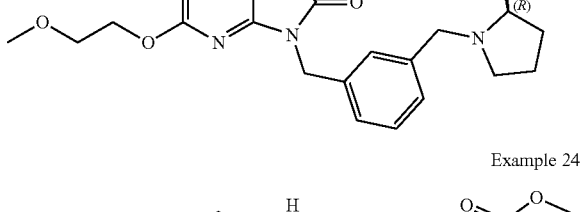
Example 25
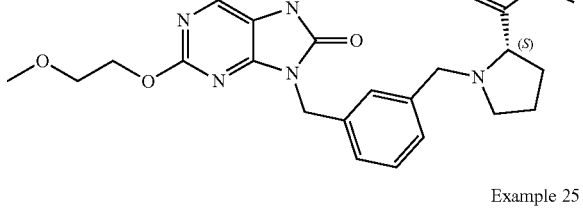
Example 26
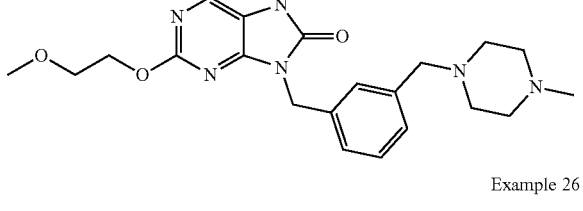
Example 27
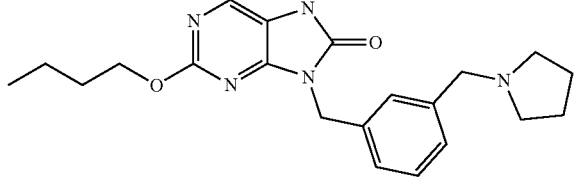

Example 28
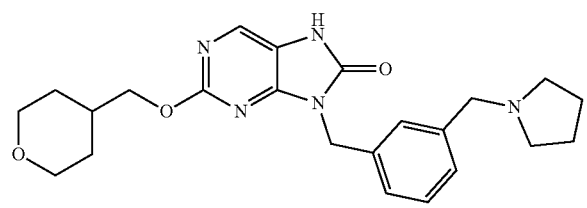
Example 29
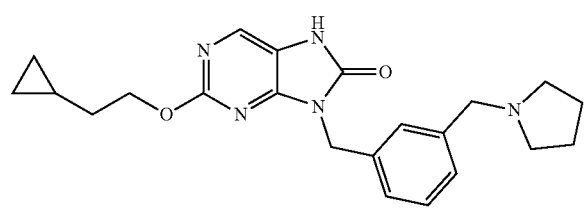
Example 30
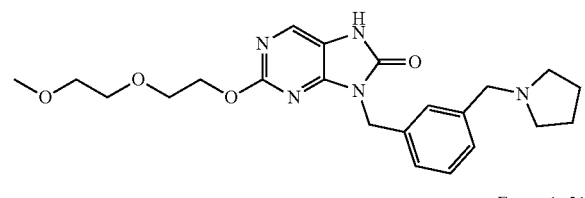
Example 31
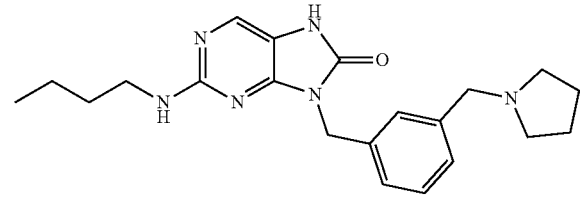
Example 32
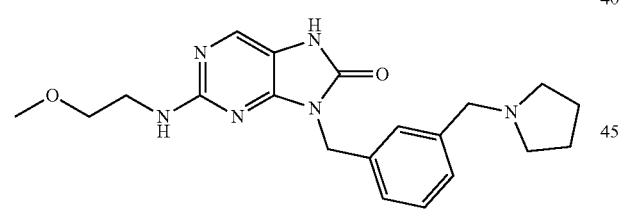
Example 33
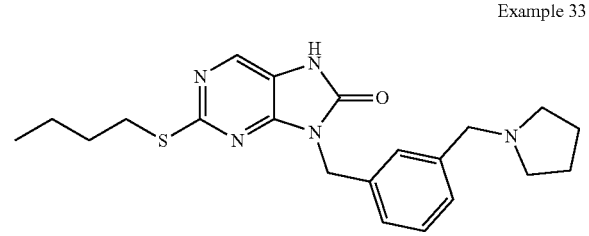
Example 34
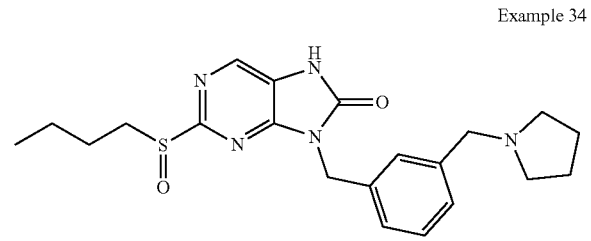
Example 35
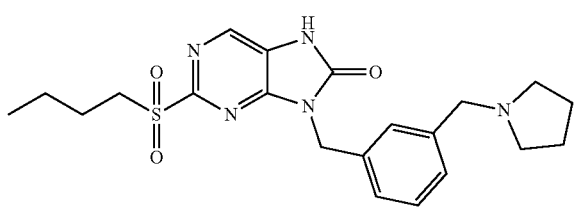
Example 36
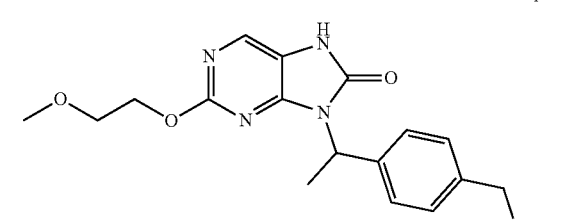
Example 37
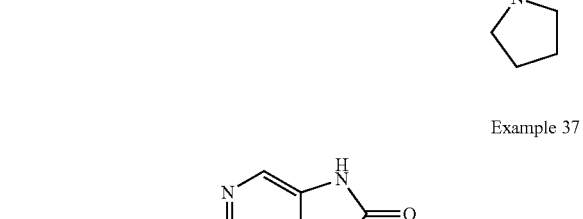
Example 38
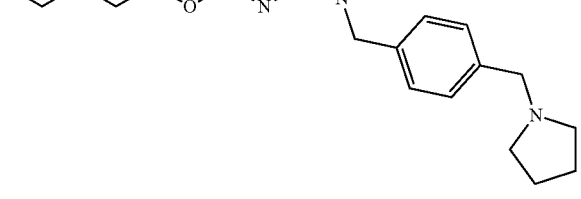
Example 39
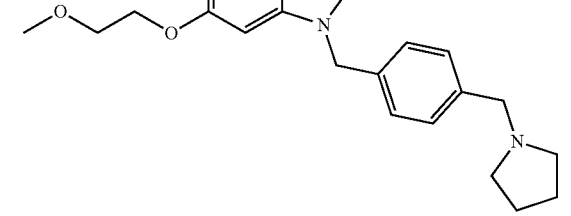

Example 40
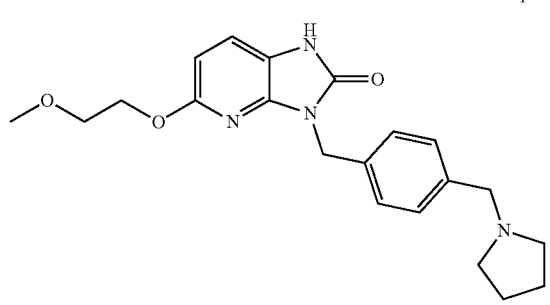
Example 41
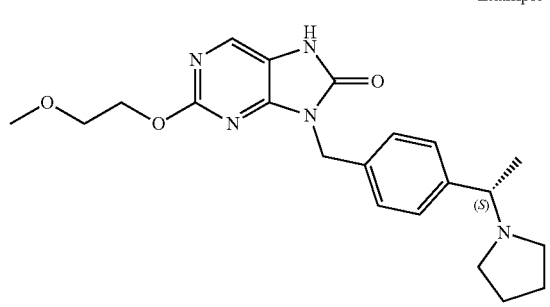
Example 42
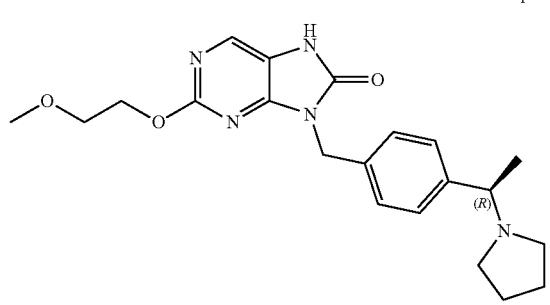
Example 43
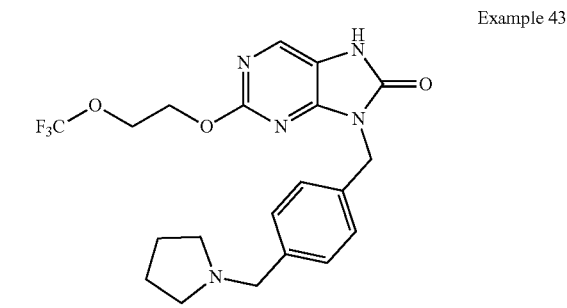
Example 44
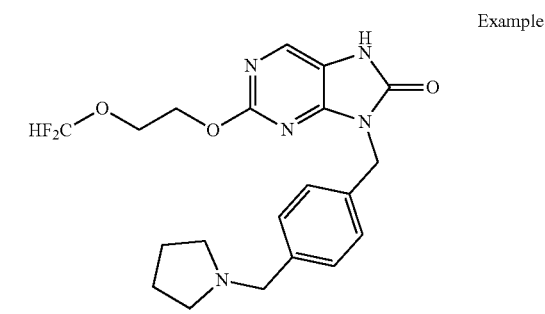
Example 45
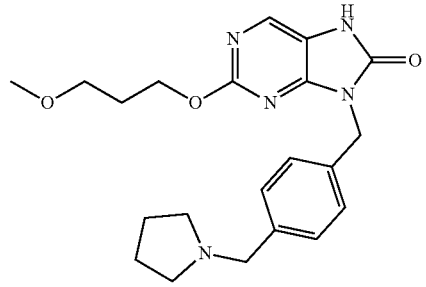
Example 46
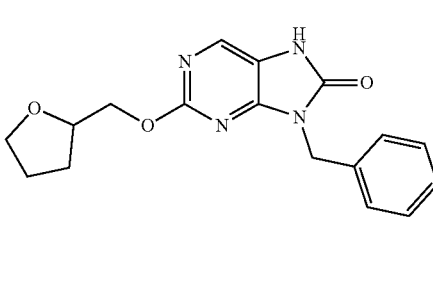
Example 47
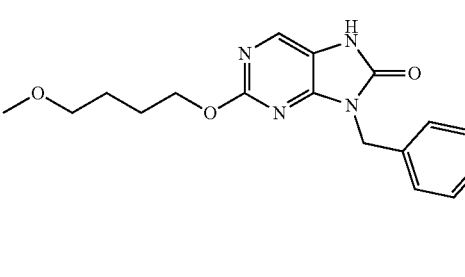
Example 48
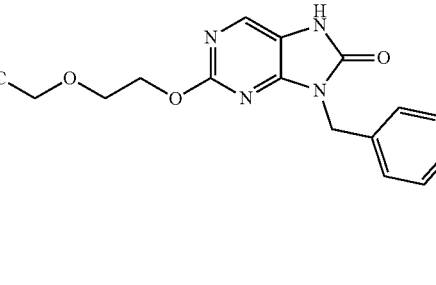
Example 49
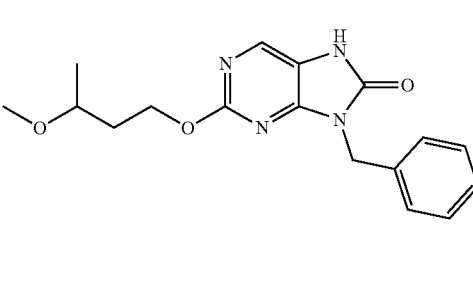

Example 50
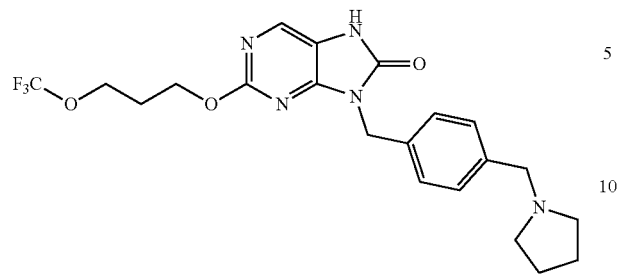
Example 51
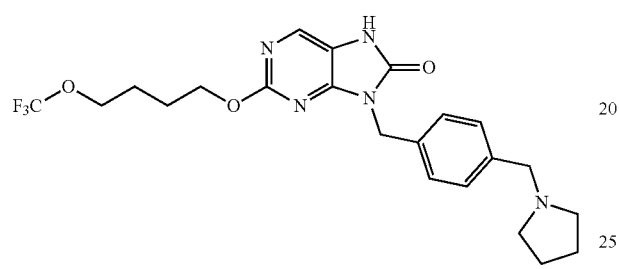
Example 52
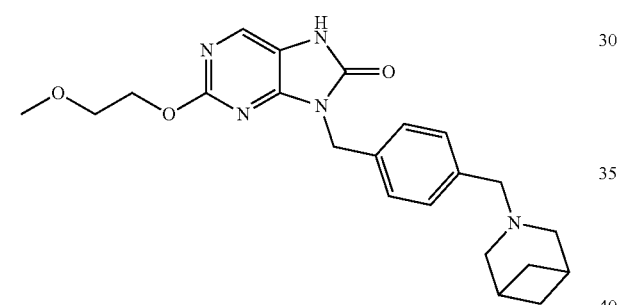
Example 53
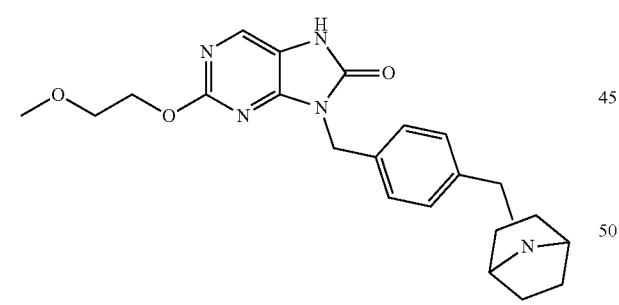
Example 54
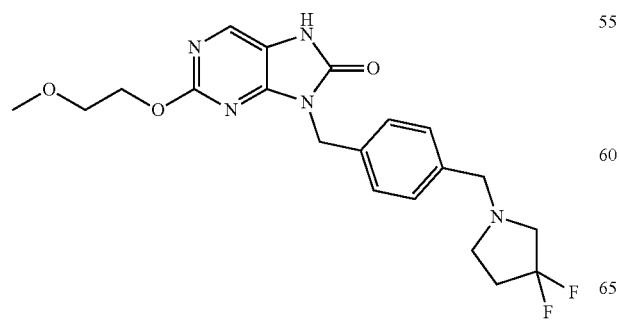
Example 55
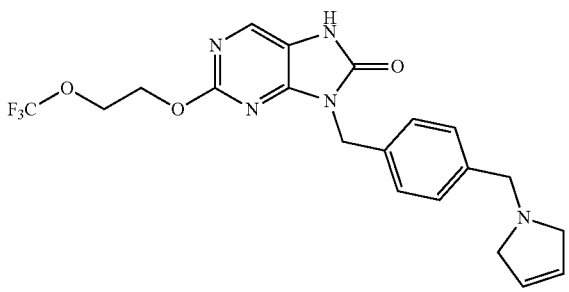
Example 56
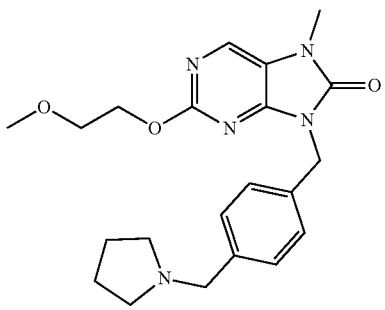
Example 57
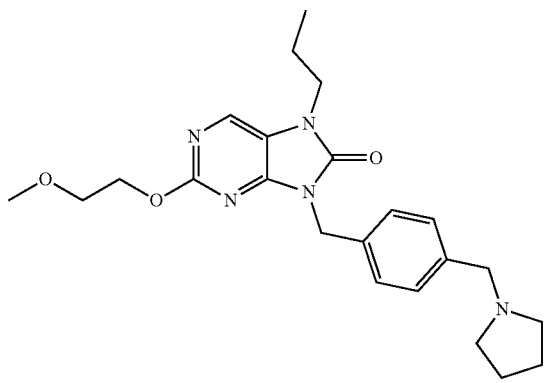
Example 58
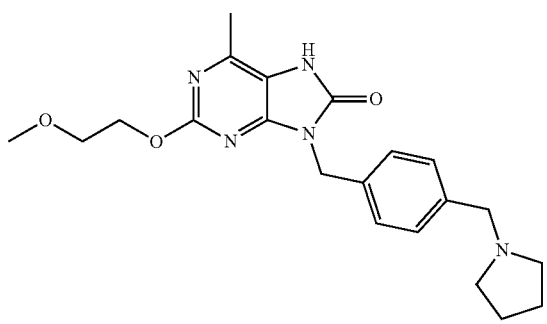

Example 59
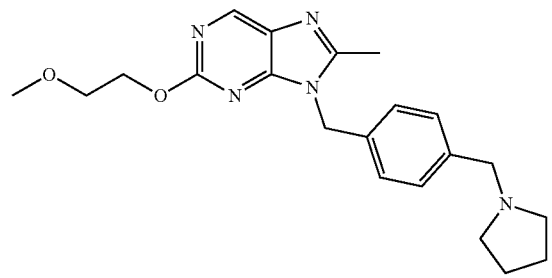
Example 60
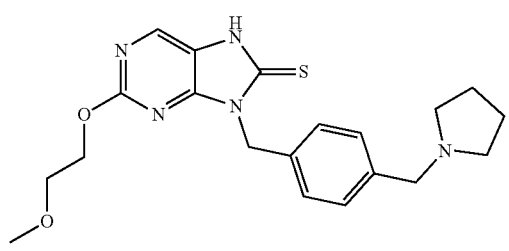
Example 61
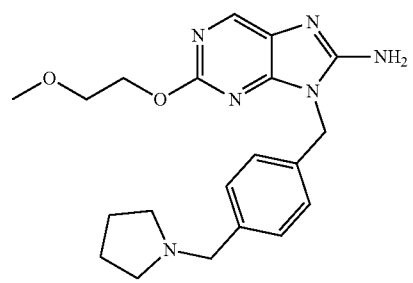
Example 62
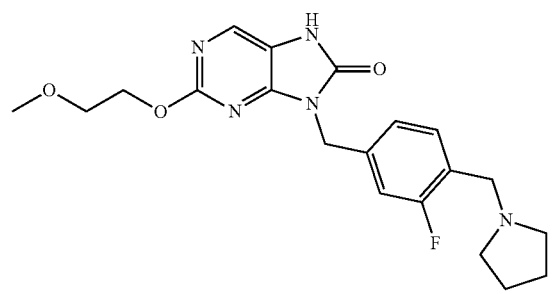
Example 63
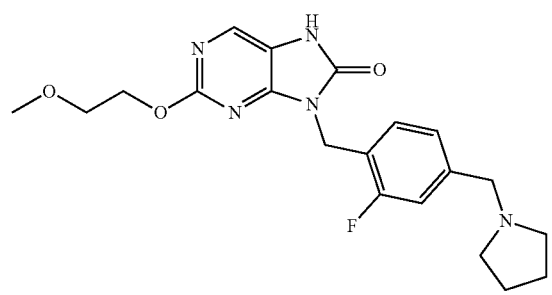
Example 64
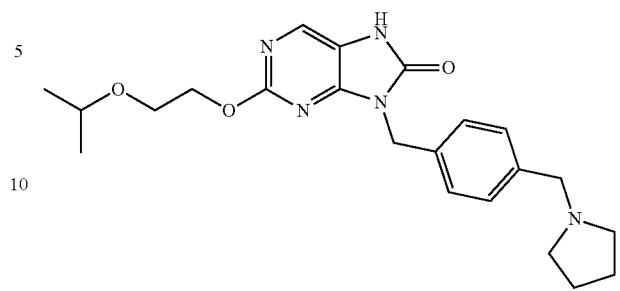
Example 65
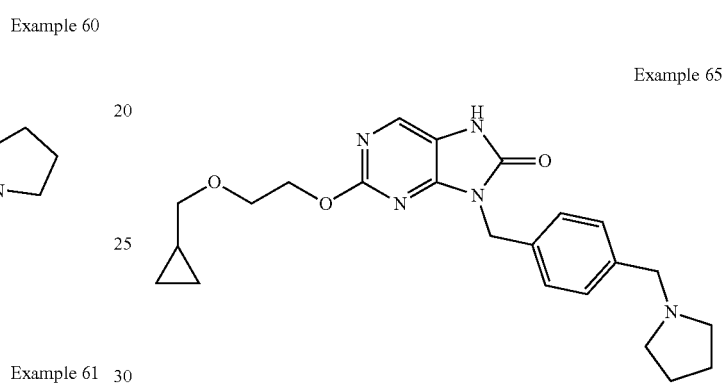
Example 66
Example 67
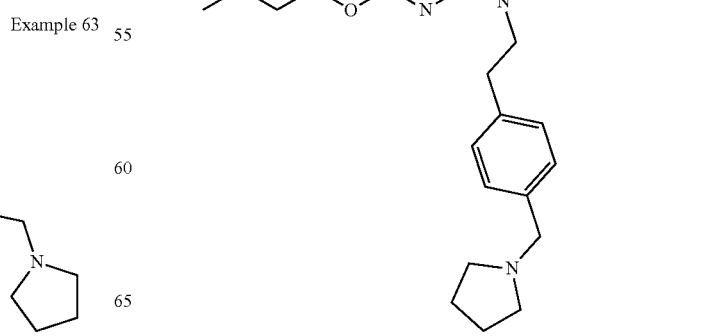

Example 68

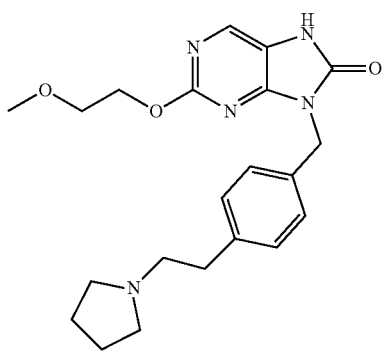

Example 69

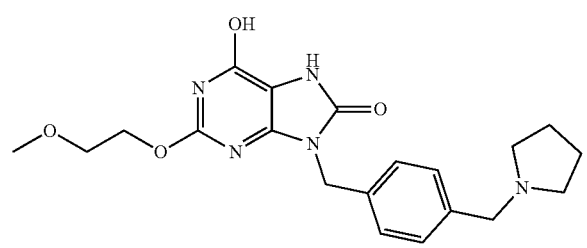

Example 70

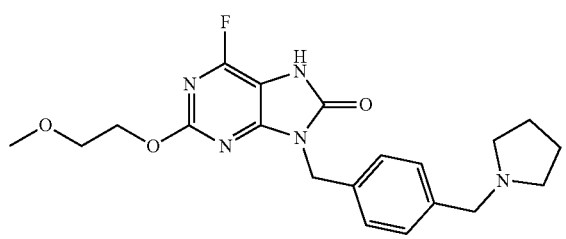

The compound of formula I and the compound of formula II can be prepared by those skilled in the art by adjusting the structure of the reactants according to the disclosure of the specific embodiments of the present invention combined with common knowledge in the art.

Preferably, the present invention also provides a method for preparing the compound of formula I, comprising the following procedure: carrying out a reductive amination reaction on the compound of formula A and the compound of formula B as shown below to give the compound of formula I;

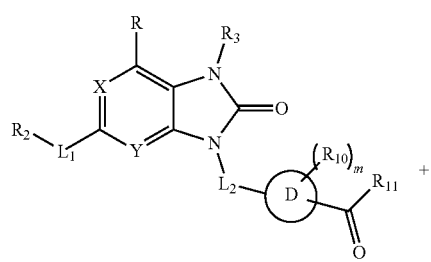

Formula A

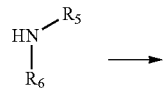

Formula B

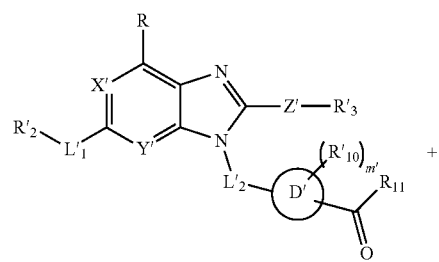

Formula I wherein, X, Y, Z, $R_2$, $R_3$, $R_5$, $R_6$, $R_{10}$, m, $L_1$, $L_2$, D and $R_{11}$ are as defined above; $L_3$ is $C_1$ alkylene.

In the preparation of the compound of formula I, the reductive amination reaction conditions can be selected according to the routine of such reactions in the art.

Preferably, the present invention also provides a method for preparing the compound of formula II, comprising the following procedure: carrying out a reductive amination reaction on the compound of formula C and the compound of formula D as shown below to give the compound of formula II;

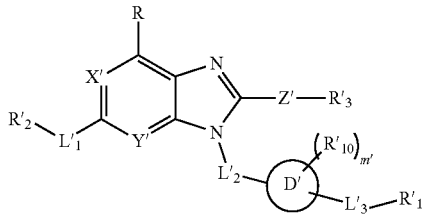

Formula C

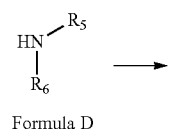

Formula D

R'<sub></sub>

Formula II wherein, X', Y', Z', $R'_2$, $R'_3$, $R_5$, $R_6$, $R'_{10}$, m', $L'_1$, $L'_2$, D' and $R_{11}$ are as defined above; $L'_3$ is $C_1$ alkylene.

In the preparation of the compound of formula II, the reductive amination reaction conditions can be selected according to the routine of such reactions in the art.

The present invention also provides any one of the following compounds:

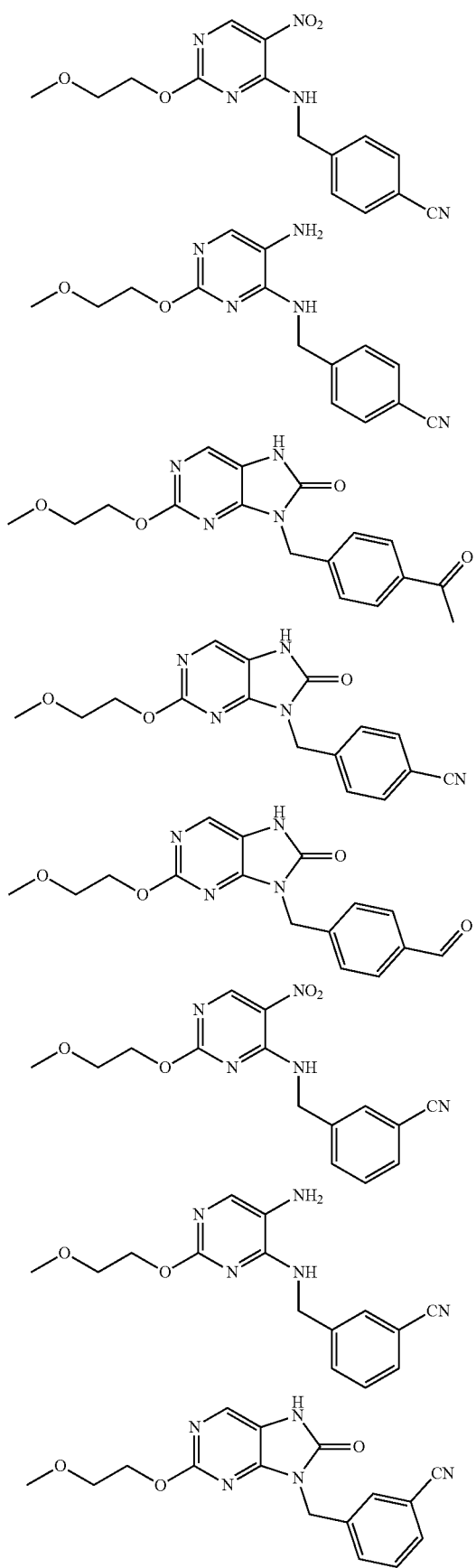
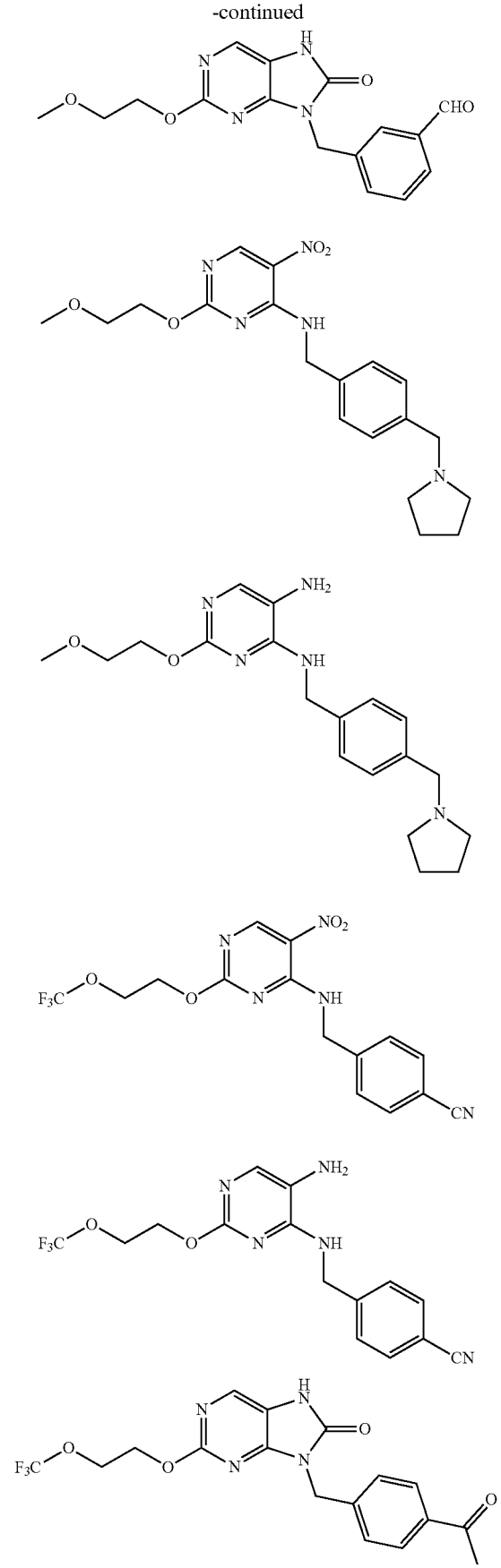

47
-continued

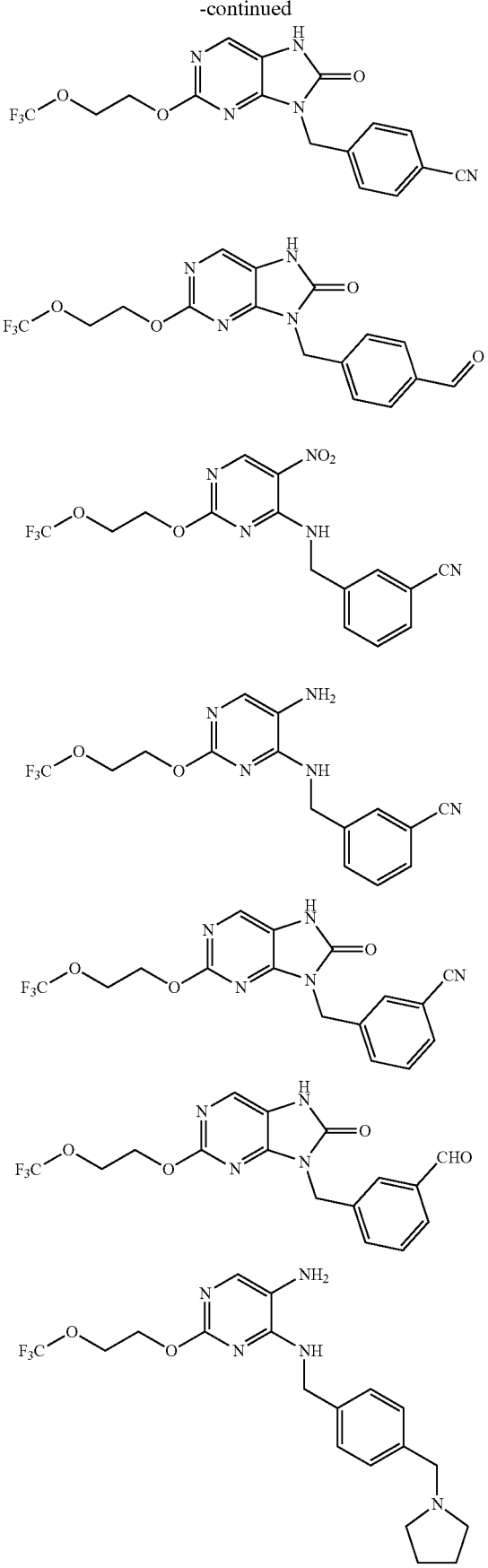

48
-continued

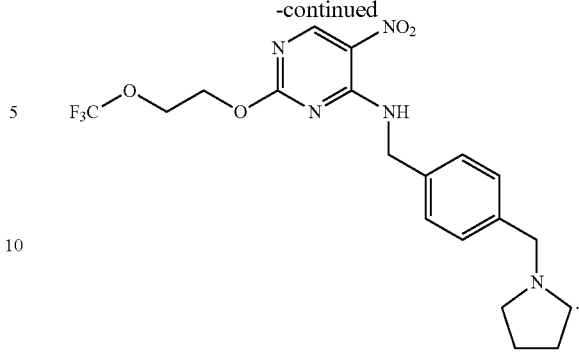

The present invention also provides a use of the compound of formula I, the tautomer thereof, the optical isomer thereof, the deuterated compound thereof, the hydrate thereof, the solvate thereof, the polymorph thereof, the pharmaceutically acceptable salt thereof or the prodrug thereof in manufacturing a TLR7 agonist.

The present invention also provides a use of the compound of formula II, the tautomer thereof, the optical isomer thereof, the deuterated compound thereof, the hydrate thereof, the solvate thereof, the polymorph thereof, the pharmaceutically acceptable salt thereof or the prodrug thereof in manufacturing a TLR7 agonist.

The present invention also provides a use of the compound of formula I, the tautomer thereof, the optical isomer thereof, the deuterated compound thereof, the hydrate thereof, the solvate thereof, the polymorph thereof, the pharmaceutically acceptable salt thereof or the prodrug thereof in manufacturing a medicament for preventing and treating a disease associated with TLR7 activity.

The present invention also provides a use of the compound of formula II, the tautomer thereof, the optical isomer thereof, the deuterated compound thereof, the hydrate thereof, the solvate thereof, the polymorph thereof, the pharmaceutically acceptable salt thereof or the prodrug thereof in manufacturing a medicament for preventing and treating a disease associated with TLR7 activity.

The "disease associated with TLR7 activity" includes, but not limited to, melanoma, non-small cell lung cancer, hepatocellular carcinoma, basal cell carcinoma, renal cell carcinoma, myeloma, allergic rhinitis, asthma, COPD, ulcerative colitis, liver fibrosis, HBV, HCV, HPV, RSV, SARS, HIV, influenza or other viral infections.

The present invention also provides a pharmaceutical composition comprising a therapeutically effective amount of the compound of formula I, the tautomer thereof, the optical isomer thereof, the deuterated compound thereof, the hydrate thereof, the solvate thereof, the polymorph thereof, the pharmaceutically acceptable salt thereof or the prodrug thereof, and one or more pharmaceutically acceptable excipients.

The present invention also provides a pharmaceutical composition comprising a therapeutically effective amount of the compound of formula II, the tautomer thereof, the optical isomer thereof, the deuterated compound thereof, the hydrate thereof, the solvate thereof, the polymorph thereof, the pharmaceutically acceptable salt thereof or the prodrug thereof, and one or more pharmaceutically acceptable excipients.

Unless otherwise specified, the following terms appearing in the description and claims of the present invention have the following meanings:

The atoms in the compound I and the compound II described in the present invention are natural atoms, that is, a mixture of their isotopes. For example, hydrogen is a mixture of protium ($^1H$), deuterium ($^2H$) and tritium ($^3H$) in a natural ratio.

The "deuterated compound" of the present invention refers to the fact that the deuterium abundance of one (or some) hydrogen atom(s) in the molecule is greater than its natural abundance of 0.0156%, up to 100%.

The term "pharmaceutically acceptable salt" refers to a salt of a compound of the present invention prepared by reacting a compound having a specific substituent of the present invention with a relatively non-toxic acid or base. When the compound of the present invention contains a relatively acidic functional group, a base addition salt may be obtained by contacting a sufficient amount of base with the neutral form of the compound in a pure solution or a suitable inert solvent. Pharmaceutically acceptable base addition salts include salts of sodium, potassium, calcium, ammonium, organic ammonia or magnesium or similar salts. When the compound of the present invention contains a relatively basic functional group, an acid addition salt may be obtained by contacting a sufficient amount of acid with the neutral form of the compound in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). When certain specific compounds of the present invention contain both a basic functional group and an acidic functional group, then they may be converted to a base or an acid addition salt.

The term "prodrug" refers to a compound that may readily undergo chemical changes under physiological conditions to convert to a compound of the invention.

For a medicament or a pharmacologically active agent, the term "effective amount" or "therapeutically effective amount" refers to a sufficient amount of the medicament or the agent that is nontoxic but achieves a desired effect. For the oral dosage form of the present invention, an "effective amount" of an active substance in a composition refers to an amount required to achieve a desired effect when used in combination with another active substance in the composition. The effective amount varies from person to person and depends on the age and general condition of the recipient as well as the specific active substance. Appropriate effective amount in an individual case may be determined by a person skilled in the art based on routine experiment.

The term "alkyl" refers to a branched-chain or linear-chain saturated aliphatic hydrocarbon group having a specified number of carbon atoms; for example, "$C_1$-$C_{10}$ alkyl" generally refers to a group having 1, 2, 3, 4, 5, 6, 7, 8, 9 or 10 carbon atoms in a branched-chain or linear-chain structure. For example, "$C_1$-$C_{10}$ alkyl" specifically includes methyl, ethyl, n-propyl, isopropyl, n-butyl, tert-butyl, isobutyl, pentyl, hexyl, heptyl, octyl, nonyl, decyl, etc.

The heteroalkyl (e.g., $C_2$-$C_{10}$ heteroalkyl) of the present invention generally refers to an alkyl (the alkyl may be a branched-chain or linear-chain alkyl), in which one or more (e.g., 2, 3 or 4, etc.) —$CH_2$— is replaced by one or more heteroatoms (the heteroatoms may be one or more of O, S and N). It should be understood that the heteroalkyl is attached to other groups through a carbon atom.

The heteroalkylene (e.g., $C_2$-$C_6$ heteroalkylene) of the present invention generally refers to an alkylene (the alkylene group may be a branched-chain or a linear-chain alkylene), in which one or more (e.g., 2, 3 or 4, etc.) —$CH_2$— is replaced by one or more heteroatoms (the heteroatoms may be one or more of O, S and N). It should be understood that the heteroalkylene is attached to other groups through a carbon atom; when substituents are present on the heteroalkylene, the substituents may be attached to carbon atoms and/or nitrogen atoms.

The term "cycloalkyl" refers to a monovalent non-aromatic saturated or partially unsaturated cyclic hydrocarbon radical having three to ten carbon atoms (e.g., $C_3$-$C_6$ cycloalkyl). Examples of monocyclic carbon ring radicals include, but are not limited to, cyclopropyl, cyclobutyl, cyclopentyl, cyclohexyl, cycloheptyl, cyclooctyl, cyclodecyl, cyclodecyl, cycloundecyl and cyclododecyl. The term "cycloalkyl" also includes polycyclic (e.g., bicyclic and tricyclic) cycloalkyl structures. A bicyclic carbon ring having 7 to 12 atoms may be arranged, for example, as bicyclo [4,5], [5,5], [5,6] or [6,6] system, or as a bridged ring system such as bicyclo [2.2.1] heptane, bicyclo [2.2.2] octane and bicyclo [3.2.2] decane.

The term "heterocycloalkyl" refers to a saturated carbocyclic radical having 3 to 8 ring atoms, wherein at least one of the ring atoms (e.g., 1 to 5) is a heteroatom independently selected from N, O, S, SO and $SO_2$, the remaining ring atoms are C. The radical may be a carbon radical or heteroatom radical. Examples of heterocycloalkyl include, but are not limited to, pyrrolidinyl, tetrahydrofuranyl, dihydrofuranyl, tetrahydrothiophenyl, tetrahydropyranyl, dihydropyranyl, tetrahydrothiopyranyl, piperidinyl, morpholinyl, 4-thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl and N-pyridylurea. Spiro moieties and bridge moieties are also included within the scope of this definition. The heterocycloalkyl may be C-attached or N-attached as long as it is possible (Certain instances of the present application can only be connected via N. For example, $R_5$ and $R_6$ together with the nitrogen atom to which they are attached form a substituted or unsubstituted heterocyclic ring.)

The term "alkenyl" refers to a linear-chain or a branched-chain monovalent hydrocarbon radical of 2 to 12 carbon atoms having at least one site of unsaturation, i.e., carbon-carbon $SP^2$ double bond (e.g., $C_2$-$C_6$ alkenyl, and e.g., $C_2$-$C_4$ alkenyl), and having "cis" and "trans" orientations, or alternatively, "E" and "Z" orientations. Examples include, but are not limited to, vinyl, allyl, 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl.

The term "alkynyl" refers to a linear-chain or a branched-chain monovalent hydrocarbon radical of 2 to 12 carbon atoms having at least one site of unsaturation, i.e., carbon-carbon $SP^3$ triple bond (e.g., $C_2$-$C_6$ alkynyl, and e.g., $C_2$-$C_4$ alkynyl). Examples include, but are not limited to, ethynyl and propinyl.

The term "halogen" refers to fluoro, chloro, bromo or iodo.

The terms "heterocyclic ring" and "heterocyclyl" are used interchangeably and refer to a saturated or partially unsaturated carbocyclic radical having 3 to 8 ring atoms, wherein at least one of the ring atoms is a heteroatom independently selected from N, O, S, SO and $SO_2$, the remaining ring atoms are C. The radical may be a carbon radical or a heteroatom radical. The term "heterocyclyl" includes heterocycloalkoxy. "Heterocyclyl" also includes radicals where a heterocyclyl is fused to a saturated, partially unsaturated, or completely unsaturated (i.e. aromatic) carbocyclic or heterocyclic ring. Examples of the heterocyclyl include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, 4-thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl and N-pyridylurea. Spiro moieties are also included within the scope of this definition. The heterocyclyl may be C-attached or N-attached as long as it is possible. For example, a radical derived from pyrrole may be pyrrol-1-yl (N-attached) or pyrrol-3-yl (C-attached). Further, a radical derived from imidazole may be imidazol-1-yl (N-attached) or imidazol-3-yl (C-attached). Examples of the heterocyclyl in which two ring carbon atoms are substituted by oxo (—O) moieties are dihydroisoindolyl-1,3-dione and 1,1-dioxo-thiomorpholinyl.

By way of example and without limitation, a C-attached heterocyclic ring is attached at 2-, 3-, 4-, 5- or 6-position of pyridine; attached at 3-, 4-, 5- or 6-position of pyridazine; attached at 2-, 4-, 5- or 6-position of pyrimidine; attached at the 2-, 3-, 5- or 6-position of pyrazine; attached at 2-, 3-, 4- or 5-position of furan, tetrahydrofuran, thiophene, pyrrole or tetrahydropyrrole; attached at 2-, 4- or 5-position of oxazole, imidazole or thiazole; attached at 3-, 4- or 5-position of isoxazole, pyrazole or isothiazole; attached at 2- or 3-position of aziridine; attached at the 2-, 3- or 4-position of azetidine; attached at 2-, 3-, 4-, 5-, 6-, 7-, or 8-position of quinoline; or attached at 1-, 3-, 4-, 5-, 6-, 7-, or 8-position of isoquinoline. Additional examples of the C-attached heterocyclic ring include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and without limitation, a N-attached heterocyclic ring is attached at the 1-position of aziridine, azetidine, pyrrole, pyrrolidine, 2-pyrroline, 3-pyrroline, imidazole, imidazolene, 2-imidazoline, 3-imidazoline, pyrazole, pyrazoline, 2-pyrazoline, 3-pyrazoline, piperidine, piperazine, indole, indoline, 1H-carbazole; attached at 2-position of isoindole or dihydroisoindole; attached at the 4 position of morpholine and attached at the 9-position of carbazole or β-oxazoline. More typically, the N-attached heterocyclic ring includes 1-aziridine, 1-azetidinyl, 1-pyrrolyl, 1-imidazolyl, 1-pyrazolyl, and 1-piperidinyl.

The above preferred conditions of can be arbitrarily combined without departing from the general knowledge in the art to obtain the preferred embodiments of the present invention.

The reagents and starting materials used in the present invention are commercially available.

The positive progress of the present invention is that the nitrogen-containing heterocyclic compound of the present invention has high TLR7 agonistic activity, high selectivity and good safety.

DETAILED DESCRIPTION OF THE PREFERRED EMBODIMENT

The following examples further illustrate the present invention, but the present invention is not limited thereto. The experimental methods in the following example of which conditions are not specified, refer to the conventional methods and conditions, or the product specification.

Example 1: Preparation of 2-(2-methoxyethoxy)-9-(4-(pyrrolidin-1-ylmethyl)benzyl)-7,9-dihydro-8H-purin-8-one

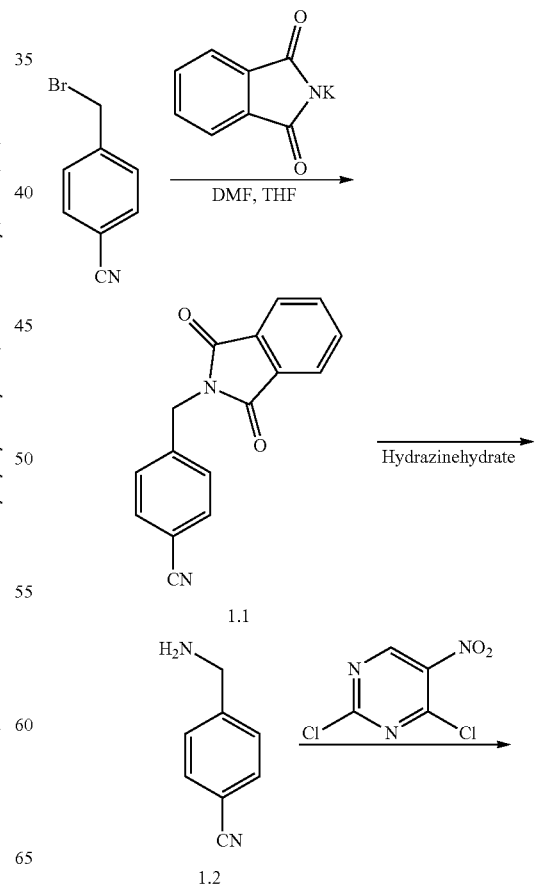

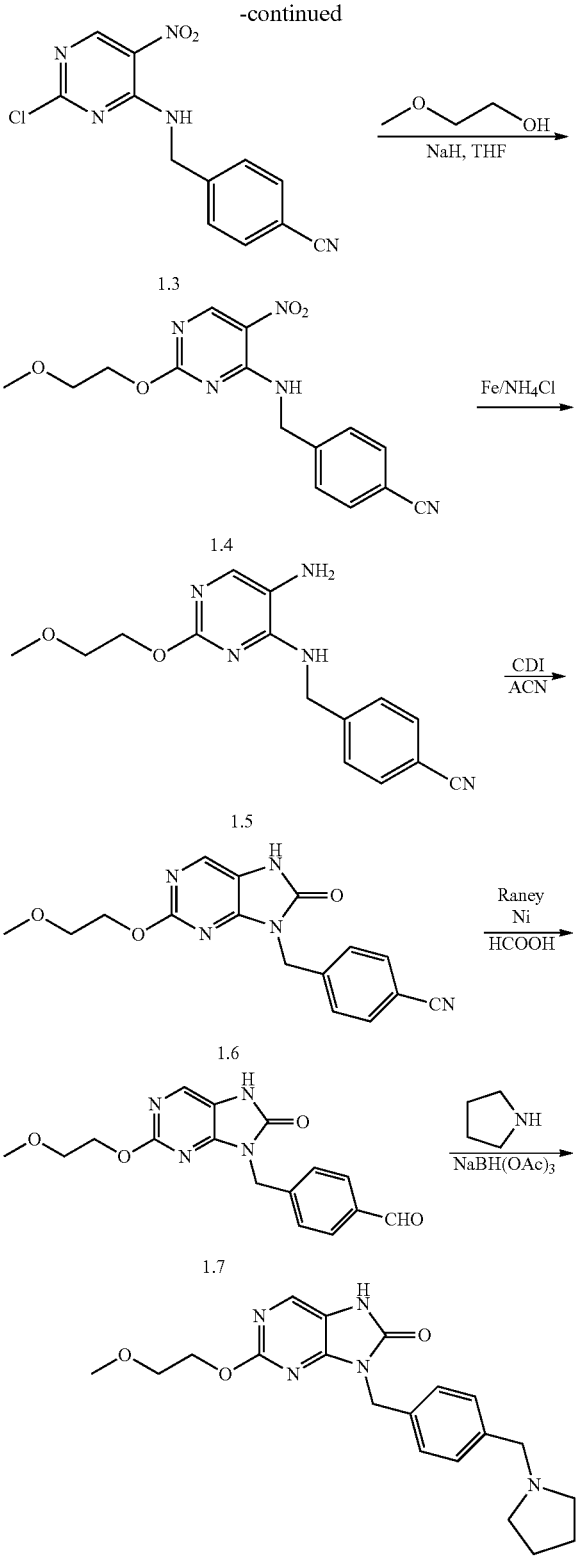

Example 1

1. Synthesis of Intermediate 1.1

Potassium phthalimide (7.3 g, 37 mmol) was added to 25 mL of anhydrous DMF, and 25 mL of a mixture of p-cyanobenzyl bromide (7.6 g, 41 mmol) and anhydrous THF was added thereto with stirring at room temperature, after the addition, the mixture was heated to 60° C. and reacted for 3 hours, and the disappearance of the starting materials was confirmed by TLC (PE/EA=5/1). The reaction mixture was cooled to room temperature and 50 mL of water was added thereto with stirring. The mixture was stirred for 30 min, followed by filtration.

The filter cake was washed with water and rinsed with ethanol, followed by drying to give Intermediate 1.1 (white solid: 9 g, yield: 93%). LC-MS: M+H$^+$=263.

2. Synthesis of Intermediate 1.2

Intermediate 1.1 (9 g, 34 mmol) was added to 200 mL of ethanol, and 9 mL of 85% hydrazine hydrate was added thereto. The mixture was heated under reflux for 2 hours with mechanical stirring, and a large amount of white solid was precipitated, and the disappearance of the starting materials was confirmed by LCMS.

The reaction mixture was cooled to room temperature, followed by filtration. The filtrate was concentrated, and 100 mL of 1N sodium hydroxide solution was added thereto, followed by extraction with dichloromethane (50 mL*3) The organic phase was dried and concentrated to give Intermediate 1.2 (colorless liquid: 4 g, yield: 88%). LC-MS: M+H$^+$=132.

3. Synthesis of Intermediate 1.3

2,4-Dichloro-5-nitropyrimidine (90%, 6.2 g, 28.9 mmol) was added into a 250 mL three-necked flask, and 50 mL of anhydrous THF was added thereto under nitrogen. The mixture was cooled to −70° C., and DIPEA (7.46 g, 57.8 mmol) was slowly added dropwise, then 50 mL of a mixture of Intermediate 1.2 (4 g, 30 mmol) in THF was added dropwise, the reaction temperature was maintained no more than −60° C. After the addition, the reaction was carried out at −60° C. for 2 hours, and the disappearance of the starting materials was confirmed by TLC/EA=2/1). The reaction mixture was slowly poured into 100 mL of iced water, and extracted with ethyl acetate (50 mL*3). The organic phase was washed with water and saturated brine, dried, concentrated, and followed by slurry with 20 mL of ethyl acetate at room temperature to give Intermediate 1.3 (brown solid: 6 g, yield: 72%). LC-MS: M+H$^+$=290.

4. Synthesis of Intermediate 1.4

NaH (0.91 g, 22.8 mmol) was added into a 100 mL three-necked flask, and 10 mL of anhydrous THF was added thereto under ice bath, followed by addition of ultra-dry 2-methoxyethanol (4.73 g, 62.1 mmol) dropwise. After the addition, the mixture was stirred under ice bath for 30 minutes. The reaction mixture was slowly added dropwise to 50 mL of a mixture of Intermediate 1.3 (6 g, 20.7 mmol) in anhydrous THF. The reaction temperature was maintained no more 10° C. After the addition, the reaction was carried out at room temperature for 2 hours, and the disappearance of the starting materials was confirmed by TLC (PE/EA=2/1). The reaction solution was slowly poured into 50 mL of iced water and extracted with ethyl acetate (30 mL*3). The organic phase was combined, washed with saturated brine, dried over anhydrous sodium sulfate, concentrated and followed by slurry with 20 mL of ethyl acetate to give Intermediate 1.4 (brown solid: 5 g, yield: 73%). LC-MS: M+H$^+$=330.

5. Synthesis of Intermediate 1.5

80 mL of ethanol and 40 mL of water were added into a 250 mL three-necked flask, and ammonium chloride solid (4.87 g, 91.1 mmol) and reduced iron powder (4.24 g, 75.9 mmol) were added thereto with stirring. After the addition, the mixture was heated to reflux and reacted for 30 minutes, and then Intermediate 1.4 (5 g, 15.2 mmol) was added thereto. The reaction was refluxed for 2 hours, and the disappearance of the starting materials was confirmed by TLC (DCM/MeOH=20/1), followed by hot filtration. The filter cake was washed with ethanol, and the filtrate was concentrated to remove ethanol and extracted with ethyl acetate (30 mL*3). The organic phase was washed with water and saturated brine, dried and concentrated to give Intermediate 1.5 (reddish brown solid: 3.2 g, yield: 70%). LC-MS: $M+H^+=300$.

6. Synthesis of Intermediate 1.6

Intermediate 1.5 (3.2 g, 10.7 mmol) was added to 60 mL of dry acetonitrile, and carbonyldiimidazole (3.45 g, 21.4 mmol) was added with stirring at room temperature. After the addition, the reaction was refluxed for 16 hours, and the disappearance of the starting materials was confirmed by TLC (DCM/MeOH=20/1). The reaction solution was concentrated, and water was added thereto with stirring for 30 minutes, followed by extraction with ethyl acetate (30 mL*3). The organic phase was washed with water and saturated brine, dried and concentrated. The crude product then followed by slurry with ethyl acetate to give Intermediate 1.6 (yellowish brown solid: 2.5 g, yield: 72%). LC-MS: $M+H^+=326$.

7. Synthesis of Intermediate 1.7

Intermediate 1.6 (2.5 g, 7.7 mmol) was added to 20 mL of a 75% aqueous solution of formic acid, and wet Raney Ni was added thereto. The reaction was heated to reflux for 1 hour, and the disappearance of the starting materials was confirmed by TLC (DCM/MeOH=20:1), followed by filtration. The filtrate was concentrated and the residue was poured into 50 mL of a saturated aqueous solution of sodium bicarbonate, followed by extraction with ethyl acetate (20 mL*3). The organic phase was washed with water and saturated brine, dried and concentrated. The crude product was purified by silica gel column chromatography to give Intermediate 1.7 (white solid: 1.3 g, yield: 40%). LC-MS: $M+H^+=329$.

8. Synthesis of the Compound of Example 1

Intermediate 1.7 (100 mg, 0.3 mmol), tetrahydropyrrole (43 mg, 0.6 mmol) and glacial acetic acid (55 mg, 0.9 mmol) were added to 1,2-dichloroethane (5 mL), and sodium triacetoxyborohydride (194 mg, 0.9 mmol) was added thereto with stirring. After the addition, the mixture was stirred overnight, and then addition sodium triacetoxyborohydride (65 mg, 0.3 mmol) was added. The reaction was carried out at room temperature for 2 hours, and the disappearance of the starting materials was confirmed by TLC (DCM/MeOH=10:1). 10 mL of a saturated aqueous solution of sodium bicarbonate was added to the reaction solution, followed by extraction with DCM (10 mL*3). The organic phase was dried and purified by preparative silica gel plate to give Example 1 (white solid: 20 mg, yield: 17%). $^1$H-NMR (400 MHz, $d_6$-DMSO) δ 11.25 (s, 1H), 7.97 (s, 1H), 7.34 (m, 4H), 4.93 (s, 2H), 4.29 (m, 2H), 3.62-3.54 (m, 2H), 3.27 (s, 2H), 3.24 (s, 3H), 3.07-2.77 (m, 4H), 1.78 (m, 4H). LC-MS: $M+H^+=384$.

Example 2: Preparation of 2-(2-methoxyethoxy)-9-(4-(azetidin-1-ylmethyl)benzyl)-7,9-dihydro-8H-purin-8-one

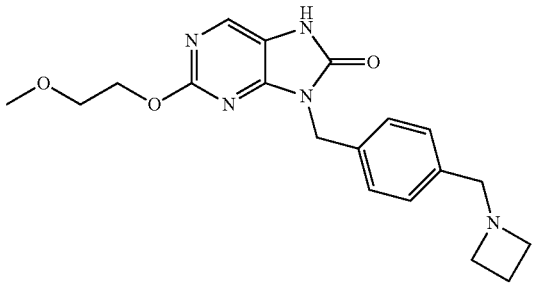 [SMILES: COCCOc1ncc2[nH]c(=O)n(Cc3ccc(CN4CCC4)cc3)c2n1]

According to the procedure of Example 1, Intermediate 1.7 and azetidine were subjected to reductive amination to give the compound of Example 2. $^1$H-NMR (400 MHz, $d_6$-DMSO) δ 11.24 (s, 1H), 7.95 (s, 1H), 7.27 (q, J=8.3 Hz, 4H), 4.89 (s, 2H), 4.37-4.25 (m, 2H), 3.80 (s, 2H), 3.64-3.56 (m, 2H), 3.45 (s, 4H), 3.19 (s, 3H), 2.13-2.01 (m, 2H). LC-MS: $M+H^+=370$.

Example 3: Preparation of 2-(2-methoxyethoxy)-9-(4-(piperidin-1-ylmethyl)benzyl)-7,9-dihydro-8H-purin-8-one

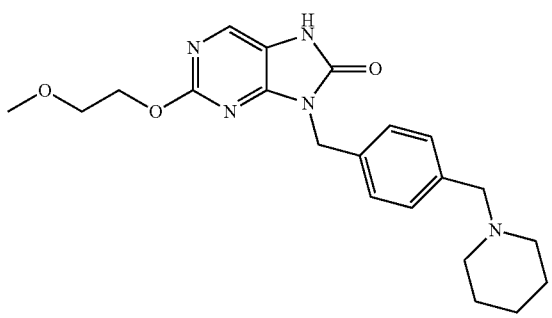 [SMILES: COCCOc1ncc2[nH]c(=O)n(Cc3ccc(CN4CCCCC4)cc3)c2n1]

According to the procedure of Example 1, Intermediate 1.7 and piperidine were subjected to reductive amination to give the compound of Example 3. $^1$H-NMR (400 MHz, $d_6$-DMSO) δ 11.26 (s, 1H), 7.95 (s, 1H), 7.26 (m, 4H), 4.91 (s, 2H), 4.33-4.26 (m, 2H), 3.61-3.55 (m, 2H), 3.27 (s, 2H), 3.24 (s, 3H), 2.63 (m, 2H), 2.02 (m, 2H), 1.75-1.24 (m, 6H). LC-MS: $M+H=398$.

Example 4: Preparation of 2-(2-methoxyethoxy)-9-(4-(azepan-1-ylmethyl)benzyl)-7,9-dihydro-8H-purin-8-one

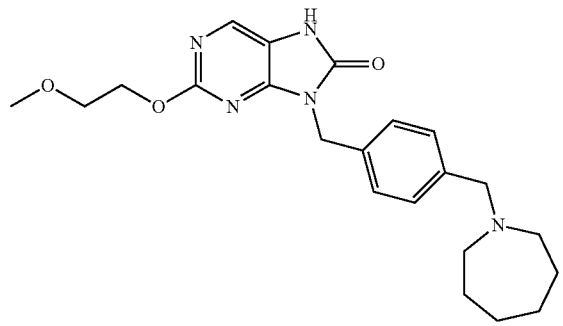 [SMILES: COCCOc1ncc2[nH]c(=O)n(Cc3ccc(CN4CCCCCC4)cc3)c2n1]

According to the procedure of Example 1, Intermediate 1.7 and azacycloheptane were subjected to reductive amination to give the compound of Example 4. $^1$H-NMR (400 MHz, d$_6$-DMSO) δ 11.27 (s, 1H), 7.95 (s, 1H), 7.40 (d, J=66.7 Hz, 4H), 4.93 (s, 2H), 4.33-4.26 (m, 2H), 3.62-3.56 (m, 2H), 3.29 (m, 4H), 3.23 (s, 3H), 2.97 (m, 2H), 1.95-1.43 (m, 8H). LC-MS: M+H$^+$=412.

Example 5: Preparation of (R)-9-(4-((3-fluoropyrrolidin-1-yl)methyl)benzyl)-2-(2-methoxyethoxy)-7,9-dihydro-8H-purin-8-one

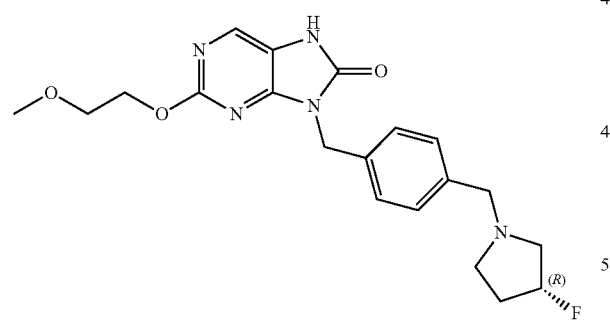

According to the procedure of Example 1, Intermediate 1.7 and (R)-3-fluoropyrrolidine were subjected to reductive amination to give the compound of Example 5. $^1$H-NMR (400 MHz, d$_6$-DMSO) δ=11.26 (s, 1H), 7.99 (s, 1H), 7.28 (s, 4H), 5.25 (s, 1H), 5.11 (s, 1H), 4.92 (s, 2H), 4.33 (t, J=4.8 Hz, 2H), 3.63 (t, J=4.8 Hz, 2H), 3.58 (s, 2H), 3.27 (s, 3H), 2.73 (s, 2H), 2.29 (s, 1H), 2.07-2.16 (m, 1H), 1.83-1.91 (m, 1H). LC-MS: M+H$^+$=402.

Example 6: Preparation of (R)-9-(4-((3-hydroxypyrrolidin-1-yl)methyl)benzyl)-2-(2-methoxyethoxy)-7,9-dihydro-8H-purin-8-one

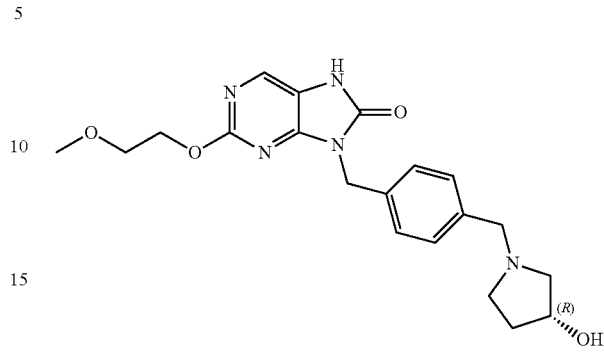

According to the procedure of Example 1, Intermediate 1.7 and (R)-pyrrolidin-3-ol were subjected to reductive amination to give the compound of Example 6. $^1$H-NMR (400 MHz, d$_6$-DMSO) δ 11.23 (s, 1H), 7.96 (s, 1H), 7.29 (t, J=12.0 Hz, 4H), 4.90 (s, 2H), 4.34-4.26 (m, 2H), 4.22 (s, 1H), 3.62-3.56 (m, 2H), 3.23 (S, 3H), 3.10-2.57 (m, 4H), 1.93 (m, 2H), 1.62 (m, 1H). LC-MS: M+H$^+$=400

Example 7: Preparation of methyl (4-((2-(2-methoxyethoxy)-8-oxo-7,8-dihydro-9H-purin-9-yl)methyl)benzyl)-D-pyrrolidine-2-carboxylate

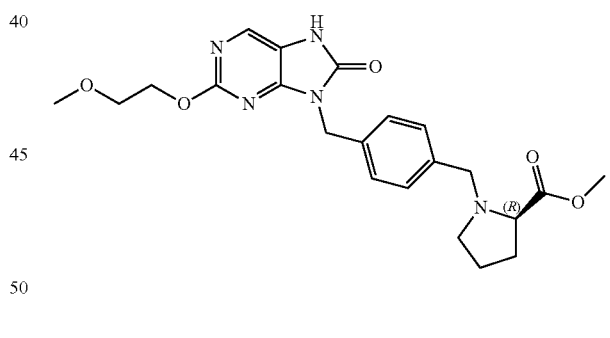

According to the procedure of Example 1, Intermediate 1.7 and D-methyl pyrrolidine-2-carboxylate hydrochloride were subjected to reductive amination to give the compound of Example 7. $^1$H-NMR (400 MHz, CDCl$_3$) δ=9.40 (s, 1H), 7.98 (s, 1H), 7.39-7.41 (d, 2H), 7.26-7.31 (m, 2H), 5.05 (s, 2H), 4.50 (t, J=4.8 Hz, 2H), 3.93 (s, 1H), 3.77 (t, J=4.8 Hz, 2H), 3.64 (s, 4H), 3.43 (s, 3H), 3.32 (s, 1H), 3.10 (s, 1H), 2.43 (s, 1H), 2.15 (s, 1H), 1.82-1.94 (m, 3H). LC-MS: M+H$^+$=442.5

Example 8: Preparation of methyl (4-((2-(2-methoxyethoxy)-8-oxo-7,8-dihydro-9H-purin-9-yl)methyl)benzyl)-L-pyrrolidine-2-carboxylate

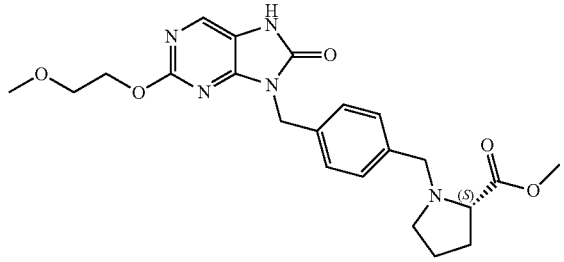

According to the procedure of Example 1, Intermediate 1.7 and L-methyl pyrrolidine-2-carboxylate hydrochloride were subjected to reductive amination to give the compound of Example 8. $^1$H-NMR (400 MHz, CDCl$_3$) δ=9.74 (s, 1H), 7.99 (s, 1H), 7.39-7.41 (d, 2H), 7.27-7.29 (d, 2H), 5.05 (s, 2H), 4.49 (t, J=4.8 Hz, 2H), 3.87-3.92 (m, 1H), 3.77 (t, J=4.8 Hz, 2H), 3.61-3.61 (m, 4H), 3.43 (s, 3H), 3.31 (s, 1H), 3.09 (s, 1H), 2.43 (s, 1H), 2.15 (s, 1H), 1.81-1.96 (m, 3H). LC-MS: M+H$^+$=442.

Example 9: Preparation of 9-(4-((dimethylamino)methyl)benzyl)-2-(2-methoxyethoxy)-7,9-dihydro-8H-purin-8-one

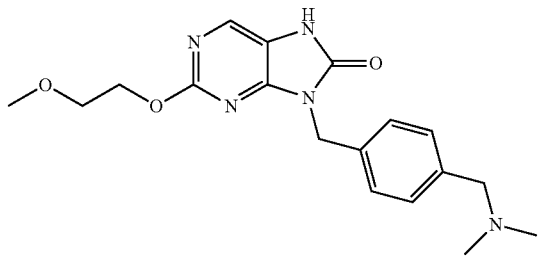

According to the procedure of Example 1, Intermediate 1.7 and dimethylamine hydrochloride were subjected to reductive amination to give the compound of Example 9. $^1$H-NMR (400 MHz, d$_6$-DMSO) δ=11.29 (s, 1H), 7.99 (s, 1H), 7.29-7.38 (m, 4H), 4.94 (s, 2H), 4.33 (t, J=4.8 Hz, 2H), 3.52-3.64 (m, 4H), 3.33 (s, 3H) 2.27 (s, 6H). LC-MS: M+H$^+$=358.

Example 10: Preparation of 9-(4-((dimethylamino)methyl)benzyl)-2-(2-methoxyethoxy)-7,9-dihydro-8H-purin-8-one

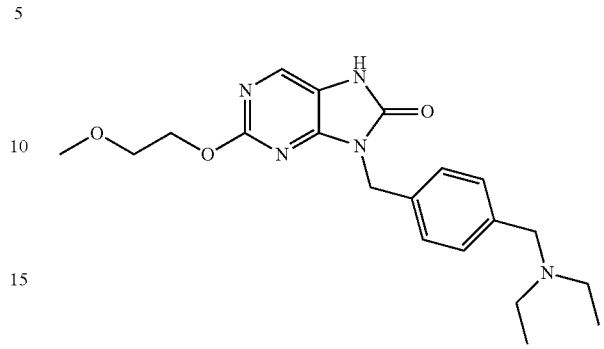

According to the procedure of Example 1, Intermediate 1.7 and diethylamine were subjected to reductive amination to give the compound of Example 10. $^1$H-NMR (400 MHz, d$_6$-DMSO) δ 11.26 (s, 1H), 7.96 (s, 1H), 7.58-7.17 (m, 4H), 4.9 (s, 2H), 4.29 (dd, J=5.4, 3.9 Hz, 2H), 3.59 (dd, J=5.3, 3.9 Hz, 2H), 3.23 (s, 3H), 2.99 (m, 4H), 1.34-0.94 (m, 6H). LC-MS: M+H$^+$=386.

Example 11: Preparation of 9-(4-((2-oxa-7-azaspiro[3.5]nonan-7-yl)methyl)benzyl)-2-(2-methoxyethoxy)-7,9-dihydro-8H-purin-8-one

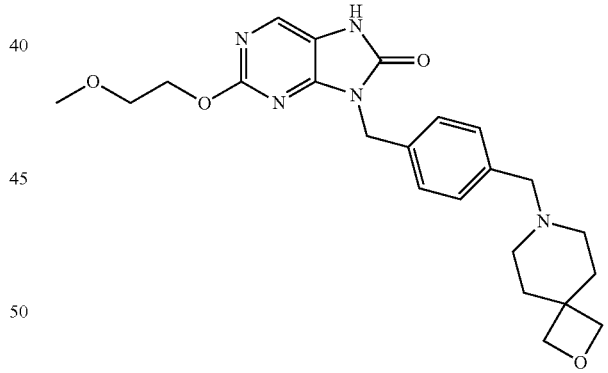

According to the procedure of Example 1, Intermediate 1.7 and 2-oxa-7-azaspiro[3.5]nonane hemioxalate were subjected to reductive amination to give the compound of Example 11. $^1$H-NMR (CDCl$_3$, 400 MHz) δ 9.10 (s, 1H), 7.93 (s, 1H), 7.39 (d, J=8.1 Hz, 2H), 7.30-7.24 (m, 2H), 5.03 (s, 2H), 4.48 (dd, J=5.4, 4.2 Hz, 2H), 4.37 (s, 4H), 3.81-3.73 (m, 2H), 3.49 (s, 2H), 3.42 (s, 3H), 2.37 (s, 4H), 1.91 (s, 4H). LC-MS: M+H$^+$=440.

Example 12: Preparation of 2-(2-methoxyethoxy)-9-(4-(((cis-5-methylhexahydropyrrolo[3,4-c]pyrrole-2(1H)-yl)methyl))benzyl)-7,9-dihydro-8H-purin-8-one

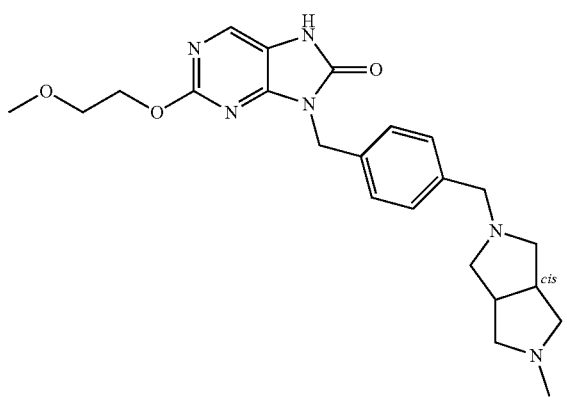 [SMILES: COCCOc1ncc2[nH]c(=O)n(Cc3ccc(CN4CC5CN(C)CC5C4)cc3)c2n1]

According to the procedure of Example 1, Intermediate 1.7 and cis-2-methylhexahydropyrrolo[3,4-c]pyrrole were subjected to reductive amination to give the compound of Example 12. $^1$H-NMR (400 MHz, d$_6$-DMSO) δ=11.25 (s, 1H), 7.99 (s, 1H), 7.28 (s, 4H), 4.92 (s, 2H), 4.33 (t, J=4.8 Hz, 2H), 3.63 (t, J=4.8 Hz, 2H), 3.53 (s, 2H), 3.28 (s, 3H), 2.67-2.79 (m, 4H), 2.31-2.48 (m, 9H). LC-MS: M+H$^+$=439.

Example 13: Preparation of 2-(2-methoxyethoxy)-9-(4-((2-aza-bicyclo[2,2,1]heptan-2-yl)methyl)benzyl)-7,9-dihydro-8H-purin-8-one

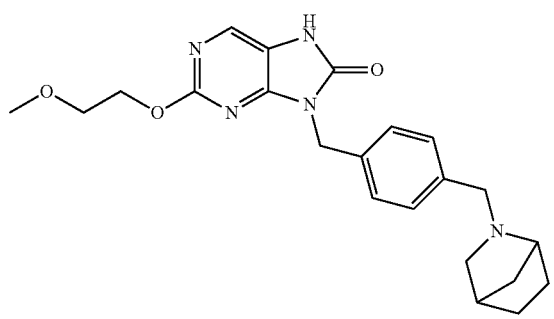 [SMILES: COCCOc1ncc2[nH]c(=O)n(Cc3ccc(CN4CC5CCC4C5)cc3)c2n1]

According to the procedure of Example 1, Intermediate 1.7 and 2-aza-bicyclo[2,2,1]heptane were subjected to reductive amination to give the compound of Example 13. $^1$H-NMR (400 MHz, d$_6$-DMSO) δ 11.27 (s, 1H), 7.96 (s, 1H), 7.54 (d, J=6.8 Hz, 2H), 7.33 (d, J=7.7 Hz, 2H), 4.93 (s, 2H), 4.32-4.27 (m, 2H), 4.10 (s, 1H), 3.85 (s, 1H), 3.65-3.53 (m, 2H), 3.28 (s, 2H), 3.24 (s, 3H), 2.98 (m, 2H), 2.07 (s, 1H), 1.88 (m, 1H), 1.68-1.37 (m, 4H). LC-MS: M+H$^+$=410

Example 14: Preparation of 2-(2-methoxyethoxy)-9-(4-(1-(pyrrolidin-1-yl)ethyl)benzyl)-7,9-dihydro-8H-purin-8-one

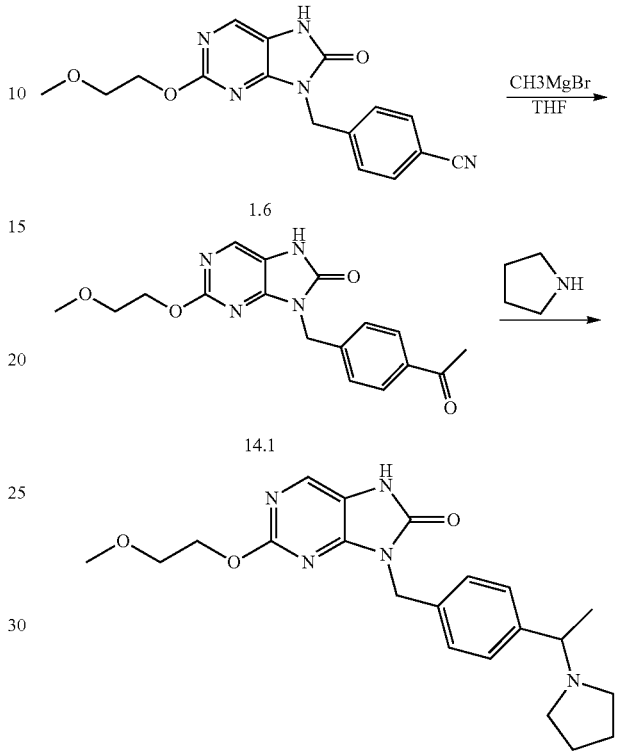

1. Synthesis of Intermediate 14.1

Intermediate 1.6 was given according to the synthesis procedure of Example 1. Intermediate 1.6 (600 mg, 1.84 mmol) was added to anhydrous THF, and a solution of 3M methylmagnesium bromide in THF (3.7 mL, 11.1 mmol) was added thereto dropwise under ice bath. After the addition, the mixture was stirred at room temperature for 1 hour, and then refluxed overnight. The disappearance of the starting materials was confirmed by LCMS. The reaction mixture was cooled to room temperature, and then slowly added to a saturated aqueous solution of ammonium chloride to quench, followed by extraction with ethyl acetate (15 mL*3). The organic phase was combined, washed with saturated brine, dried over anhydrous sodium sulfate, concentrated and purified by silica gel column chromatography to give the product 9-(4-acetylbenzyl)-2-(2-methoxyethoxy)-7,9-dihydro-8H-purin-8-one (colorless viscous liquid: 300 mg, yield: 47.5%). LC-MS: M+H$^+$=343.

2. Synthesis of Example 14

Intermediate 14.1 (100 mg, 0.29 mmol) was added to 5 mL of dry tetrahydrofuran, and tetrahydropyrrole (62 mg, 0.88 mmol) and tetraisopropyltitanium oxide (250 mg, 0.88 mmol) were added. The mixture was heated to 60° C. in a sealed tube and reacted overnight, and then the reaction mixture was cooled to room temperature, followed by addition of sodium triacetoxyborohydride (186 mg, 0.88 mmol). After the addition, the reaction mixture was stirred at 60° C. for 6 hours, and a small amount of the residue of the starting materials was confirmed by LCMS. Ethyl acetate was added to the reaction mixture, and the reaction mixture was washed with water and saturated brine and dried. The crude product was purified by preparative silica gel plate to give Example 14 (30 mg, 25.8%). $^1$H-NMR (400 MHz, d$_6$-DMSO) δ 11.27 (s, 1H), 7.97 (s, 1H), 7.52 (d, J=6.8 Hz, 2H), 7.34 (d, J=8.0 Hz, 2H), 4.93 (s, 2H), 4.41-4.21 (m, 3H), 4.08 (q, J=5.3 Hz, 1H), 3.64-3.54 (m, 3H), 3.24 (s, 3H), 3.13 (d, J=5.2 Hz, 3H), 2.83-2.73 (m, 2H), 1.97-1.73 (m, 4H), 1.54-1.52 (m, 2H). LC-MS: M+H$^+$=398.

Example 15: Preparation of 2-(2-methoxyethoxy)-9-(4-(1-(piperidin-1-yl)ethyl)benzyl)-7,9-dihydro-8H-purin-8-one

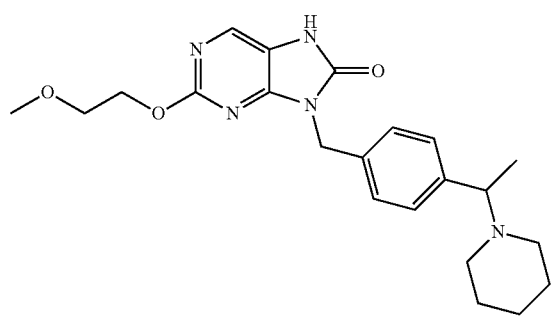 [SMILES: COCCOc1ncc2[nH]c(=O)n(Cc3ccc(C(C)N4CCCCC4)cc3)c2n1]

According to the synthesis procedure of Example 14, Intermediate 14.1 and piperidine were subjected to reductive amination to give the compound of Example 15. $^1$H-NMR (400 MHz, d$_6$-DMSO) δ=11.31 (s, 1H), 10.29 (s, 1H), 8.01 (s, 1H), 7.56 (s, 2H), 7.39 (s, 2H), 4.97 (s, 2H), 4.41 (s, 1H), 4.32-4.35 (m, 2H), 3.61-3.64 (m, 2H), 3.57 (s, 1H), 3.27 (s, 3H), 3.10 (s, 1H), 2.67 (s, 1H), 2.54 (s, 1H), 1.63-1.85 (s, 7H), 1.27-1.33 (m, 2H). LC-MS: M+H$^+$=412.

Example 16: Preparation of 2-(2-methoxyethoxy)-9-(4-(1-(azacycloheptane-1-yl)ethyl)benzyl)-7,9-dihydro-8H-purin-8-one

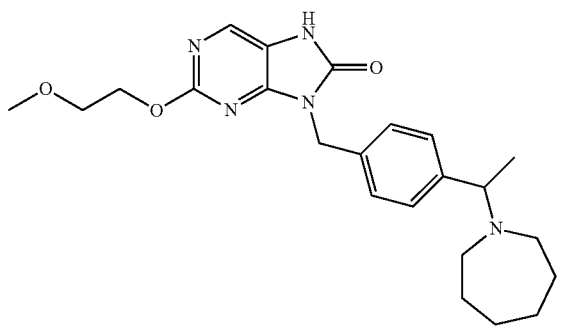 [SMILES: COCCOc1ncc2[nH]c(=O)n(Cc3ccc(C(C)N4CCCCCC4)cc3)c2n1]

According to the synthesis procedure of Example 14, Intermediate 14.1 and azacycloheptane were subjected to reductive amination to give the compound of Example 16. $^1$H-NMR (400 MHz, d$_6$-DMSO) δ=11.27 (s, 1H), 10.17 (s, 1H), 7.97 (s, 1H), 7.56-7.57 (d, 2H), 7.33-7.35 (d, 2H), 4.93 (s, 2H), 4.49 (s, 1H), 4.28-4.30 (m, 2H), 3.58-3.60 (m, 2H), 3.41 (s, 1H), 3.24 (s, 3H), 3.18 (s, 1H), 2.96 (s, 1H), 2.79 (s, 1H), 1.48-1.75 (m, 11H). LC-MS: M+H$^+$=426.

Example 17

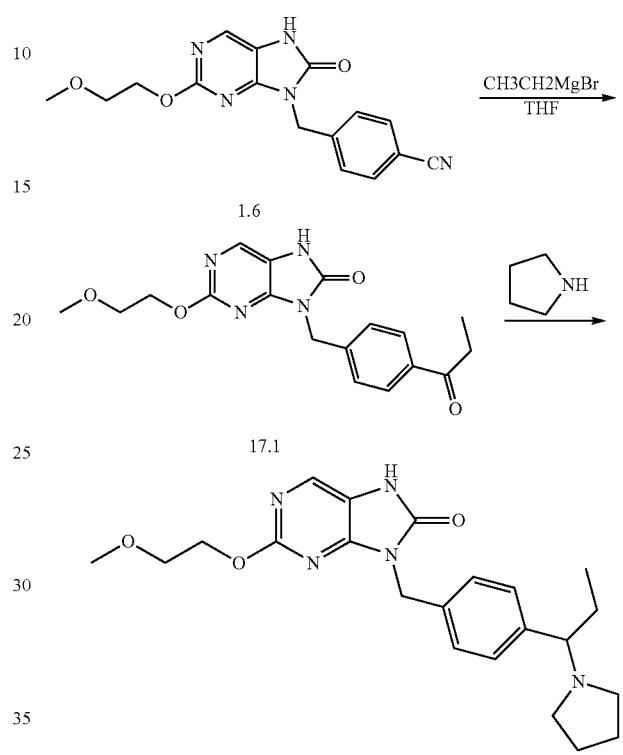

Example 17

1. Synthesis of Intermediate 17.1

Intermediate 1.6 was given according to the synthesis procedure of Example 1. Intermediate 1.6 (150 mg, 0.46 mmol) was added to anhydrous THF, and a solution of 2M ethylmagnesium bromide in THF (1.4 mL, 2.76 mmol) was added dropwise under ice bath. After the addition, the mixture was stirred at room temperature for 1 hour, and then refluxed overnight. The disappearance of the starting materials was confirmed by LCMS. The reaction mixture was cooled to room temperature, and then added to a saturated aqueous solution of ammonium chloride to quench, followed by extraction with ethyl acetate (10 mL*3). The organic phase was combined, washed with saturated brine, dried over anhydrous sodium sulfate, concentrated and purified by silica gel column chromatography to give the product 9-(4-acetylbenzyl)-2-(2-methoxyethoxy)-7,9-dihydro-8H-purin-8-one (pale yellow solid: 85 mg, yield: 52%). LC-MS: M+H$^+$=357

2. Synthesis of Example 17

Intermediate 17.1 (85 mg, 0.24 mmol) was added to 5 mL of dry tetrahydrofuran, and tetrahydropyrrole (51 mg, 0.72 mmol) and tetraisopropyltitanium oxide (204 mg, 0.72 mmol) were added. The mixture was heated to 60° C. in a sealed tube and reacted overnight, and then cooled to room temperature, followed by addition of sodium triacetoxyborohydride (153 mg, 0.72 mmol). After the addition, the reaction mixture was stirred at 60° C. for 6 hours, and a small amount of the residue of the starting materials was confirmed by LCMS. Ethyl acetate was added to the reaction mixture, and the reaction mixture was washed with water and saturated brine and dried. The crude product was purified by preparative silica gel plate to give Example 17 (20 mg, 20.4%). $^1$H-NMR (400 MHz, d$_6$-DMSO) δ 11.26 (s, 1H), 7.98 (s, 1H), 7.48 (d, J=7.2 Hz, 2H), 7.36 (d, J=8.1 Hz, 2H), 4.95 (s, 2H), 4.31-4.29 (m, 2H), 3.69-3.62 (m, 1H), 3.60-3.58 (m, 2H), 3.24 (s, 3H), 2.87-2.66 (m, 4H), 2.13-1.64 (m, 6H), 0.56 (t, J=7.3 Hz, 3H). LC-MS: M+H$^+$=412.

Example 18

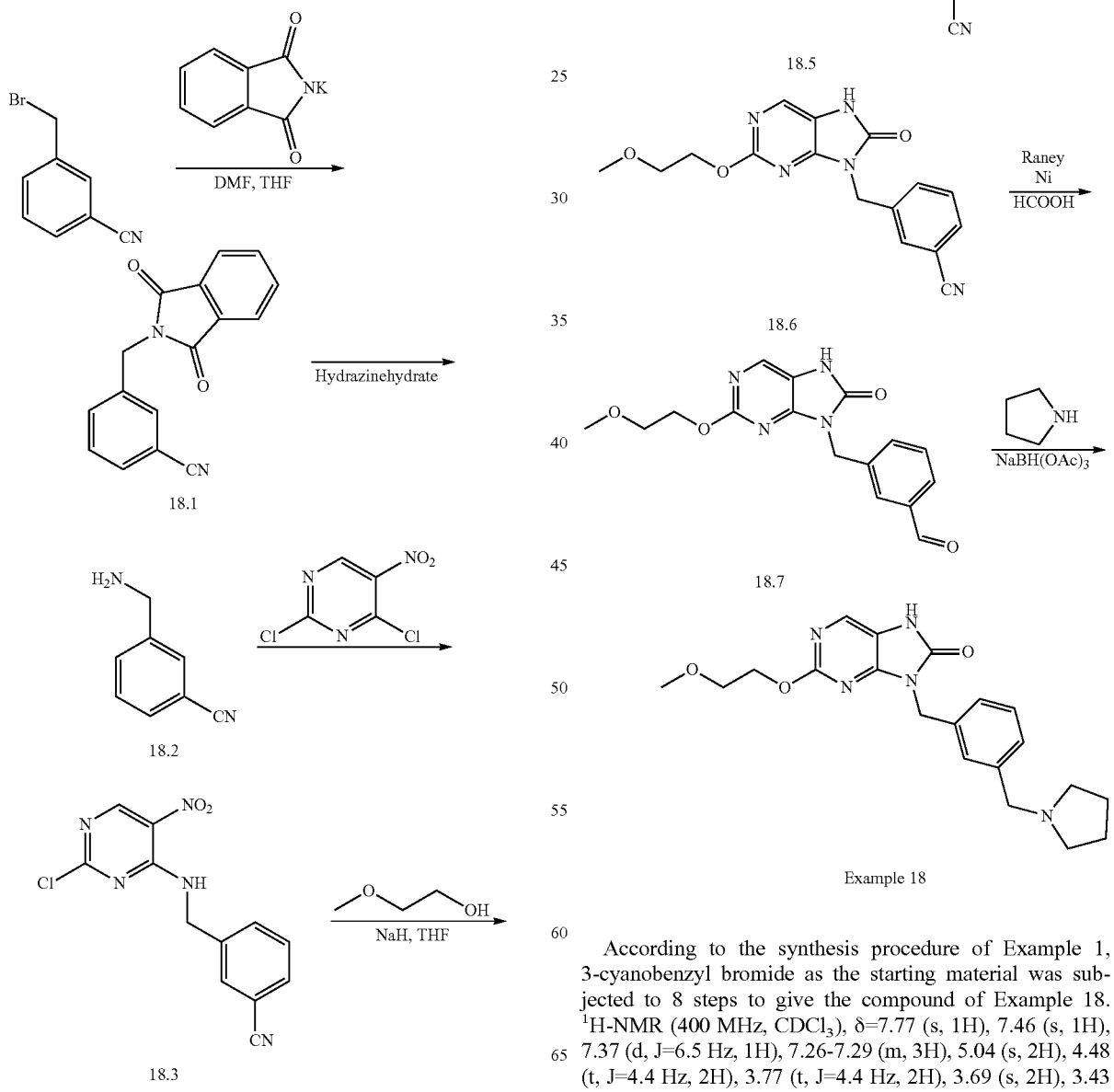

Example 18

According to the synthesis procedure of Example 1, 3-cyanobenzyl bromide as the starting material was subjected to 8 steps to give the compound of Example 18. $^1$H-NMR (400 MHz, CDCl$_3$), δ=7.77 (s, 1H), 7.46 (s, 1H), 7.37 (d, J=6.5 Hz, 1H), 7.26-7.29 (m, 3H), 5.04 (s, 2H), 4.48 (t, J=4.4 Hz, 2H), 3.77 (t, J=4.4 Hz, 2H), 3.69 (s, 2H), 3.43 (s, 3H), 2.62 (s, 4H), 1.80 (s, 4H). LC-MS: M+H$^+$=384.

Example 19: Preparation of 2-(2-methoxyethoxy)-9-(3-(azetidin-1-ylmethyl)benzyl)-7,9-dihydro-8H-purin-8-one

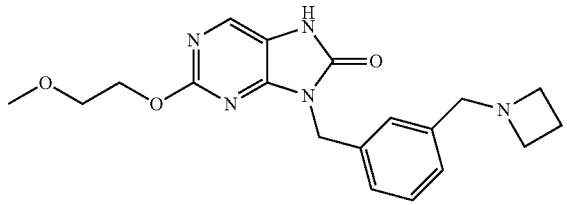 [SMILES: COCCOc1ncc2[nH]c(=O)n(Cc3cccc(CN4CCC4)c3)c2n1]

According to the procedure of Example 18, Intermediate 18.7 and azetidine were subjected to reductive amination to give the compound of Example 19. $^1$H-NMR (400 MHz, d$_6$-DMSO) δ=7.99 (s, 1H), 7.23-7.27 (m, 2H), 7.13-7.17 (m, 3H), 4.92 (s, 2H), 4.34 (t, J=4.4 Hz, 2H), 3.63 (t, J=4.4 Hz, 2H), 3.47 (s, 2H), 3.28 (s, 3H), 3.07 (t, J=6.8 Hz, 4H), 1.91-1.98 (m, 2H). LC-MS: M+H$^+$=370.

Example 20: Preparation of 2-(2-methoxyethoxy)-9-(3-(piperidin-1-ylmethyl)benzyl)-7,9-dihydro-8H-purin-8-one

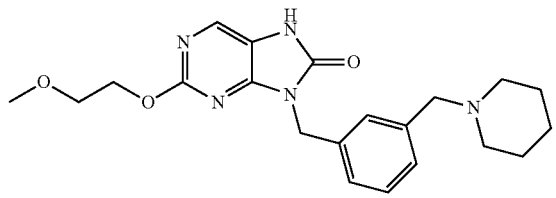 [SMILES: COCCOc1ncc2[nH]c(=O)n(Cc3cccc(CN4CCCCC4)c3)c2n1]

According to the procedure of Example 18, Intermediate 18.7 and piperidin were subjected to reductive amination to give the compound of Example 20. $^1$H-NMR (400 MHz, d$_6$-DMSO) δ=11.23 (s, 1H), 7.99 (s, 1H), 7.25-7.28 (m, 2H), 7.16-7.18 (m, 2H), 4.93 (s, 2H), 4.33 (t, J=4.8 Hz, 2H), 3.62 (t, J=4.8 Hz, 2H), 3.37 (s, 2H), 3.27 (s, 3H), 2.26 (s, 4H), 1.41-1.47 (m, 4H), 1.33-1.38 (m, 2H). LC-MS: M+H$^+$=398.

Example 21: Preparation of 2-(2-methoxyethoxy)-9-(3-(azepan-1-ylmethyl)benzyl)-7,9-dihydro-8H-purin-8-one

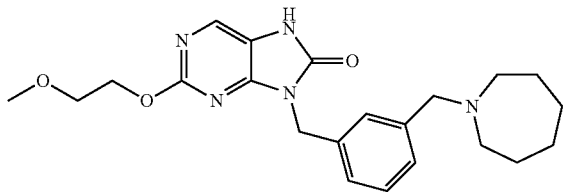 [SMILES: COCCOc1ncc2[nH]c(=O)n(Cc3cccc(CN4CCCCCC4)c3)c2n1]

According to the procedure of Example 18, Intermediate 18.7 and azacycloheptane were subjected to reductive amination to give the compound of Example 21. —NMR (400 MHz, d$_6$-DMSO) δ=11.33 (s, 1H), 8.00 (s, 1H), 7.33-7.46 (m, 4H), 4.96 (s, 2H), 4.32 (t, J=4.8 Hz, 2H), 3.60-3.63 (m, 4H), 2.97 (s, 4H), 1.70 (m, 4H), 1.57 (m, 4H). LC-MS: M+H$^+$=412.

Example 22: Preparation of (R)-9-(3-((3-fluoropyrrolidin-1-yl)methyl)benzyl)-2-(2-methoxyethoxy)-7,9-dihydro-8H-purin-8-one

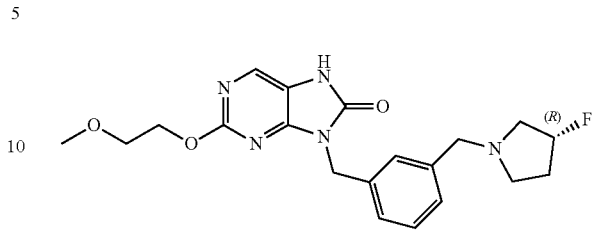

According to the procedure of Example 18, Intermediate 18.7 and (R)-3-fluoropyrrolidine were subjected to reductive amination to give the compound of Example 22. $^1$H-NMR (400 MHz, d$_6$-DMSO) δ 11.22 (s, 1H), 7.95 (s, 1H), 7.25-7.22 (m, 2H), 7.18-7.12 (m, 2H), 5.22-5.14 (m, 0.5H), 5.10-5.02 (m, 0.5H), 4.90 (s, 2H), 4.34-4.24 (m, 2H), 3.61-3.56 (m, 2H), 3.53 (s, 2H), 3.24 (s, 3H), 2.75-2.65 (m, 2H), 2.60-2.50 (m, 1H), 2.28-2.22 (m, 1H), 2.15-2.00 (m, 1H), 1.91-1.71 (m, 1H). LC-MS: M+H$^+$=402.

Example 23: Preparation of methyl (3-((2-(2-methoxyethoxy)-8-oxo-7,8-dihydro-9H-purin-9-yl)methyl)benzyl)-D-pyrrolidine-2-carboxylate

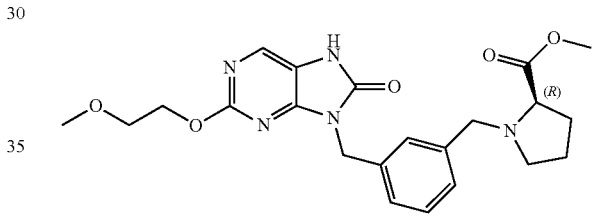

According to the procedure of Example 18, Intermediate 18.7 and D-methyl pyrrolidine-2-carboxylate hydrochloride were subjected to reductive amination to give the compound of Example 23. $^1$H-NMR (400 MHz, d$_6$-DMSO) δ 11.21 (s, 1H), 7.95 (s, 1H), 7.25-7.22 (m, 2H), 7.18-7.12 (m, 2H), 4.89 (s, 2H), 4.32-4.25 (m, 2H), 3.78 (d, J=13.4 Hz, 1H), 3.61-3.56 (m, 2H), 3.50 (s, 3H), 3.43 (d, J=13.4 Hz, 1H), 3.24 (s, 3H), 3.21-3.17 (m, 1H), 2.78-2.73 (m, 1H), 2.29 (dd, J=16.4, 8.2 Hz, 1H), 2.02-1.95 (m, 1H), 1.80-1.70 (m, 1H), 1.66 (dd, J=14.4, 7.3 Hz, 2H). LC-MS: M+H$^+$=442.

Example 24: Preparation of methyl (3-((2-(2-methoxyethoxy)-8-oxo-7,8-dihydro-9H-purin-9-yl)methyl)benzyl)-L-pyrrolidine-2-carboxylate

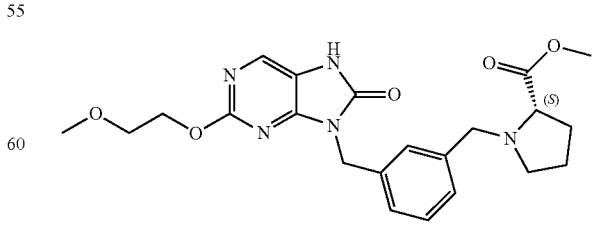

According to the procedure of Example 18, Intermediate 18.7 and L-methyl pyrrolidine-2-carboxylate hydrochloride were subjected to reductive amination to give the compound of Example 24. ¹H-NMR (400 MHz, $d_6$-DMSO) δ 11.21 (s, 1H), 7.95 (s, 1H), 7.25-7.22 (m, 2H), 7.18-7.12 (m, 2H), 4.89 (s, 2H), 4.32-4.25 (m, 2H), 3.78 (d, J=13.4 Hz, 1H), 3.61-3.56 (m, 2H), 3.50 (s, 3H), 3.43 (d, J=13.4 Hz, 1H), 3.24 (s, 3H), 3.21-3.17 (m, 1H), 2.78-2.73 (m, 1H), 2.29 (dd, J=16.4, 8.2 Hz, 1H), 2.02-1.95 (m, 1H), 1.80-1.70 (m, 1H), 1.66 (dd, J=14.4, 7.3 Hz, 2H). LC-MS: M+H⁺=442.

Example 25: Preparation of 2-(2-methoxyethoxy)-9-(3-((4-methylpiperazin-1-yl)methyl)benzyl)-7,9-dihydro-8H-purin-8-one

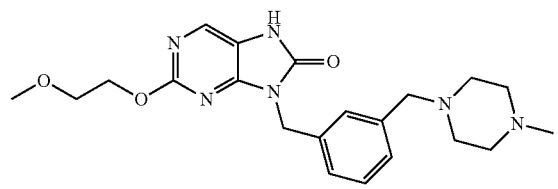

According to the procedure of Example 18, Intermediate 18.7 and N-methylpiperazine were subjected to reductive amination to give the compound of Example 25. ¹H-NMR (400 MHz, CDCl₃) δ=7.85 (s, 1H), 7.41 (s, 1H), 7.35 (d, J=7.2 Hz, 1H), 7.21-7.28 (m, 3H), 5.05 (s, 2H), 4.49 (t, J=4.4 Hz, 2H), 3.77 (t, J=4.4 Hz, 2H), 3.51 (s, 2H), 3.43 (s, 3H), 2.52 (s, 8H), 2.34 (s, 3H). LC-MS: M+H⁺=413.

Example 26: Preparation of 2-(2-methoxyethoxy)-9-(3-(1-(pyrrolidin-1-yl)ethyl)benzyl)-7,9-dihydro-8H-purin-8-one

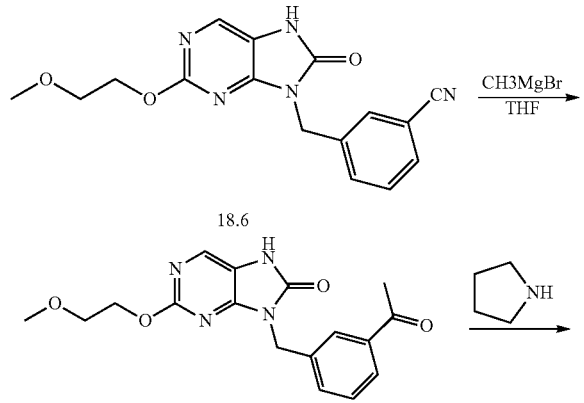

Example 26

According to the synthesis procedure of Example 14, Intermediate 18.6 was subjected to Grignard reaction, followed by reductive amination to give the compound of Example 26. ¹H-NMR (400 MHz, $d_6$-DMSO) δ 11.20 (s, 1H), 7.96 (s, 1H), 7.30 (s, 1H), 7.30-7.22 (m, 2H), 7.16 (d, J=6.5 Hz, 1H), 4.89 (s, 2H), 4.34-4.23 (m, 2H), 3.63-3.55 (m, 2H), 3.23 (s, 3H), 2.65-2.52 (m, 4H), 1.60-1.40 (m, 4H), 1.21 (d, J=9.7 Hz, 3H). LC-MS: M+H⁺=398.

Example 27: Preparation of 2-butoxy-9-(3-(pyrrolidin-1-ylmethyl)benzyl)-7,9-dihydro-8H-purin-8-one

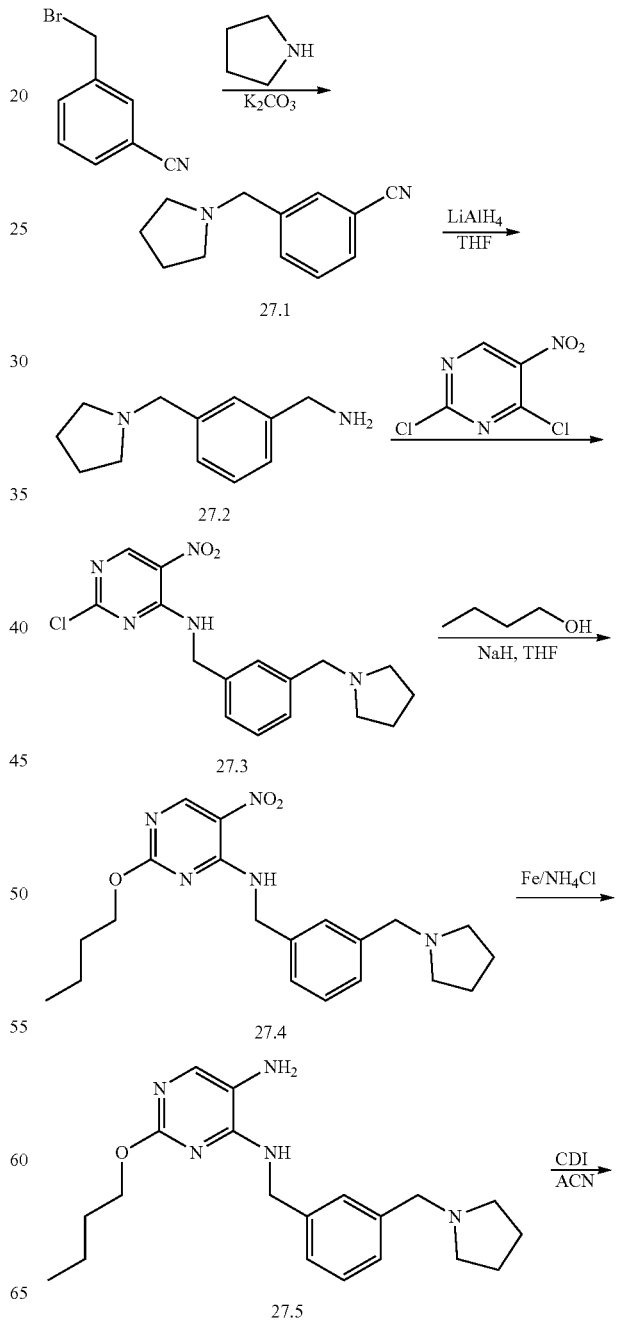

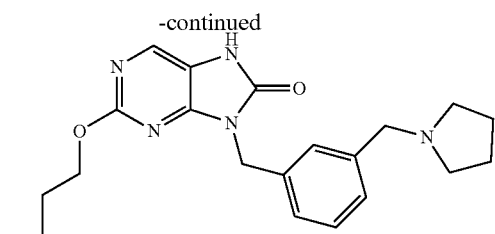

Example 27

1. Synthesis of Intermediate 27.1

3-Cyanobenzyl bromide (15 g, 76.51 mmol), tetrahydropyrrole (5.99 g, 84.15 mmol) and potassium carbonate (31.7 g, 229.5 mmol) were sequentially added to 150 mL of anhydrous ethanol. Then the mixture was heated to 65° C. and reacted for 2 hours, and the disappearance of the starting materials was confirmed by TLC (DCM/MeOH=10:1). The reaction mixture was cooled to room temperature, followed by filtration. The filtrate was concentrated, added with dichloromethane, washed with water, dried and purified by silica gel column chromatography to give Intermediate 27.1 (yellow oil: 12 g, yield: 84%). LC-MS: M+H$^+$=187.

2. Synthesis of Intermediate 27.2

Lithium aluminum hydride (4.9 g, 129 mmol) was added to anhydrous THF, and then cooled to 0° C. under nitrogen atmosphere. A solution of Intermediate 27.1 in THF was slowly added dropwise with stirring. The temperature was maintained no more than 10° C. After the addition, the reaction was carried out at room temperature for 2 hours with stirring, and the disappearance of the starting materials was confirmed by LCMS. 4.9 mL of water, 4.9 mL of 15% aqueous solution of sodium hydroxide and 14.7 mL of water were slowly added dropwise to the reaction mixture with stirring for 30 minutes under ice bath, followed by filtration. The filter cake was washed with dichloromethane. The organic phase was concentrated and evaporated to dryness to give Intermediate 27.2 (yellow oily liquid: 9.9 g, yield: 81%). LC-MS: M+H$^+$=191.

3. Synthesis of Intermediate 27.3

2,4-Dichloro-5-nitropyrimidine (9.62 g, 49.5 mmol) was added to 50 mL of anhydrous THF and cooled to −70° C., followed by addition of DIPEA (9.62 g, 74.4 mmol) dropwise. After the addition, a mixture of Intermediate 27.2 (9.9 g, 52.1 mmol) in THF was added dropwise, the temperature was maintained no more than −60° C. After the addition, the reaction was carried out at −70° C. for 2 hours, and the disappearance of the starting materials was confirmed by LCMS. The reaction solution was slowly poured into iced water and extracted with ethyl acetate (50 mL*3). The organic phase was washed with saturated brine, dried and concentrated. The crude product followed by slurry with ethyl acetate to give Intermediate 27.3 (yellow solid: 4.1 g, yield: 24%). LC-MS: M+H$^+$=348

4. Synthesis of Intermediate 27.4

NaH (31 mg, 1.3 mmol) was added into a 50 mL three-necked flask, and 5 mL of anhydrous THF was added thereto under ice bath, and then ultra-dry n-butanol (2.62 g, 35 mmol) was slowly added dropwise. After the addition, the mixture was stirred for 30 minutes under ice bath. The reaction mixture was slowly added dropwise to 10 mL of a solution of Intermediate 27.3 (410 mg, 1.18 mmol) in anhydrous THF, the temperature was maintained no more than 10° C. After the addition, the reaction was carried out at room temperature for 2 hours, and the disappearance of the starting materials was confirmed by TLC (DCM/MeOH=20/1). The reaction mixture was slowly poured into 20 mL of iced water and extracted with ethyl acetate (10 mL*3). The organic phase was combined, washed with saturated brine, dried over anhydrous sodium sulfate, concentrated and purified by silica gel column chromatography to give Intermediate 27.4 (brown solid: 300 mg, yield: 66%). LC-MS: M+H$^+$=386

5. Synthesis of Intermediate 27.5

20 mL of ethanol and 10 mL of water were added into a 100 mL three-necked flask, and ammonium chloride solid (250 mg, 4.67 mmol) and reduced iron powder (217 mg, 3.89 mmol) were added thereto with stirring, followed by heating to reflux. The reaction was carried out for 30 minutes, and then Intermediate 27.4 (300 mg, 0.78 mmol) was added. The reaction was refluxed for 2 hours, and the disappearance of the starting materials was confirmed by TLC (DCM/MeOH=20/1), followed by hot filtration. The filter cake was washed with ethanol, and the filtrate was concentrated to remove ethanol and extracted with ethyl acetate (30 mL*3). The organic phase was washed with water and saturated brine, dried and concentrated. The crude product was purified by silica gel column chromatography to give Intermediate 27.5 (reddish brown solid: 150 mg, yield: 54%). LC-MS: M+H$^+$=356

6. Synthesis of Example 27

Intermediate 27.5 (150 mg, 0.42 mmol) was added to 5 mL of anhydrous acetonitrile, and carbonyldiimidazole (137 mg, 0.84 mmol) was added at room temperature with stirring. After the addition, the reaction was carried out at an external temperature of 90° C. in a sealed tube for 16 hours, and the disappearance of the starting materials was confirmed by TLC (DCM/MeOH=20/1). Water was added to the reaction solution and stirred for 30 minutes, followed by extraction with ethyl acetate (10 mL*3). The organic phase was washed with saturated brine, dried, concentrated and purified by silica gel column chromatography to give Example 27 (yellowish brown solid: 40 mg, yield: 25%). $^1$H-NMR (400 MHz, CDCl$_3$), δ=8.32 (s, 1H), 7.89 (s, 1H), 7.49 (s, 1H), 7.42 (d, J=7.4 Hz, 1H), 7.24-7.31 (m, 2H), 5.01 (s, 2H), 4.47 (s, 2H), 3.56 (t, J=6.6 Hz, 4H), 3.45 (t, J=6.6 Hz, 2H), 1.99 (m, 4H), 1.54-1.61 (m, 2H), 1.32-1.41 (m, 2H), 0.90 (t, J=7.4 Hz, 3H). LC-MS: M+H$^+$=382.

Example 28: Preparation of 9-(3-(pyrrolidin-1-ylmethyl)benzyl)-2-((tetrahydro-2H-pyran-4-yl)methoxy)-7,9-dihydro-8H-purin-8-one

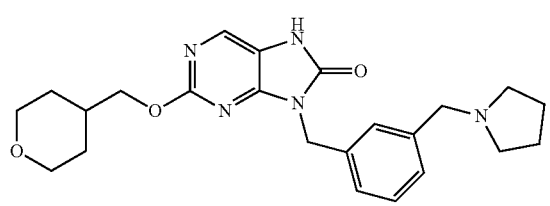 [SMILES: O=c1[nH]c2cnc(OCC3CCOCC3)nc2n1Cc1cccc(CN2CCCC2)c1]

According to the procedure of Example 27, wherein n-butanol was replaced by (tetrahydro-2H-pyran-4-yl) methanol, which was reacted with Intermediate 27.3 by reduction and cyclization to give the compound of Example 28. ¹H-NMR (400 MHz, d₆-DMSO) δ 10.72 (s, 1H), 7.82 (s, 1H), 7.30 (s, 1H), 7.30-7.22 (m, 2H), 7.16 (d, J=6.5 Hz, 1H), 4.86 (s, 2H), 4.39 (s, 2H), 3.77 (dd, J=11.1, 3.1 Hz, 2H), 3.40 (t, J=6.4 Hz, 4H), 3.25-3.17 (m, 4H), 1.87 (t, J=6.6 Hz, 4H), 1.75-1.67 (m, 1H), 1.47 (d, J=12.9 Hz, 2H), 1.11 (dt, J=12.0, 7.6 Hz, 2H). LC-MS: M+H⁺=424.

Example 29: Preparation of 2-(2-cyclopropyl-ethoxy)-9-(3-(pyrrolidin-1-ylmethyl)benzyl)-7,9-dihydro-8H-purin-8-one

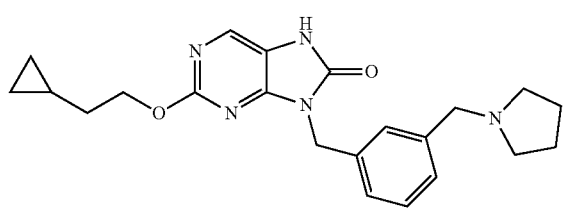 [SMILES: O=c1[nH]c2cnc(OCCC3CC3)nc2n1Cc1cccc(CN2CCCC2)c1]

According to the procedure of Example 27, wherein n-butanol was replaced by 2-cyclopropylethanol, which was reacted with Intermediate 27.3 by reduction and cyclization to give the compound of Example 29. ¹H-NMR (400 MHz, d₆-DMSO) δ 10.72 (s, 1H), 7.82 (s, 1H), 7.34 (s, 1H), 7.30-7.22 (m, 2H), 7.17 (d, J=6.7 Hz, 1H), 4.85 (s, 2H), 4.40 (s, 2H), 3.43-3.37 (m, 6H), 1.87 (t, J=6.6 Hz, 4H), 1.37 (q, J=6.7 Hz, 2H), 0.70-0.59 (m, 1H), 0.38-0.27 (m, 2H), 0.01-0.08 (m, 2H). LC-MS: M+H⁺=394.

Example 30: Preparation of 2-(2-(2-methoxyethoxy) ethoxy)-9-(3-(pyrrolidin-1-ylmethyl)benzyl)-7,9-dihydro-8H-purin-8-one

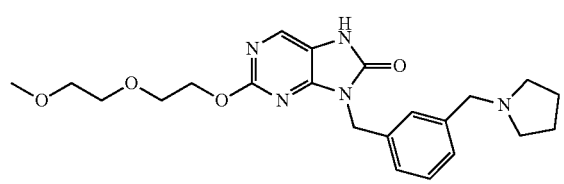 [SMILES: COCCOCCOc1ncc2[nH]c(=O)n(Cc3cccc(CN4CCCC4)c3)c2n1]

According to the procedure of Example 27, wherein n-butanol was replaced by (2-(2-methoxyethoxy)ethanol, which was reacted with Intermediate 27.3 by reduction and cyclization to give the compound of Example 30. ¹H-NMR (400 MHz, d₆-DMSO) δ 10.73 (s, 1H), 7.82 (s, 1H), 7.25 (ddd, J=30.6, 20.9, 9.1 Hz, 4H), 4.85 (s, 2H), 4.42 (s, 2H), 3.57-3.46 (m, 5H), 3.39 (dt, J=6.7, 5.4 Hz, 6H), 3.28 (d, J=9.6 Hz, 6H), 1.97-1.78 (m, 4H). LC-MS: M+H⁺=428.

Example 31: 2-(butylamino)-9-(3-(pyrrolidin-1-ylmethyl)benzyl)-7,9-dihydro-8H-purin-8-one

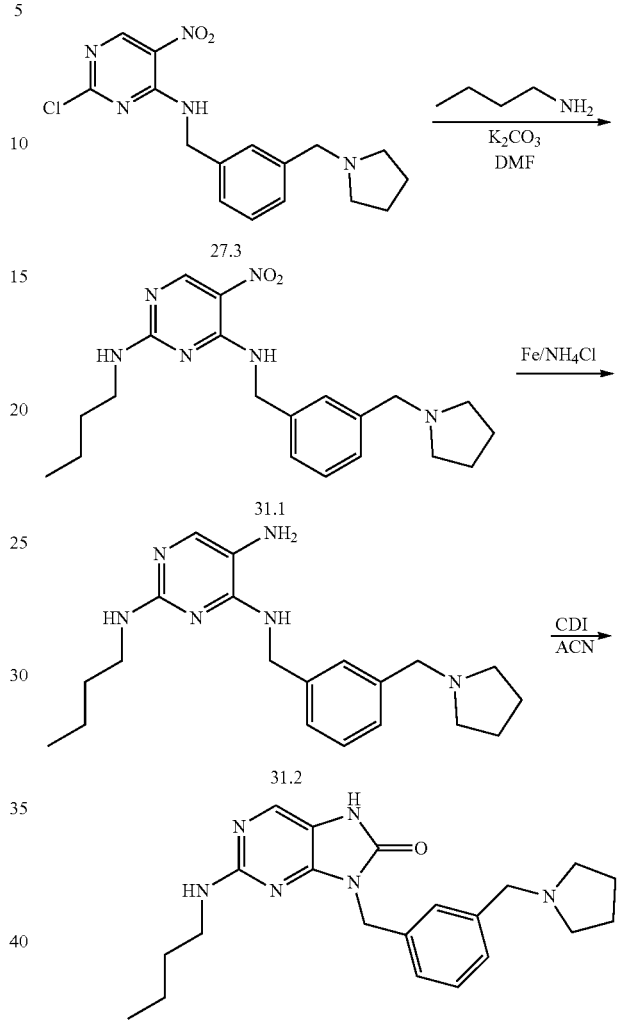

Example 31

1. Synthesis of Intermediate 31.1

Intermediate 27.1 (500 mg, 1.44 mmol), n-butylamine (126 mg, 1.72 mmol) and potassium carbonate (597 mg, 4.32 mmol) were added to 5 mL of anhydrous DMF and heated to 50° C. The reaction was carried out for 16 hours, and the disappearance of the starting materials was confirmed by LCMS. The reaction solution was added to 20 mL of water, and extracted with ethyl acetate (10 mL*3). The organic phase was washed with saturated aqueous solution of sodium chloride, dried and purified by silica gel column chromatography to give Intermediate 31.1 (brown solid: 290 mg, 52.4%). LC-MS: M+H⁺=384.

2. Synthesis of Intermediate 31.2

20 mL of ethanol and 10 mL of water were added into a 100 mL three-necked flask, and ammonium chloride solid (242 mg, 4.53 mmol) and reduced iron powder (211 mg, 3.77 mmol) were added thereto with stirring. After addition, the mixture was heated to reflux and reacted for 30 minutes, and then Intermediate 31.1 (290 mg, 0.75 mmol) was added. The reaction was refluxed for 2 hours, and the disappearance of the starting materials was confirmed by TLC (DCM/MeOH=20/1), followed by hot filtration. The filter cake was washed with ethanol, the filtrate was concentrated to remove ethanol and extracted with ethyl acetate (30 mL*3). The organic phase was washed with water and saturated brine, dried and concentrated. The crude product was purified by silica gel column chromatography to give Intermediate 31.2 (reddish brown solid: 210 mg, yield: 78.5%). LC-MS: M+H$^+$=355.

3. Synthesis of Example 31

Intermediate 31.2 (210 mg, 0.59 mmol) was added to 5 mL of anhydrous acetonitrile, and carbonyldiimidazole (144 mg, 0.89 mmol) was added at room temperature with stirring. After the addition, the reaction was carried out at an external temperature of 90° C. in a sealed tube for 16 hours, and the disappearance of the starting materials was confirmed by TLC (DCM/MeOH=20/1). Water was added to the reaction mixture and stirred for 30 minutes, followed by extraction with ethyl acetate (10 mL*3). The organic phase was washed with saturated brine, dried, concentrated and purified by silica gel column chromatography to give Example 31 (yellowish brown solid: 30 mg, yield: 13%). $^1$H-NMR (400 MHz, d-DMSO), δ=10.83 (s, 1H), 8.93 (s, 1H), 7.87 (s, 1H), 7.41-7.45 (m, 4H), 4.91 (s, 2H), 4.07 (s, 2H), 3.42 (s, 4H), 2.80-2.84 (m, 2H), 1.89 (s, 4H), 1.53-1.61 (m, 2H), 1.25-1.33 (m, 2H), 0.86 (t, J=7.4 Hz, 3H). LC-MS: M+H$^+$=381.

Example 32: Preparation of 2-((2-methoxyethyl)amine)-9-(3-(pyrrolidin-1-ylmethyl)benzyl)-7,9-dihydro-8H-purin-8-one

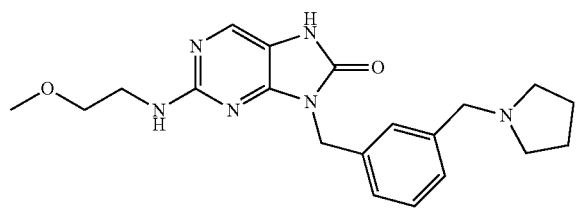 [SMILES: COCCNc1ncc2[nH]c(=O)n(Cc3cccc(CN4CCCC4)c3)c2n1]

According to the procedure of Example 31, wherein n-butylamine was replaced by 2-methoxyethylamine, which was reacted with Intermediate 27.3 by reduction and cyclization to give the compound of Example 32. $^1$H-NMR (400 MHz, d-DMSO), δ=11.26 (s, 1H), 7.99 (s, 1H), 7.28 (s, 4H), 5.25 (s, 1H), 5.11 (s, 1H), 4.92 (s, 2H), 4.33 (t, J=4.8 Hz, 2H), 3.58-3.64 (m, 4H), 3.27 (s, 3H), 2.73 (s, 2H), 2.29 (s, 1H), 2.07-2.16 (m, 1H), 1.83-1.91 (m, 1H). LC-MS: M+H$^+$=383.

Example 33: Preparation of 2-butylthio-9-(3-(pyrrolidin-1-ylmethyl)benzyl)-7,9-dihydro-8H-purin-8-one

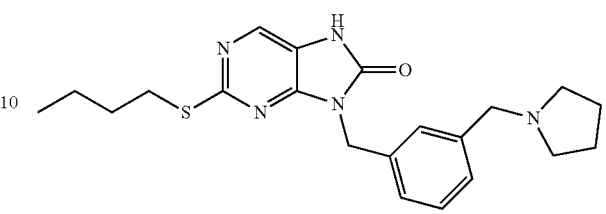

According to the procedure of Example 27, n-butanol was replaced by thiobutanol, which was reacted with Intermediate 27.3 by reduction and cyclization to give the compound of Example 33. $^1$H-NMR (400 MHz, d-DMSO), δ=10.79 (s, 1H), 9.75 (s, 1H), 7.85 (s, 1H), 7.33 (s, 1H), 7.19-7.33 (m, 3H), 4.87 (s, 2H), 3.67 (s, 2H), 3.44 (t, J=6.4 Hz, 4H), 2.32 (t, J=7.2 Hz, 2H), 1.90 (t, J=6.6 Hz, 4H), 1.34-1.44 (m, 2H), 1.21-1.29 (m, 2H), 0.78 (t, J=7.2 Hz, 3H). LC-MS: M+H$^+$=398.

Example 34: Preparation of 2-butylsulfinyl-9-(3-(pyrrolidin-1-ylmethyl)benzyl)-7,9-dihydro-8H-purin-8-one

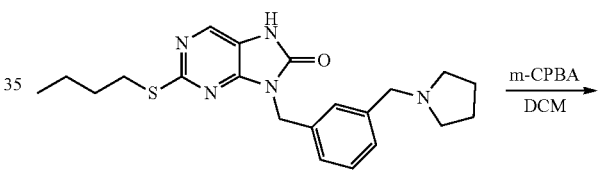

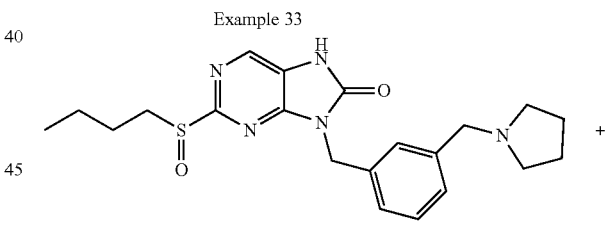

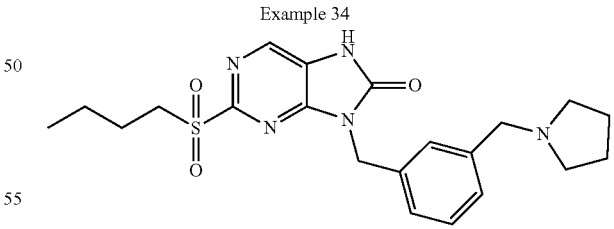

The compound of Example 33 (160 mg, 0.40 mmol) was dissolved in 5 mL of dichloromethane, and m-CPBA (122 mg, 0.60 mmol) was added thereto at room temperature. After the addition, the mixture was stirred for 2 hours, and the disappearance of the starting materials was confirmed by TLC. 20 mL of dichloromethane was added to the reaction mixture, and the reaction mixture was washed with 10 mL of saturated aqueous solution of sodium bicarbonate, dried

¹H-NMR (400 MHz, d-DMSO), δ=10.74 (s, 1H), 7.82 (s, 1H), 7.29-7.30 (m, 3H), 7.17-7.21 (m, 1H), 4.86 (s, 2H), 4.07 (d, J=12.8 Hz, 1H), 3.88 (d, J=12.8 Hz, 1H), 3.40 (t, J=6.4 Hz, 4H), 2.60-2.68 (m, 1H), 2.50-2.55 (m, 1H), 1.86 (t, J=6.6 Hz, 4H), 1.50-1.58 (m, 2H), 1.24-1.38 (m, 2H), 0.83 (t, J=7.2 Hz, 3H). LC-MS: M+H⁺=414.

Example 35: 2-butylsulfonyl-9-(3-(pyrrolidin-1-ylmethyl)benzyl)-7,9-dihydro-8H-purin-8-one

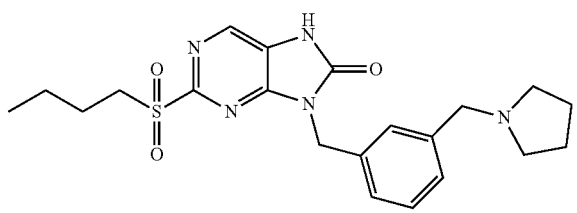 [SMILES: CCCCS(=O)(=O)c1ncc2[nH]c(=O)n(Cc3cccc(CN4CCCC4)c3)c2n1]

The preparation method was the same as that of Example 34. ¹H-NMR (400 MHz, d-DMSO), δ=10.77 (s, 1H), 7.86 (s, 1H), 7.34-7.39 (m, 3H), 7.29-7.31 (m, 1H), 4.90 (s, 2H), 4.44 (s, 2H), 3.43 (t, J=6.4 Hz, 4H), 2.95 (m, 2H), 1.89 (t, J=6.4 Hz, 4H), 1.56-1.64 (m, 2H), 1.27-1.37 (m, 2H), 0.84 (t, J=7.2 Hz, 3H). LC-MS: M+H⁺=430.

Example 36: Preparation of 2-(2-methoxyethyl)-9-(1-(4-pyrrolidin-1-ylmethyl)phenyl)ethyl)-7,9-dihydro-8H-purin-8-one

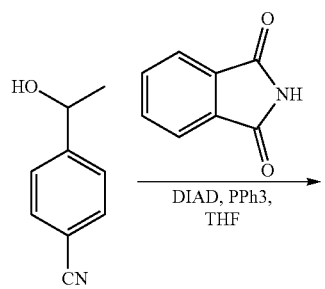

-continued

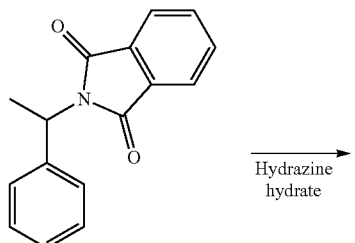

36.1

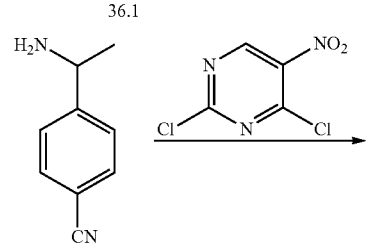

36.2

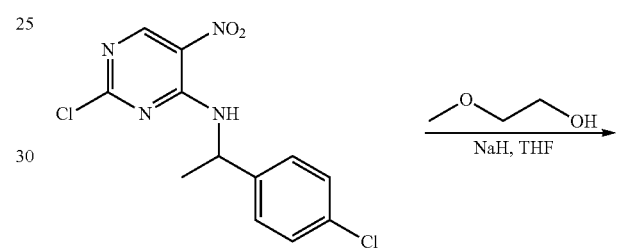

36.3

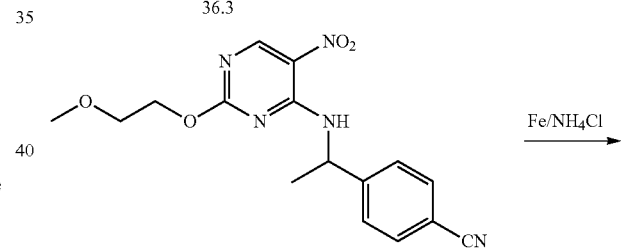

36.4

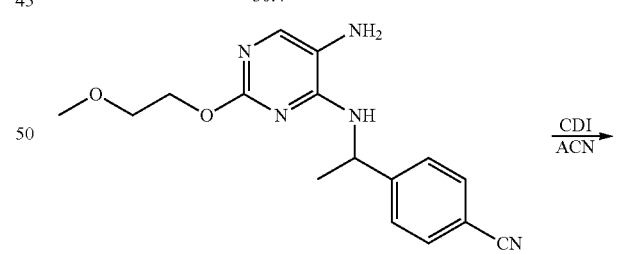

36.5

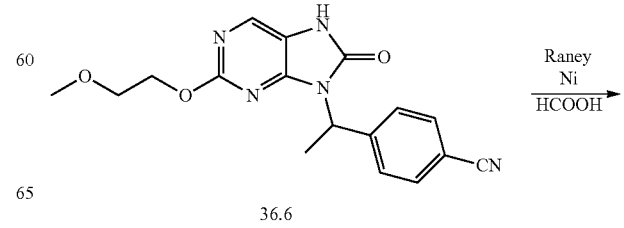

36.6

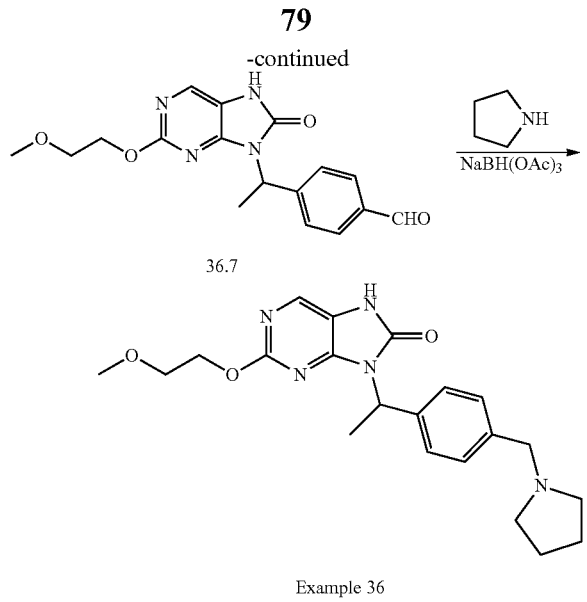

Example 36

1. Synthesis of Intermediate 36.1

Phthalimide (76.29 g, 43 mmol), triphenylphosphine (11.22 g, 43 mmol) and 4-(1-hydroxyethyl)benzonitrile (4.34 g, 29 mmol) were added to 200 mL anhydrous THF. DIAD (8.65 g, 43 mmol) was added dropwise under ice bath and stirred at room temperature for 16 hours, and the disappearance of the starting materials was confirmed by TLC (PE/EA=2/1). The reaction mixture was concentrated and replaced with methanol twice, and then the obtained mixture was concentrated to about 100 mL. The mixture was stirred at room temperature for 30 minutes, followed by filtration. The filter cake was washed with methanol and dried to give intermediate 36.1 (white solid: 5.6 g, yield: 70%). LC-MS: M+H$^+$=277.

2. Synthesis of Intermediate 36.2

Intermediate 36.1 (5.6 g, 20 mmol) was added to 200 mL of ethanol, and 2.1 g of 85% hydrazine hydrate was added thereto. The mixture was heated to reflux for 2 hours with mechanical stirring, followed by precipitation of large amounts of white solid, and the disappearance of the starting materials was confirmed by LCMS. The reaction mixture was cooled to room temperature, followed by filtration. The filtrate was concentrated, and 100 mL of 1N sodium hydroxide solution was added thereto, followed by extraction with dichloromethane (50 mL*3). The organic phase was dried and concentrated to give Intermediate 36.2 (colorless liquid: 2.9 g, yield: 99%). LC-MS: M+H$^+$=147

3. Synthesis of Intermediate 36.3

2,4-Dichloro-5-nitropyrimidine (90%, 4.7 g, 22 mmol) was added into a 250 mL three-necked flask, and 50 mL of anhydrous THF was added thereto under nitrogen. The reaction solution was cooled to −70° C., and DIPEA (7.46 g, 57.8 mmol) was slowly added dropwise. After the addition, 50 mL of a solution of Intermediate 36.2 (3.4 g, 23 mmol) in THF was added and the reaction temperature was maintained no more than −60° C. After the addition, the reaction was carried out at −60° C. for 2 hours, and the disappearance of the starting materials was confirmed by TLC/EA=2/1). The reaction mixture was slowly poured into 100 mL of iced water, and extracted with ethyl acetate (50 mL*3). The organic phase was washed with water and saturated brine, dried, concentrated, and followed by slurry with 20 mL of ethyl acetate at room temperature to give Intermediate 1.3 (brown solid: 4.7 g, yield: 70%). LC-MS: M+H$^+$=3 04.

4. Synthesis of Intermediate 36.4

NaH (0.68 g, 17 mmol) was added into a 100 mL three-necked flask, and 10 mL of anhydrous THF was added thereto under ice bath, then ultra-dry 2-methoxyethanol (3.53 g, 46 mmol) was slowly added dropwise. After the addition, the reaction mixture was stirred under ice bath for 30 minutes. The reaction solution was slowly added dropwise to 50 mL of a solution of Intermediate 36.3 (4.7 g, 15 mmol) in anhydrous THF, and the mixture was maintained no more than 10° C. After the addition, the reaction was carried out at room temperature for 2 hours, and the disappearance of the starting materials was confirmed by TLC (PE/EA=2/1). The reaction mixture was slowly poured into 50 mL of iced water and extracted with ethyl acetate (30 mL*3). The organic phase was combined, washed with saturated brine, dried over anhydrous sodium sulfate, concentrated and followed by slurry with 20 mL of ethyl acetate to give Intermediate 36.4 (brown solid: 3.4 g, yield: 65%). LC-MS: M+H$^+$=344.

5. Synthesis of Intermediate 36.5

80 mL of ethanol and 40 mL of water were added into a 250 mL three-necked flask, and ammonium chloride solid (2.68 g, 50 mmol) and reduced iron powder (3.36 g, 60 mmol) were added thereto with stirring. After the addition, the mixture was heated to reflux and reacted for 30 minutes, and then Intermediate 36.4 (3.4 g, 10 mmol) was added thereto. The reaction was refluxed for 2 hours, and the disappearance of the starting materials was confirmed by TLC (DCM/MeOH=20/1), followed by hot filtration. The filter cake was washed with ethanol, and the filtrate was concentrated to remove ethanol and extracted with ethyl acetate (30 mL*3). The organic phase was washed with water and saturated brine, dried and concentrated to give Intermediate 36.5 (reddish brown oil: 3.1 g, yield: 99%). LC-MS: M+H$^+$=314.

6. Synthesis of Intermediate 36.6

Intermediate 36.5 (3.13 g, 10 mmol) was added to 60 mL of dry acetonitrile, and carbonyldiimidazole (3.24 g, 20 mmol) was added with stirring at room temperature. After the addition, the reaction was refluxed for 16 hours, and the disappearance of the starting materials was confirmed by TLC (DCM/MeOH=20/1). The reaction mixture was concentrated, and water was added thereto with stirring for 30 minutes, followed by extraction with ethyl acetate (30 mL*3). The organic phase was washed with water and saturated brine, dried and concentrated. The crude product was purified by silica gel column chromatography to give Intermediate 36.6 (yellowish brown solid: 1.3 g, yield: 38%). LC-MS: M+H$^+$=340.

7. Synthesis of Intermediate 36.7

Intermediate 36.6 (0.6 g, 1.8 mmol) was added to 20 mL of a 75% aqueous solution of formic acid, and wet Raney Ni was added thereto. The mixture was heated to reflux for 1 hour, and the disappearance of the starting materials was confirmed by TLC (DCM/MeOH=20:1), followed by filtration. The filtrate was concentrated and the residue was mixed with 50 mL of a saturated aqueous solution of sodium bicarbonate, followed by extraction with ethyl acetate (20 mL*3). The organic phase was washed with water and saturated brine, dried and concentrated. The crude product was purified by silica gel column chromatography to give Intermediate 36.7 (white solid: 0.3 g, yield: 50%). LC-MS: M+H$^+$=343.

8. Synthesis of the Compound of Example 36

Intermediate 36.7 (100 mg, 0.3 mmol), tetrahydropyrrole (43 mg, 0.6 mmol) and glacial acetic acid (55 mg, 0.9 mmol) were added to 1,2-dichloroethane (5 mL), and additional amount of sodium triacetoxyborohydride (194 mg, 0.9 mmol) was added thereto with stirring. After the addition, the reaction mixture was stirred overnight, and then addition amount of sodium triacetoxyborohydride (65 mg, 0.3 mmol) was added. The mixture was stirred at room temperature for 2 hours, and the disappearance of the starting materials was confirmed by TLC (DCM/MeOH=10:1). 10 mL of a saturated aqueous solution of sodium bicarbonate was added to the reaction mixture, followed by extraction with DCM (10 mL*3). The organic phase was dried and purified by preparative silica gel plate to give Example 36 (white solid: 30 mg, yield: 26%). $^1$H-NMR (400 MHz, d$_6$-DMSO) δ 11.25 (s, 1H), 7.95 (s, 1H), 7.48 (d, J=7.4 Hz, 2H), 7.41 (d, J=8.1 Hz, 2H), 5.58 (q, J=7.2 Hz, 1H), 4.28-4.26 (m, 2H), 4.23-4.10 (m, 1H), 3.61-3.55 (m, 2H), 3.24 (s, 3H), 3.12-2.85 (m, 4H), 1.88 (d, J=7.3 Hz, 3H), 1.89-1.86 (m, 4H). LC-MS: M+H$^+$=398.

Example 37: Preparation of 2-(2-ethoxyethoxy)-9-(4-(pyrrolidin-1-ylmethyl)benzyl)-7,9-dihydro-8H-purin-8-one

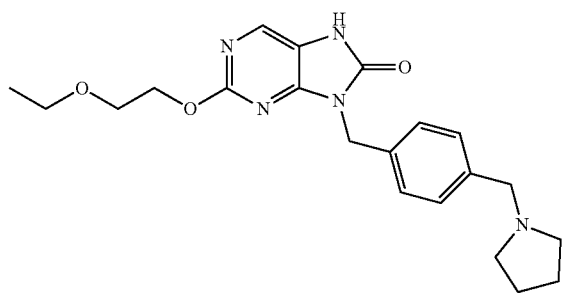 [SMILES: CCOCCOc1ncc2[nH]c(=O)n(Cc3ccc(CN4CCCC4)cc3)c2n1]

According to the procedure of Example 1, Intermediate 1.3 and 2-ethoxyethanol were subjected to nitro reduction, ring-closing reaction, reaction of cyano to aldehyde and reductive amination to give Example 37. $^1$H-NMR (400 MHz, d$_6$-DMSO) δ 11.26 (s, 1H), 7.97 (s, 1H), 7.46 (d, J=6.6 Hz, 2H), 7.34 (d, J=8.5 Hz, 2H), 4.94 (s, 2H), 4.33-4.25 (m, 2H), 3.66-3.59 (m, 2H), 3.43 (q, J=7.0 Hz, 2H), 3.27 (s, 3H), 2.99 (s, 2H), 1.76 (d, J=28.9 Hz, 4H), 1.07 (t, J=7.0 Hz, 3H). LC-MS: M+H=398.

Example 38: Preparation of 2-(2-hydroxyethoxy)-9-(4-(pyrrolidin-1-ylmethyl)benzyl)-7,9-dihydro-8H-purin-8-one

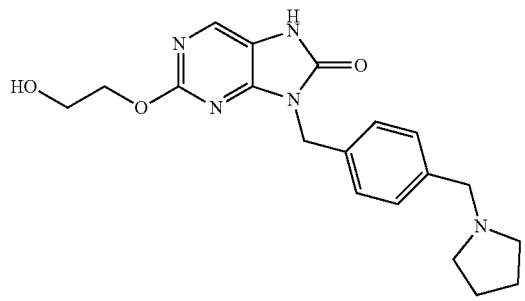 [SMILES: O=c1[nH]c2cnc(OCCO)nc2n1Cc1ccc(CN2CCCC2)cc1]

According to the procedure of Example 1, Intermediate 1.3 and ethylene glycol were subjected to nitro reduction, ring-closing reaction, reaction of cyano to aldehyde and reductive amination to give Example 38. $^1$H-NMR (400 MHz, d$_6$-DMSO) δ 11.24 (s, 1H), 7.97 (s, 1H), 7.43 (s, 2H), 7.32 (d, J=7.8 Hz, 2H), 4.93 (s, 2H), 4.82 (t, J=5.5 Hz, 1H), 4.23-4.16 (m, 2H), 3.65 (dd, J=10.3, 5.5 Hz, 2H), 3.26 (s, 2H), 2.93 (s, 4H), 1.81 (s, 4H). LC-MS: M+H=370.

Example 39: Preparation of 6-(2-methoxyethoxy)-1-(4-(pyrrolidin-1-ylmethyl)benzyl)-1,3-dihydro-2H-imidazole-[4,5-c]pyridin-2-one

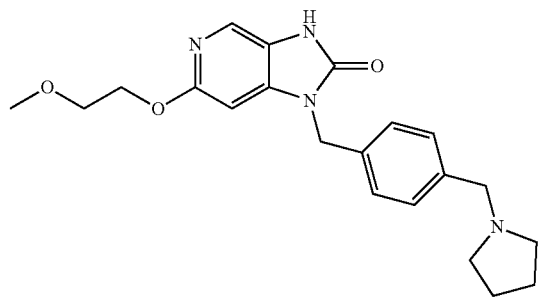 [SMILES: COCCOc1cc2c(cn1)[nH]c(=O)n2Cc1ccc(CN2CCCC2)cc1]

According to the procedure of Example 1, intermediate 1.2 and 2,4-dichloro-5-nitropyridine were subjected to substitution reaction of 2-ethoxyethanol, nitro reduction, ring-closing reaction, reaction of cyano to aldehyde and reductive amination to give Example 39. $^1$H-NMR (400 MHz, d$_6$-DMSO) δ 10.96 (s, 1H), 7.66 (s, 1H), 7.24 (s, 4H), 6.50 (s, 1H), 4.90 (s, 2H), 4.34-4.12 (m, 2H), 3.66-3.55 (m, 2H), 3.53 (s, 2H), 3.22 (s, 3H), 2.40 (s, 4H), 1.64 (s, 4H). LC-MS: M+H=383.

Example 40: Preparation of 5-(2-methoxyethoxy)-3-(4-(pyrrolidin-1-ylmethyl)benzyl)-1,3-dihydro-2H-imidazole[4,5-b]pyridin-2-one

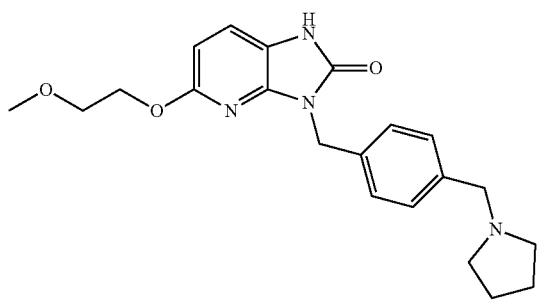 [SMILES: COCCOc1ccc2[nH]c(=O)n(Cc3ccc(CN4CCCC4)cc3)c2n1]

According to the procedure of Example 1, intermediate 1.2 and 2,6-dichloro-3-nitropyridine were subjected to substitution reaction of 2-methoxyethanol, nitro reduction, ring-closing reaction, reaction of cyano to aldehyde and reductive amination to give Example 40. $^1$H-NMR (400 MHz, d$_6$-DMSO) δ 10.97 (s, 1H), 7.35 (s, 4H), 7.27 (d, J=8.3 Hz, 1H), 6.39 (d, J=8.3 Hz, 1H), 4.93 (s, 2H), 4.35-4.20 (m, 2H), 3.97 (s, 2H), 3.65-3.52 (m, 2H), 3.23 (s, 3H), 2.83 (s, 4H), 1.78 (s, 4H). LC-MS: M+H=383.

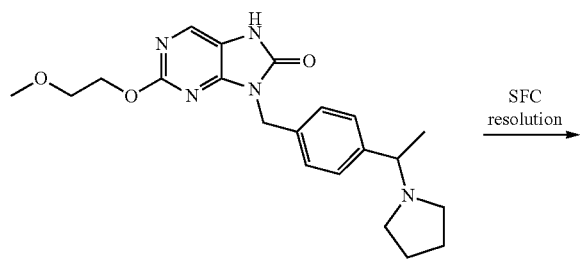

Example 14

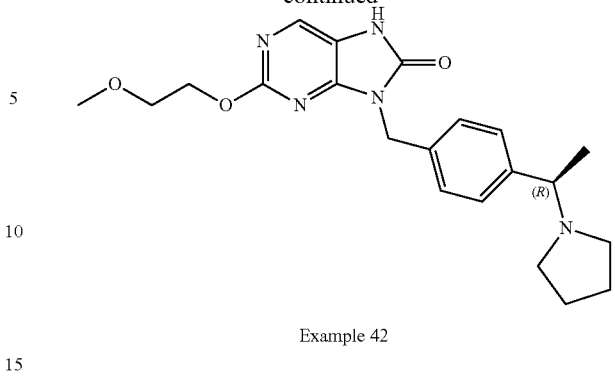

Example 42

Example 14 was subjected to SFC resolution to give Example 41 and Example 42.

Example 41: Preparation of (S)-2-(2-methoxyethoxy)-9-(4-(1-(pyrrolidin-1-yl)ethyl)benzyl)-7,9-dihydro-8H-purin-8-one $^1$H-NMR (400 MHz, d$_6$-DMSO) δ 11.27 (s, 1H), 7.97 (s, 1H), 7.52 (d, J=6.8 Hz, 2H), 7.34 (d, J=8.0 Hz, 2H), 4.93 (s, 2H), 4.41-4.21 (m, 3H), 4.08 (q, J=5.3 Hz, 1H), 3.64-3.54 (m, 3H), 3.24 (s, 3H), 3.13 (d, J=5.2 Hz, 3H), 2.83-2.73 (m, 2H), 1.97-1.73 (m, 4H), 1.54-1.52 (m, 2H). LC-MS: M+H$^+$= 398.

Example 42: Preparation of (R)-2-(2-methoxyethoxy)-9-(4-(1-(pyrrolidin-1-yl)ethyl)benzyl)-7,9-dihydro-8H-purin-8-one $^1$H-NMR (400 MHz, d$_6$-DMSO) δ 11.27 (s, 1H), 7.97 (s, 1H), 7.52 (d, J=6.8 Hz, 2H), 7.34 (d, J=8.0 Hz, 2H), 4.93 (s, 2H), 4.41-4.21 (m, 3H), 4.08 (q, J=5.3 Hz, 1H), 3.64-3.54 (m, 3H), 3.24 (s, 3H), 3.13 (d, J=5.2 Hz, 3H), 2.83-2.73 (m, 2H), 1.97-1.73 (m, 4H), 1.54-1.52 (m, 2H). LC-MS: M+H$^+$= 398.

Example 43: Preparation of 9-(4-(pyrrolidin-1-ylmethyl)benzyl)-2-(2-(trifluoromethyl)ethoxy)-7,9-dihydro-8H-purin-8-one

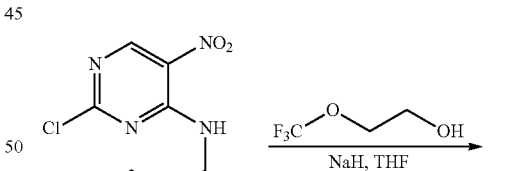

1.3

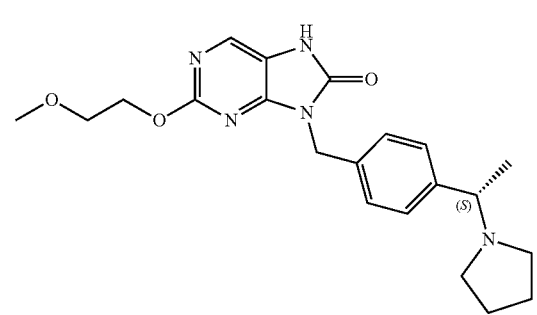

Example 41

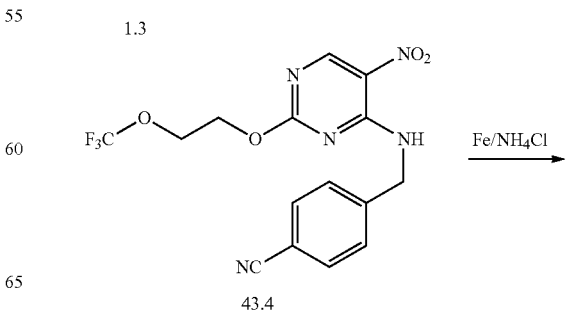

43.4

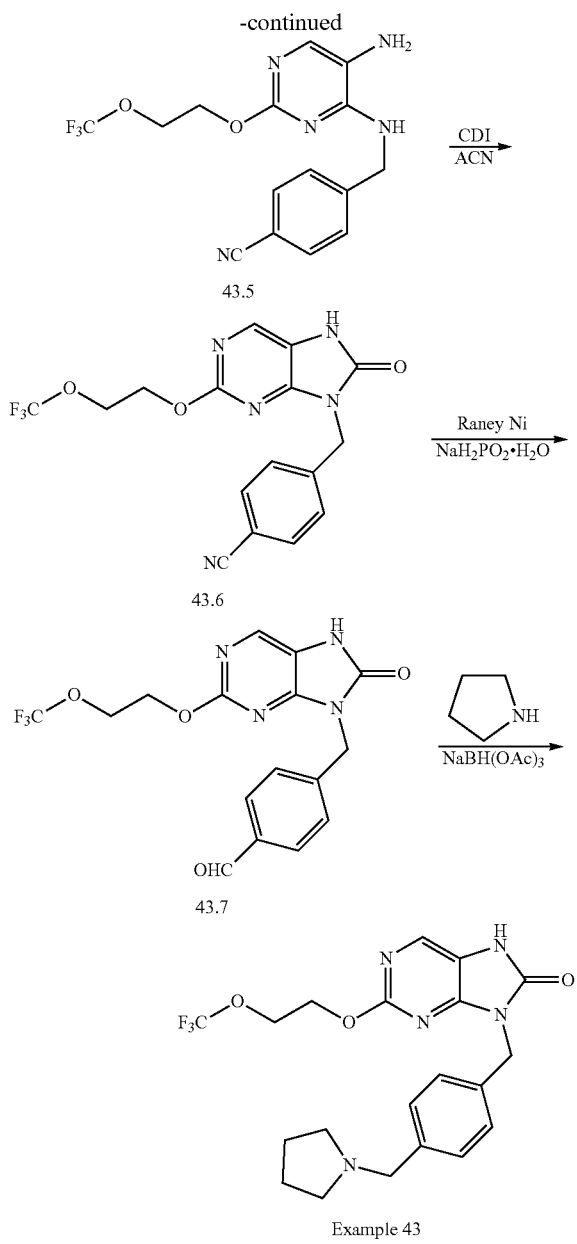

Example 43

1. Synthesis of Intermediate 43.4

NaH (0.41 g, 10.4 mmol) was added into a 100 mL three-necked flask, and 10 mL of anhydrous THF was added thereto under ice bath, followed by slow addition of 10 mL of a solution of 2-trifluoromethoxy-1-ethanol (2.69 g, 20.7 mmol) in anhydrous THF dropwise. After the addition, the reaction solution was stirred under ice bath for 30 minutes. The reaction mixture was slowly added dropwise to 50 mL of a solution of Intermediate 1.3 (2 g, 6.90 mmol) in anhydrous THF, the temperature was maintained no more than 10° C. After the addition, the reaction was carried out at room temperature for 2 hours, and the disappearance of the starting materials was confirmed by TLC (PE/EA=2/1). The reaction mixture was slowly poured into 50 mL of iced water and extracted with ethyl acetate (30 mL*3). The organic phases were combined, washed with saturated brine, dried over anhydrous sodium sulfate and concentrated. The crude product was purified by silica gel column chromatography to give Intermediate 43.4 (yellow solid: 1.9 g, yield: 72%). LC-MS: M+H$^+$=3 84.

2. Synthesis of Intermediate 43.5

20 mL of ethanol and 10 mL of water were added into a 100 mL three-necked flask, and ammonium chloride solid (0.26 g, 4.96 mmol) and reduced iron powder (1.38 g, 24.8 mmol) were added thereto with stirring. After the addition, the mixture was heated to reflux and activated for 30 minutes. And then Intermediate 43.4 (1.90 g, 4.96 mmol) was added thereto. The reaction was carried out at 50° C. for 2 hours, and the disappearance of the starting materials was confirmed by TLC (DCM/MeOH=20/1), followed by hot filtration. The filter cake was washed with ethanol, and the filtrate was concentrated to remove ethanol and extracted with ethyl acetate (30 mL*3). The organic phase was washed with water and saturated brine, dried. The crude product was purified by silica gel column chromatography to give Intermediate 36.5 (reddish brown solid: 1.4 g, yield: 80%). LC-MS: M+H$^+$=354.

3. Synthesis of Intermediate 43.6

Intermediate 43.5 (1.4 g, 3.96 mmol) was added to 30 mL of dry acetonitrile, and carbonyldiimidazole (1.29 g, 7.93 mmol) was added with stirring at room temperature. After the addition, the reaction was carried out at 50° C. for 2 hours, and the disappearance of the starting materials was confirmed by TLC (DCM/MeOH=20/1). The reaction mixture was concentrated, and the concentrated liquor was poured into water with stirring for 30 minutes, followed by extraction with ethyl acetate (20 mL*3). The organic phase was washed with water and saturated brine, dried and concentrated. The crude product was purified by silica gel column chromatography to give Intermediate 43.6 (off-white solid: 0.9 g, yield: 60%). LC-MS: M+H$^+$=380.

4. Synthesis of Intermediate 43.7

5 mL of water was added to 5 mL of acetic acid under ice bath. After the addition, 10 mL of pyridine was slowly added, and then Intermediate 43.6 (0.9 g, 2.37 mmol) and sodium hypophosphite monohydrate (5 g, 475 mmol) were added thereto.

After stirring and dissolving, wet Raney Ni (about 1 g) was added in portions. The reaction was carried out at 45° C. for 2 hours, and the completion of the reaction was confirmed by LCMS, followed by filtration. 30 mL of water was added to the filtrate and extracted with ethyl acetate (20 mL*3). The organic phase was washed with 1N hydrochloric acid, water, and saturated brine, dried and concentrated to give Intermediate 43.7 (pale yellow solid: 0.58 g, yield: 64%). LC-MS: M+H$^+$=383.

5. Synthesis of Example 43

Intermediate 43.7 (580 mg, 1.52 mmol) and tetrahydropyrrole (216 mg, 3.03 mmol) were added to ultra-dry THF (10 mL). After stirring at room temperature for 30 minutes, sodium triacetoxyborohydride (965 mg, 4.55 mmol) was added thereto. After the addition, the reaction mixture was stirred at room temperature for 2 hours, and the disappearance of the starting materials was confirmed by TLC (DCM/MeOH=10:1). 20 mL of a half-saturated aqueous solution of sodium bicarbonate was added to the reaction mixture, followed by extraction with ethyl acetate (20 mL*3). The organic phase was dried and purified by silica gel column chromatography to give Example 43 (white solid: 340 mg, yield: 51%). $^1$H-NMR (400 MHz, CDCl3): δ 7.93 (s, 1H), 7.41 (d, J=7.9 Hz, 2H), 7.32 (d, J=7.9 Hz, 2H), 5.06 (s, 2H), 4.59 (t, J=4.8 Hz, 2H), 4.32 (t, J=4.8 Hz, 2H), 3.67 (s, 2H), 2.60 (s, 4H), 1.81 (s, 4H). LC-MS: M+H$^+$=438.

Example 44: Preparation of 9-(4-(pyrrolidin-1-ylmethyl)benzyl)-2-(2-(difluoromethyl)ethoxy)-7,9-dihydro-8H-purin-8-one

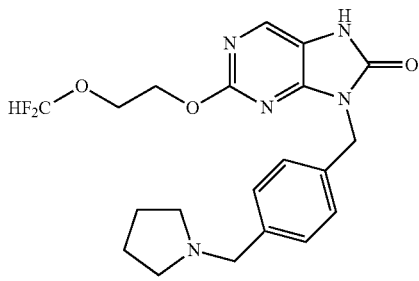

Example 44 was obtained according to the synthesis procedure of Example 43, wherein 2-trifluoromethoxy-1-ethanol was replaced by 2-difluoromethoxy-1-ethanol. $^1$H-NMR (400 MHz, CDCl$_3$): δ 8.31 (s, 1H), 7.92 (s, 1H), 7.53 (d, J=8.0 Hz, 2H), 7.31 (d, J=8.0 Hz, 2H), 6.28 (t, J=74.7 Hz, 1H), 5.04 (s, 2H), 4.56 (s, 2H), 4.02 (t, J=4.8 Hz, 2H), 3.67 (t, J=4.8 Hz, 2H), 3.59 (t, J=6.6 Hz, 4H), 2.08-1.93 (m, 4H). LC-MS: M+H$^+$=420.

Example 45: Preparation of 9-(4-(pyrrolidin-1-ylmethyl)benzyl)-2-(3-methoxypropoxy)-7,9-dihydro-8H-purin-8-one

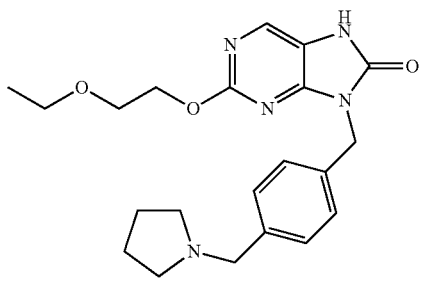 [SMILES: CCOCCOc1ncc2[nH]c(=O)n(Cc3ccc(CN4CCCC4)cc3)c2n1]

Example 45 was obtained according to the synthesis procedure of Example 43, wherein 2-trifluoromethoxy-1-ethanol was replaced by 3-methoxy-1-propanol. $^1$H-NMR (400 MHz, CDCl$_3$): δ 8.01 (s, 1H), 7.47 (s, 4H), 5.08 (s, 2H), 4.45 (t, J=6.5 Hz, 2H), 3.99 (s, 2H), 3.60 (t, J=6.2 Hz, 2H), 3.38 (s, 3H), 2.97 (s, 4H), 2.18-2.07 (m, 2H), 2.00 (s, 4H). LC-MS: M+H$^+$=398.

Example 46: Preparation of 9-(4-(pyrrolidin-1-ylmethyl)benzyl)-2-((tetrahydrofuran-2-yl)methoxy)-7,9-dihydro-8H-purin-8-one

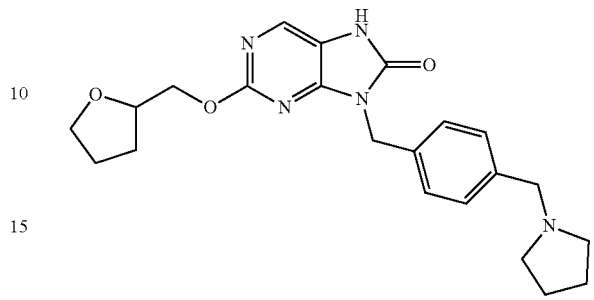

Example 46 was obtained according to the synthesis procedure of Example 43, wherein 2-trifluoromethoxy-1-ethanol was replaced by tetrahydrofuran-2-methanol. $^1$H-NMR (400 MHz, CDCl$_3$): δ 7.87 (s, 1H), 7.42 (d, J=7.9 Hz, 2H), 7.30 (d, J=7.9 Hz, 2H), 5.04 (s, 2H), 4.38-4.31 (m, 3H), 3.94 (dd, J=14.6, 6.8 Hz, 1H), 3.83 (dd, J=14.4, 7.5 Hz, 1H), 3.66 (s, 2H), 2.59 (s, 4H), 2.13-1.86 (m, 4H), 1.80 (s, 4H). LC-MS: M+H$^+$=410.

Example 47: Preparation of 9-(4-(pyrrolidin-1-ylmethyl)benzyl)-2-(4-methoxybutoxy)-7,9-dihydro-8H-purin-8-one

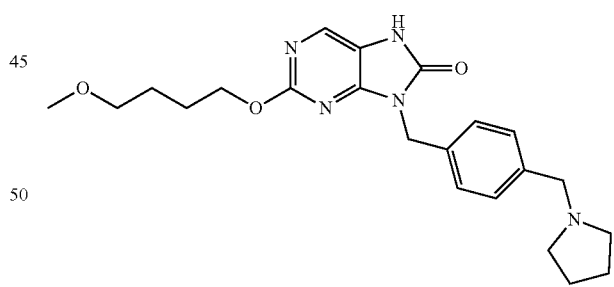

Example 47 was obtained according to the synthesis procedure of Example 43, wherein 2-trifluoromethoxy-1-ethanol was replaced by 4-methoxy-1-butanol. $^1$H-NMR (400 MHz, CDCl$_3$): δ 7.96 (s, 1H), 7.44 (d, J=8.0 Hz, 2H), 7.37 (d, J=7.9 Hz, 2H), 5.06 (s, 2H), 4.36 (t, J=6.5 Hz, 2H), 3.77 (s, 2H), 3.45 (t, J=6.4 Hz, 2H), 3.35 (s, 3H), 2.72 (s, 4H), 1.91-1.86 (m, 6H), 1.80-1.73 (m, 2H). LC-MS: M+H$^+$=412.

Example 48: Preparation of 9-(4-(pyrrolidin-1-ylmethyl)benzyl)-2-(2-(2,2,2-trifluoroethoxy)ethoxy)-7,9-dihydro-8H-purin-8-one

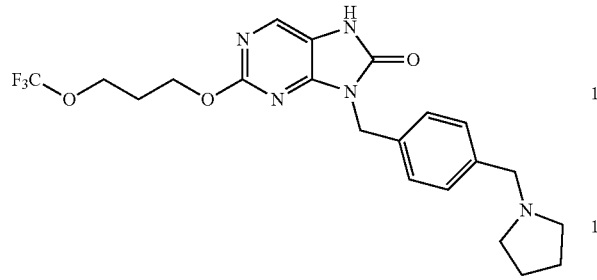

Example 48 was obtained according to the synthesis procedure of Example 43, wherein 2-trifluoromethoxy-1-ethanol was replaced by 2-(2,2,2-trifluoroethoxy)-1-ethanol. $^1$H-NMR (400 MHz, CDCl$_3$): δ 7.92 (s, 1H), 7.41 (d, J=7.9 Hz, 2H), 7.30 (d, J=7.9 Hz, 2H), 5.06 (s, 2H), 4.53 (t, J=4.8 Hz, 2H), 4.01 (t, J=4.8 Hz, 2H), 3.95 (q, J=8.8 Hz, 2H), 3.63 (s, 2H), 2.56 (s, 4H), 1.79 (s, 4H). LC-MS: M+H$^+$=452.

Example 49: Preparation of 9-(4-(pyrrolidin-1-ylmethyl)benzyl)-2-(3-methoxybutoxy)-7,9-dihydro-8H-purin-8-one

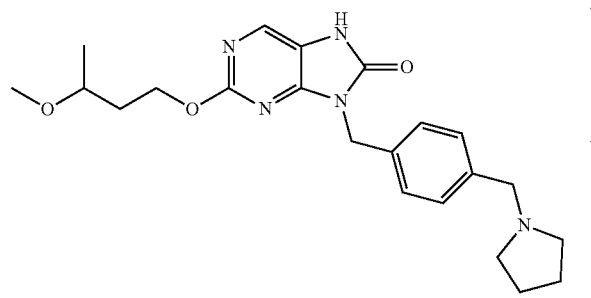

Example 49 was obtained according to the synthesis procedure of Example 43, wherein 2-trifluoromethoxy-1-ethanol was replaced by 3-methoxy-1-butanol $^1$H-NMR (400 MHz, CDCl$_3$): δ 7.97 (s, 1H), 7.45 (d, J=8.0 Hz, 2H), 7.38 (d, J=7.9 Hz, 2H), 5.07 (s, 2H), 4.45-4.41 (m, 2H), 3.80 (s, 2H), 3.62-3.57 (m, 1H), 3.34 (s, 3H), 2.76 (br, 4H), 2.05-1.94 (m, 2H), 1.89 (br, 4H), 1.21 (d, J=6.1 Hz, 3H). LC-MS: M+H$^+$=412.

Example 50: Preparation of 9-(4-(pyrrolidin-1-ylmethyl)benzyl)-2-(3-(trifluoromethoxy)propoxy)-7,9-dihydro-8H-purin-8-one

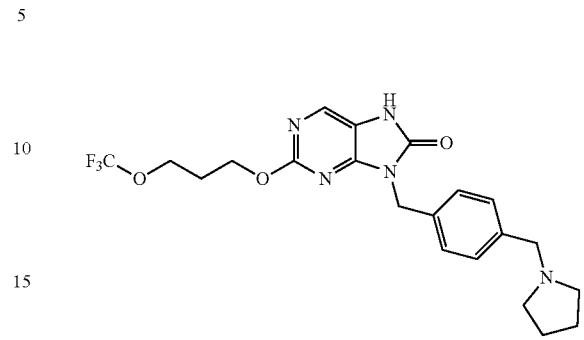

Example 50 was obtained according to the synthesis procedure of Example 43, wherein 2-trifluoromethoxy-1-ethanol was replaced by 3-trifluoromethoxy-1-propanol. $^1$H-NMR (400 MHz, CDCl$_3$): δ 7.99 (s, 1H), 7.47 (s, 4H), 5.07 (s, 2H), 4.46 (t, J=6.1 Hz, 2H), 4.19 (t, J=6.2 Hz, 2H), 3.96 (s, 2H), 2.94 (s, 4H), 2.24-2.18 (m, 2H), 1.99 (s, 4H). LC-MS: M+H$^+$=452.

Example 51: Preparation of 9-(4-(pyrrolidin-1-ylmethyl)benzyl)-2-(3-(trifluoromethoxy)butoxy)-7,9-dihydro-8H-purin-8-one

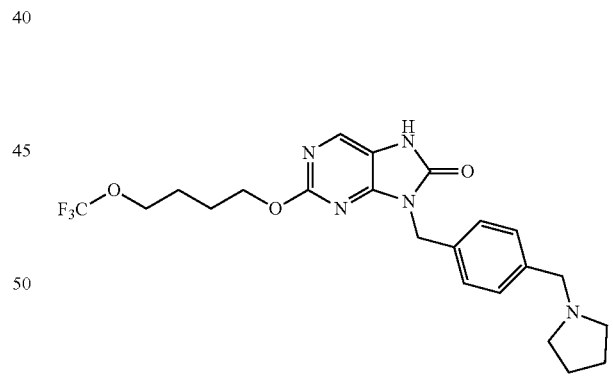

Example 51 was obtained according to the synthesis procedure of Example 43, wherein 2-trifluoromethoxy-1-ethanol was replaced by 3-trifluoromethoxy-1-butanol. $^1$H-NMR (400 MHz, CDCl3): δ 7.97 (s, 1H), 7.44 (d, J=7.9 Hz, 2H), 7.39 (d, J=8.1 Hz, 2H), 5.06 (s, 2H), 4.38 (t, J=5.6 Hz, 2H), 4.04 (t, J=5.7 Hz, 2H), 3.80 (s, 2H), 2.75 (br, 4H), 1.92-1.89 (m, 2H). LC-MS: M+H$^+$=466.

Example 52: Preparation of 9-(4-((3-azabicyclo[3.1.1]heptan-3-yl)methyl)benzyl)-2-(2-methoxyethoxy)-7,9-dihydro-8H-purin-8-one

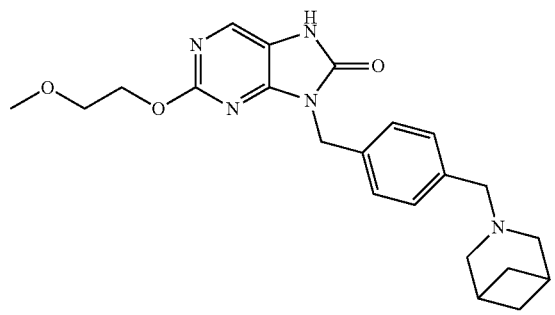 [SMILES: COCCOc1ncc2[nH]c(=O)n(Cc3ccc(CN4CC5CC(C5)C4)cc3)c2n1]

Example 52 was obtained according to the synthesis procedure of Example 1, wherein in the step of reductive amination, tetrahydropyrrole was replaced by 3-azabicyclo[3.1.1]heptane. $^1$H-NMR (400 MHz, CDCl$_3$): δ 8.03 (s, 1H), 7.53 (s, 2H), 7.47 (d, J=7.9 Hz, 2H), 5.08 (s, 2H), 4.54-4.50 (m, 2H), 4.04 (s, 2H), 3.82-3.78 (m, 2H), 3.46 (s, 3H), 3.24 (s, 4H), 2.42 (s, 2H), 2.16-2.04 (m, 4H). LC-MS: M+H$^+$=410.

Example 53: Preparation of 9-(4-((7-azabicyclo[2.2.1]heptan-7-yl)methyl)benzyl)-2-(2-methoxyethoxy)-7,9-dihydro-8H-purin-8-one

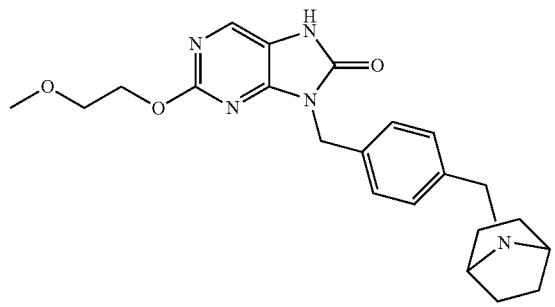

Example 53 was obtained according to the synthesis procedure of Example 1, wherein in the step of reductive amination, tetrahydropyrrole was replaced by 7-azabicyclo[2.2.1]heptane. $^1$H-NMR (400 MHz, CDCl$_3$): δ 7.99 (s, 1H), 7.62 (d, J=7.2 Hz, 2H), 7.44 (d, J=8.1 Hz, 2H), 5.03 (s, 2H), 4.52-4.43 (m, 2H), 4.04 (s, 2H), 3.84-3.74 (m, 4H), 3.42 (s, 3H), 2.33-2.19 (m, 8H). LC-MS: M+H$^+$=410.

Example 54: Preparation of 9-(4-((3,3-difluoropyrrolidin-1-yl)methyl)benzyl)-2-(2-methoxyethoxy)-7,9-dihydro-8H-purin-8-one

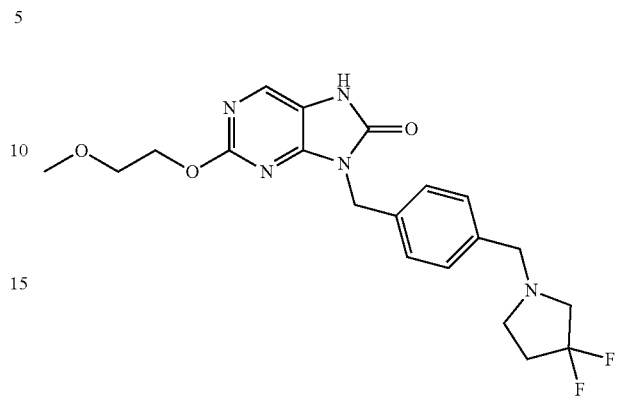

Example 54 was obtained according to the synthesis procedure of Example 1, wherein in the step of reductive amination, tetrahydropyrrole was replaced by 3,3-difluoropyrrolidine. $^1$H-NMR (400 MHz, CDCl$_3$): δ 8.76 (s, 1H), 7.96 (s, 1H), 7.42 (d, J=8.1 Hz, 2H), 7.24 (d, J=8.1 Hz, 2H), 5.05 (s, 2H), 4.53-4.43 (m, 2H), 3.80-3.70 (m, 2H), 3.57 (s, 2H), 3.42 (s, 3H), 2.82 (t, J=13.2 Hz, 2H), 2.68 (t, J=6.9 Hz, 2H), 2.31-2.15 (m, 2H). LC-MS: M+H$^+$=420.

Example 55: Preparation of 9-(4-((2,5-dihydro-1H-pyrrol-1-yl)methyl)benzyl)-2-(2-methoxyethoxy)-7,9-dihydro-8H-purin-8-one

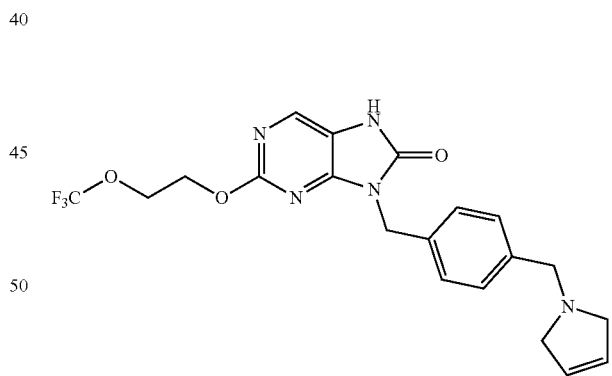

Example 55 was obtained according to the synthesis procedure of Example 43, wherein in the step of reductive amination, tetrahydropyrrole was replaced by 2,5-dihydro-1H-pyrrole. $^1$H-NMR (400 MHz, CDCl$_3$): δ 7.85 (s, 1H), 7.34 (d, J=8.0 Hz, 2H), 7.26 (d, J=8.0 Hz, 2H), 5.71 (s, 2H), 5.00 (s, 2H), 4.52 (t, J=4.8 Hz, 2H), 4.29-4.21 (m, 2H), 3.74 (s, 2H), 3.42 (s, 4H). LC-MS: M+H$^+$=436.

Example 56: Preparation of 9-(4-(pyrrolidin-1-ylmethyl)benzyl)-7-methyl-2-(2-methoxyethoxy)-7,9-dihydro-8H-purin-8-one

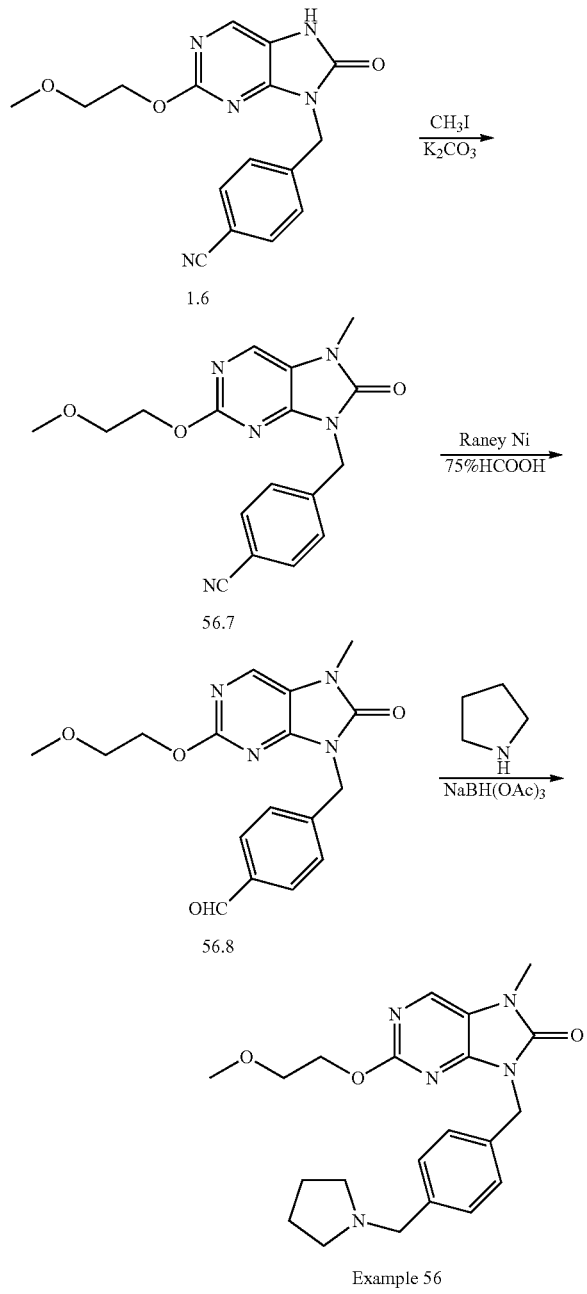

1. Synthesis of Intermediate 56.7

Intermediate 1.6 (500 mg, 1.54 mmol) was added to 10 mL of anhydrous DMF, and the mixture was stirred at room temperature for dissolving, followed by addition of potassium carbonate (319 mg, 2.31 mmol) and iodomethane (262 mg, 1.84 mmol). The reaction was carried out at an external temperature of 70° C. for 16 hours, and the disappearance of the starting materials was confirmed by LCMS. The reaction mixture was cooled to room temperature, poured into 50 mL of water, and extracted with ethyl acetate (20 mL*3). The organic phases were combined, washed with water and saturated brine, dried and purified by silica gel column chromatography to give Intermediate 56.7 (brown solid: 300 mg, yield: 58%). LC-MS: M+H$^+$=340.

2. Synthesis of Intermediate 56.8

Intermediate 56.7 (300 mg, 0.88 mmol) was added to 10 mL of a 75% aqueous solution of formic acid, and wet Raney Ni (about 0.5 g) was added thereto. The reaction was carried out at 50° C. for 4 hours, and the disappearance of the starting materials was confirmed by LCMS, followed by filtration. The filtrate was concentrated and the residue was poured into 50 mL of a saturated aqueous solution of sodium bicarbonate, followed by extraction with ethyl acetate (20 mL*3). The organic phase was washed with water and saturated brine, dried and concentrated. The crude product was purified by silica gel column chromatography to give Intermediate 56.8 (white solid: 0.2 g, yield: 66%). LC-MS: M+H$^+$=329

3. Preparation of Example 56

Intermediate 56.8 (200 mg, 0.58 mmol) and tetrahydropyrrole (83 mg, 1.17 mmol) was added to dry THF (10 mL). The reaction was carried out at room temperature for 30 minutes, and sodium triacetoxyborohydride (371 mg, 1.75 mmol) was added thereto with stirring. After the addition, the reaction was carried out at room temperature for 2 hours, and the disappearance of the starting materials was confirmed by TLC (DCM/MeOH=10:1). 20 mL of a half-saturated aqueous solution of sodium bicarbonate was added to the reaction solution, and extracted with DCM (10 mL*3). The organic phase was dried and purified by preparative silica gel plate to give Example 56 (brown solid, 100 mg, yield 43%). $^1$H-NMR (400 MHz, CDCl3): δ 7.85 (s, 1H), 7.46 (s, 4H), 5.05 (s, 2H), 4.49 (t, J=4.8 Hz, 2H), 3.77 (t, J=4.8 Hz, 2H), 3.42 (s, 3H), 3.39 (s, 3H), 2.66 (s, 4H), 1.99 (s, 4H). LC-MS: M+H$^+$=398.

Example 57: Preparation of 9-(4-(pyrrolidin-1-ylmethyl)benzyl)-7-propyl-2-(2-methoxyethoxy)-7,9-dihydro-8H-purin-8-one

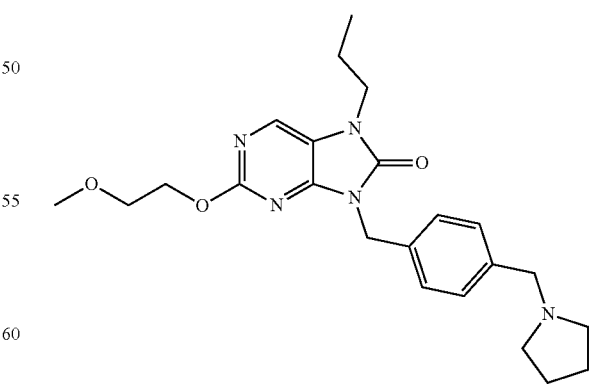

Example 57 was obtained according to the synthesis procedure of Example 56, iodomethane was replaced by 1-iodopropane. $^1$H-NMR (400 MHz, CDCl$_3$): δ 7.87 (s, 1H), 7.53-7.40 (m, 4H), 5.05 (s, 2H), 4.53-4.42 (m, 2H), 3.94 (s, 2H), 3.84-3.71 (m, 4H), 3.41 (s, 3H), 2.95 (s, 4H), 1.98 (s, 4H), 1.76 (dd, J=14.5, 7.3 Hz, 2H), 0.94 (t, J=7.4 Hz, 3H). LC-MS: M+H$^+$=426.

Example 58: Preparation of 9-(4-(pyrrolidin-1-ylmethyl)benzyl)-6-methyl-2-(2-methoxyethoxy)-7,9-dihydro-8H-purin-8-one

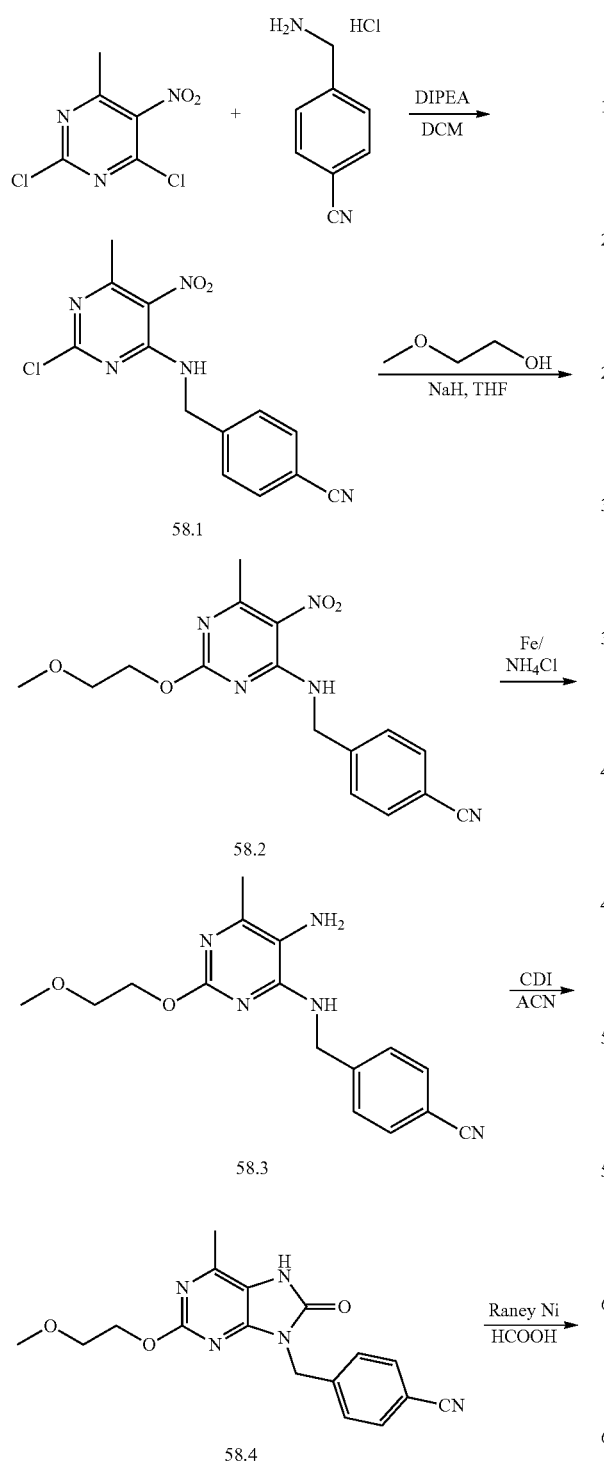

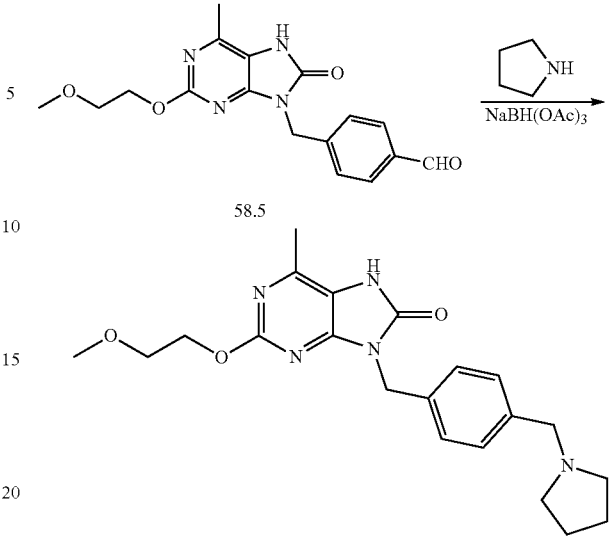

Example 58

1. Synthesis of Intermediate 58.1

4-Cyanobenzylamine hydrochloride (4.18 g, 24.8 mmol) and 6-methyl-2,4-dichloro-5-nitropyrimidine (5.67 g, 27.3 mmol) was added to 70 mL DCM, DIPEA (7.05 g, 54.5 mmol) was added dropwise at −78° C., followed by warming to room temperature. The reaction was carried out for 2 hours and detected by TLC. The reaction mixture was concentrated to remove DCM, and then 50 mL of water was added thereto with stirring, followed by filtration. The filter cake was washed with water and cold EA and dried to give Intermediate 58.1 (yellow solid: 4.8 g, yield: 64%). LC-MS: M+H$^+$=304.

2. Synthesis of Intermediate 58.2

NaH (60% in oil, 695 mg, 17.4 mmol) was suspended in 10 mL of THF, and 2-methoxyethanol (3.61 g, 47.4 mmol) was added dropwise at 0° C. under nitrogen. The mixture was stirred for 30 minutes and 20 mL of a solution of Intermediate of 58.1 (4.8 g, 15.8 mmol) in THF was added thereto. After the addition, the reaction was carried out at room temperature for 2 hours, and the complete conversion of the starting materials was confirmed by TLC. The reaction solution was poured into a half-saturated ammonium chloride solution and extracted with EA. The organic layer was dried over anhydrous sodium sulfate and evaporated to dryness. The crude product was then followed by slurry with EA to give Intermediate 58.2 (yellow solid: 5.15 g, yield: 95%). LC-MS: M+H$^+$=344.

3. Synthesis of Intermediate 58.3

Intermediate 58.2 (5.15 g, 15 mmol), Fe (4.2 g, 75 mmol) and NH$_4$Cl (4.8 g, 90 mmol) were added to 150 mL EtOH and 75 mL H$_2$O. The reaction was carried out at 50° C. for 4 hours, and the completion of the reaction was confirmed by TLC, followed by hot suction filtration through diatomite. The filtrate was concentrated, and 50 mL of water was added thereto, followed by extraction with EA (50 mL*3). The organic phase was dried over anhydrous sodium sulfate and purified by silica gel column chromatography to give Intermediate 58.3 (reddish brown solid: 2 g, yield: 43%). LC-MS: M+H+=314.

4. Synthesis of Intermediate 58.4

Intermediate 58.3 (2.0 g, 6.38 mmol) and CDI (2.07 g, 12.8 mmol) was placed in a sealed tube, followed by addition of 30 mL of ACN. The reaction was carried out at 80° C. for 2 hours, and the complete conversion was confirmed by TLC. The reaction solution was concentrated, followed by slurry with EA, suction filtration and water washing. The filter cake was washed with EA to give Intermediate 58.4 (off-white solid: 1.35 g, yield: 62%). LC-MS: M+H+=340.

5. Synthesis of Intermediate 58.5

Intermediate 58.4 (1.35 g, 3.98 mmol) was added to 75% formic acid (15 mL), followed by addition of wet Raney Ni (about 1 g) at room temperature. The reaction was carried out at 80° C. for 4 hours, and the complete conversion of the starting materials was confirmed by TLC, followed by filtration. The filter cake was washed with EA, and the filtrate was poured into a saturated NaHCO3 solution, followed by extraction with EA. The organic layer was washed with saturated brine, dried over anhydrous sodium sulfate and evaporated to dryness to give Intermediate 58.5 (off-white solid: 700 mg, yield: 51%). LC-MS: M+H+=343

6. Synthesis of Example 58

Intermediate 58.5 (675 mg, 1.97 mmol) and pyrrolidine (280 mg, 3.94 mmol) was dissolved in 20 mL DCM and stirred for 15 minutes, and sodium triacetoxyborohydride (1.25 g, 5.91 mmol) was added in batches at 0° C. After the addition, the reaction was carried out at room temperature for 3 hours, and the complete conversion of the starting materials was confirmed by TLC. Water was added thereto and extracted with DCM. The organic layer was washed with saturated NaCl solution, dried over anhydrous sodium sulfate, evaporated to dryness and purified by preparative plate to give Example 58 (pale yellow solid: 350 mg, yield: 45%). 1H-NMR (400 MHz, CDCl3): δ 7.44 (d, J=8.2 Hz, 2H), 7.40 (d, J=8.1 Hz, 2H), 5.04 (s, 2H), 4.49 (t, J=4.5 Hz, 2H), 3.91 (s, 2H), 3.77 (t, J=4.5 Hz, 2H), 3.43 (s, 3H), 2.88 (s, 4H), 2.45 (s, 3H), 1.94 (s, 4H). LC-MS: M+H+=398.

Example 59: Preparation of 2-(2-methoxyethoxy)-8-methyl-9-(4-(pyrrolidin-1-ylmethyl)benzyl)-9H-purine

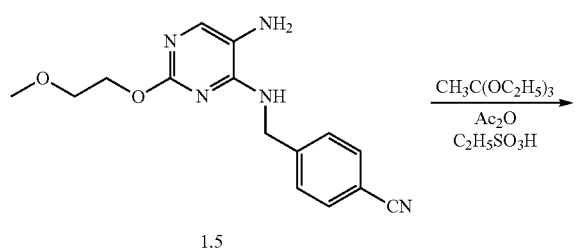

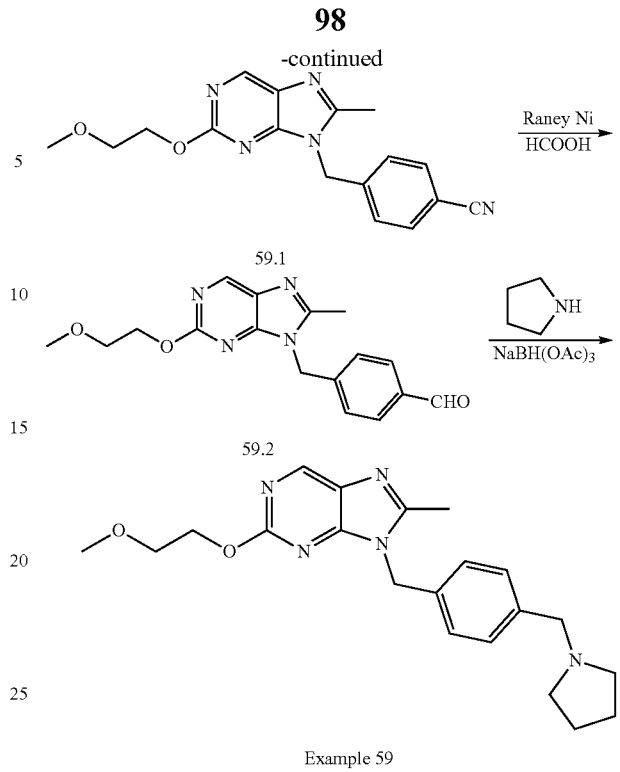

Example 59

1. Synthesis of Intermediate 59.1

Intermediate 1.5 (1.80 g, 6 mmol), triethyl orthoacetate (2.93 g, 18 mmol) and ethyl sulfonic acid (199 mg, 1.8 mmol) were added to 15 mL of acetic anhydride. The reaction was carried out at 120° C. under microwave for 2 hours, detected by TLC. After completion of the reaction, water was added, and extracted with DCM. The organic layer was washed with saturated NaCl solution, dried over anhydrous sodium sulfate and evaporated to dryness to give the intermediate containing some impurities by column chromatography (yellow solid: 756 mg, yield: 39%). LC-MS: M+H+=324.

2. Synthesis of Intermediate 59.2

Intermediate 59.1 (756 mg, 2.34 mmol) was dissolved in 75% formic acid (15 mL), and wet Raney Ni (about 1 g) was added thereto. The reaction was carried out at 50° C. for 4 hours, detected by TLC. After completion of the reaction, diatomite was added for suction filtration. The filter cake was washed with EA, and the filtrate was poured into a saturated NaHCO3 solution, followed by extraction with EA. The organic layer was washed with saturated NaCl solution, dried over anhydrous sodium sulfate, evaporated to dryness and purified by preparative plate to give Intermediate 59.2 (off-white solid: 132 mg, yield: 17%).

3. Synthesis of the Compound of Example 59

Intermediate 59.2 (278 mg, 0.85 mmol) and pyrrolidine (123 mg, 1.7 mmol) were dissolved in 6 mL DCM and stirred for 15 minutes, followed by addition of sodium triacetoxyborohydride (541 mg, 2.55 mmol) at 0° C. After the addition, the reaction was carried out at room temperature for 3 hours, detected by TLC. After completion of the reaction, water was added, and extracted with DCM. The organic layer was washed with saturated NaCl solution, dried over anhydrous sodium sulfate, evaporated to dryness and purified by preparative plate to give the compound of Example 59 (pale yellow solid: 180 mg, yield: 55%). $^1$H-NMR (400 MHz, CDCl$_3$): δ 8.73 (s, 1H), 7.44 (d, J=7.8 Hz, 2H), 7.17 (d, J=7.9 Hz, 2H), 5.34 (s, 2H), 4.58 (t, J=4.5 Hz, 2H), 3.84 (s, 2H), 3.81 (t, J=4.5 Hz, 2H), 3.44 (s, 3H), 2.80 (s, 4H), 2.50 (s, 3H), 1.93 (s, 4H). LC-MS: M+H$^+$=382.

Example 60: Preparation of 2-(2-methoxyethoxy)-9-(4-(pyrrolidin-1-ylmethyl)benzyl)-7,9-dihydro-8H-purin-8-thione

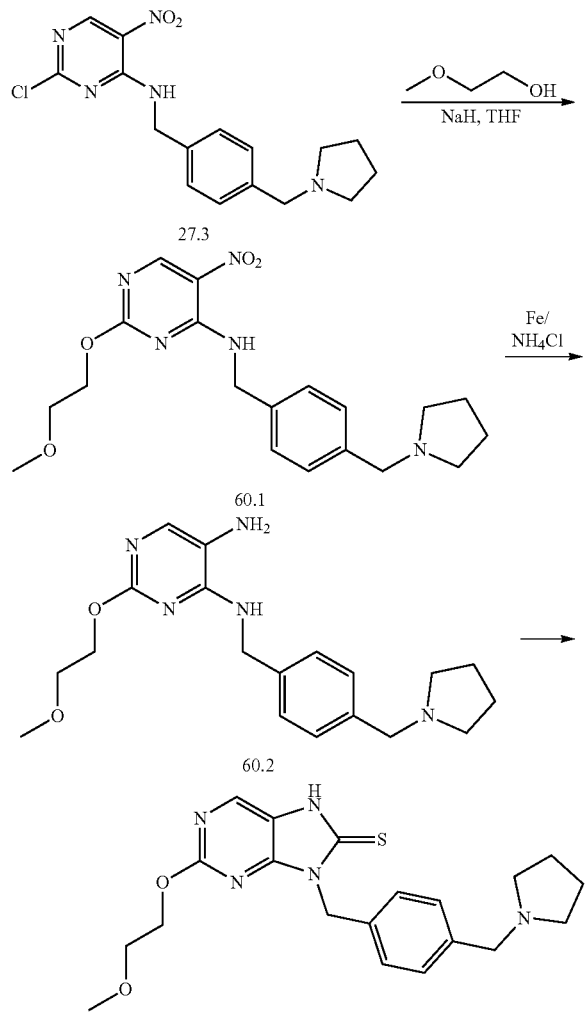

1. Synthesis of Intermediate 60.1

NaH (276 mg, 6.9 mmol) was added into a 100 mL three-necked flask, and 10 mL of anhydrous THF was added thereto under ice bath and then ultra-dry 2-methoxyethanol (1.31 g, 17.25 mmol) was slowly added dropwise. After the addition, the mixture was stirred under ice bath for 30 minutes. The reaction mixture was slowly added dropwise to 10 mL of a solution of Intermediate 27.3 (2 g, 5.75 mmol) in anhydrous THF, the temperature was maintained no more than 10° C. After the addition, the reaction was carried out at room temperature for 2 hours, and the disappearance of the starting materials was confirmed by TLC (DCM/MeOH=20/1). The reaction solution was slowly poured into 30 mL of iced water and extracted with ethyl acetate (20 mL*3). The organic phases were combined, washed with saturated brine, dried over anhydrous sodium sulfate, concentrated and purified by silica gel column chromatography to give Intermediate 60.1 (brown solid: 800 mg, yield: 36%). LC-MS: M+H$^+$=388

2. Synthesis of Intermediate 60.2

20 mL of ethanol and 10 mL of water were added into a 100 mL three-necked flask, and ammonium chloride solid (663 mg, 12.4 mmol) and reduced iron powder (576 mg, 10.32 mmol) were added thereto with stirring. After the addition, the mixture was heated to reflux and reacted for 30 minutes, and then Intermediate 60.1 (800 mg, 2.06 mmol) was added thereto. The reaction was carried out at 80° C. for 2 hours, and the disappearance of the starting materials was confirmed by TLC (DCM/MeOH=20/1), followed by hot filtration. The filter cake was washed with ethanol, and the filtrate was concentrated to remove ethanol and extracted with ethyl acetate (30 mL*3). The organic phase was washed with water and saturated brine, dried, concentrated and purified by silica gel column chromatography to give Intermediate 60.2 (reddish brown solid: 400 mg, yield: 54%). LC-MS: M+H$^+$=358.

3. Synthesis of the Compound of Example 60

Intermediate 60.2 (100 mg, 0.28 mmol) was added to 10 mL of ethanol, and potassium ethylxanthate (90 mg, 0.56 mmol) was added thereto with stirring at room temperature. After the addition, the reaction was carried out at an external temperature of 90° C. for 16 hours, and the disappearance of the starting materials was confirmed by TLC (DCM/MeOH=20/1), followed by suction filtration with diatomite. The filter cake was washed with EA, and the filtrate was evaporated to dryness. Water was added thereto and extracted with EA. The organic phase was dried and concentrated. The crude product was purified by silica gel column chromatography to give the compound of Example 60 (yellowish brown solid: 56 mg, yield: 50%). $^1$H-NMR (400 MHz, CDCl3), δ 9.28 (s, 1H), 8.08 (s, 1H), 7.62 (d, J=7.9 Hz, 2H), 7.29 (d, J=8.0 Hz, 2H), 5.40 (s, 2H), 4.53 (s, 2H), 3.66-3.50 (m, 8H), 3.38 (s, 3H), 2.01 (t, J=6.6 Hz, 4H). LC-MS: M+H$^+$=400.

Example 61: Preparation of 2-(2-methoxyethoxy)-9-(4-(pyrrolidin-1-ylmethyl)benzyl)-7,9-dihydro-8H-purin-8-amine

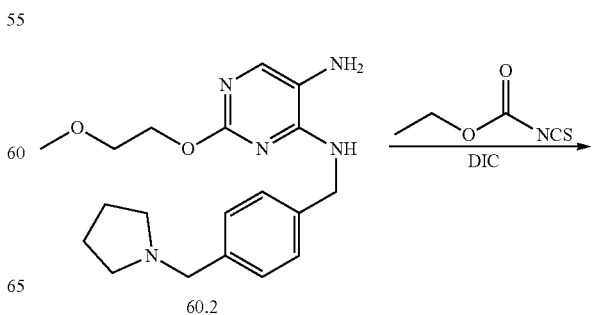

102

Example 62: Preparation of 2-(2-methoxyethoxy)-9-(3-fluoro-4-(pyrrolidin-1-ylmethyl)benzyl)-7,9-dihydro-8H-purin-8-one

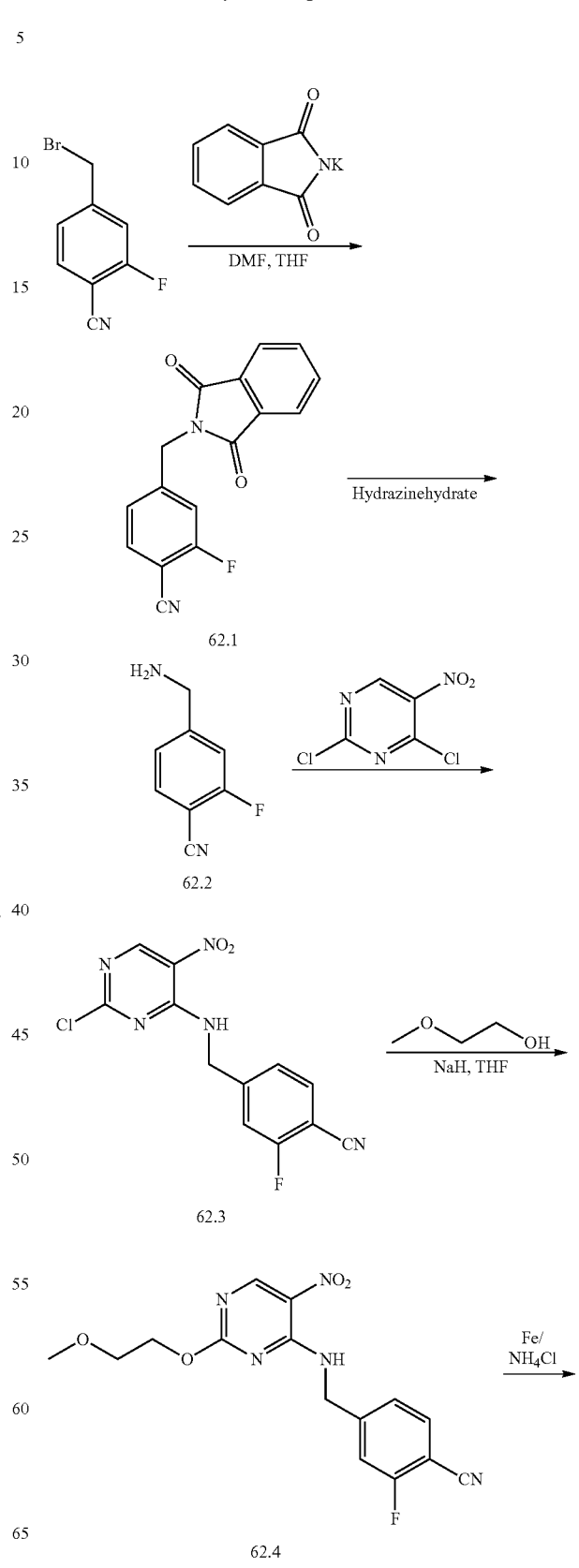

101

-continued

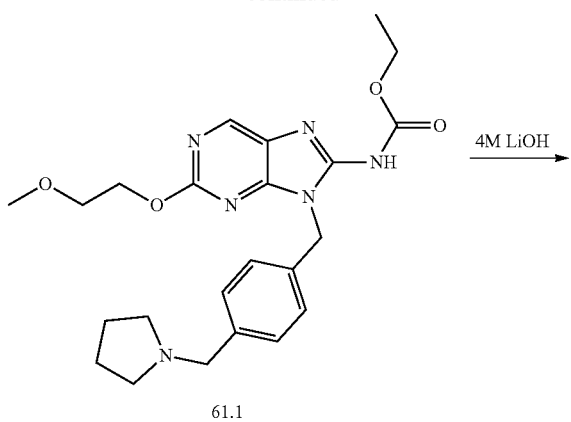

61.1

Example 61

1. Synthesis of Intermediate 61.1

Intermediate 60.2 (666 mg, 1.87 mmol) was added to 10 mL of ACN, and then Et$_3$N (566.6 mg, 5.61 mmol) was added. 6 mL of a solution of ethyl isothiocyanate (294 mg, 2.24 mmol) in ACN was added thereto at 0° C. and stirred at room temperature for 30 minutes, followed by addition of N,N-diisopropylcarbodiimide (306.3 mg, 2.43 mmol). After the addition, the reaction was carried out under reflux and detected by TLC. After completion of the reaction, water was added, and extracted with DCM. The organic layer was evaporated to dryness and purified by silica gel column chromatography to give Intermediate 61.1 (brown oil: 298 mg, yield: 35%). LC-MS: M+H$^+$=400.

2. Synthesis of the Compound of Example 61

Intermediate 61.1 (132 mg, 0.29 mmol) was dissolved in 5 mL of methanol, and then 5 mL of 4M aqueous solution of LiOH (20 mmol) was added. The reaction was carried out at 90° C. for 48 hours, detected by TLC. After completion of the reaction, water was added, and extracted with DCM. The organic layer was evaporated to dryness and purified by preparative plate to give the compound of Example 61 (brown solid: 29 mg, yield: 26%). $^1$H-NMR (400 MHz, d$_6$-DMSO), δ 8.06 (s, 1H), 7.32-7.25 (m, 4H), 6.80 (br, 2H), 5.15 (s, 2H), 4.43 (s, 2H), 3.53-3.41 (m, 8H), 3.23 (s, 3H), 1.90 (br, 4H). LC-MS: M+H$^+$=383.

103

-continued

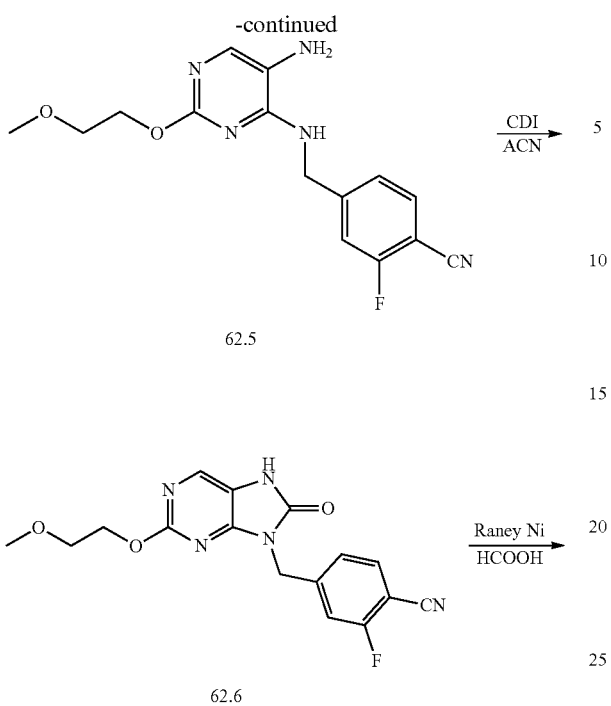

62.5

62.6

62.7

Example 62

The compound of Example 62 was obtained according to the synthesis procedure of Example 1, wherein the starting material of 4-cyanobenzyl bromide was replaced by 4-cyano-3-fluorobenzyl bromide. $^1$H-NMR (400 MHz, CDCl$_3$) δ 7.96 (s, 1H), 7.59 (s, 1H), 7.22 (d, J=7.9 Hz, 1H), 7.15 (d, J=10.7 Hz, 1H), 5.02 (s, 2H), 4.48 (d, J=4.8 Hz, 1H), 3.95 (s, 2H), 3.76 (d, J=4.8 Hz, 1H), 3.42 (s, 3H), 2.89 (s, 4H), 1.94 (s, 4H). LC-MS: M+H$^+$=402.

104

Example 63: Preparation of 2-(2-methoxyethoxy)-9-(2-fluoro-4-(pyrrolidin-1-ylmethyl)benzyl)-7,9-dihydro-8H-purin-8-one

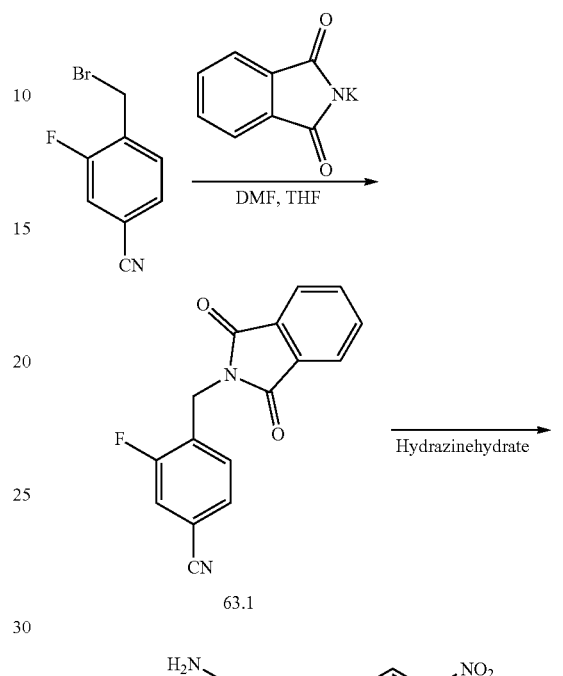

63.1

63.2

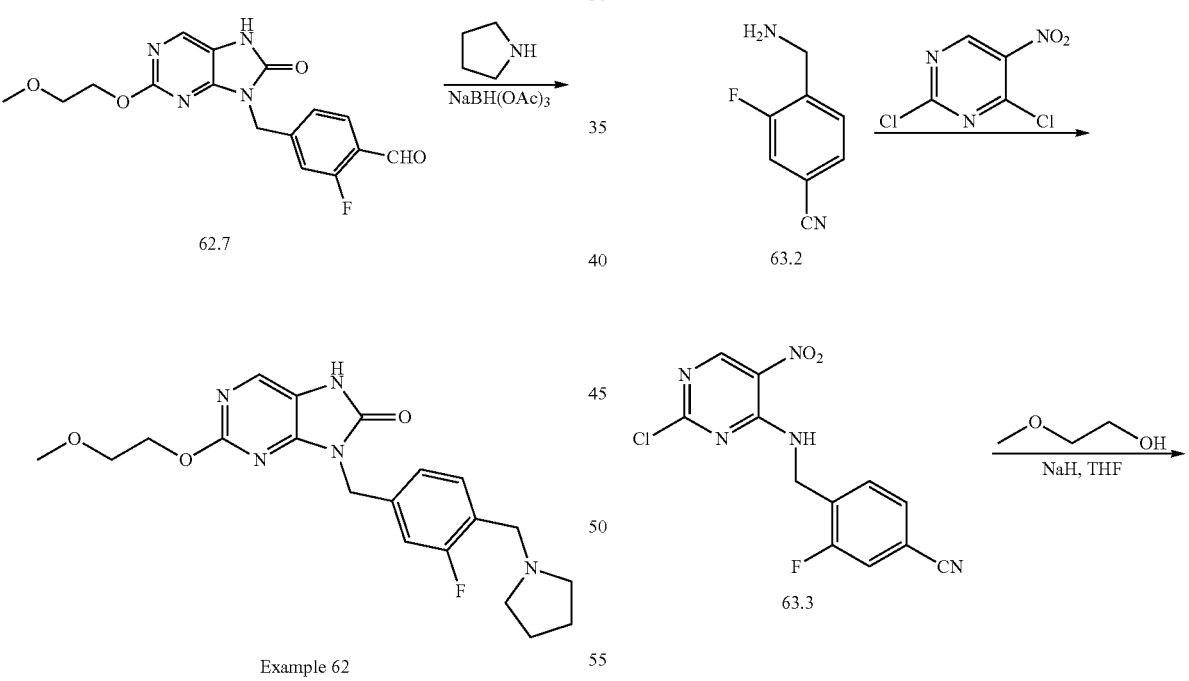

63.3

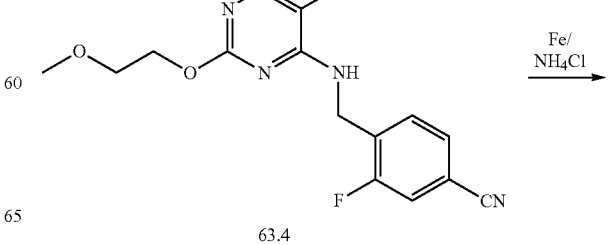

63.4

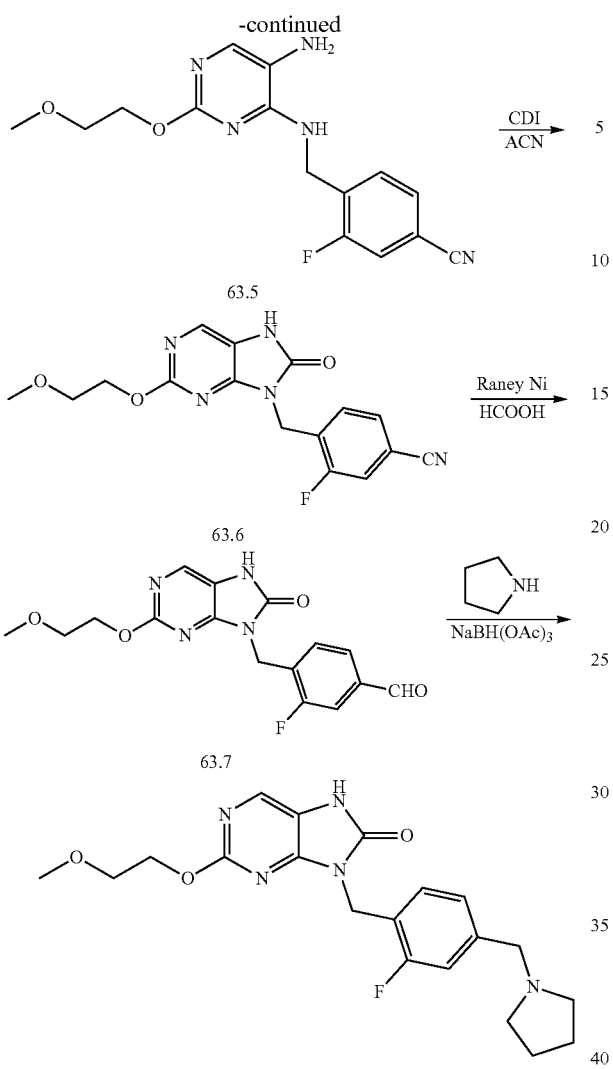

Example 63

The compound of Example 63 was obtained according to the synthesis procedure of Example 1, wherein the starting material of 4-cyanobenzyl bromide was replaced by 4-cyano-2-fluorobenzyl bromide. ¹H-NMR (400 MHz, CDCl₃) δ 7.98 (s, 1H), 7.23-7.19 (m, 1H), 7.17-7.08 (m, 2H), 5.11 (s, 2H), 4.50-4.40 (m, 2H), 3.77-3.73 (m, 4H), 3.40 (s, 3H), 2.73 (s, 4H), 1.88 (s, 4H). LC-MS: M+H⁺=402.

Example 64: Preparation of 9-(4-(pyrrolidin-1-ylmethyl)benzyl)-2-(2-isopropoxyethoxy)-7,9-dihydro-8H-purin-8-one

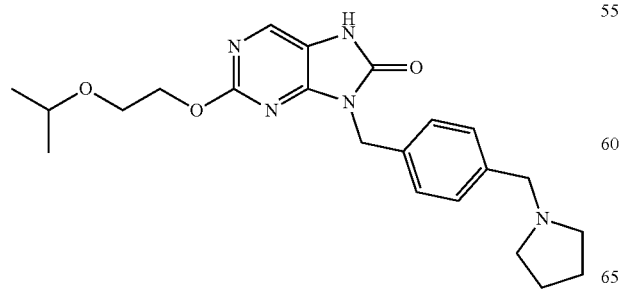

The compound of Example 64 was obtained according to the synthesis procedure of Example 43, wherein 2-trifluoromethoxy-1-ethanol was replaced by 2-isopropoxy-1-ethanol. ¹H-NMR (400 MHz, CDCl₃): δ 7.95 (s, 1H), 7.45 (d, J=8.2 Hz, 2H), 7.41 (d, J=8.1 Hz, 2H), 5.07 (s, 2H), 4.50 (d, J=4.9 Hz, 2H), 3.87 (s, 2H), 3.83 (d, J=4.9 Hz, 2H), 3.76-3.67 (m, 1H), 2.84 (s, 4H), 1.94 (s, 4H), 1.22 (d, J=6.1 Hz, 6H). LC-MS: M+H⁺=412.

Example 65: Preparation of 9-(4-(pyrrolidin-1-ylmethyl)benzyl)-2-(2-(cyclopropylmethoxy)ethoxy)-7,9-dihydro-8H-purin-8-one

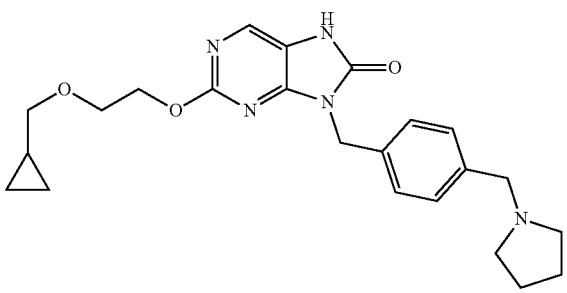 [SMILES: O=c1[nH]c2cnc(OCCOCC3CC3)nc2n1Cc1ccc(CN2CCCC2)cc1]

The compound of Example 65 was obtained according to the synthesis procedure of Example 43, wherein 2-trifluoromethoxy-1-ethanol was replaced by 2-cyclopropoxy-1-ethanol. ¹H-NMR (400 MHz, CDCl₃): δ 7.95 (s, 1H), 7.43 (s, 4H), 5.05 (s, 2H), 4.51 (t, J=4.9 Hz, 2H), 3.94 (s, 2H), 3.85 (t, J=4.9 Hz, 2H), 3.39 (d, J=6.9 Hz, 2H), 2.93 (s, 4H), 1.97 (s, 4H), 1.14-1.01 (m, 1H), 0.54 (d, J=7.6 Hz, 2H), 0.22 (d, J=5.0 Hz, 2H). LC-MS: M+H⁺=424.

Example 66: Preparation of 9-(4-(pyrrolidin-1-ylmethyl)benzyl)-2-butoxy-7,9-dihydro-8H-purin-8-one

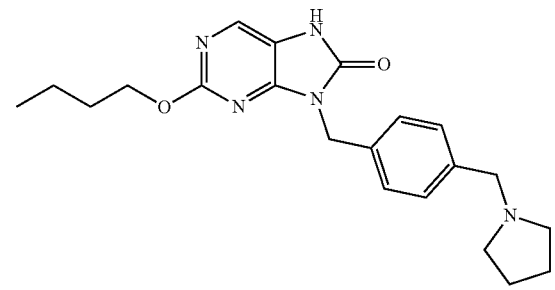 [SMILES: CCCCOc1ncc2[nH]c(=O)n(Cc3ccc(CN4CCCC4)cc3)c2n1]

The compound of Example 66 was according to the synthesis procedure of Example 43, wherein 2-trifluoromethoxy-1-ethanol was replaced by n-butanol. ¹H-NMR (400 MHz, d₆-DMSO): δ 10.74 (s, 1H), 7.82 (s, 1H), 7.30 (d, J=7.6 Hz, 2H), 7.22 (d, J=7.6 Hz, 2H), 4.84 (s, 2H), 4.36 (s, 2H), 3.39-3.33 (m, 6H), 1.86 (br, 4H), 1.47-1.43 (m, 2H), 1.30-1.19 (m, 2H), 0.82 (t, J=7.2 Hz, 3H). LC-MS: M+H⁺=382.

Example 67: Preparation of 9-(4-(pyrrolidin-1-ylm-ethyl)phenethyl)-2-(2-methoxyethoxy)-7,9-dihydro-8H-purin-8-one

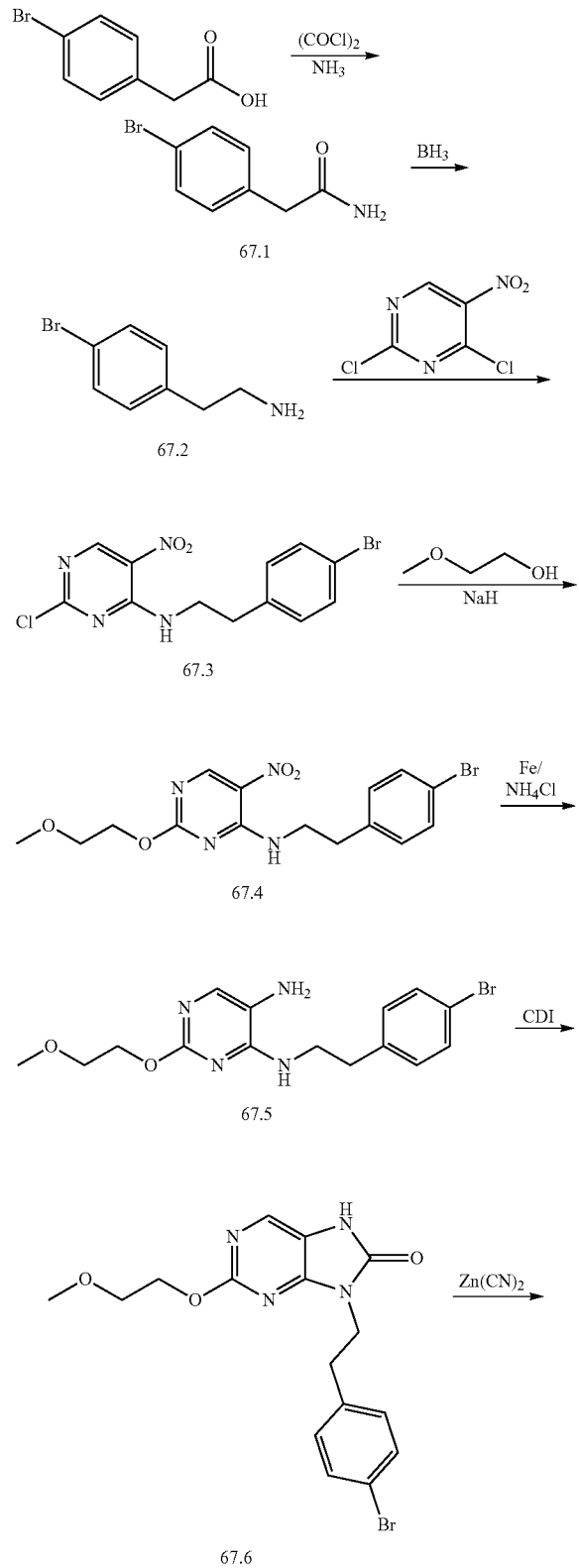

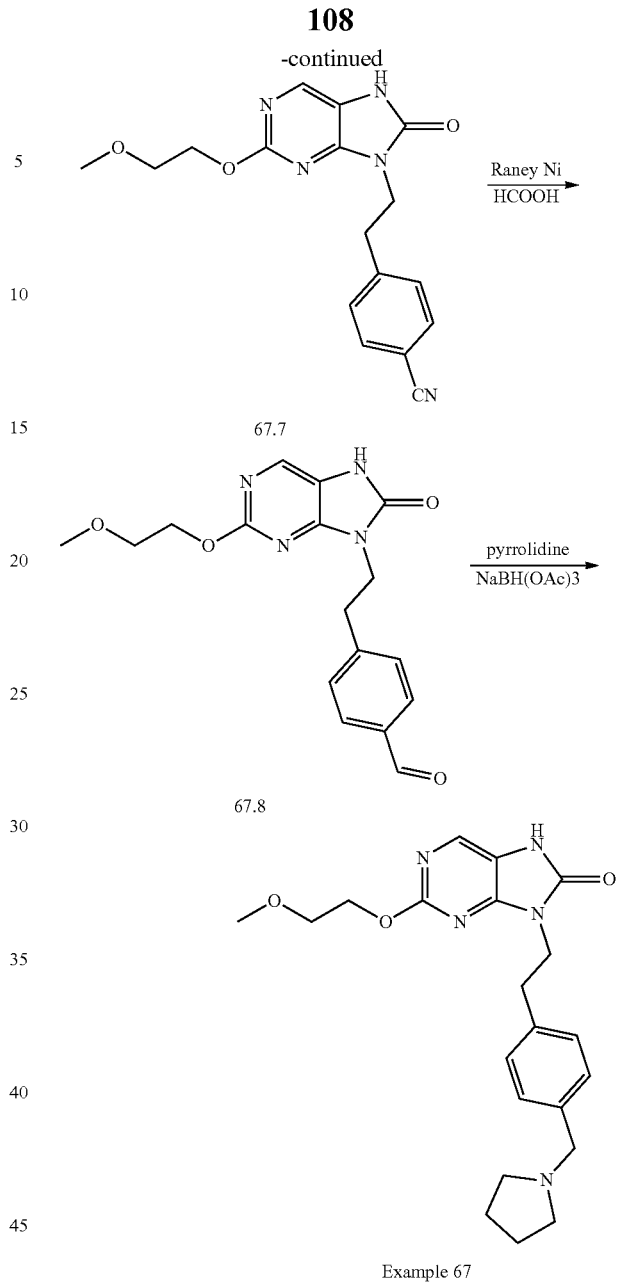

Example 67

1. Synthesis of Intermediate 67.1

2-(4-Bromophenyl)acetic acid (10 g, 46 mmol) was added to 50 mL DCM, and oxalyl chloride (7.08 g, 56 mmol) was added thereto dropwise. The reaction mixture was heated to 45° C., stirred for 3 hours, and then cooled to room temperature and concentrated. The remaining mixture was added to 50 mL of THF to form a solution. The solution was slowly added dropwise to 50 mL of ammonium hydroxide at 0° C., and stirred at room temperature for 3 hours, followed by filtration. The filter cake was washed with water, rinsed with ethanol and dried to give Intermediate 67.1 (white solid: 9.9 g, yield: 99%). LC-MS: M+H$^+$=214, 216.

2. Synthesis of Intermediate 67.2

Intermediate 67.1 (10 g, 46 mmol) was added to 150 mL of THF, followed by addition of BH$_3$/THF (150 mL). After the addition, the reaction solution was heated to 80° C. and stirred overnight. The reaction mixture was cooled to room temperature, and methanol was added thereto for quenching, followed by filtration. The filtrate was concentrated, and water was added thereto and extracted with dichloromethane three times. The dichloromethane phases were combined, washed with water three times, dried over anhydrous sodium sulfate and concentrated to give Intermediate 67.2 (colorless liquid: 5 g, yield: 56%). LC-MS: M+H$^+$=200, 202.

3. Synthesis of Intermediate 67.3

2,4-Dichloro-5-nitropyrimidine (5 g, 25.8 mmol) was dissolved in 50 mL of THF and cooled to −78° C., followed by addition of Intermediate 67.2 (5 g, 25.8 mmol) and DIPEA (6.6 g, 51.6 mmol). The reaction mixture was then stirred at −78° C. for 1 hour. The reaction mixture was poured into ice water, and extracted with DCM three times. The organic layers were combined, washed with brine, dried over anhydrous sodium sulfate and concentrated. The residue then followed by slurry with methanol and filtration to give Intermediate 67.3 (pale yellow solid: 3 g, yield: 35%). LC-MS: M+H$^+$=357, 359.

4. Synthesis of Intermediate 67.4

NaH (0.5 g, 12 mmol) was added to 2-methoxyethanol (10 mL) in portions, and the mixture was stirred at room temperature for 0.5 hour. A solution Intermediate 67.3 (3 g, 8.39 mmol) in tetrahydrofuran was then added thereto and stirred at room temperature for 1 hour. After completion of reaction detected by TLC, the reaction solution was poured into ice water, filtered and dried to give Intermediate 67.4 (yellow solid: 3 g, yield: 88%). LC-MS: M+H$^+$=397, 399.

5. Synthesis of Intermediate 67.5

Intermediate 67.4 (3 g, 7.5 mmol) was dissolved in 30 mL of ethanol and 20 mL of water, followed by sequential addition of iron powder (2.1 g, 37.7 mmol) and ammonium chloride (0.4 g, 7.5 mmol). The mixture was heated to 80° C. and stirred for 2 hours. After completion of reaction detected by TLC, the reaction mixture was removed from heating, followed by hot filtration. The solvent was evaporated to dryness. The crude product was purified by silica gel column chromatography to give Intermediate 67.5 (reddish brown solid: 3 g, yield: 96%). LC-MS: M+H$^+$=367, 369.

6. Synthesis of Intermediate 67.6

Intermediate 67.5 (3 g, 8.17 mmol) was dissolved in 100 mL of ACN, followed by addition of carbodiimidazole (2.3 g, 16.35 mmol) at room temperature. After the addition, the mixture was heated to reflux and stirred overnight. After completion of the reaction, the solvent was evaporated to dryness. The residue was purified by silica gel column chromatography to give Intermediate 67.6 (yellow solid: 2 g, yield: 62%). LC-MS: M+H$^+$=393, 395.

7. Synthesis of Intermediate 67.7

Intermediate 67.6 (500 mg, 1.27 mmol), zinc cyanide (232 mg, 2.5 mmol) and Pd(PPh$_3$)$_4$ (80 mg, 0.07 mmol) were added to 6 mL of DMF. The mixture was heated to 120° C. and stirred overnight under nitrogen. After completion of reaction, water was added, and extracted with ethyl acetate. The residue was purified by silica gel column chromatography to give Intermediate 67.7 (yellow solid: 300 mg, yield: 69%). LC-MS: M+H$^+$=340.

8. Synthesis of Intermediate 67.8

Intermediate 67.7 (0.3 g, 0.8 mmol) was dissolved in 3 mL of 75% formic acid, followed by addition of Raney Ni (10 mg) at room temperature. After the addition, the mixture was heated to reflux and stirred for 0.5 hour. After completion of the reaction, the solvent was evaporated to dryness. The residue was poured into saturated aqueous solution of sodium bicarbonate, extracted with DCM three times, dried over anhydrous sodium sulfate and concentrated to give Intermediate 67.8 (yellow solid: 150 mg, yield: 49%). LC-MS: M+H$^+$=343.

9. Synthesis of the Compound of Example 67

Intermediate 67.8 (100 mg, 0.29 mmol) and tetrahydropyrrole (42 mg, 0.58 mmol) were dissolved in 3 mL THF and stirred at room temperature for 4 hours, followed by addition of sodium triacetoxyborohydride (76 mg, 0.36 mmol). After the addition, the mixture was stirred at room temperature overnight. After completion of the reaction, the reaction mixture was quenched with saturated NaHCO$_3$ and extracted with DCM. The solvent was then evaporated to dryness.

The residue was purified by silica gel column chromatography to give the compound of Example 67 (yellow solid: 20 mg, yield: 17%). $^1$H-NMR (400 MHz, d$_6$-DMSO) δ 8.01 (s, 1H), 7.43 (d, J=8.1 Hz, 2H), 7.10 (d, J=8.1 Hz, 2H), 4.52-4.50 (m, 2H), 4.14-4.13 (m, 2H), 4.11 (s, 2H), 3.47 (s, 2H), 3.13 (m, 2H), 3.12-3.10 (m, 2H), 2.13 (m, 4H), 1.31-1.28 (m, 2H). LC-MS: M+H$^+$=398.

Example 68: Preparation of 9-(4-(2-(pyrrolidin-1-yl)ethyl)benzyl)-2-(2-methoxyethoxy)-7,9-dihydro-8H-purin-8-one

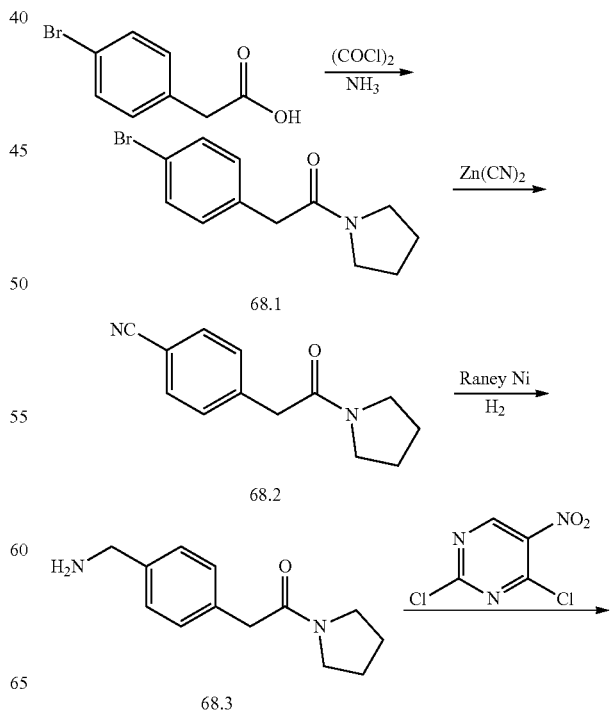

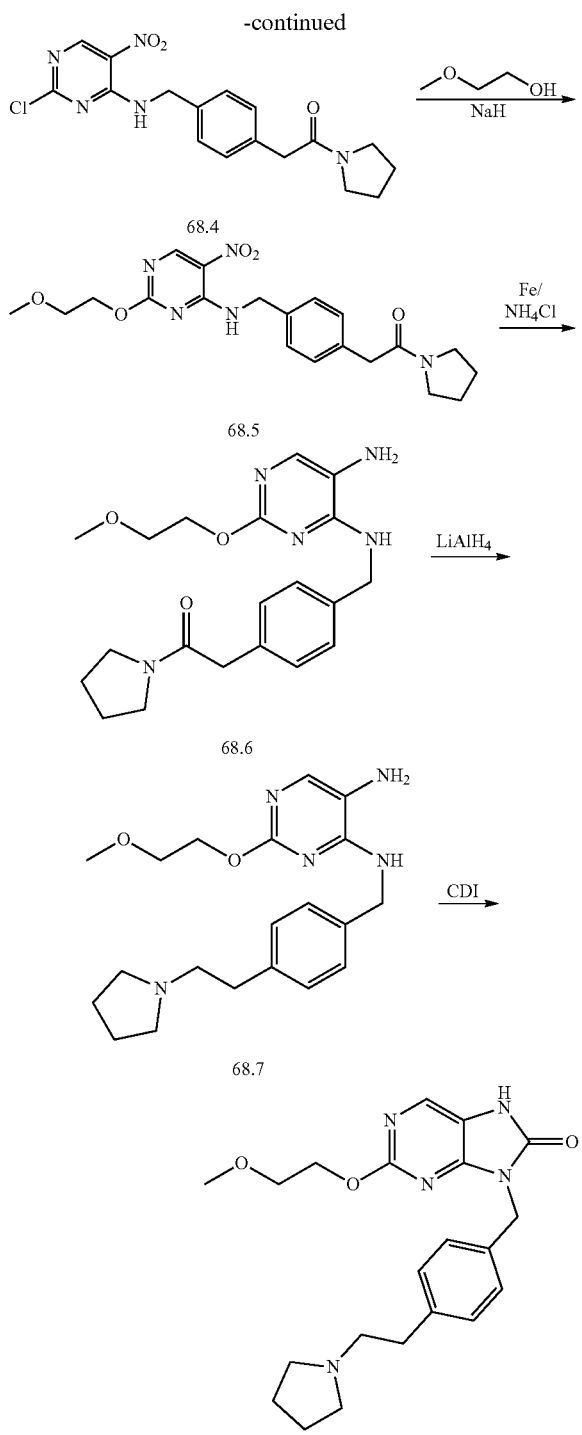

Example 68

1. Synthesis of Intermediate 68.1

2-(4-Bromophenyl)acetic acid (10 g, 46 mmol) was added to 50 mL DCM, oxalyl chloride (7.08 g, 56 mmol) was added thereto dropwise. The mixture was heated to 45° C., stirred for 3 hours, and then cooled to room temperature and concentrated. The remaining mixture was added to 50 mL of THF to form a solution. The solution was slowly added dropwise to 50 mL of a solution of tetrahydropyrrole (6.61 g, 93 mmol) in THF, and stirred at room temperature overnight, followed by filtration. The filter cake was washed with water, rinsed with ethanol and dried to give Intermediate 68.1 (white solid: 10 g, yield: 80%). LC-MS: M+H$^+$= 268, 270.

2. Synthesis of Intermediate 68.2

Intermediate 68.1, zinc cyanide (2.73 g, 29.83 mmol) and Pd(PPh$_3$)$_4$ (0.86 g, 0.75 mmol) were added to 40 mL of DMF. The mixture was heated to 120° C. and stirred overnight under nitrogen. After completion of the reaction, water was added thereto, and extracted with ethyl acetate. The residue was purified by silica gel column chromatography to give Intermediate 68.2 (yellow solid: 3 g, yield: 90%). LC-MS: M+H$^+$=215.

3. Synthesis of Intermediate 68.3

Intermediate 68.2 (3 g, 466 mmol) was dissolved in 20 mL of NH$_3$/MeOH, followed by addition of Raney Nickel (0.2 g). The mixture was stirred at room temperature under hydrogen (2 atm) overnight, and the complete conversion of the starting materials was confirmed by TLC. The reaction mixture was filtered, concentrated and dried to give Intermediate 68.3 (brown oil: 2 g, yield: 65%). LC-MS: M+H$^+$=219.

4. Synthesis of Intermediate 68.4

2,4-Dichloro-5-nitropyrimidine (0.5 g, 2.58 mmol) was dissolved in 5 mL of THF and then cooled to −78° C. Intermediate 68.3 (0.5 g, 2.3 mmol) and DIPEA (0.6 g, 4.6 mmol) were added thereto, and then stirred at −78° C. for 1 hour. The reaction mixture was poured into ice water and extracted with DCM three times. The organic phases were combined, washed with saturated brine and dried over anhydrous sodium sulfate. The crude product was followed by slurry with methanol and filtration to give Intermediate 68.4 (pale yellow solid: 0.5 g, yield: 58%). LC-MS: M+H$^+$=376.

5. Synthesis of Intermediate 68.5

NaH (0.13 g, 3.2 mmol) was added to 2-methoxyethanol (5 mL) in portions, and stirred at room temperature for 0.5 hour. Intermediate 68.4 (1 g, 2.66 mmol) was then added thereto in portions and stirred at room temperature for 1 hour. After completion of reaction detected by TLC, the reaction mixture was poured into ice water, filtered and dried to give Intermediate 68.5 (yellow solid: 0.9 g, yield: 81%). LC-MS: M+H$^+$=416

6. Synthesis of Intermediate 68.6

Intermediate 68.5 (0.9 g, 2.17 mmol) was dissolved in 9 mL of ethanol and 5 mL of water, followed by sequential addition of iron powder (0.6 g, 10.8 mmol) and ammonium chloride (0.7 g, 13 mmol). The mixture was heated to 80° C. and stirred for 2 hours. After completion of reaction detected by TLC, the reaction mixture was removed from heating and cooled to room temperature, followed by filtration. The solvent was evaporated to dryness. The residue was purified by silica gel column chromatography to give Intermediate 68.6 (reddish brown solid: 0.6 g, yield: 70%). LC-MS: M+H$^+$=386.

7. Synthesis of Intermediate 68.7

Intermediate 68.7 (300 mg, 0.78 mmol) was added to 10 mL of THF, followed by addition of lithium aluminum hydride (90 mg, 2.34 mmol) at 0° C. The mixture was stirred at 10° C. under nitrogen for 1 hour. After completion of the reaction, water was added thereto, and extracted with ethyl acetate. The residue was purified by silica gel column chromatography to give Intermediate 68.7 (yellow solid: 250 mg, yield: 80%). LC-MS: M+H$^+$=372.

8. Synthesis of the Compound of Example 68

Intermediate 68.7 (200 mg, 0.53 mmol) and CDI (175 mg, 1.08 mmol) were dissolved in 5 mL of ACN and stirred at 50° C. for 2 hours. After completion of the reaction, the solvent was evaporated to dryness. The residue was purified by silica gel column chromatography to give the compound of Example 68 (yellow solid: 60 mg, yield: 30%). $^1$H-NMR (400 MHz, CDCl$_3$) 7.91 (s, 1H), 7.65 (s, 1H), 7.28 (d, J=8.1 Hz, 2H), 7.05 (d, J=8.1 Hz, 2H), 4.94 (s, 2H), 4.43-4.40 (m, 2H), 3.71-3.69 (m, 2H), 3.3 (s, 3H), 3.18-3.06 (m, 8H), 2.01 (s, 4H). LC-MS: M+H$^+$=398.

Example 69: Preparation of 6-hydroxy-2-(2-methoxyethoxy)-9-(4-(pyrrolidin-1-ylmethyl)benzyl)-7,9-dihydro-8H-purin-8-one

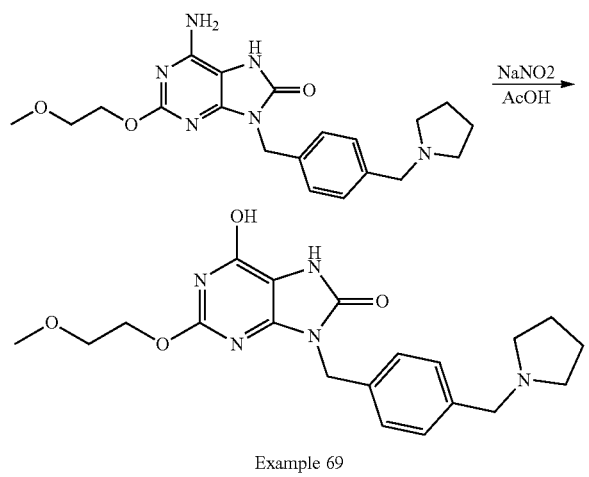

Example 69

6-Amino-2-(2-methoxyethoxy)-9-(4-(pyrrolidin-1-ylmethyl)benzyl)-7,9-dihydro-purin-8-one (150 mg, 0.37 mmol, the synthesis method referred to CN01784548B) was dissolved in 5 mL of 95% acetic acid. Sodium nitrite (78 mg, 1.13 mmol) was added thereto at 0° C. and stirred at room temperature for 3 hours. After completion of the reaction, sodium carbonate was added for quenching and extraction. The solvent was evaporated to dryness. The residue was purified by silica gel column chromatography to give the compound of Example 69 (yellow solid: 60 mg, yield: 39%). $^1$H-NMR (400 MHz, DMSO) δ 10.94 (s, 1H), 7.26 (m, 4H), 4.82 (s, 2H), 4.42 (t, J=4.0 Hz, 2H), 3.61 (t, J=4.0 Hz, 2H), 3.52 (s, 2H), 3.26 (s, 3H), 2.39 (br, 4H), 1.66 (br, 4H). LC-MS: M+H$^+$=400.

Example 70: Preparation of 6-fluoro-2-(2-methoxyethoxy)-9-(4-(pyrrolidin-1-ylmethyl)benzyl)-7,9-dihydro-8H-purin-8-one

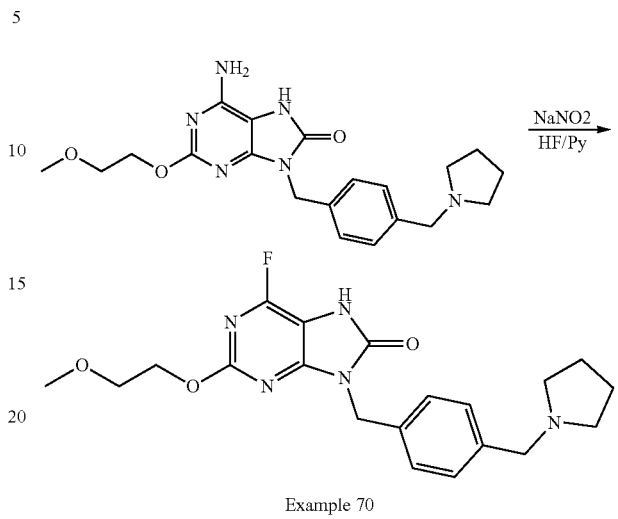

Example 70

6-Amino-2-(2-methoxyethoxy)-9-(4-(pyrrolidin-1-ylmethyl)benzyl)-7,9-dihydro-purin-8-one (150 mg, 0.37 mmol, the synthesis method referred to CN01784548B) was dissolved in 5 mL of 70% hydrogen fluoride pyridine. Sodium nitrite (78 mg, 1.13 mmol) was added thereto at 0° C. and stirred at room temperature for 3 hours. After completion of the reaction, sodium hydroxide was added for quenching and extraction. The solvent was evaporated to dryness. The residue was purified by silica gel column chromatography to give the compound of Example 70 (yellow solid: 80 mg, yield: 52%). $^1$H-NMR (400 MHz, CDCl3) δ 7.46 (d, J=8.0 Hz, 2H), 7.38 (d, J=8.0 Hz, 2H), 4.98 (s, 2H), 4.42 (t, J=4.0 Hz, 2H), 4.05 (s, 2H), 3.70 (t, J=4.0 Hz, 2H), 3.37 (s, 3H), 3.08 (br, 4H), 2.01 (br, 4H). LC-MS: M+H$^+$=402.

Effect Example 1: Activation Activity Test of hTLR7 and hTLR8

1. Reagents and Materials:

Cell lines: HEK-Blue™ hTLR7 and HEK-Blue™ hTLR8 (InvivoGen Co.)

Primary reagents: QUANTI-Blue™ (InvivoGen) and ATPlite 1 Step (PerkinElmer)

Primary instruments: Automatic Liquid Handling Workstation (Labcyte, Model: Echo), Cell Counter (Countstar, IC$_{1000}$) and Multifunctional Enzyme Marker (Molecular Device, Flexstation III).

2. Experimental Method 2.1 The tested compounds were formulated into a 60 mM concentrated stock solution in DMSO and stored in a nitrogen cabinet. The positive control compound R848 was formulated into a 2 mg/mL concentrated stock solution in DMSO and stored at −20° C. in a fridge.

2.2 Each tested compounds was added into the cell plates in a 3-fold gradient with Echo for a total of 10 concentrations, double wells per concentration. The negative control wells were filled with 1 μL of DMSO per well, and the positive control wells were filled with 1 μL of 2 mg/mL of R848 per well.

2.3 The T150 cultured cells were taken out from the CO$_2$ incubator and the cell culture supernatant was discarded. The cells were washed with PBS once, followed by addition of about 10 mL of the culture solution. The cells were dissociated by patting the cell culture flask, and gently blown to even by a pipette.

The cells were counted, and the cell suspension was adjusted to 200,000 cells/mL by the culture solution. Thereafter, 200 μL of diluted cells was added to each well in a 96-well plate containing the compound (40,000 cells/well).

2.4 The compounds and cells were incubated in a 5% $CO_2$ incubator at 37° C. for 24 hours.

2.5 Compound activity assay: 20 μl of the cell supernatant of each well after induction was added to a cell culture plate containing 180 μL of reagent QUANTI-Blue™, and incubated at 37° C. for 1.5 hours. Thereafter, the optical density absorption ($OD_{650}$) of each well at 650 nm was measured using a Multifunctional Enzyme Marker: Flexstation III.

2.6 Compound Activity: $OD_{650}$ values were analyzed using GraphPad Prism software and the dose-response curves for the compound were fitted to calculate the $EC_{50}$ values of the compound.

The experimental results were shown in Table 1:

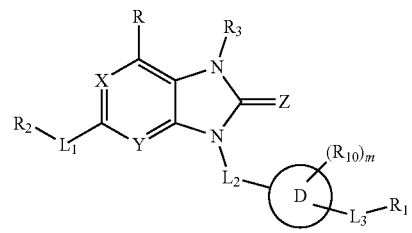

Formula I

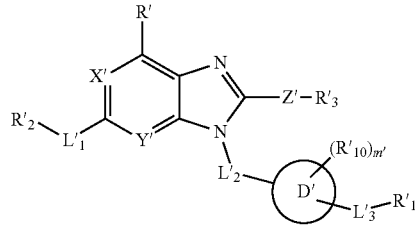

Formula II wherein, each of X, Y, X' and Y' is independently selected from C or N;

TABLE 1

| Compound | TLR7 ($EC_{50}$) | TLR8 ($EC_{50}$) | Compound | TLR7 ($EC_{50}$) | TLR8 ($EC_{50}$) | Compound | TLR7 ($EC_{50}$) | TLR8 ($EC_{50}$) |
|---|---|---|---|---|---|---|---|---|
| Example 1 | B | D | Example 2 | C | D | Example 3 | B | D |
| Example 4 | B | D | Example 5 | B | D | Example 6 | C | D |
| Example 7 | C | D | Example 8 | C | D | Example 9 | B | D |
| Example 10 | B | D | Example 11 | B | D | Example 12 | B | D |
| Example 13 | B | D | Example 14 | A | D | Example 15 | A | D |
| Example 16 | A | D | Example 17 | B | D | Example 18 | B | D |
| Example 19 | B | D | Example 20 | C | D | Example 21 | C | D |
| Example 22 | C | D | Example 23 | C | D | Example 24 | D | D |
| Example 25 | C | D | Example 26 | C | D | Example 27 | D | C |
| Example 28 | D | D | Example 29 | D | D | Example 30 | D | D |
| Example 31 | D | D | Example 32 | D | D | Example 33 | D | D |
| Example 34 | D | D | Example 35 | D | D | Example 36 | C | D |
| Example 37 | B | D | Example 38 | C | D | Example 39 | C | D |
| Example 40 | D | D | Example 41 | A | D | Example 42 | A | D |
| Example 43 | A | D | Example 45 | A | D | Example 46 | B | D |
| Example 47 | B | D | Example 48 | A | D | Example 49 | A | D |
| Example 50 | A | D | Example 51 | B | D | Example 52 | B | D |
| Example 53 | B | D | Example 54 | C | D | Example 55 | A | D |
| Example 56 | D | D | Example 57 | D | D | Example 58 | D | D |
| Example 59 | D | D | Example 60 | D | D | Example 61 | C | D |
| Example 62 | B | D | Example 63 | B | D | Example 64 | B | D |
| Example 65 | B | D | Example 66 | D | D | Example 67 | D | D |
| Example 68 | B | D | Example 69 | C | D | Example 70 | C | D |
| R848 | A | B | | | | | | |

Note:
1 nM ≤ A ≤ 1000 nM; 1 μM < B ≤ 10 μM; 10 μM < C ≤ 100 μM; 100 μM < D.

As the results shown in Table 1, the positive control R848 showed strong agonistic activity against TLR8, indicating its poor selectivity and low safety. However, some of the compounds of the present application not only have higher agonistic activity on TLR7, but also have much better selectivity than the positive control R848, and the safety is higher.

What is claimed is:

1. A compound of formula I or formula II, a tautomer thereof, an optical isomer thereof, a deuterated compound thereof, a hydrate thereof, a solvate thereof or a pharmaceutically acceptable salt thereof, each of $R_2$ and $R'_2$ is independently hydrogen, a $C_1$-$C_{10}$ alkyl, a $C_2$-$C_{10}$ heteroalkyl, a $C_3$-$C_{10}$ cycloalkyl, a $C_3$-$C_{10}$ heterocycloalkyl, a $C_2$-$C_{10}$ alkenyl or a $C_2$-$C_{10}$ alkynyl; wherein, each of the $C_1$-$C_{10}$ alkyl, the $C_2$-$C_{10}$ heteroalkyl, the $C_3$-$C_{10}$ cycloalkyl, the $C_3$-$C_{10}$ heterocycloalkyl, the $C_2$-$C_{10}$ alkenyl and the $C_2$-$C_{10}$ alkynyl is independently substituted by one or more $R_4$; when a plurality of $R_4$ substituents are present, the substituents are the same or different; $R_4$ is selected from the group consisting of hydrogen, hydroxyl, a halogen, a $C_1$-$C_6$ alkyl, a $C_3$-$C_{10}$ cycloalkyl and a $C_3$-$C_{10}$ heterocycloalkyl;

each of $L_1$ and $L'_1$ is independently —O—, —C($R_{a1}R_{a2}$)—, —C(O)—, —S—, —S(O)—, —S(O)$_2$—, —N($R_{a3}$)—, —N($R_{a4}$)C(O)— or —N(R$_{a5}$)S(O)$_2$—; wherein, each of R$_{a1}$, R$_{a2}$, R$_{a3}$, R$_{a4}$ and R$_{a5}$ is independently hydrogen or a C$_1$-C$_6$ alkyl;

each of R$_1$ and R'$_1$ is independently —NR$_5$R$_6$;

each of R$_5$ and R$_6$ is independently hydrogen or a C$_1$-C$_{10}$ alkyl; wherein the C$_1$-C$_{10}$ alkyl is substituted by one or more R$_7$; when a plurality of R$_7$ substituents are present, the substituents are the same or different; R$_7$ is selected from the group consisting of hydrogen, hydroxyl, a halogen, a C$_3$-C$_{10}$ cycloalkyl and a C$_3$-C$_{10}$ heterocycloalkyl;

alternatively, R$_5$ and R$_6$ together with the nitrogen atom to which they are attached form a substituted or unsubstituted heterocyclic ring; the substituted heterocyclic ring is substituted by one or more R$_8$; when a plurality of R$_8$ substituents are present, the substituents are the same or different; R$_8$ is selected from the group consisting of a halogen, hydroxyl, a C$_1$-C$_6$ alkyl, a C$_3$-C$_{10}$ cycloalkyl, —C(O)OR$_{b1}$, —C(O)R$_{b2}$, —NR$_{b3}$R$_{b4}$, —C(O)NR$_{b5}$, —OC(O)NR$_{b6}$ or —NR$_{b7}$C(O)NR$_{b8}$; wherein, each of R$_{b1}$, R$_{b2}$, R$_{b3}$, R$_{b4}$, R$_{b5}$, R$_{b6}$, R$_{b7}$ and R$_{b8}$ is independently hydrogen or a C$_1$-C$_6$ alkyl;

Z is C, N, O or S;

Z' is —O—, —S—, —N(R'$_4$)— or —C(R'$_5$R'$_6$)—;

each of R$_3$, R'$_3$, R'$_4$, R'$_5$ and R'$_6$ is independently hydrogen, a C$_1$-C$_{10}$ alkyl or a C$_3$-C$_{10}$ cycloalkyl; wherein each of the C$_1$-C$_{10}$ alkyl and the C$_3$-C$_{10}$ cycloalkyl is independently substituted by one or more R$_9$; when a plurality of R$_9$ substituents are present, the substituents are the same or different; R$_9$ is selected from the group consisting of hydrogen, a halogen, a C$_1$-C$_6$ alkyl, a C$_3$-C$_{10}$ cycloalkyl and a C$_3$-C$_{10}$ heterocycloalkyl;

each of D and D' is independently phenylene;

each of R$_{10}$ and R'$_{10}$ is independently a halogen, nitro, cyano, hydroxyl, sulfhydryl, a C$_1$-C$_6$ alkyl, a C$_1$-C$_6$ alkoxy, a C$_3$-C$_{10}$ cycloalkyl, a C$_3$-C$_{10}$ heterocycloalkyl, —C(O)OR$_{c1}$, —C(O)R$_{c2}$, —OC(O)R$_{c3}$, —NR$_{c4}$R$_{c5}$, —NR$_{c6}$C(O)R$_{c7}$, —C(O)NR$_{c8}$, —OC(O)NR$_{c9}$, —NR$_{c10}$C(O)NR$_{c11}$, —SR$_{c12}$, —S(O)NR$_{c13}$R$_{c14}$, —S(O)$_2$NR$_{c15}$R$_{c16}$, —NR$_{c17}$S(O)$_2$R$_{c18}$ or —NR$_{c19}$S(O)R$_{c20}$; wherein each of R$_{c1}$, R$_{c2}$, R$_{c3}$, R$_{c4}$, R$_{c5}$, R$_{c6}$, R$_{c7}$, R$_{c8}$, R$_{c9}$, R$_{c10}$, R$_{c11}$, R$_{c12}$, R$_{c13}$, R$_{c14}$, R$_{c15}$, R$_{c16}$, R$_{c17}$, R$_{c18}$, R$_{c19}$ and R$_{c20}$ is independently hydrogen or a C$_1$-C$_6$ alkyl;

each of m and m' is independently 0, 1, 2, 3 or 4; when a plurality of R$_{10}$ substituents are present on D, the substituents are the same or different; when a plurality of R'$_{10}$ substitutions are present on D', the substituents are the same or different;

each of L$_2$ and L'$_2$ is independently a C$_1$-C$_3$ alkylene;

each of L$_3$ and L'$_3$ is independently a C$_1$-C$_6$ alkylene or a C$_2$-C$_6$ heteroalkylene; each of the C$_1$-C$_6$ alkylene and the C$_2$-C$_6$ heteroalkylene is independently substituted by one or more R$_{11}$; when a plurality of R$_{11}$ substitutions are present, the substituents are the same or different; R$_{11}$ is selected from the group consisting of hydrogen, a halogen, cyano, a C$_1$-C$_6$ alkyl, a C$_3$-C$_{10}$ cycloalkyl, a C$_3$-C$_{10}$ heterocycloalkyl, —OR$_{d1}$, —SR$_{d2}$, —NR$_{d3}$R$_{d4}$; wherein each of R$_{d1}$, R$_{d2}$, R$_{d3}$ and R$_{d4}$ is independently hydrogen or a C$_1$-C$_6$ alkyl;

each of R and R' is independently hydrogen, a halogen, hydroxyl, a C$_1$-C$_3$ alkyl.

2. The compound of formula I or formula II, the tautomer thereof, the optical isomer thereof, the deuterated compound thereof, the hydrate thereof, the solvate thereof or the pharmaceutically acceptable salt thereof of claim 1, wherein, both X and Y are N;

or, both X' and Y' are N;

or, when R$_2$, R'$_2$, R$_3$, R'$_3$, R'$_4$, R'$_5$, R'$_6$, R$_5$ or R$_6$ is a C$_1$-C$_{10}$ alkyl; then the C$_1$-C$_{10}$ alkyl is a C$_1$-C$_6$ alkyl;

or when R$_2$, R'$_2$ is a C$_2$-C$_{10}$ heteroalkyl, then the heteroatom in the C$_2$-C$_{10}$ heteroalkyl group is selected from the group consisting of O, S and N; the number of heteroatom is 1, 2, 3, 4 or 5;

or, when R$_2$, R'$_2$, R$_3$, R'$_3$, R'$_4$, R'$_5$, R'$_6$ is a C$_3$-C$_{10}$ cycloalkyl, then the C$_3$-C$_{10}$ cycloalkyl is cyclopropyl, cyclopentyl or cyclohexyl;

or, when R$_2$, R'$_2$ is a C$_3$-C$_{10}$ heterocycloalkyl, then the heteroatom in the C$_3$-C$_{10}$ heterocycloalkyl is selected from the group consisting of O, S and N; the number of the heteroatom is 1, 2, or 3;

or, when R$_2$, R'$_2$ is a C$_2$-C$_{10}$ alkenyl, then the C$_2$-C$_{10}$ alkenyl is vinyl;

or, when R$_2$, R'$_2$ is a C$_2$-C$_{10}$ alkynyl, then the C$_2$-C$_{10}$ alkynyl is ethynyl;

or, when R$_4$, R$_7$, R$_8$, R$_9$, R$_{10}$, R'$_{10}$, or R$_{11}$ is a halogen, then the halogen is preferably F, Cl, Br or I;

or, when R$_4$, R$_8$, R$_9$, R$_{10}$, R'$_{10}$, or R$_{11}$ is a C$_1$-C$_6$ alkyl, then the C$_1$-C$_6$ alkyl is methyl, ethyl, n-propyl, isopropyl, n-butyl, isobutyl or tert-butyl;

or, when R$_4$, R$_7$, R$_8$, R$_9$, R$_{10}$, R'$_{10}$, or R$_{11}$ is a C$_3$-C$_{10}$ cycloalkyl, then the C$_3$-C$_{10}$ cycloalkyl is cyclopropyl, cyclopentyl or cyclohexyl;

or, when R$_4$, R$_7$, R$_9$, R$_{10}$, R'$_{10}$, or R$_{11}$ is a C$_3$-C$_{10}$ heterocycloalkyl, then the heteroatom in the C$_3$-C$_{10}$ heterocycloalkyl is selected from the group consisting of O, S and N; the number of the heteroatom is 1, 2 or 3;

or, when the R$_{10}$ or R'$_{10}$ is a C$_1$-C$_6$ alkoxy, then the C$_1$-C$_6$ alkoxy is methoxy, ethoxy, n-propoxy, isobutoxy, n-butoxy, isobutoxy or tert-butoxy;

or, when R$_{a1}$, R$_{a2}$, R$_{a3}$, R$_{a4}$ or R$_{a5}$ is a C$_1$-C$_6$ alkyl, then the C$_1$-C$_6$ alkyl is methyl, ethyl, n-propyl, isopropyl, n-butyl, isobutyl or tert-butyl;

or, in R$_1$ or R'$_1$, when R$_5$ and R$_6$ together with the nitrogen atom to which they are attached form a substituted or unsubstituted heterocyclic ring; then the heterocyclic ring is a 3-10 membered heterocyclic ring; the heteroatom is selected from the group consisting of O, S and N; the number of the heteroatom is 1-3;

or, when R$_{b1}$, R$_{b2}$, R$_{b3}$, R$_{b4}$, R$_{b5}$, R$_{b6}$, R$_{b7}$ or R$_{b8}$ is a C$_1$-C$_6$ alkyl, then the C$_1$-C$_6$ alkyl is methyl, ethyl, n-propyl, isopropyl, n-butyl, isobutyl or tert-butyl;

or, when R$_{c1}$, R$_{c2}$, R$_{c3}$, R$_{c4}$, R$_{c5}$, R$_{c6}$, R$_{c7}$, R$_{c8}$, R$_{c9}$, R$_{c10}$, R$_{c11}$, R$_{c12}$, R$_{c13}$, R$_{c14}$, R$_{c15}$, R$_{c16}$, R$_{c17}$, R$_{c18}$, R$_{c19}$ or R$_{c20}$ is a C$_1$-C$_6$ alkyl, then the C$_1$-C$_6$ alkyl is methyl, ethyl, n-propyl, isopropyl, n-butyl, isobutyl or tert-butyl;

or, when L$_2$ or L'$_2$ is a C$_1$-C$_3$ alkylene, then the C$_1$-C$_3$ alkylene is —CH$_2$—, —CH$_2$CH$_2$—, —CH(CH$_3$)—, —CH$_2$CH$_2$CH$_2$—, —CH(CH$_3$)CH$_2$— or —CH(CH$_2$CH$_3$)—;

or, when L$_3$ or L'$_3$ is a C$_1$-C$_6$ alkylene, then the C$_1$-C$_6$ alkylene is —CH$_2$—, —CH$_2$CH$_2$—, —CH(CH$_3$)—, —CH$_2$CH$_2$CH$_2$—, —CH(CH$_3$)CH$_2$— or —CH(CH$_2$CH$_3$)—;

or, when L$_3$ or L'$_3$ is a C$_2$-C$_6$ heteroalkylene, then the heteroatom in the C$_2$-C$_6$ heteroalkylene is selected from the group consisting of O, S and N; the number of the heteroatom is 1, 2 or 3;

or, when R$_{d1}$, R$_{d2}$, R$_{d3}$ or R$_{d4}$ is a C$_1$-C$_6$ alkyl, then the C$_1$-C$_6$ alkyl is methyl, ethyl, n-propyl, isopropyl, n-butyl, isobutyl or tert-butyl.

3. The compound of formula I or formula II, the tautomer thereof, the optical isomer thereof, the deuterated compound thereof, the hydrate thereof, the solvate thereof or the pharmaceutically acceptable salt thereof of claim 2, wherein,
when $R_2$, $R'_2$, $R_3$, $R'_3$, $R_4$, $R'_4$, $R'_5$, $R'_6$, $R_5$ or $R_6$ is a $C_1$-$C_6$ alkyl; then the $C_1$-$C_6$ alkyl is methyl, ethyl, n-propyl, isopropyl, n-butyl, isobutyl or tert-butyl;
or, when R or R' is a $C_1$-$C_3$ alkyl; then the $C_1$-$C_3$ alkyl is methyl, ethyl, n-propyl or isopropyl;
or, when $R_2$ or $R'_2$ is a $C_2$-$C_{10}$ heteroalkyl, then the $C_2$-$C_{10}$ heteroalkyl is

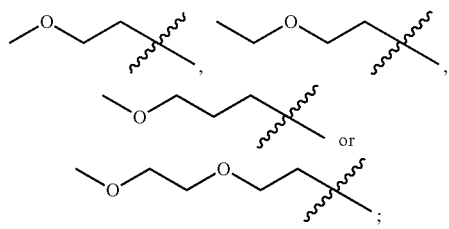

or when $R_2$ or $R'_2$ is a $C_3$-$C_{10}$ heterocycloalkyl, then the $C_3$-$C_{10}$ heterocycloalkyl is

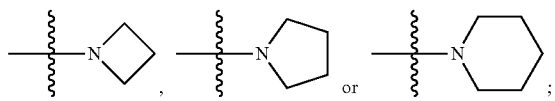

or when $R_4$, $R_7$, $R_9$, $R_{10}$, $R'_{10}$, or $R_{11}$ is a $C_3$-$C_{10}$ heterocycloalkyl, then the $C_3$-$C_{10}$ heterocycloalkyl is

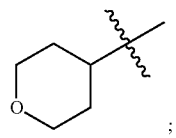

or, in $R_1$ or $R'_1$, when $R_5$ and $R_6$ together with the nitrogen atom to which they are attached form a substituted or unsubstituted heterocyclic ring; then the heterocyclic ring is selected from any one of the following structures:

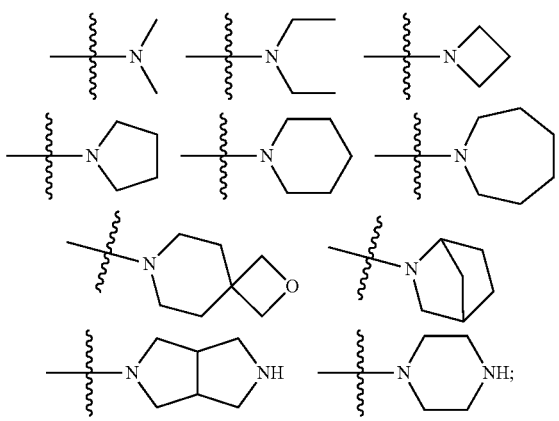

or, $L_3$-$R_1$ is located at the ortho-, meta- or para-position of $L_2$;
or, $L'_3$-$R'_1$ is at the ortho-, meta- or para-position of $L'_2$.

4. The compound of formula I or formula II, the tautomer thereof, the optical isomer thereof, the deuterated compound thereof, the hydrate thereof, the solvate thereof or the pharmaceutically acceptable salt thereof of claim 3, wherein,
in $R_1$ or $R'_1$, when $R_5$ and $R_6$ together with the nitrogen atom to which they are attached form a substituted or unsubstituted heterocyclic ring; the substituted heterocyclic ring is selected from any one of the following structures:

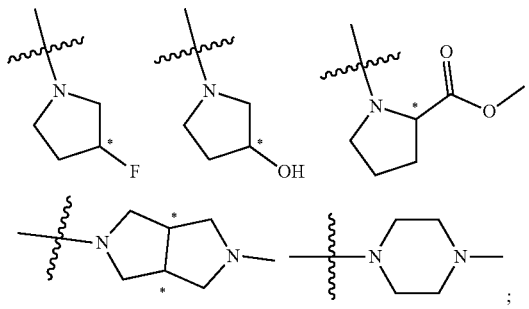

or, the $R_2$-$L_1$- is selected from any one of the following structures:

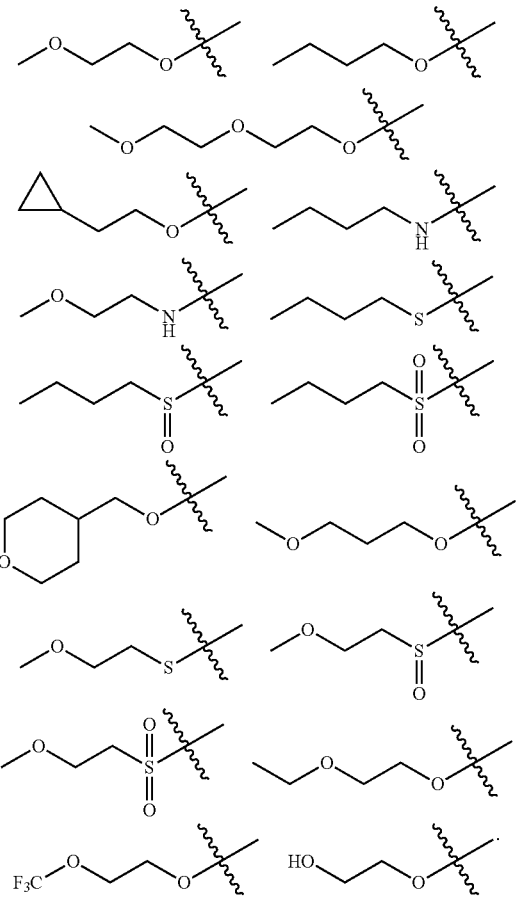

5. The compound of formula I, the tautomer thereof, the optical isomer thereof, the deuterated compound thereof, the hydrate thereof, the solvate thereof or the pharmaceutically acceptable salt thereof of claim 1, wherein, X and Y are independently C or N;

$R_2$ is hydrogen, a $C_1$-$C_{10}$ alkyl, a $C_2$-$C_{10}$ heteroalkyl, a $C_3$-$C_{10}$ cycloalkyl, a $C_3$-$C_{10}$ heterocycloalkyl, a $C_2$-$C_{10}$ alkenyl or a $C_2$-$C_{10}$ alkynyl; wherein, the $C_1$-$C_{10}$ alkyl, the $C_2$-$C_{10}$ heteroalkyl, the $C_3$-$C_{10}$ cycloalkyl, the $C_3$-$C_{10}$ heterocycloalkyl, the $C_2$-$C_{10}$ alkenyl and the $C_2$-$C_{10}$ alkynyl are independently substituted by one or more $R_4$; when a plurality of $R_4$ substituents are present, each $R_4$ is the same or different; $R_4$ is independently selected from the group consisting of hydrogen, hydroxyl, a halogen, a $C_1$-$C_6$ alkyl, a $C_3$-$C_{10}$ cycloalkyl and a $C_3$-$C_{10}$ heterocycloalkyl; however, not all the $R_4$ on the $C_1$-$C_{10}$ alkyl is hydrogen;

$L_1$ is —O—, —C($R_{a1}R_{a2}$)—, —C(O)—, —S—, —S(O)—, —S(O)$_2$—, —N($R_{a3}$)—, —N($R_{a4}$)C(O)— or —N($R_{a5}$)S(O)$_2$—; wherein, $R_{a1}$, $R_{a2}$, $R_{a3}$, $R_{a4}$ and $R_{a5}$ are independently hydrogen or a $C_1$-$C_6$ alkyl;

$R_3$ is hydrogen, a $C_1$-$C_{10}$ alkyl or a $C_3$-$C_{10}$ cycloalkyl; wherein the $C_1$-$C_{10}$ alkyl and the $C_3$-$C_{10}$ cycloalkyl are independently substituted by one or more $R_9$; when a plurality of $R_9$ substitutions are present, each $R_9$ is the same or different; $R_9$ is independently selected from the group consisting of hydrogen, a halogen, a $C_1$-$C_6$ alkyl, a $C_3$-$C_{10}$ cycloalkyl and a $C_3$-$C_{10}$ heterocycloalkyl;

Z is $CH_2$, NH, O or S;

$L_3$ is a $C_1$-$C_6$ alkylene or a $C_2$-$C_6$ heteroalkylene; the $C_1$-$C_6$ alkylene and the $C_2$-$C_6$ heteroalkylene are independently substituted by one or more $R_{11}$; when a plurality of $R_{11}$ substitutions are present, each $R_{11}$ is the same or different; $R_{11}$ is independently selected from the group consisting of hydrogen, a halogen, cyano, a $C_1$-$C_6$ alkyl, a $C_3$-$C_{10}$ cycloalkyl, a $C_3$-$C_{10}$ heterocycloalkyl, —O$R_{d1}$, —S$R_{d2}$, —N$R_{d3}R_{d4}$; wherein $R_{d1}$, $R_{d2}$, $R_{d3}$ and $R_{d4}$ are independently hydrogen or a $C_1$-$C_6$ alkyl;

D is phenylene;

m is 0, 1, 2, 3 or 4; when a plurality of $R_{10}$ substituents are present on D, each $R_{10}$ is the same or different;

$R_{10}$ is independently a halogen, nitro, cyano, hydroxyl, sulfhydryl, a $R_{10-1}$ substituted or unsubstituted $C_1$-$C_6$ alkyl, a $R_{10-2}$ substituted or unsubstituted $C_1$-$C_6$ alkoxy, a $R_{10-3}$ substituted or unsubstituted $C_3$-$C_{10}$ cycloalkyl, a $R_{10-4}$ substituted or unsubstituted $C_3$-$C_{10}$ heterocycloalkyl, —C(O)O$R_{c1}$, —C(O)$R_{c2}$, —OC(O)$R_{c3}$, —N$R_{c4}R_{c5}$, —N$R_{c6}$C(O)$R_{c7}$, —C(O)N$R_{c8}$, —OC(O)N$R_{c9}$, —N$R_{c10}$C(O)N$R_{c11}$, —S$R_{c12}$, —S(O)N$R_{c13}R_{c14}$, —S(O)$_2R_{c15}R_{c16}$, —N$R_{c17}$S(O)$_2R_{c18}$ or —N$R_{c19}$S(O)$R_{c20}$; wherein, all of $R_{10-1}$, $R_{10-2}$, $R_{10-3}$ and $R_{10-4}$ are independently F, Cl, Br or I; $R_{c1}$, $R_{c2}$, $R_{c3}$, $R_{c4}$, $R_{c5}$, $R_{c6}$, $R_{c7}$, $R_{c8}$, $R_{c9}$, $R_{c10}$, $R_{c11}$, $R_{c12}$, $R_{c13}$, $R_{c14}$, $R_{c15}$, $R_{c16}$, $R_{c17}$, $R_{c18}$, $R_{c19}$ and $R_{c20}$ are independently hydrogen or a $C_1$-$C_6$ alkyl;

$R_1$ is —N$R_5R_6$;

$R_5$ and $R_6$ are independently hydrogen or a $C_1$-$C_{10}$ alkyl; wherein the $C_1$-$C_{10}$ alkyl is substituted by one or more $R_7$; when a plurality of $R_7$ substituents are present, each $R_7$ is the same or different; $R_7$ is independently selected from the group consisting of hydrogen, hydroxyl, a halogen, a $C_3$-$C_{10}$ cycloalkyl and a $C_3$-$C_{10}$ heterocycloalkyl;

alternatively, $R_5$ and $R_6$ together with the nitrogen atom to which they are attached form a substituted or unsubstituted heterocyclic ring; the substituted heterocyclic ring is substituted by one or more $R_8$; when a plurality of $R_8$ substituents are present, each $R_8$ is the same or different; $R_8$ is independently selected from the group consisting of a halogen, hydroxyl, a $C_1$-$C_6$ alkyl, a $C_3$-$C_{10}$ cycloalkyl, —C(O)O$R_{b1}$, —C(O)$R_{b2}$, —N$R_{b3}R_{b4}$, —C(O)N$R_{b5}$, —OC(O)N$R_{b6}$ or —N$R_{b7}$C(O)N$R_{b8}$; wherein, $R_{b1}$, $R_{b2}$, $R_{b3}$, $R_{b4}$, $R_{b5}$, $R_{b6}$, $R_{b7}$ and $R_{b8}$ are independently hydrogen or a $C_1$-$C_6$ alkyl.

6. The compound of formula I, the tautomer thereof, the optical isomer thereof, the deuterated compound thereof, the hydrate thereof, the solvate thereof or the pharmaceutically acceptable salt thereof of claim 5, wherein, when the $R_2$ is a $C_1$-$C_{10}$ alkyl, then the $C_1$-$C_{10}$ alkyl is a $C_1$-$C_6$ alkyl;

or, when the $R_2$ is a $C_2$-$C_{10}$ heteroalkyl, then the heteroatom is selected from the group consisting of O, S and N;

or, when the $R_2$ is a $C_2$-$C_{10}$ heteroalkyl, then the number of the heteroatom is 1, 2, 3, 4 or 5;

or, when the $R_2$ is a $C_2$-$C_{10}$ heteroalkyl, then the $C_2$-$C_{10}$ heteroalkyl is a $C_2$-$C_5$ heteroalkyl;

or, in the $R_2$, when the $C_1$-$C_{10}$ alkyl, the $C_2$-$C_{10}$ heteroalkyl, the $C_3$-$C_{10}$ cycloalkyl, the $C_3$-$C_{10}$ heterocycloalkyl, the $C_2$-$C_{10}$ alkenyl and the $C_2$-$C_{10}$ alkynyl are independently substituted by one or more $R_4$, the "more" is independently 2, 3 or 4;

or, when the $R_4$ is independently a halogen, then the halogen is independently F, Cl, Br or I;

or, when the $R_4$ is independently a $C_3$-$C_{10}$ cycloalkyl, then the $C_3$-$C_{10}$ cycloalkyl is independently a $C_3$-$C_6$ cycloalkyl;

or, when the $R_4$ is independently a $C_3$-$C_{10}$ heterocycloalkyl, then the heteroatom is selected from the group consisting of O, S and N;

or, when the $R_4$ is independently a $C_3$-$C_{10}$ heterocycloalkyl, then the number of the heteroatom is 1, 2, 3, 4 or 5;

or, when the $R_4$ is independently a $C_3$-$C_{10}$ heterocycloalkyl, then the $C_3$-$C_{10}$ heterocycloalkyl is a $C_4$-$C_5$ heterocycloalkyl;

or, when the $L_1$ is —C($R_{a1}R_{a2}$)— and the $R_{a1}$ is a $C_1$-$C_6$ alkyl, then the $C_1$-$C_6$ alkyl is methyl, ethyl, n-propyl, isopropyl, n-butyl, isobutyl or tert-butyl;

or, when the $L_1$ is —C($R_{a1}R_{a2}$)— and the $R_{a2}$ is a $C_1$-$C_6$ alkyl, then the $C_1$-$C_6$ alkyl is methyl, ethyl, n-propyl, isopropyl, n-butyl, isobutyl or tert-butyl;

or, when the $L_1$ is —N($R_{a3}$)— and the $R_{a3}$ is a $C_1$-$C_6$ alkyl, then the $C_1$-$C_6$ alkyl is methyl, ethyl, n-propyl, isopropyl, n-butyl, isobutyl or tert-butyl;

or, when the $L_1$ is —N($R_{a4}$)C(O)— and the $R_{a4}$ is a $C_1$-$C_6$ alkyl, then the $C_1$-$C_6$ alkyl is methyl, ethyl, n-propyl, isopropyl, n-butyl, isobutyl or tert-butyl;

or, when the $L_1$ is —N($R_{a5}$)S(O)$_2$— and the $R_{a5}$ is a $C_1$-$C_6$ alkyl, then the $C_1$-$C_6$ alkyl is methyl, ethyl, n-propyl, isopropyl, n-butyl, isobutyl or tert-butyl;

or, when $R_3$ is a $C_1$-$C_{10}$ alkyl, then the $C_1$-$C_{10}$ alkyl is a $C_1$-$C_6$ alkyl;

or, in the $R_3$, when the $C_1$-$C_{10}$ alkyl and the $C_3$-$C_{10}$ cycloalkyl are independently substituted by one or more $R_9$, the "more" is independently 2, 3 or 4;

or, when the $L_2$ is a $C_1$-$C_1$ alkylene, then the $C_1$-$C_3$ alkylene is —$CH_2$—, —$CH_2CH_2$—, —CH($CH_3$)—, —$CH_2CH_2CH_2$—, —CH($CH_3$)$CH_2$— or —CH($CH_2CH_3$)—;

or, when the $L_2$ is a $C_1$-$C_3$ alkylene and the $C_1$-$C_3$ alkylene contains a chiral carbon atom, the chiral carbon atom is in R-configuration, S-configuration or a mixture thereof;

or, when the L$_3$ is a C$_1$-C$_6$ alkylene, then the C$_1$-C$_6$ alkylene is —CH$_2$—, —CH$_2$CH$_2$—, —CH(CH$_3$)—, —CH$_2$CH$_2$CH$_2$—, —CH(CH$_3$)CH$_2$— or —CH(CH$_2$CH$_3$)—;

or, when the L$_3$ is a C$_1$-C$_6$ alkylene and the C$_1$-C$_6$ alkylene contains a chiral carbon atom, then the chiral carbon atom is in R-configuration, S-configuration or a mixture thereof;

or, when the L$_3$ is a C$_2$-C$_6$ heteroalkylene, then the heteroatom is selected from the group consisting of O, S and N;

or, when the L$_3$ is a C$_2$-C$_6$ heteroalkylene, then the number of the heteroatom is 1, 2 or 3;

or, in the L$_3$, when the C$_1$-C$_6$ alkylene and the C$_2$-C$_6$ heteroalkylene are independently substituted by one or more R$_{11}$, the "more" is independently 2, 3 or 4;

or, in the L$_3$, when R$_{11}$ is independently selected from —OR$_{d1}$ and the R$_{d1}$ is independently a C$_1$-C$_6$ alkyl, then the C$_1$-C$_6$ alkyl is methyl, ethyl, n-propyl, isopropyl, n-butyl, isobutyl or tert-butyl;

or, in the L$_3$, when R$_{11}$ is independently selected from —SR$_{d2}$ and the R$_{d2}$ is independently a C$_1$-C$_6$ alkyl, then the C$_1$-C$_6$ alkyl is methyl, ethyl, n-propyl, isopropyl, n-butyl, isobutyl or tert-butyl;

or, in the L$_3$, when R$_{11}$ is independently selected from —NR$_{d3}$R$_{d4}$ and the R$_{d3}$ is independently a C$_1$-C$_6$ alkyl, then the C$_1$-C$_6$ alkyl is methyl, ethyl, n-propyl, isopropyl, n-butyl, isobutyl or tert-butyl;

or, in the L$_3$, when R$_{11}$ is independently selected from —NR$_{d3}$R$_{d4}$ and the R$_{d4}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently a halogen, then the halogen is F, Cl, Br or I;

or, when m is not 0 and the R$_{10}$ is independently a R$_{10-1}$ substituted or unsubstituted C$_1$-C$_6$ alkyl, then the number of the R$_{10-1}$ is one or more; when a plurality of R$_{10-1}$ substituents are present, each R$_{10-1}$ is the same or different;

or, when m is not 0 and the R$_{10}$ is independently a R$_{10-1}$ substituted or unsubstituted C$_1$-C$_6$ alkyl, then the C$_1$-C$_6$ alkyl is a C$_1$-C$_4$ alkyl;

or, when m is not 0 and the R$_{10}$ is independently a R$_{10-1}$ substituted or unsubstituted C$_1$-C$_6$ alkyl, then the R$_{10-1}$ is F;

or, when m is not 0 and the R$_{10}$ is independently a R$_{10-2}$ substituted or unsubstituted C$_1$-C$_6$ alkoxy, then the number of the R$_{10-2}$ is one or more; when a plurality of R$_{10-2}$ substituents are present, each R$_{10-2}$ is the same or different;

or, when m is not 0 and the R$_{10}$ is independently a R$_{10-2}$ substituted or unsubstituted C$_1$-C$_6$ alkoxy, then the C$_1$-C$_6$ alkoxy is a C$_1$-C$_4$ alkoxy;

or, when m is not 0 and the R$_{10}$ is independently a R$_{10-2}$ substituted or unsubstituted C$_1$-C$_6$ alkoxy, then the R$_{10-2}$ is F;

or, when m is not 0 and the R$_{10}$ is independently a R$_{10-3}$ substituted or unsubstituted C$_3$-C$_{10}$ cycloalkyl, then the number of the R$_{10-3}$ is one or more; when a plurality of R$_{10-3}$ substituents are present, each R$_{10-3}$ is the same or different;

or, when m is not 0 and the R$_{10}$ is independently a R$_{10-3}$ substituted or unsubstituted C$_3$-C$_{10}$ cycloalkyl, then the C$_3$-C$_{10}$ cycloalkyl is a C$_3$-C$_6$ cycloalkyl;

or, when m is not 0 and the R$_{10}$ is independently a R$_{10-3}$ substituted or unsubstituted C$_3$-C$_{10}$ cycloalkyl, then the R$_{10-3}$ is F;

or, when m is not 0 and the R$_{10}$ is independently a R$_{10-4}$ substituted or unsubstituted C$_3$-C$_{10}$ heterocycloalkyl, then the number of the R$_{10-4}$ is one or more; when a plurality of R$_{10-4}$ substituents are present, each R$_{10-4}$ is the same or different;

or, when m is not 0 and the R$_{10}$ is independently a R$_{10-4}$ substituted or unsubstituted C$_3$-C$_{10}$ heterocycloalkyl, then the R$_{10-4}$ is F;

or, when m is not 0 and the R$_{10}$ is independently —C(O)OR$_{c1}$ and the R$_{c1}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —C(O)R$_{c2}$ and the R$_{c2}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —OC(O)R$_{c3}$ and the R$_{c3}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —NR$_{c4}$R$_{c5}$ and the R$_{c4}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —NR$_{c4}$R$_{c5}$ and the R$_{c5}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —NR$_{c6}$C(O)R$_{c7}$ and the R$_{c6}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —NR$_{c6}$C(O)R$_{c7}$ and the R$_{c7}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —C(O)NR$_{c8}$ and the R$_{c8}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —OC(O)NR$_{c9}$ and the R$_{c9}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —NR$_{c10}$C(O)NR$_{c11}$ and the R$_{c10}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —NR$_{c10}$C(O)NR$_{c11}$ and the R$_{c11}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —SR$_{c12}$ and the R$_{c12}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —S(O)NR$_{c13}$R$_{c14}$ and the R$_{c13}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —S(O)NR$_{c13}$R$_{c14}$ and the R$_{c14}$ is independently a C$_1$-C$_6$ alkyl, then the C$_1$-C$_6$ alkyl is methyl, ethyl, n-propyl, isopropyl, n-butyl, isobutyl or tert-butyl;

or, when m is not 0 and the R$_{10}$ is independently —S(O)$_2$NR$_{c15}$R$_{c16}$ and the R$_{c15}$ is independently a C$_1$-C$_6$ alkyl, then the $C_1$-$C_6$ alkyl is methyl, ethyl, n-propyl, isopropyl, n-butyl, isobutyl or tert-butyl;

or, when m is not 0 and the $R_{10}$ is independently —S(O)$_2$NR$_{c15}$R$_{c16}$ and the R$_{c16}$ is independently a $C_1$-$C_6$ alkyl, then the $C_1$-$C_6$ alkyl is methyl, ethyl, n-propyl, isopropyl, n-butyl, isobutyl or tert-butyl;

or, when m is not 0 and the $R_{10}$ is independently —NR$_{c17}$S(O)$_2$R$_{c18}$ and the R$_{c17}$ is independently a $C_1$-$C_6$ alkyl, then the $C_1$-$C_6$ alkyl is methyl, ethyl, n-propyl, isopropyl, n-butyl, isobutyl or tert-butyl;

or, when m is not 0 and the $R_{10}$ is independently —NR$_{c17}$S(O)$_2$R$_{c18}$ and the R$_{c18}$ is independently a $C_1$-$C_6$ alkyl, then the $C_1$-$C_6$ alkyl is methyl, ethyl, n-propyl, isopropyl, n-butyl, isobutyl or tert-butyl;

or, when m is not 0 and the $R_{10}$ is independently —NR$_{c19}$S(O)R$_{c20}$ and the R$_{c19}$ is independently a $C_1$-$C_6$ alkyl, then the $C_1$-$C_6$ alkyl is methyl, ethyl, n-propyl, isopropyl, n-butyl, isobutyl or tert-butyl;

or, when m is not 0 and the $R_{10}$ is independently —NR$_{c19}$S(O)R$_{c20}$ and the R$_{c20}$ is independently a $C_1$-$C_6$ alkyl, then the $C_1$-$C_6$ alkyl is methyl, ethyl, n-propyl, isopropyl, n-butyl, isobutyl or tert-butyl;

or, when the $R_5$ is a $C_1$-$C_{10}$ alkyl, then the $C_1$-$C_{10}$ alkyl is $C_1$-$C_6$ alkyl;

or, in the $R_5$, when is the $C_1$-$C_{10}$ alkyl is substituted by one or more $R_7$, the "more" is independently 2, 3 or 4;

or, when the $R_6$ is a $C_1$-$C_{10}$ alkyl, then the $C_1$-$C_{10}$ alkyl is a $C_1$-$C_6$ alkyl;

or, in the $R_6$, when is the $C_1$-$C_{10}$ alkyl is substituted by one or more $R_7$, the "more" is independently 2, 3 or 4;

or, when the $R_5$ and the $R_6$ together with the nitrogen atom to which they are attached form a substituted or unsubstituted heterocyclic ring, then the heterocyclic ring is a monocyclic ring, a fused ring, a spiro ring or a bridged ring;

or, when the $R_5$ and the $R_6$ together with the nitrogen atom to which they are attached form a substituted or unsubstituted heterocyclic ring, the heterocyclic ring is a heteroaromatic ring or a heteroalicyclic ring;

or, when the $R_5$ and the $R_6$ together with the nitrogen atom to which they are attached form a substituted or unsubstituted heterocyclic ring, then the heterocyclic ring is a 3-10 membered heterocyclic ring;

or, when the $R_5$ and the $R_6$ together with the nitrogen atom to which they are attached form a substituted or unsubstituted heterocyclic ring, then the heteroatom is selected from the group consisting of O, S and N;

or, when the $R_5$ and the $R_6$ together with the nitrogen atom to which they are attached form a substituted or unsubstituted heterocyclic ring, then the number of the heteroatom is 1, 2 or 3;

or, when the $R_5$ and the $R_6$ together with the nitrogen atom to which they are attached form a substituted heterocyclic ring and the $R_8$ is independently a halogen, then the halogen is F, Cl, Br or I;

or, when the $R_5$ and the $R_6$ together with the nitrogen atom to which they are attached form a substituted heterocyclic ring and the $R_8$ is independently a $C_1$-$C_6$ alkyl, then the $C_1$-$C_6$ alkyl is a $C_1$-$C_4$ alkyl;

or, when the $R_5$ and the $R_6$ together with the nitrogen atom to which they are attached form a substituted heterocyclic ring, the $R_8$ is —C(O)OR$_{b1}$ and the R$_{b1}$ is a $C_1$-$C_6$ alkyl, then the $C_1$-$C_6$ alkyl is methyl, ethyl, n-propyl, isopropyl, n-butyl, isobutyl or tert-butyl;

or, when the $R_5$ and the $R_6$ together with the nitrogen atom to which they are attached form a substituted heterocyclic ring, the $R_8$ is —C(O)R$_{b2}$ and the R$_{b2}$ is a $C_1$-$C_6$ alkyl, then the $C_1$-$C_6$ alkyl is methyl, ethyl, n-propyl, isopropyl, n-butyl, isobutyl or tert-butyl;

or, when the $R_5$ and the $R_6$ together with the nitrogen atom to which they are attached form a substituted heterocyclic ring, the $R_8$ is —NR$_{b3}$R$_{b4}$ and the R$_{b3}$ is a $C_1$-$C_6$ alkyl, then the $C_1$-$C_6$ alkyl is methyl, ethyl, n-propyl, isopropyl, n-butyl, isobutyl or tert-butyl;

or, when the $R_5$ and the $R_6$ together with the nitrogen atom to which they are attached form a substituted heterocyclic ring, the $R_8$ is —NR$_{b3}$R$_{b4}$ and the R$_{b4}$ is a $C_1$-$C_6$ alkyl, then the $C_1$-$C_6$ alkyl is methyl, ethyl, n-propyl, isopropyl, n-butyl, isobutyl or tert-butyl;

or, when the $R_5$ and the $R_6$ together with the nitrogen atom to which they are attached form a substituted heterocyclic ring, the $R_8$ is —C(O)NR$_{b5}$ and the R$_{b5}$ is a $C_1$-$C_6$ alkyl, then the $C_1$-$C_6$ alkyl is methyl, ethyl, n-propyl, isopropyl, n-butyl, isobutyl or tert-butyl;

or, when the $R_5$ and the $R_6$ together with the nitrogen atom to which they are attached form a substituted heterocyclic ring, the $R_8$ is —OC(O)NR$_{b6}$ and the R$_{b6}$ is a $C_1$-$C_6$ alkyl, the $C_1$-$C_6$ alkyl is methyl, ethyl, n-propyl, isopropyl, n-butyl, isobutyl or tert-butyl;

or, when the $R_5$ and the $R_6$ together with the nitrogen atom to which they are attached form a substituted heterocyclic ring, the $R_8$ is NR$_{b7}$C(O)NR$_{b8}$ and the R$_{b7}$ is a $C_1$-$C_6$ alkyl, the $C_1$-$C_6$ alkyl is methyl, ethyl, n-propyl, isopropyl, n-butyl, isobutyl or tert-butyl;

or, when the $R_5$ and the $R_6$ together with the nitrogen atom to which they are attached form a substituted heterocyclic ring, the $R_8$ is NR$_{b7}$C(O)NR$_{b8}$ and the R$_{b8}$ is a $C_1$-$C_6$ alkyl, the $C_1$-$C_6$ alkyl is methyl, ethyl, n-propyl, isopropyl, n-butyl, isobutyl or tert-butyl.

7. The compound of formula I, the tautomer thereof, the optical isomer thereof, the deuterated compound thereof, the hydrate thereof, the solvate thereof or the pharmaceutically acceptable salt thereof of claim 6, wherein, when the $R_2$ is a $C_1$-$C_{10}$ alkyl, the $C_1$-$C_{10}$ alkyl is a $C_1$-$C_4$ alkyl;

or, when the $R_2$ is a $C_2$-$C_{10}$ heteroalkyl, the $C_2$-$C_{10}$ heteroalkyl is

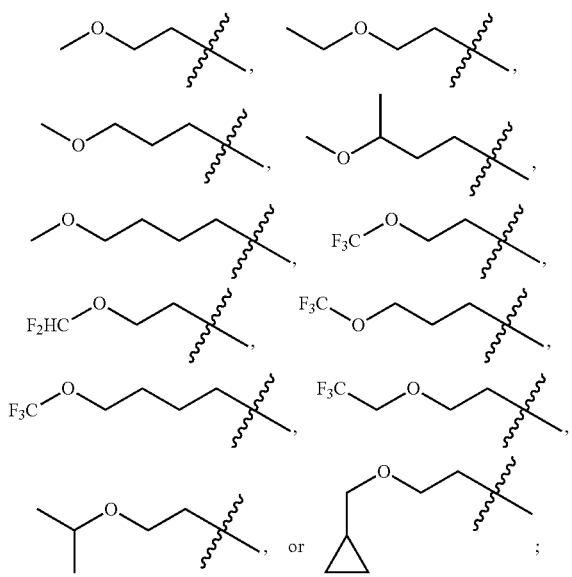

or, when the $R_4$ is independently a halogen, then the halogen is independently F;

or, when the $R_4$ is independently a $C_3$-$C_{10}$ cycloalkyl, then the $C_3$-$C_{10}$ cycloalkyl is independently cyclopropyl, cyclobutyl, cyclopentyl or cyclohexyl;

or, when the $R_4$ is independently a $C_3$-$C_{10}$ heterocycloalkyl, then the $C_3$-$C_{10}$ heterocycloalkyl is a tetrahydropyranyl or a tetrahydrofuranyl;

or, when the $R_3$ is a $C_1$-$C_{10}$ alkyl, then the $C_1$-$C_{10}$ alkyl is a $C_1$-$C_4$ alkyl;

or, when the $L_2$ is a $C_1$-$C_3$ alkylene, then the $C_1$-$C_3$ alkylene is —$CH_2$—;

or, when the $L_3$ is a $C_1$-$C_6$ alkylene, the $C_1$-$C_6$ alkylene is —$CH_2$—, —$CH_2CH_2$—, —$CH(CH_3)$— or —CH($CH_2CH_3$)—;

or, when the $L_3$ is a $C_2$-$C_6$ heteroalkylene, then the $C_2$-$C_6$ heteroalkylene is —$CH_2OCH_2$—;

or, the $L_2$ and the $L_3$ is at the para-position or meta-position to each other;

or, when m is not 0 and the $R_{10}$ is independently a halogen, then the halogen is F or Cl;

or, when m is not 0 and the $R_{10}$ is independently a $R_{10-1}$ substituted or unsubstituted $C_1$-$C_6$ alkyl, then the $C_1$-$C_6$ alkyl is methyl, ethyl, n-propyl, isopropyl, n-butyl, sec-butyl, isobutyl or tert-butyl;

or, when m is not 0 and the $R_{10}$ is independently a $R_{10-2}$ substituted or unsubstituted $C_1$-$C_6$ alkoxy, then the $C_1$-$C_6$ alkoxy is methoxy, ethoxy, n-propoxy, isopropoxy, n-butoxy, sec-butoxy, isobutoxy or tert-butoxy;

or, when m is not 0 and the $R_{10}$ is independently a $R_{10-3}$ substituted or unsubstituted $C_3$-$C_{10}$ cycloalkyl, then the $C_3$-$C_{10}$ cycloalkyl is cyclopropyl, cyclobutyl, cyclopentyl or cyclohexyl;

or, when the $R_5$ is a $C_1$-$C_{10}$ alkyl, then the $C_1$-$C_{10}$ alkyl is a $C_1$-$C_4$ alkyl;

or, when the $R_6$ is a $C_1$-$C_{10}$ alkyl, then the $C_1$-$C_{10}$ alkyl is a $C_1$-$C_4$ alkyl;

or, when the $R_5$ and the $R_6$ together with the nitrogen atom to which they are attached form a substituted or unsubstituted heterocyclic ring, the heterocyclic ring is a monocyclic ring;

or, when the $R_5$ and the $R_6$ together with the nitrogen atom to which they are attached form a substituted or unsubstituted heterocyclic ring and the heterocyclic ring is a heteroalicyclic ring, then the heteroalicyclic ring is a heterocycloalkyl or a heterocycloalkenyl;

or, when the $R_5$ and the $R_6$ together with the nitrogen atom to which they are attached form a substituted or unsubstituted heterocyclic ring, then the heterocyclic ring is a 4-9 membered heterocyclic ring;

or, when the $R_5$ and the $R_6$ together with the nitrogen atom to which they are attached form a substituted or unsubstituted heterocyclic ring, then the heteroatom is only nitrogen atom;

or, when the $R_5$ and the $R_6$ together with the nitrogen atom to which they are attached form a substituted or unsubstituted heterocyclic ring, then the number of the heteroatom is 1 or 2;

or, when the $R_5$ and the $R_6$ together with the nitrogen atom to which they are attached form a substituted heterocyclic ring and the $R_8$ is independently a halogen, then the halogen is F;

or, when the $R_5$ and the $R_6$ together with the nitrogen atom to which they are attached form a substituted heterocyclic ring and the $R_8$ is independently a $C_1$-$C_6$ alkyl, then the $C_1$-$C_6$ alkyl is methyl, ethyl, n-propyl, isopropyl, n-butyl, isobutyl or tert-butyl.

8. The compound of formula I, the tautomer thereof, the optical isomer thereof, the deuterated compound thereof, the hydrate thereof, the solvate thereof or the pharmaceutically acceptable salt thereof of claim 7, wherein, when the $R_2$ is a $C_1$-$C_{10}$ alkyl, then the $C_1$-$C_{10}$ alkyl is methyl, ethyl, n-propyl, isopropyl, n-butyl, isobutyl or tert-butyl;

or, when the $R_4$ is independently a $C_3$-$C_{10}$ cycloalkyl, then the $C_3$-$C_{10}$ cycloalkyl is independently cyclopropyl;

or, when the $R_4$ is independently a $C_3$-$C_{10}$ heterocycloalkyl and the $C_3$-$C_{10}$ heterocycloalkyl is a tetrahydropyranyl, then the tetrahydropyranyl is tetrahydropyran-4-yl;

or, when the $R_4$ is independently a $C_3$-$C_{10}$ heterocycloalkyl and the $C_3$-$C_{10}$ heterocycloalkyl is a tetrahydrofuranyl, then the tetrahydrofuranyl is tetrahydrofuran-2-yl;

or, when the R is a $C_1$-$C_3$ alkyl, then the $C_1$-$C_3$ alkyl is methyl, ethyl, n-propyl or isopropyl;

or, when $R_3$ is a $C_1$-$C_{10}$ alkyl, then the $C_1$-$C_{10}$ alkyl is methyl, ethyl, n-propyl, isopropyl, n-butyl, sec-butyl, isobutyl or tert-butyl;

or, when the $L_3$ is a $C_1$-$C_6$ alkylene, then the $C_1$-$C_6$ alkylene is —$CH_2$—;

or, the $L_2$ and the $L_3$ is at the para-position to each other, or, when m is not 0 and the $R_{10}$ is independently a $R_{10-1}$ substituted or unsubstituted $C_1$-$C_6$ alkyl, then the $R_{10-1}$ substituted $C_1$-$C_6$ alkyl is trifluoromethyl;

or, when m is not 0 and the $R_{10}$ is independently a $R_{10-2}$ substituted or unsubstituted $C_1$-$C_6$ alkoxy, then the $R_{10-2}$ substituted $C_1$-$C_6$ alkoxy is trifluoromethoxy;

or, when the $R_5$ is a $C_1$-$C_{10}$ alkyl, then the $C_1$-$C_{10}$ alkyl is methyl, ethyl, n-propyl, isopropyl, n-butyl, isobutyl or tert-butyl;

or, when the $R_6$ is a $C_1$-$C_{10}$ alkyl, then the $C_1$-$C_{10}$ alkyl is methyl, ethyl, n-propyl, isopropyl, n-butyl, isobutyl or tert-butyl;

or, when the $R_5$ and the $R_6$ together with the nitrogen atom to which they are attached form a substituted or unsubstituted heterocyclic ring and the heterocyclic ring is a heteroalicyclic ring, then the heteroalicyclic ring is a heterocycloalkyl;

or, when the $R_5$ and the $R_6$ together with the nitrogen atom to which they are attached form a substituted or unsubstituted heterocyclic ring, then the heterocyclic ring is a 5-7 membered heterocyclic ring;

or, when the $R_5$ and the $R_6$ together with the nitrogen atom to which they are attached form a substituted or unsubstituted heterocyclic ring, then the number of the heteroatom is 1.

9. The compound of formula I, the tautomer thereof, the optical isomer thereof, the deuterated compound thereof, the hydrate thereof, the solvate thereof or the pharmaceutically acceptable salt thereof of claim 8, wherein, when the $R_2$ is a $R_4$ substituted $C_1$-$C_{10}$ alkyl, then the $R_4$ substituted $C_1$-$C_{10}$ alkyl is

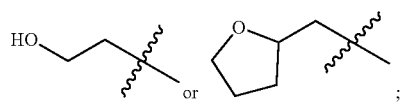

or, when the R is a $C_1$-$C_3$ alkyl, then the $C_1$-$C_3$ alkyl is methyl;

or, when the $R_3$ is a $C_1$-$C_{10}$ alkyl, then the $C_1$-$C_{10}$ alkyl is methyl or n-propyl;

or, when the $R_5$ is a $C_1$-$C_{10}$ alkyl, then the $C_1$-$C_{10}$ alkyl is methyl or ethyl;

or, when the $R_6$ is a $C_1$-$C_{10}$ alkyl, then the $C_1$-$C_{10}$ alkyl is methyl or ethyl;

or, when the $R_5$ and the $R_6$ together with the nitrogen atom to which they are attached form a substituted or unsubstituted heterocyclic ring, then the heterocyclic ring is any one of the following structures:

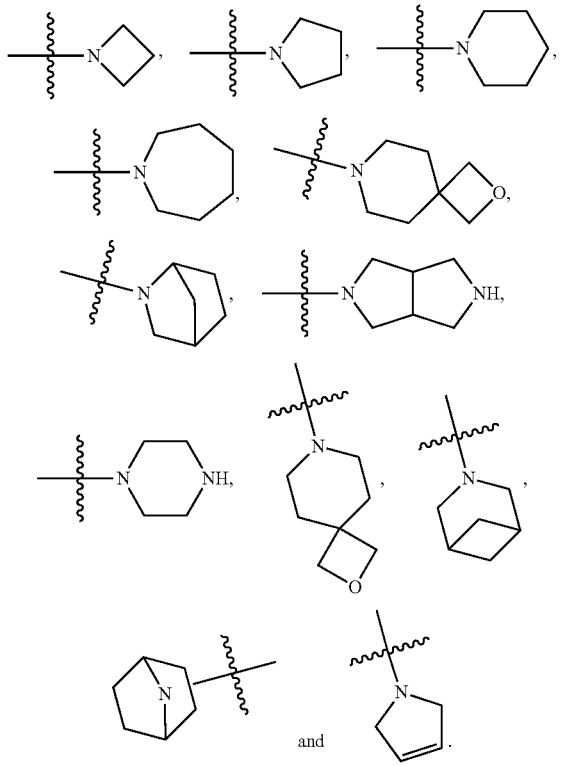

10. The compound of formula I, the tautomer thereof, the optical isomer thereof, the deuterated compound thereof, the hydrate thereof, the solvate thereof or the pharmaceutically acceptable salt thereof of claim 9, wherein, when the $R_5$ and the $R_6$ together with the nitrogen atom to which they are attached form a substituted or unsubstituted heterocyclic ring, then the "substituted heterocyclic ring" is selected from any one of the following structures:

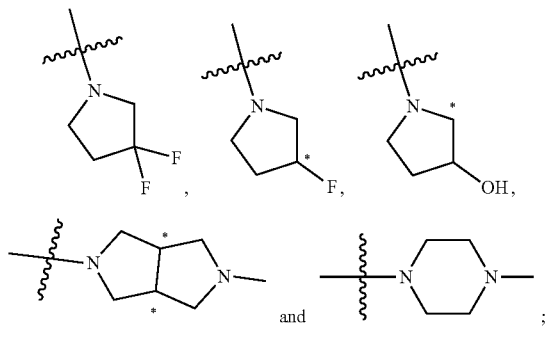

wherein the

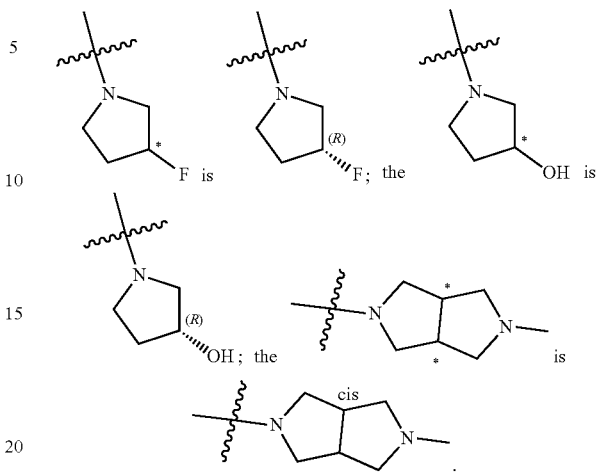

11. The compound of formula I, the tautomer thereof, the optical isomer thereof, the deuterated compound thereof, the hydrate thereof, the solvate thereof or the pharmaceutically acceptable salt thereof of claim 5, wherein, both X and Y are N; or X is N and Y is C;

or, $R_2$ is hydrogen, a $C_1$-$C_{10}$ alkyl, a $C_2$-$C_{10}$ heteroalkyl, a $C_3$-$C_{10}$ cycloalkyl, or, a $C_3$-$C_{10}$ heterocycloalkyl; wherein, the $C_1$-$C_{10}$ alkyl, the $C_2$-$C_{10}$ heteroalkyl, the $C_3$-$C_{10}$ cycloalkyl, and, the $C_3$-$C_{10}$ heterocycloalkyl are independently substituted by one or more $R_4$; when a plurality of $R_4$ substituents are present, each $R_4$ is the same or different; $R_4$ is independently selected from the group consisting of hydrogen, hydroxyl, a halogen, a $C_1$-$C_6$ alkyl, a $C_3$-$C_{10}$ cycloalkyl and a $C_3$-$C_{10}$ heterocycloalkyl;

or, $L_1$ is —O—;

or, R is hydrogen, a halogen, or, hydroxyl;

or, $R_3$ is hydrogen;

or, Z is NH or O;

or, $L_2$ is a $C_1$-$C_3$ alkylene;

or, $L_3$ is a $C_1$-$C_6$ alkylene;

or, D is phenylene;

or, m is 0 or 1;

or, $R_{10}$ is a halogen, cyano, a $R_{10-1}$ substituted or unsubstituted $C_1$-$C_6$ alkyl, a $R_{10-2}$ substituted or unsubstituted $C_1$-$C_6$ alkoxy, a $R_{10-3}$ substituted or unsubstituted $C_3$-$C_{10}$ cycloalkyl, or, a $R_{10-4}$ substituted or unsubstituted $C_3$-$C_{10}$ heterocycloalkyl; all of $R_{10-1}$, $R_{10-2}$, $R_{10-3}$ and $R_{10-4}$ are independently F, Cl, Br or I;

or, $R_1$ is —$NR_5R_6$; $R_5$ and $R_6$ together with the nitrogen atom to which they are attached form a substituted or unsubstituted heterocyclic ring.

12. The compound of formula I, the tautomer thereof, the optical isomer thereof, the deuterated compound thereof, the hydrate thereof, the solvate thereof or the pharmaceutically acceptable salt thereof of claim 11, wherein, both X and Y are N;

or, $R_2$ is a $C_1$-$C_{10}$ alkyl, or, a $C_2$-$C_{10}$ heteroalkyl containing one heteroatom; wherein, the $C_1$-$C_{10}$ alkyl is substituted by one or more $R_4$; when a plurality of $R_4$ substituents are present, each $R_4$ is the same or different; the $C_2$-$C_{10}$ heteroalkyl is substituted by one or more $R_4$; when a plurality of $R_4$ substituents are present, each $R_4$ is the same or different; wherein, the $R_4$ on the $C_1$-$C_{10}$ alkyl is independently hydroxyl or a $C_3$-$C_4$ heterocycloalkyl; the $R_4$ on the $C_2$-$C_{10}$ heteroalkyl is independently hydrogen or a halogen;

or, R is hydrogen;

or, Z is O;

or, $R_{11}$ is independently hydrogen;

or, $R_{10}$ is a halogen.

13. The compound of formula I, the tautomer thereof, the optical isomer thereof, the deuterated compound thereof, the hydrate thereof, the solvate thereof or the pharmaceutically acceptable salt thereof of claim 5, wherein, X and Y are independently C or N;

$R_2$ is hydrogen, a $C_1$-$C_{10}$ alkyl, a $C_2$-$C_{10}$ heteroalkyl, a $C_3$-$C_{10}$ cycloalkyl, or, a $C_3$-$C_{10}$ heterocycloalkyl; wherein, the $C_1$-$C_{10}$ alkyl, the $C_2$-$C_{10}$ heteroalkyl, the $C_3$-$C_{10}$ cycloalkyl, and, the $C_3$-$C_{10}$ heterocycloalkyl are independently substituted by one or more $R_4$; when a plurality of $R_4$ substituents are present, each $R_4$ is the same or different; $R_4$ is independently selected from the group consisting of hydrogen, hydroxyl, a halogen, a $C_1$-$C_6$ alkyl, a $C_3$-$C_{10}$ cycloalkyl and a $C_3$-$C_{10}$ heterocycloalkyl; however, not all the $R_4$ on the $C_1$-$C_{10}$ alkyl is hydrogen;

$L_1$ is —O—;

R is hydrogen, a halogen, or, hydroxyl;

$R_3$ is hydrogen;

Z is $CH_2$, NH, O or S;

$L_2$ is a $C_1$-$C_3$ alkylene;

$L_3$ is a $C_1$-$C_6$ alkylene;

D is phenylene;

m is 0, 1, 2, 3 or 4; when a plurality of $R_{10}$ substituents are present on D, each $R_{10}$ is the same or different;

$R_{10}$ is independently a halogen, cyano, a $R_{10\text{-}1}$ substituted or unsubstituted $C_1$-$C_6$ alkyl, a $R_{10\text{-}2}$ substituted or unsubstituted $C_1$-$C_6$ alkoxy, a $R_{10\text{-}3}$ substituted or unsubstituted $C_3$-$C_{10}$ cycloalkyl, or, a $R_{10\text{-}4}$ substituted or unsubstituted $C_3$-$C_{10}$ heterocycloalkyl; all of $R_{10\text{-}1}$, $R_{10\text{-}2}$, $R_{10\text{-}3}$ and $R_{10\text{-}4}$ are independently F, Cl, Br or I;

$R_1$ is —$NR_5R_6$;

$R_5$ and $R_6$ are independently hydrogen or a $C_1$-$C_{10}$ alkyl; wherein the $C_1$-$C_{10}$ alkyl is substituted by one or more $R_7$; when a plurality of $R_7$ substituents are present, each $R_7$ is the same or different; $R_7$ is independently selected from the group consisting of hydrogen, hydroxyl, a halogen, a $C_3$-$C_{10}$ cycloalkyl and a $C_3$-$C_{10}$ heterocycloalkyl;

alternatively, $R_5$ and $R_6$ together with the nitrogen atom to which they are attached form a substituted or unsubstituted heterocyclic ring; the substituted heterocyclic ring is substituted by one or more $R_8$; when a plurality of $R_8$ substituents are present, each $R_8$ is the same or different; $R_8$ is independently a halogen, hydroxyl, a $C_1$-$C_6$ alkyl, or, a $C_3$-$C_{10}$ cycloalkyl.

14. The compound of formula I, the tautomer thereof, the optical isomer thereof, the deuterated compound thereof, the hydrate thereof, the solvate thereof or the pharmaceutically acceptable salt thereof of claim 5, wherein, X and Y are selected from N;

$R_2$ is a $C_1$-$C_{10}$ alkyl, or, a $C_2$-$C_{10}$ heteroalkyl containing one heteroatom; wherein, the $C_1$-$C_{10}$ alkyl is substituted by one or more $R_4$; when a plurality of $R_4$ substituents are present, each $R_4$ is the same or different; the $C_2$-$C_{10}$ heteroalkyl is substituted by one or more $R_4$; when a plurality of $R_4$ substituents are present, each $R_4$ is the same or different; wherein, the $R_4$ on the $C_1$-$C_{10}$ alkyl is independently hydroxyl or a $C_3$-$C_4$ heterocycloalkyl; the $R_4$ on the $C_2$-$C_{10}$ heteroalkyl is independently hydrogen or a halogen;

$L_1$ is —O—;

R is hydrogen, a halogen, or, hydroxyl;

$R_3$ is hydrogen;

Z is NH or O;

$L_2$ is —$CH_2$—;

$L_3$ is a $C_1$-$C_6$ alkylene;

D is phenylene;

m is 0 or 1;

$R_{10}$ is a halogen, a $R_{10\text{-}1}$ substituted or unsubstituted $C_1$-$C_6$ alkyl, a $R_{10\text{-}2}$ substituted or unsubstituted $C_1$-$C_6$ alkoxy, a $R_{10\text{-}3}$ substituted or unsubstituted $C_3$-$C_{10}$ cycloalkyl, or, a $R_{10\text{-}4}$ substituted or unsubstituted $C_3$-$C_{10}$ heterocycloalkyl; all of $R_{10\text{-}1}$, $R_{10\text{-}2}$, $R_{10\text{-}3}$ and $R_{10\text{-}4}$ are independently F, Cl, Br or I;

$R_1$ is —$NR_5R_6$;

$R_5$ and $R_6$ are independently a $C_1$-$C_{10}$ alkyl;

alternatively, $R_5$ and $R_6$ together with the nitrogen atom to which they are attached form a substituted or unsubstituted heterocyclic ring; the substituted heterocyclic ring is substituted by one or more $R_8$; when a plurality of $R_8$ substituents are present, each $R_8$ is the same or different; $R_8$ is independently a halogen, hydroxyl, or, a $C_1$-$C_6$ alkyl.

15. The compound of formula I, the tautomer thereof, the optical isomer thereof, the deuterated compound thereof, the hydrate thereof, the solvate thereof or the pharmaceutically acceptable salt thereof of claim 5, wherein, X and Y are selected from N;

$R_2$ is a $C_1$-$C_{10}$ alkyl, or, a $C_2$-$C_{10}$ heteroalkyl containing one heteroatom; wherein, the $C_1$-$C_{10}$ alkyl is substituted by one or more $R_4$; when a plurality of $R_4$ substituents are present, each $R_4$ is the same or different; the $C_2$-$C_{10}$ heteroalkyl is substituted by one or more $R_4$; when a plurality of $R_4$ substituents are present, each $R_4$ is the same or different; wherein, the $R_4$ in the $C_1$-$C_{10}$ alkyl is independently hydroxyl or a $C_3$-$C_4$ heterocycloalkyl; the $R_4$ in the $C_2$-$C_{10}$ heteroalkyl is independently hydrogen or a halogen;

$L_1$ is —O—;

R is hydrogen;

$R_3$ is hydrogen;

Z is O;

$L_2$ is —$CH_2$—;

$L_3$ is a $C_1$-$C_6$ alkylene;

D is phenylene;

m is 0 or 1;

$R_{10}$ is a halogen;

$R_1$ is —$NR_5R_6$;

$R_5$ and $R_6$ are independently a $C_1$-$C_{10}$ alkyl;

alternatively, $R_5$ and $R_6$ together with the nitrogen atom to which they are attached form a substituted or unsubstituted heterocyclic ring; the substituted heterocyclic ring is substituted by one or more $R_8$; when a plurality of $R_8$ substituents are present, each $R_8$ is the same or different; $R_8$ is independently a halogen, hydroxyl, or, a $C_1$-$C_6$ alkyl.

16. The compound of formula I or formula II, the tautomer thereof, the optical isomer thereof, the deuterated compound thereof, the hydrate thereof, the solvate thereof or the pharmaceutically acceptable salt thereof of claim 1, wherein, the compound of formula I is selected from any one of the following structures:

133
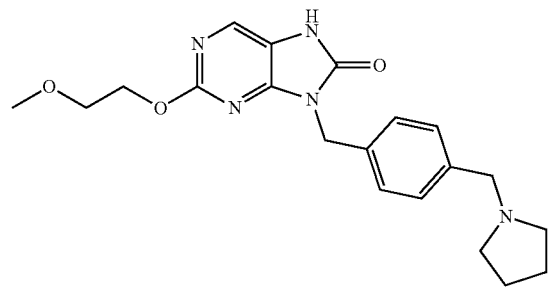
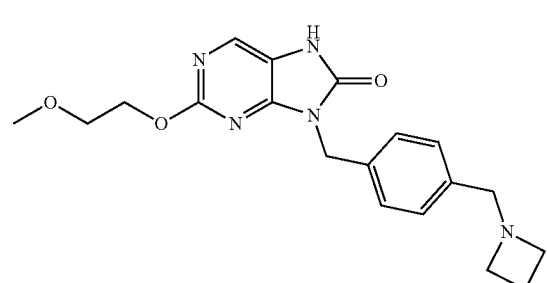
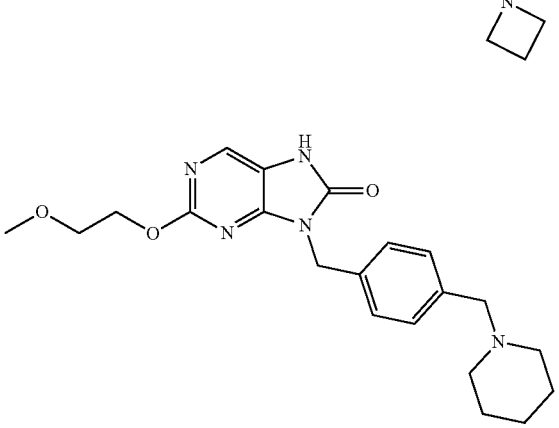
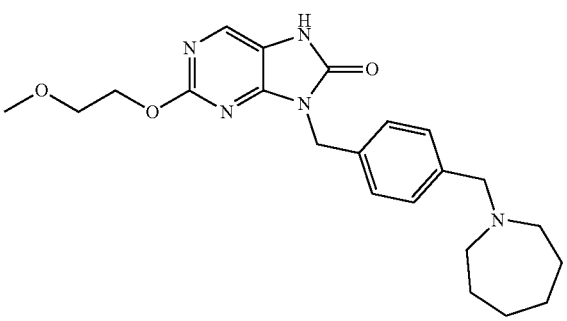
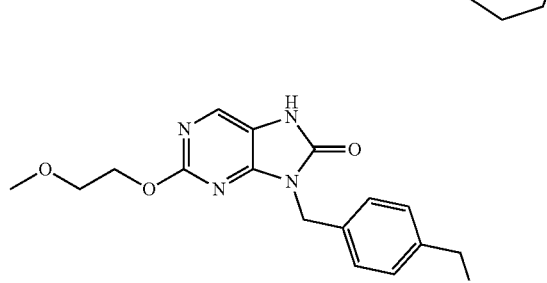
134
-continued
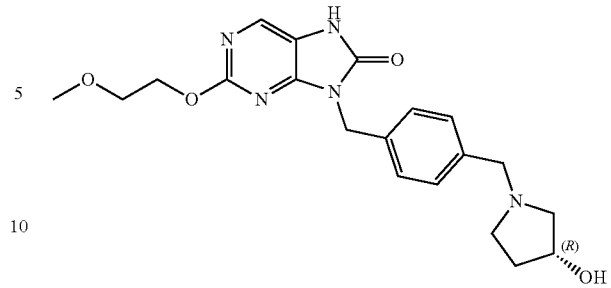
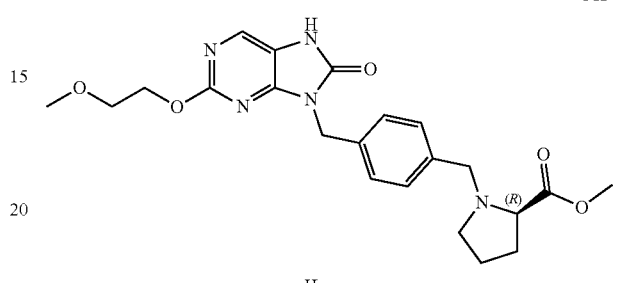

135
-continued
136
-continued
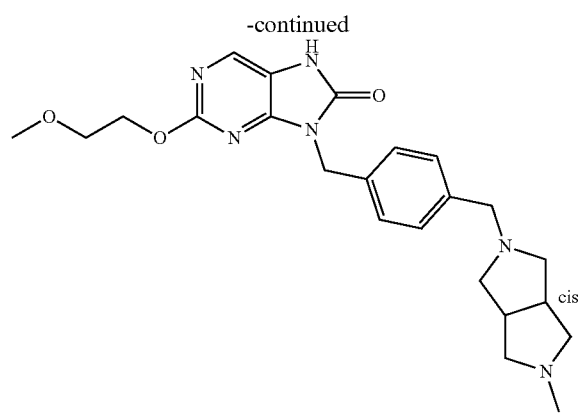
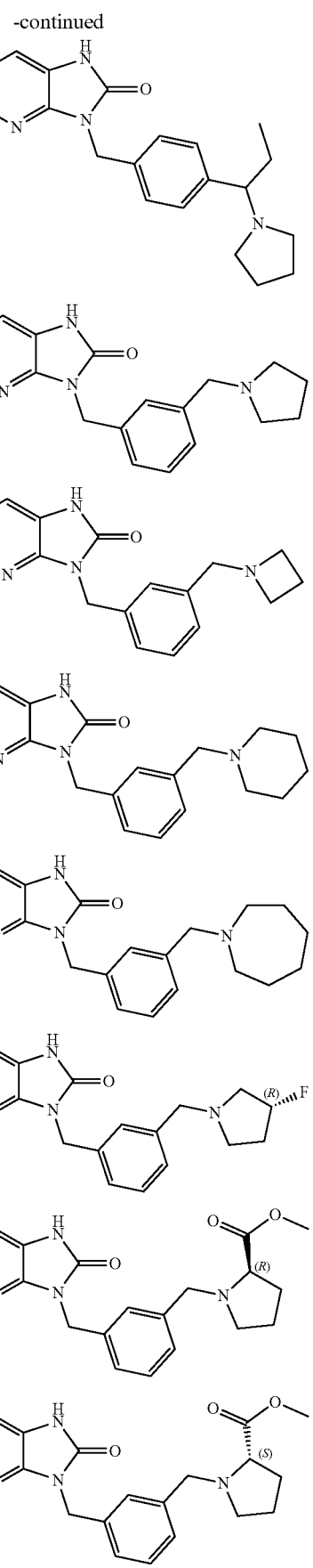

137
-continued
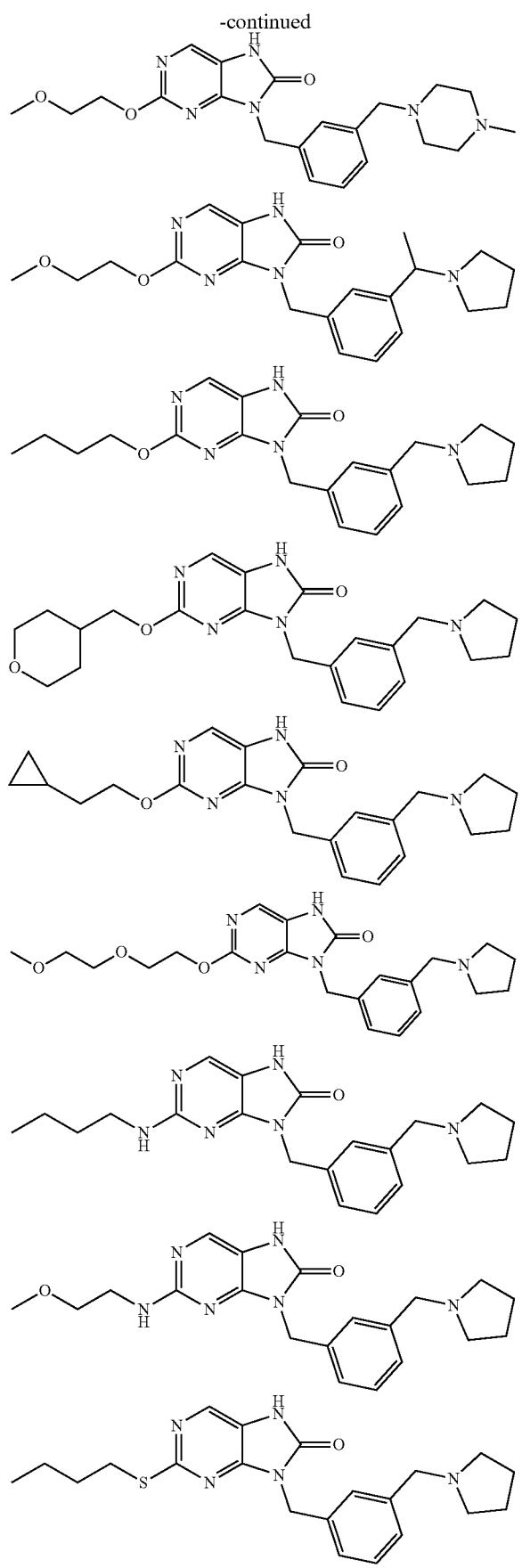
138
-continued
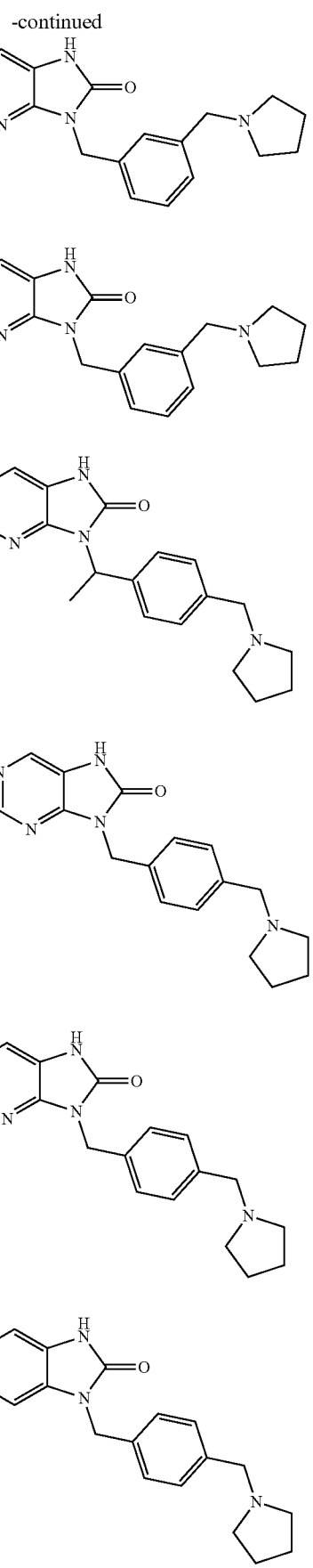

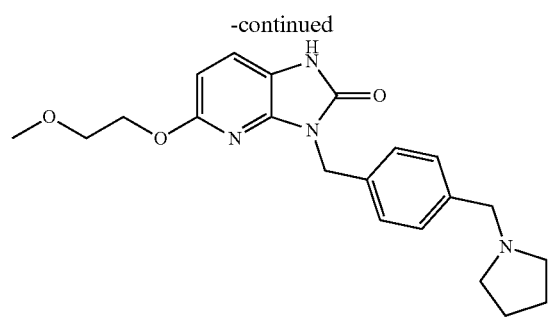
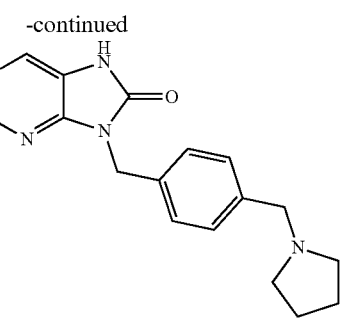
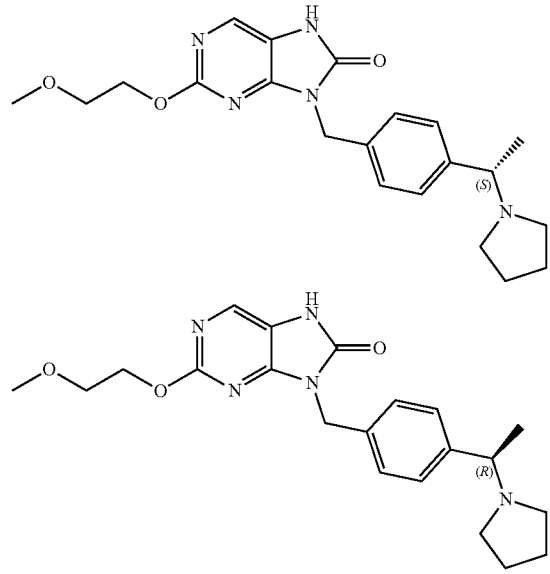
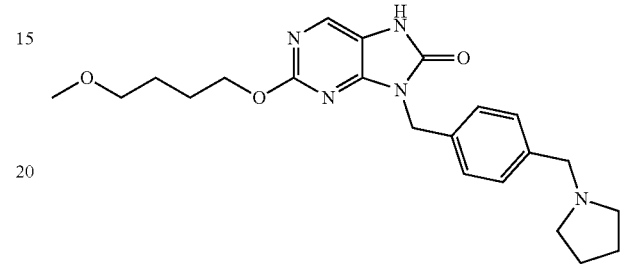
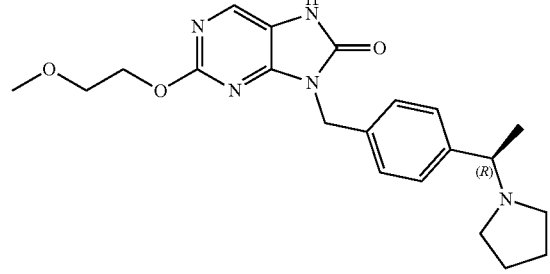
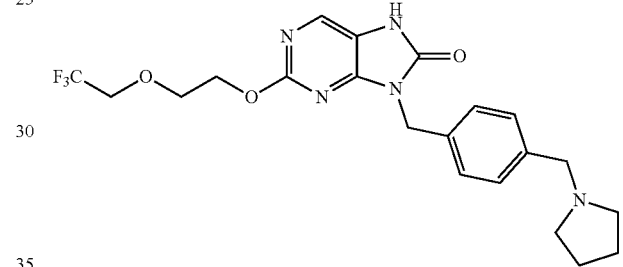
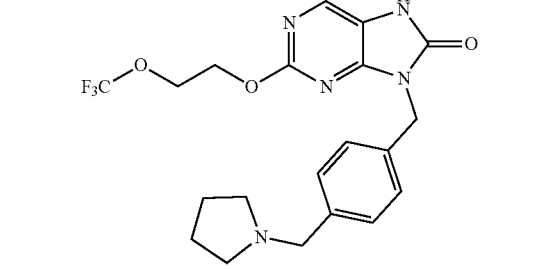
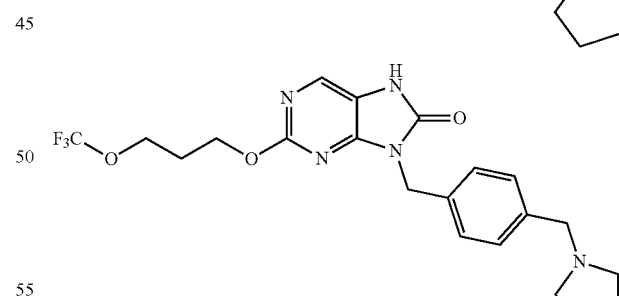
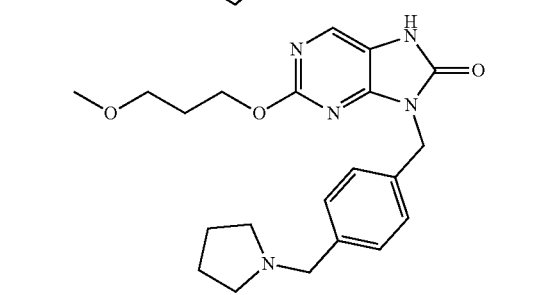
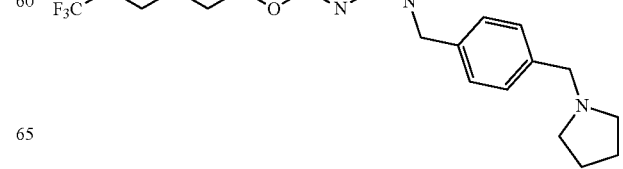

141
-continued
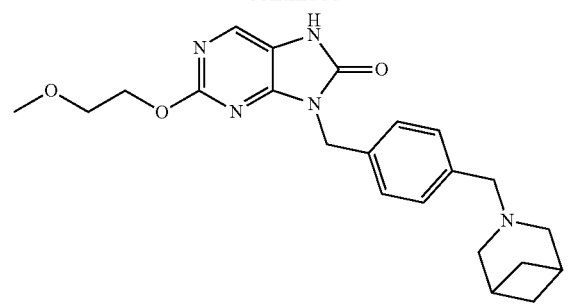
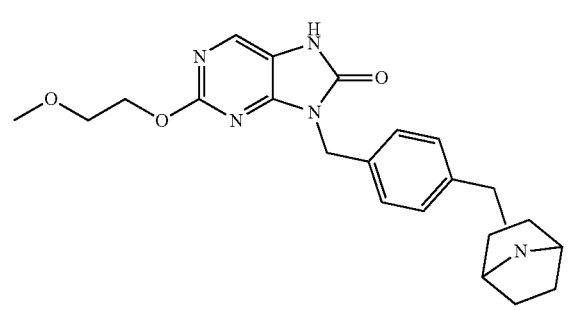
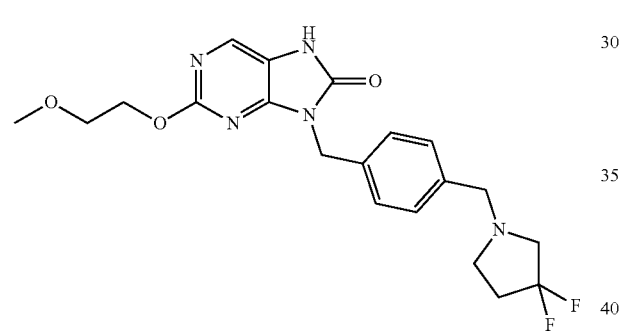
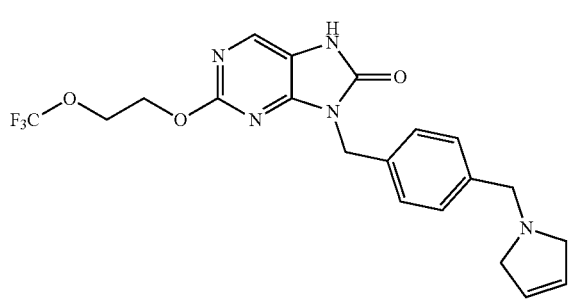
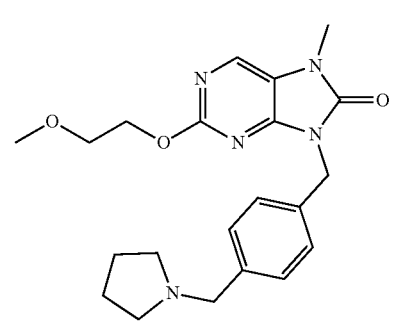
142
-continued
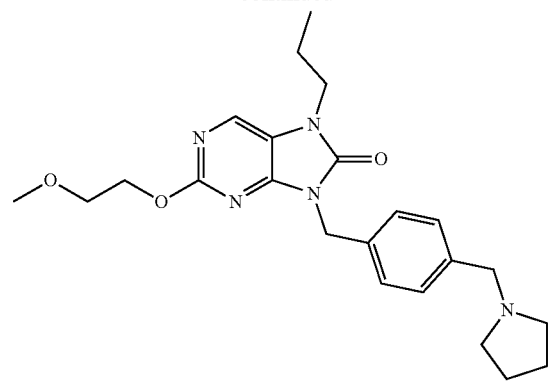
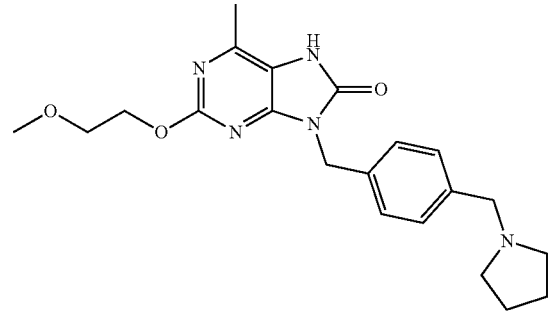
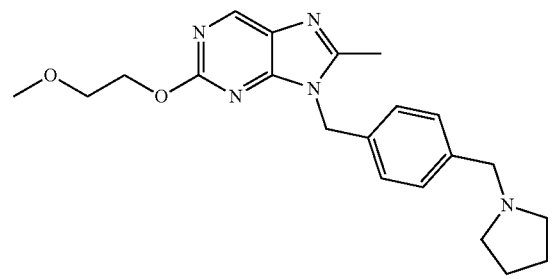
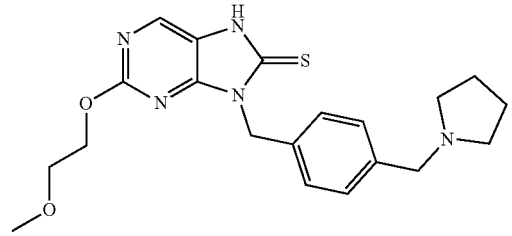
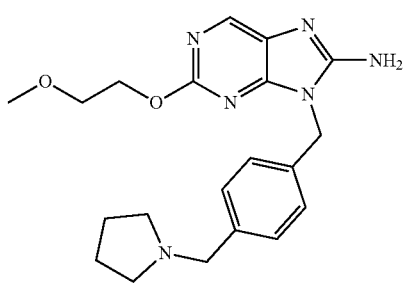

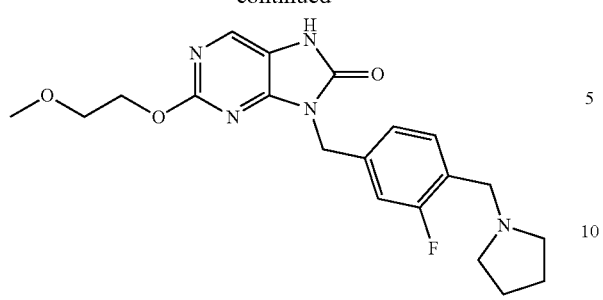

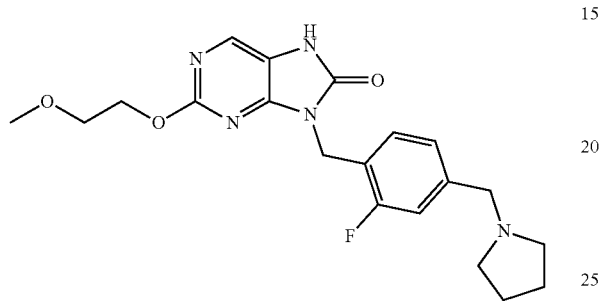

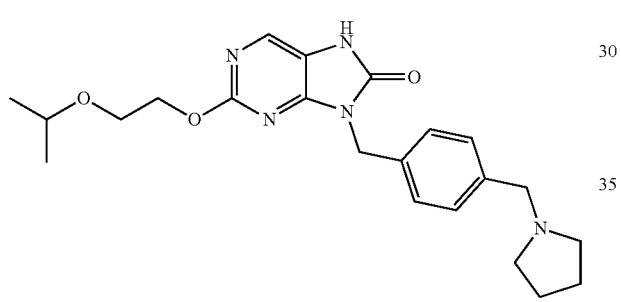

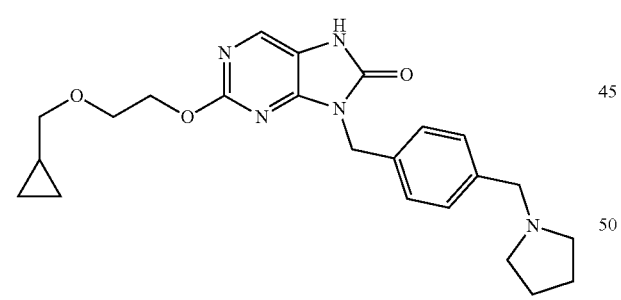

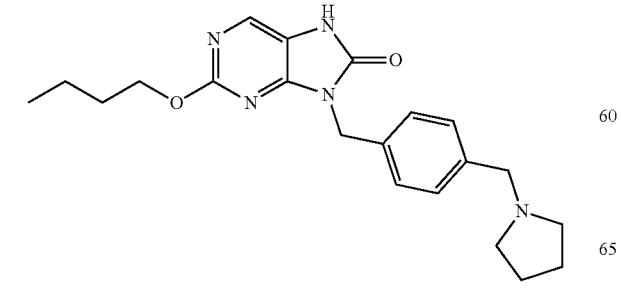

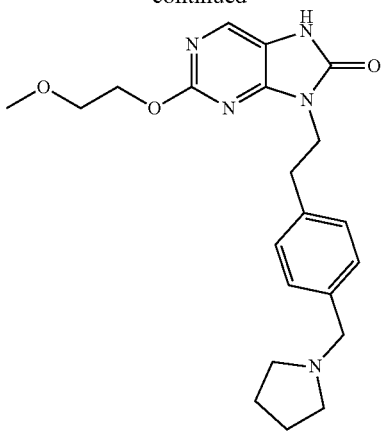

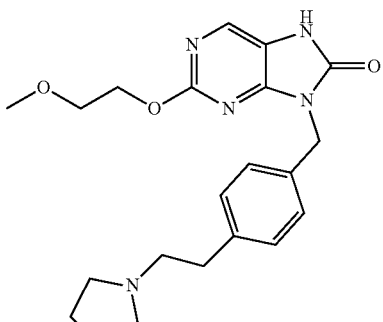

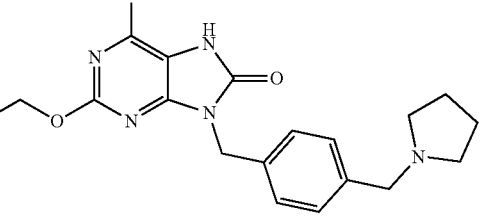

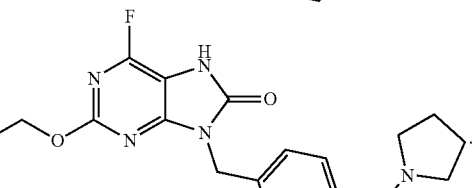

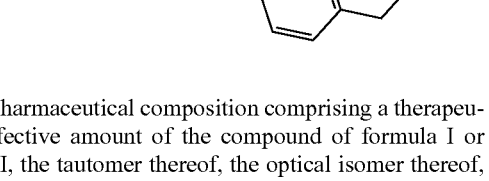

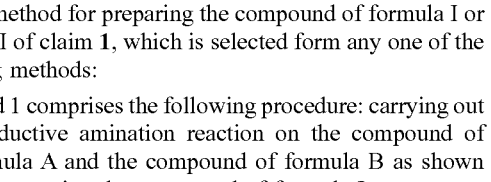

17. A pharmaceutical composition comprising a therapeutically effective amount of the compound of formula I or formula II, the tautomer thereof, the optical isomer thereof, the deuterated compound thereof, the hydrate thereof, the solvate thereof or the pharmaceutically acceptable salt thereof of claim 1, and one or more pharmaceutically acceptable excipients.

18. A method for preparing the compound of formula I or formula II of claim 1, which is selected form any one of the following methods:

method 1 comprises the following procedure: carrying out a reductive amination reaction on the compound of formula A and the compound of formula B as shown below to give the compound of formula I;

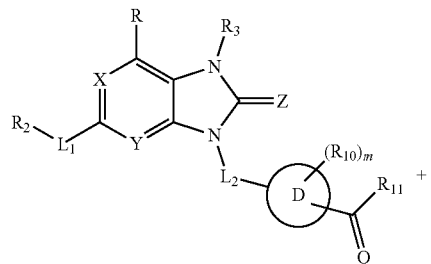

Formula A

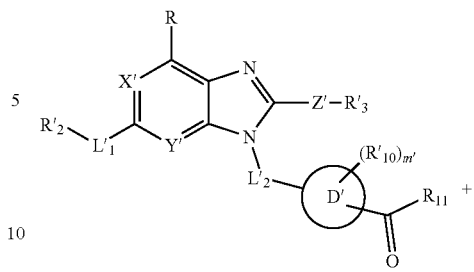

Formula C

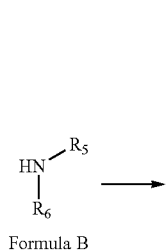

Formula B

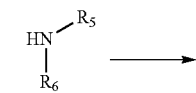

Formula D

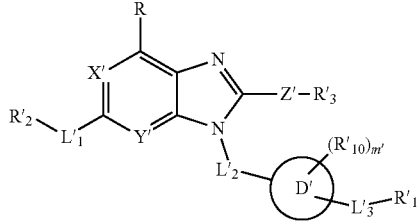

Formula II

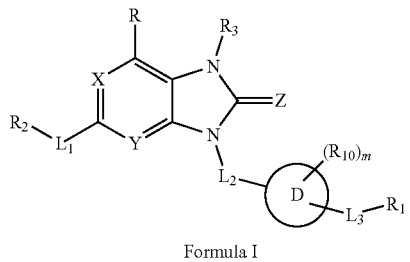

Formula I wherein, X, Y, Z, $R_2$, $R_3$, $R_5$, $R_6$, $R_{10}$, m, $L_1$, $L_2$, D and $R_{11}$ are as defined in claim 1; $L_3$ is $C_1$ alkylene;

or method 2 comprises the following procedure: carrying out a reductive amination reaction on the compound of formula C and the compound of formula D as shown below to give the compound of formula II;

wherein, X', Y', Z', $R'_2$, $R'_3$, $R_5$, $R_6$, $R'_{10}$, m', $L'_1$, $L'_2$, D' and $R_{11}$ are as defined in claim 1; $L'_3$ is $C_1$ alkylene.

19. A method for treating a disease associated with TLR7 activity in a subject in need thereof, comprising administering a therapeutically effective amount of the compound of formula I or formula II, the tautomer thereof, the optical isomer thereof, the deuterated compound thereof, the hydrate thereof, the solvate thereof or the pharmaceutically acceptable salt thereof of claim 1 to the subject, wherein the disease associated with TLR7 activity is a disease selected from the group consisting of melanoma, non-small cell lung cancer, hepatocellular carcinoma, basal cell carcinoma, renal cell carcinoma, myeloma, allergic rhinitis, asthma, COPD, ulcerative colitis, liver fibrosis, HBV, HCV, HPV, RSV, SARS, HIV and influenza.

\* \* \* \* \*